US011739142B2

(12) United States Patent
Fischer et al.

(10) Patent No.: US 11,739,142 B2
(45) Date of Patent: Aug. 29, 2023

(54) BISPECIFIC ANTI-CCL2 ANTIBODIES

(71) Applicant: Hoffmann-La Roche Inc., Little Falls, NJ (US)

(72) Inventors: Jens Fischer, Penzberg (DE); Guy Georges, Penzberg (DE); Anton Jochner, Penzberg (DE); Gregor Jordan, Penzberg (DE); Hubert Kettenberger, Penzberg (DE); Joerg Moelleken, Penzberg (DE); Tilman Schlothauer, Penzberg (DE); Georg Tiefenthaler, Penzberg (DE); Valeria Runza, Penzberg (DE); Meher Majety, Penzberg (DE); Martin Schaefer, Penzberg (DE); Maria Viert, Penzberg (DE); Shu Feng, Singapore (SG); Wei Shiong Adrian Ho, Singapore (SG); Siok Wan Gan, Singapore (SG); Runyi Adeline Lam, Singapore (SG); Michael Gertz, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 192 days.

(21) Appl. No.: 17/123,465

(22) Filed: Dec. 16, 2020

(65) Prior Publication Data

US 2021/0188960 A1     Jun. 24, 2021

(30) Foreign Application Priority Data

Dec. 18, 2019   (EP) ..................................... 19217665

(51) Int. Cl.
 *C07K 16/24*  (2006.01)
 *A61K 39/00*  (2006.01)

(52) U.S. Cl.
 CPC ........ *C07K 16/24* (2013.01); *A61K 2039/505* (2013.01); *C07K 2317/31* (2013.01); *C07K 2317/565* (2013.01)

(58) Field of Classification Search
 None
 See application file for complete search history.

(56) References Cited

U.S. PATENT DOCUMENTS

| 4,676,980 | A | 6/1987 | Segal et al. |
| 4,737,456 | A | 4/1988 | Weng et al. |
| 5,648,237 | A | 7/1997 | Carter |
| 5,731,168 | A | 3/1998 | Carter et al. |
| 5,789,199 | A | 8/1998 | Joly et al. |
| 5,840,523 | A | 11/1998 | Simmons et al. |
| 5,959,177 | A | 9/1999 | Hein et al. |
| 6,040,498 | A | 3/2000 | Stomp et al. |
| 6,171,586 | B1 | 1/2001 | Lam et al. |
| 6,267,958 | B1 | 7/2001 | Andya et al. |
| 6,417,429 | B1 | 7/2002 | Hein et al. |
| 6,420,548 | B1 | 7/2002 | Vezina et al. |
| 7,125,978 | B1 | 10/2006 | Vezina et al. |
| 7,695,936 | B2 | 4/2010 | Carter et al. |
| 2005/0260186 | A1 | 11/2005 | Bookbinder et al. |
| 2006/0104968 | A1 | 5/2006 | Bookbinder et al. |
| 2008/0069820 | A1 | 3/2008 | Fuh et al. |
| 2009/0035836 | A1 | 2/2009 | Deepshikaha et al. |

FOREIGN PATENT DOCUMENTS

| EP | 1752471 A1 | 2/2007 |
| EP | 1772465 B1 | 2/2009 |
| EP | 1870459 B1 | 6/2016 |
| WO | 96/027011 A1 | 9/1996 |
| WO | 98/050431 A3 | 11/1998 |
| WO | 98/050431 A2 | 12/1998 |
| WO | 01/77342 A1 | 10/2001 |
| WO | 02/060919 A2 | 8/2002 |
| WO | 2004/035752 A2 | 4/2004 |
| WO | 2005/037867 A1 | 4/2005 |
| WO | 2005/047327 A2 | 5/2005 |
| WO | 2005/123780 A2 | 12/2005 |
| WO | 2006/019447 A1 | 2/2006 |
| WO | 2006/031370 A2 | 3/2006 |
| WO | 2006/044908 A2 | 4/2006 |
| WO | 2006/053301 A2 | 5/2006 |
| WO | 2006/105338 A2 | 5/2006 |
| WO | 2006/050166 A2 | 11/2006 |
| WO | 2007/041635 A2 | 4/2007 |
| WO | 2007/110205 A2 | 4/2007 |
| WO | 2007/147901 A1 | 12/2007 |
| WO | 2008/022152 A2 | 2/2008 |
| WO | 2008/024715 A2 | 2/2008 |
| WO | 2008/077945 A2 | 3/2008 |

(Continued)

OTHER PUBLICATIONS

Loberg et al. Targeting CCL2 with Systemic Delivery of Neutralizing Antibodies Induces Prostate Cancer Tumor Regression In vivo. Cancer Res vol. 67/19:9417-9424, (Oct. 1, 2007). (Year: 2007).*
Lutgens et al. (Gene Profiling in Atherosclerosis Reveals a Key Role for Small Inducible Cytokines. Validation Using a Novel Monocyte Chemoattractant Protein Monoclonal Antibody. Circulation vol. 111:3443-342, (2005). (Year: 2005).*
Atwell, S., et al., "Stable heterodimers from remodeling the domain interface of a homodimer using a phage display library" J Mol Biol 270(1):26-35 (Jul. 4, 1997).
Brennan, M. et al., "Preparation of bispecific antibodies by chemical recombination of monoclonal immunoglobulin G1 fragments" Science 229( SUPPL 4708):81-83 (Jul. 5, 1985).
Bussiere, J., et al., "Alternative strategies for toxicity testing of species-specific biopharmaceuticals" Int J Toxicol 28(3):230-253 (May 31, 2009).

(Continued)

*Primary Examiner* — Joanne Hama
*Assistant Examiner* — Regina M DeBerry
(74) *Attorney, Agent, or Firm* — Yan Qi

(57) ABSTRACT

The present invention relates to bispecific anti-CCL2 antibodies binding to two different epitopes on human CCL2, pharmaceutical compositions thereof, their manufacture, and use as medicaments for the treatment of cancers, inflammatory, autoimmune and ophthalmologic diseases.

2 Claims, 35 Drawing Sheets

Specification includes a Sequence Listing.

(56) References Cited

FOREIGN PATENT DOCUMENTS

| WO | 2008/092117 A2 | 7/2008 |
| --- | --- | --- |
| WO | 2009/041613 A1 | 2/2009 |
| WO | 2009/080251 A1 | 2/2009 |
| WO | 2009/058492 A2 | 7/2009 |
| WO | 2009/080252 A1 | 7/2009 |
| WO | 2009/080253 A1 | 7/2009 |
| WO | 2009/086320 A1 | 7/2009 |
| WO | 2009/089004 A1 | 7/2009 |
| WO | 2009/125825 A1 | 10/2009 |
| WO | 2010/045193 A1 | 4/2010 |
| WO | 2010/106180 A1 | 9/2010 |
| WO | 2010/112193 A1 | 10/2010 |
| WO | 2010/115589 A1 | 10/2010 |
| WO | 2010/136172 A1 | 12/2010 |
| WO | 2010/145792 A1 | 12/2010 |
| WO | 2010/129304 A2 | 2/2011 |
| WO | 2011/034605 A2 | 3/2011 |
| WO | 2011/090754 A1 | 7/2011 |
| WO | 2011/090762 A1 | 7/2011 |
| WO | 2011/122011 A2 | 10/2011 |
| WO | 2011/143545 A1 | 11/2011 |
| WO | 2012/016227 A1 | 2/2012 |
| WO | 2012/058768 A1 | 6/2012 |
| WO | 2012/058768 A8 | 6/2012 |
| WO | 2012/073992 A1 | 6/2012 |
| WO | 2012/115241 A1 | 8/2012 |
| WO | 2012/122011 A2 | 9/2012 |
| WO | 2012/132067 A1 | 10/2012 |
| WO | 2013/026831 A1 | 2/2013 |
| WO | 2013/046704 A2 | 4/2013 |
| WO | 2013/046722 A1 | 4/2013 |
| WO | 2013/047752 A1 | 4/2013 |
| WO | 2013/081143 A1 | 6/2013 |
| WO | 2013/096291 A2 | 6/2013 |
| WO | 2013/096291 A3 | 6/2013 |
| WO | 2013/125667 A1 | 8/2013 |
| WO | 2013/157953 A1 | 10/2013 |
| WO | 2013/157954 A1 | 10/2013 |
| WO | 2013/180200 A1 | 12/2013 |
| WO | 2013/180201 A1 | 12/2013 |
| WO | 2014/030728 A1 | 2/2014 |
| WO | 2014/145159 A2 | 9/2014 |
| WO | 2015/095539 A1 | 6/2015 |
| WO | 2015/150447 A1 | 10/2015 |
| WO | 2016/016299 A1 | 2/2016 |
| WO | 2016/098357 A1 | 6/2016 |
| WO | 2016/125495 A1 | 8/2016 |
| WO | 2016/172485 A2 | 10/2016 |
| WO | 2017/046994 A1 | 3/2017 |

OTHER PUBLICATIONS

Carter, Paul, "Bispecific human IgG by design" J Immunol Methods 248(1-2):7-15 (Feb. 1, 2001).
Charlton, K.A., "Expression and isolation of recombinant antibody fragments in *E. coli*" Methods Mol Biol 248:245-254 (2003).
Chothia, C., et al., "Canonical structures for the hypervariable regions of immunoglobulins" J Mol Biol 196(4):901-917 (Aug. 20, 1987).
Clackson, T., et al., "Making antibody fragments using phage display libraries" Nature 352(6336):624-628 (Aug. 15, 1991).
Connolly, J ., "Analytical Molecular Surface Calculation" J Appl Cryst 16:548-558 (Oct. 1, 1983).
Dall'acqua, W., et al., "Properties of human I gG1s engineered for enhanced binding to the neonatal Fc receptor (FcRn)" J Biol Chem 281(33):23514-23524 (Aug. 18, 2006).
Davis, J., et al., "SEEDbodies: fusion proteins based on strand-exchange engineered domain (SEED) CH3 heterodiniers in an Fe analogue platform for asymmetric binders or imrnunofusions and bispeeifie antibodies" Protein Eng Des Sel 23(4):195-202 (Apr. 1, 2010).

Deng, R., et al., "Pharmacokinetics of Humanized Monoclonal Anti-Tumor Necrosis Factor-α Antibody and Its Neonatal Fc Receptor Variants in Mice and Cynomolgus Monkeys" Drug Metab Dispos 38(4):600-605 (Apr. 1, 2010).
Devanaboyina, S.C., et al., "The effect of pH dependence of antibody-antigen interactions on subcellular trafficking dynamics" MABS 5(6):851-859 (Nov. 1, 2013).
Fetterly, G., et al., "Utilizing pharmacokinetics/pharmacodynamics modeling to simultaneously examine free CCL2, total CCL2 and carlumab (CNTO 888) concentration time data" J Clin Pharmacol 53(10): 1020-1027 (Oct. 1, 2013).
Flatman, S., et al., "Process analytics for purification of monoclonal antibodies" J Chromatogr 848(1):79-87 (Mar 15, 2007).
Gerngross, T., "Advances in the Production of Human Therapeutic Proteins in Yeasts and Filamentous Fungi" Nat Biotechnol 22(11):1409-1414 (Nov 22, 2004).
Graham, F., et al., "Characteristics of a Human Cell Line Transformed by DNA from Human Adenovirus Type 5" J Gen Virol 36(1):59-74 (Feb. 1, 1977).
Gruber, M. et al., "Efficient tumor cell lysis mediated by a bispecific single chain antibody expressed in *Escheiiehia coli*" J Immunol 152(11):5368-5374 (Jun. 1, 1994).
Handel, T., et al., "Heteronuelear (1H, 13C, 15N) NMR Assignments and Solution Structure of the Monoeyte Chemoattraetant Protein-1 (MCP-1) Dimer" Biochemistry 35(21):6569-6584 (May 28, 1996).
Haringman, J., et al., "A randomized controlled trial with an anti-CCL2 (anti-monoeyte chemotaetie protein 1) monoclonal antibody in patients with rheumatoid arthritis" Arthritis Rheum 54(8):2387-2392 (Aug. 1, 2006).
Heyl, D., et al., "pKa and volume of residue one influence delta/mu opioid binding: QSAR analysis of tyrosine replacement in a non-selective deltorphin analogue" Bioorg Med Chem 11(17):3761-3768 (Aug. 15, 2003).
Hinton, P., et al., "An Engineered Human IgG1 Antibody with Longer Serum Half-life" J Immunol 176(1):346-356 (Jan. 1, 2006).
Holliger, P., et al, "Diabodies: Small Bivalent and Bispecific Antibody Fragments" PNAS 90(14):6444-6448 (Jul. 15, 1993).
Igawa, T., et al, "Antibody recycling by engineered pH-dependent antigen binding improves the duration of antigen neutralization" Nat Biotechnol 28(11):1203-1207 (Nov. 1, 2010).
Igawa, T., et al., "Sweeping antibody as a novel therapeutic antibody modality capable of eliminating soluble antigens from circulation" Immunol Rev 270(1): 132-151 (Mar. 1, 2016).
Junghans, R., et al., "Anti-Tac-H, a Humanized Antibody to the Interleukin 2 Receptor with New Features for Imrnunotherapy in Malignant and Immune Disorders" Cancer Res 50(5):1495-1502 (Mar. 1, 1990).
Kabat, E., et al. U.S. Dept. of Health and Human Services, Public Health Services, NIH Publ. No. 91-32423 "Sequences of Proteins of Immunological Interest" ( 1983).
Klein, C. et al., "The use of CrossMAb technology for the generation of bi- and multispecific antibodies" MABS 8(6):1010-1020 (Aug. 31, 2016).
Kostelny, S., et al., "Formation of a bispecific antibody by the use of leucine zippers" J Immunol 148(5):1547-1553 (Mar. 1, 1992).
Lee, B., et al., "The interpretation of protein structures: Estimation of static accessibility" J Mol Biol 55(3):379-400 (Feb. 14, 1971).
Li, H., et al., "Optimization of humanized IgGs in glycoengineered Pichia paston's" Nat Biotechnol 24(2):210-215 (Feb. 1, 2006).
Lubkowski, J ., et al., "The structure of MCP-1 in two crystal forms provides a rare example of variable quaternary interactions" Nat Struct Biol 4(1):64-69 (Jan. 1, 1997).
MacCallum, R., et al., "Antibody-antigen Interactions: Contact Analysis and Binding Site Topography" J Mol Biol 262:732-745 (Oct. 11, 1996).
Mather, J., "Establishment and characterization of two distinct mouse testicular epithelial cell lines" Biol Reprod 23(1):243-252 (Aug. 1, 1980).
Mather, J ., et al, "Culture of Testicular Cells in Hormone-Supplemented Serum-Free Medium" Ann NY Acad Sci 383:44-68 (Jan. 1, 1982).

(56) References Cited

OTHER PUBLICATIONS

Meissner, P. et al., "Transient gene expression: recombinant protein production with suspension-adapted HEK293-EBNA cells" Biotechnol Bioeng 75(2):197-203 (Oct. 20, 2001).
Menne, J., "C-C motif-ligand 2 inhibition with emaptieap pegol (NOX-E36) in type 2 diabetic patients with albuminuria" Nephrol Dial Transplant 32(2):307-315 (Feb. 1, 2017).
Meyer, C., et al., "Frequencies of circulating MDSC correlate with clinical outcome of melanoma patients treated with ipilimumab" Cancer Immunol Immunother 63(3):247-257 (Mar. 1, 2014).
Milstein, C., et al., "Hybrid hybridomas and their use in immunohistochemistry" Nature 305(5934):537-539 (Oct. 6, 1983).
Ng, C., et al., "Pharmacokinetics/pharmacodynamics of nondepleting anti-CD4 monoclonal antibody (TRX1) in healthy human volunteers" Pharm Res 23(1):95-103 (Jan. 1, 2006).
Obmolova, G., et 211., "Structural basis for high selectivity of anti-CCL2 neutralizing antibody CNTO 888" Mol Immunol 51(2):227-233 (Jun. 1, 2012).
Pacios, L., et al., "Arvomol/Contour: molecular surface areas and volumes on personal computers" Computers Chem 18(4):377-385 (Dec. 1, 1994).
Pacios, L., "Variations of Surface Areas and Volumes in Distinct Molecular Surfaces of Biomolecules" J Mol Model 1(2):46-53 (May 1, 1995).
Paolini, J, et al, "The chemokines IL-8, monoeyte chemoattraetant protein-1, and I-309 are monomers at physiologically relevant concentrations" J Immunol 153(6):2704-2717 (Sep. 15, 1994).
Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).
Portolano, S., et al., "Lack of promiscuity in autoantigen-specific H and L chain combinations as revealed by human H and L chain 'roulette'" J Immunol 150(3):880-887 (Feb. 1, 1993).
Presta, L., et al., "Molecular engineering and design of therapeutic antibodies" Curr Opin Immunol 20(4):460-470 (Aug 1, 2008).
Raghu, G., et al., "CC-chemokine ligand 2 inhibition in idiopathic pulmonary fibrosis: a phase 2 trial of carlumab" Eur Respir J 46(6):1740-1750 (Oct. 22, 2015).
Remington, J. Pharmaceutical Sciences (Table of Contents), Osol, 16 edition, Easton, PA: Mack Publishing Company,:TOC (1980).
Ridgway, J., et al., "Knobs-into-holes engineeiing of antibody CH3 domains for heavy chain heterodimenzation" Protein Eng 9(7):617-621 (Jul. 1, 1996).
Roopenian, D., et al., "FcRn: the neonatal Fc receptor comes of age" Nat Rev Immunol 7(9):715-725 (Sep. 1, 2007).
Sambrook et al. Molecular Cloning: A Laboratory Manual (Table of Contents only, in 32 pages), 2nd edition, Cold Spring Harbor, NY: Cold Spring Harbor Laboratory Press, (1989).
Sandhu, S., et al., "A First-in-human, first-in-class, phase I study of carlumab (CNTO 888), a human monoclonal antibody against CC-chemokine ligand 2 in patients with solid tumors" Cancer Chemother Pharmacol 71(4):1041-1050 (Apr. 1, 2013).
Schaefer, W., et al., "Immunoglobulin domain crossover as a generic approach for the production of bispecific IgG antibodies" PNAS USA 108(27):11187-11192 (Jul. 5, 2011).
Seo, Y.,, "Differentiation of CC vs CXC Chemokine Dimers with GAG Octasaccharide Binding Partners: An Ion Mobility Mass Spectrometry Approach" J Am Chem Soc 135(11):4325-4332 (Feb. 18, 2013).
Spiess, C., et al., "Alternative molecular formats and therapeutic applications for bispecific antibodies" Mol Immunol 67( Suppl 2 Pt A):95-106 (Jan. 27, 2015).
Strohl, R., et al., "Optimization of Fc-mediated effector functions of monoclonal antibodies" Curr Opin Biotechnol 20(6):685-691 (Dec. 1, 2009).
Stubenrauch, K., et al., "Impact of molecular processing in the hinge region of therapeutic IgG4 antibodies on disposition profiles in cynomolgus monkeys" Drug Metab Dispos 38(1):84-91 (Jan. 1, 2010).
Tutt, A., et al., "Trispecific F(ab')3 derivatives that use cooperative signaling via the TCR/CD3 complex and CD2 to activate and redirect resting cytotoxic T cells" J Immunol 147(1):60-69 (Jul. 1, 1991).
Urlaub, G., et al., "Isolation of chinese hamster cell mutants deficient in dihydrofolate reductase activity" PNAS US 77(7):4216-4220 (Jul. 1, 1980).
Vidarsson, G., et al., "IgG Subclasses and Allotypes: From Structure to Effector Functions" Front Immunol 5(520):1-17 (Oct. 20, 2014).
Yazaki, P. J ., et al. Methods in Molecular Biology "Expression of recombinant antibodies in mammalian cell lines" Lo, B.K.C. (ed.), Totowa, NJ: Humana Press, vol. 248:255-268 (2004).
Zalevsky, J., et al., "Enhanced antibody half-life improves in Vivo activity" Nat Biotechnol 28(2):157-159 (Feb. 1, 2010).
Zhang, Y., et al., "A dominant negative inhibitor indicates that monocyte chemoattraetant protein 1 functions as a dimer" Mol Cell Biol 15(9):4851-4855 (Sep. 1, 1995).
Zheng, Y., et al., "Translational pharmacokinetics and pharmacodynamics of an FcRn-variant anti-CD4 monoclonal antibody from preclinical model to phase I study" Clin Pharmacol Ther 89(2):283-290 (Feb. 1, 2011).
Zlotnik, A., et al., "Chemokines: a new classification system and their role in immunity" Immunity 12(2):121-127 (Feb. 1, 2000).

\* cited by examiner

BISPECIFIC ANTI-CCL2 ANTIBODIES

CROSS-REFERENCE TO RELATED APPLICATIONS

This application claims priority to EP Application No. 19217665.9, filed Dec. 18, 2019, the disclosure of which is incorporated herein by reference in its entirety.

SEQUENCE LISTING

This application contains a Sequence Listing which has been submitted electronically in ASCII format and is hereby incorporated by reference in its entirety. Said ASCII copy, created on Dec. 14, 2020, is named "P35823-US_Sequence_Listing_ST25.txt" and is 245,760 bytes in size.

FIELD OF THE INVENTION

The present invention relates to bispecific anti-CCL2 antibodies binding to two different epitopes on human CCL2, pharmaceutical compositions thereof, their manufacture, and use as medicaments for the treatment of cancers, inflammatory, autoimmune and ophthalmologic diseases.

BACKGROUND OF THE INVENTION

The CCL2/CCR2 axis is the main mediator of immature myeloid cell recruitment into the tumor. CCL2 is overexpressed by malignant cells and binds to the extracellular matrix (ECM) building up a chemoattractant gradient. Once they reach the tumor, myeloid-derived suppressive cells (MDSCs) contribute to the pro-tumorigenic milieu by secreting/up-regulating anti-inflammatory cytokines/receptors that in turn inhibit the initiation of an anti-tumor T cell response. In this way, MDSCs may reduce or even impair the efficacy of any T cell-activating therapy (Meyer et al, 2014). Therefore, the specific inhibition of the recruitment of these immature myeloid cells will boost the efficacy of checkpoint inhibitors, T cell bispecific antibodies (TCBs) or other cancer immunotherapies (CITs). In addition, CCL2 has also been implicated in the promotion of angiogenesis, metastasis and tumor growth, suggesting that neutralizing CCL2 might contribute to several lines of anti-tumor intervention.

Targeting CCL2—as opposed to its receptor—will specifically inhibit the undesired CCL2-mediated effects, sparing those that might signal through the same receptor (CCR2) but different ligands (e.g. CCL7, CCL8, CCL13) which are involved in the recruitment of other immune cell populations, like Th1 and NK cells.

Clinically, CCL2 has been a preferred antibody-target in several studies aiming at neutralizing its elevated levels caused by different inflammatory diseases, such as rheumatoid arthritis (Haringman et al, Arthritis Rheum. 2006 August; 54(8):2387-92), idiopathic pulmonary fibrosis (Raghu et al, Eur Respir J. 2015 December; 46(6):1740-50), diabetic nephropathy (Menne et al, Nephrol Dial Transplant (2017) 32: 307-315) and cancer (Sandhu et al, Cancer Chemother Pharmacol. 2013 April; 71(4):1041-50). However, its high synthesis rate together with the observed high in vivo antibody-antigen dissociation constants (KD) have proven to be the main obstacles hindering the suppression of free CCL2 by conventional antibodies at clinically viable doses (Fetterly et al, J Clin Pharmacol. 2013 October; 53(10):1020-7).

CCL2 neutralization appears to be more obviously relevant in patients with elevated serum levels of CCL2, which has been observed in several types of cancers like breast cancer (BC), ovarian cancer (OvCa), colorectal cancer (CRC), pancreatic cancer and prostate cancer. However, even patients within these indications who do not present this serology but whose tumors are highly infiltrated with immune cells of the myeloid lineage might very well profit from this novel therapy due to the many roles that CCL2 plays in the tumor context as mentioned above.

Igawa et al, Immunological Reviews 270 (2016) 132-151 describes the Sweeping technology in which the generated antibody bears pH-dependent CDRs (for antibody-antigen dissociation within the acidic endosomes, leading to antigen degradation) and an engineered Fc moiety with an optimized isoelectric point (pI) and enhanced binding to FcgammaRIIb (favoring the cellular uptake of immune complexes), and a moderate affinity to the neonatal Fc receptor, to maintain an acceptable pharmacokinetic profile.

SUMMARY OF THE INVENTION

The present invention relates to bispecific anti-CCL2 antibodies binding to two different epitopes on human CCL2, pharmaceutical compositions thereof, their manufacture, and use as medicaments for the treatment of cancers, inflammatory, autoimmune and ophthalmologic diseases.

One embodiment of the invention is a bispecific antibody comprising a first antigen-binding site that (specifically) binds to a first epitope on human CCL2 and a second different antigen-binding site that (specifically) binds a second different epitope on human CCL2, wherein bispecific antibody comprises a Fc domain of human IgG isotype.

One embodiment of the invention is a bispecific antibody comprising a first antigen-binding site that (specifically) binds to a first epitope on human CCL2 and a second different antigen-binding site that (specifically) binds a second epitope on human CCL2, wherein A) i) said first antigen-binding site comprises
a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
ii) said second antigen-binding site comprises
a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;
and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

B) i) said first antigen-binding site comprises
a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;

and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and ii) said second antigen-binding site comprises a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;

and a VL domain comprising (d) a CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22;

or

C) i) said first antigen-binding site comprises a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;

and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and ii) said second antigen-binding site comprises a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;

and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14;

or

D) i) said first antigen-binding site comprises a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;

and a VL domain comprising (d) a CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22; and ii) said second antigen-binding site comprises a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;

and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

or

E) i) said first antigen-binding site comprises a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;

and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30; and ii) said second antigen-binding site comprises a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43; and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

or

F) i) said first antigen-binding site comprises a VH domain comprising (a) a CDR-H1 comprising the amino acid sequence of SEQ ID NO: 49, (b) a CDR-H2 comprising the amino acid sequence of SEQ ID NO: 50, and (c) a CDR-H3 comprising the amino acid sequence of SEQ ID NO: 51;

and a VL domain comprising (d) a CDR-L1 comprising the amino acid sequence of SEQ ID NO: 52; (e) a CDR-L2 comprising the amino acid sequence of SEQ ID NO: 53, and (f) a CDR-L3 comprising the amino acid sequence of SEQ ID NO: 54; and ii) said second antigen-binding site comprises a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43; and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

or

G) i) said first antigen-binding site comprises a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;

and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14; and ii) said second antigen-binding site comprises a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;

and a VL domain comprising a (d) CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22;

or
H) i) said first antigen-binding site comprises
a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;
and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14; and
ii) said second antigen-binding site comprises
a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;
and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30;
or
I) i) said first antigen-binding site comprises
a VH domain comprising (a) a CDR-H1 comprising the amino acid sequence of SEQ ID NO: 1, (b) a CDR-H2 comprising the amino acid sequence of SEQ ID NO: 2, and (c) a CDR-H3 comprising the amino acid sequence of SEQ ID NO: 3;
and a VL domain comprising (d) a CDR-L1 comprising the amino acid sequence of SEQ ID NO: 4; (e) a CDR-L2 comprising the amino acid sequence of SEQ ID NO: 5, and (f) a CDR-L3 comprising the amino acid sequence of SEQ ID NO: 6; and
ii) said second antigen-binding site comprises
a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;
and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30.

In one embodiment the bispecific antibody comprises a Fc domain of human IgG isotype.

In one embodiment the bispecific antibody comprises a Fc domain of human IgG1 isotype.

In one embodiment the bispecific antibody comprises constant heavy chain domain of human IgG isotype.

In one embodiment the bispecific antibody comprises a constant heavy chain domain of human IgG1 isotype.

In one embodiment the in vivo clearance rate for human CCL2 (ml/day/kg) after administration of the bispecific antibody comprising a constant heavy chain domain of human wild type IgG1 isotype (or the Fc domain thereof) is at least two fold higher (in one embodiment at least 5 fold higher, in one embodiment at least 10 fold higher, in one embodiment at least 20 fold higher) compared to the in vivo clearance rate for human CCL2 (ml/day/kg) after administration of a bispecific antibody comprising a Fc gamma receptor silenced constant heavy chain domain of human IgG1 isotype (or the Fc domain thereof) comprising the mutations L234A, L235A, P329G (Kabat EU numbering), when a pre-formed immune complex consisting of 20 mg/kg of each bispecific antibody and 0.1 mg/kg human CCL2 was administered at a single dose of 10 ml/kg into FcRn transgenic mice.

One embodiment of the invention is an (isolated) bispecific antibody comprising a first antigen-binding site that (specifically) binds to a first epitope on human CCL2 and a second antigen-binding site that (specifically) binds a second epitope on human CCL2, wherein
i) said first antigen-binding site binds to same epitope on CCL2 as an antibody comprising
a VH domain comprising the amino acid sequence of SEQ ID NO:39 wherein the VH domain comprises (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
and a VL domain comprising the amino acid sequence of SEQ ID NO:40 wherein the VL domain comprises (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
ii) said second antigen-binding site binds to same epitope on CCL2 as an antibody comprising
a VH domain comprising the amino acid sequence of SEQ ID NO:47 wherein the VH domain comprises (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;
and a VL domain comprising the amino acid sequence of SEQ ID NO:48 wherein the VL domain comprises (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46.

In one embodiment the in vivo clearance rate for human CCL2 (ml/day/kg) after administration of the bispecific antibody comprising a constant heavy chain domain of human wild type IgG1 isotype (or the Fc domain thereof) is at least 15 fold higher, in particular at least 20 fold higher, compared to the in vivo clearance rate for human CCL2 (ml/day/kg) after administration of a bispecific antibody comprising a Fc gamma receptor silenced constant heavy chain domain of human IgG1 isotype (or the Fc domain thereof) comprising the mutations L234A, L235A, P329G (Kabat EU numbering), when a pre-formed immune complex consisting of 20 mg/kg of each bispecific antibody and 0.1 mg/kg human CCL2 was administered at a single dose of 10 ml/kg into FcRn transgenic mice.

One embodiment of the invention is an (isolated) bispecific antibody comprising a first antigen-binding site that (specifically) binds to a first epitope on human CCL2 and a second antigen-binding site that (specifically) binds a second epitope on human CCL2, wherein
i) said first antigen-binding site comprises
a VH domain comprising (a) a CDR-H1 comprising the amino acid sequence SHYGXS of SEQ ID NO: 57 wherein X is I or T, (b) a CDR-H2 comprising the amino acid sequence $GX^1IX^2IFX^3TANYAQKFQG$ of SEQ ID NO: 58 wherein $X^1$ is V, I, or H, $X^2$ is P or H, and X³ is H or G, and (c) a CDR-H3 comprising the amino acid sequence YDAHYGELDF of SEQ ID NO: 59;

and a VL domain comprising (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62;

and ii) said second antigen-binding site comprises a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain comprising (d) a CDR-L1 comprising the amino acid sequence KAX¹EDIYNRX²A of SEQ ID NO: 79 wherein X¹ is F or T and X² is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

One embodiment of the invention is an (isolated) bispecific antibody comprising a first antigen-binding site that (specifically) binds to a first epitope on human CCL2 and a second antigen-binding site that (specifically) binds a second epitope on human CCL2, wherein i) said first antigen-binding site comprises a VH domain comprising (a) a CDR-H1 comprising the amino acid sequence SHYGXS of SEQ ID NO: 57 wherein X is I or T, (b) a CDR-H2 comprising the amino acid sequence GX¹IX²IFX³TANYAQKFQG of SEQ ID NO: 58 wherein X¹ is V, I, or H, X² is P or H, and X³ is H or G, (c) a CDR-H3 comprising the amino acid sequence YDAHYGELDF of SEQ ID NO: 59, (d) a FR-H1 comprising the amino acid sequence QVQLVQSGAEVKKPGSSVKVSCK-ASGGTF of SEQ ID NO:63, (e) a FR-H2 comprising the amino acid sequence WVRQAPGQ-GLEWMG of SEQ ID NO:64, (f) a FR-H3 comprising the amino acid sequence RVTITADEST-STAYMELSSLRSEDTAVY YCAR of SEQ ID NO:65, and (g) a FR-H4 comprising the amino acid sequence WGQGTLVTVSS of SEQ ID NO:66;

and a VL domain comprising (h) a CDR-L1 comprising the amino acid sequence RASQHVSDAYLA of SEQ ID NO: 60; (i) a CDR-L2 comprising the amino acid sequence DASDRAE of SEQ ID NO: 61, and (j) a CDR-L3 comprising the amino acid sequence HQYIHLSFT of SEQ ID NO: 62, (k) a FR-L1 comprising the amino acid sequence EIVLTQSPATLSLSPGERATLSC of SEQ ID NO:67, (l) a FR-L2 comprising the amino acid sequence WYQQKPGQAPRLLIY of SEQ ID NO:68, (m) a FR-L3 comprising the amino acid sequence GVPARFSGSGSGTDFTLTISSLEPED-FAVYYC of SEQ ID NO:69, and (n) a FR-L4 comprising the amino acid sequence GQGTKVEIK of SEQ ID NO:70;

and ii) said second antigen-binding site comprises a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, (c) a CDR-H3 comprising the amino acid sequences GVFGFFXH of SEQ ID NO:78 wherein X is D or E, (d) a FR-H1 comprising the amino acid sequence QVQLVQS-GAEVKKPGSSVKVSCKASGLTIS of SEQ ID NO:82, (e) a FR-H2 comprising the amino acid sequence WVRQAPGQGLEWMG of SEQ ID NO:83, (f) a FR-H3 comprising the amino acid sequence RVTITADTSTSTAYMELSSLRSED-TAVYYCAR of SEQ ID NO:84, and (g) a FR-H4 comprising the amino acid sequence WGQGTTVTVSS of SEQ ID NO:85;

and a VL domain comprising (h) a CDR-L1 comprising the amino acid sequence KAX¹EDIYNRX²A of SEQ ID NO: 79 wherein X¹ is F or T and X² is R or L, (i) a CDR-L2 comprising the amino acid sequence GATSLEH of SEQ ID NO: 80, (j) a CDR-L3 comprising the amino acid sequence QQFXSAPYT of SEQ ID NO: 81 wherein X is W or R, (k) a FR-L1 comprising the amino acid sequence DIQMTQSPSSL-SASVGDRVTITC of SEQ ID NO:86, (l) a FR-L2 comprising the amino acid sequence WYQQKPGKAPKLLIH of SEQ ID NO:87, (m) a FR-L3 comprising the amino acid sequence GVPSRFSGSGSGTDYTLTISSLQPEDFATYYC of SEQ ID NO:88, and (n) a FR-L4 comprising the amino acid sequence FGGGTKVEIK of SEQ ID NO:89.

One embodiment of the invention is an (isolated) bispecific antibody comprising a first antigen-binding site that (specifically) binds to a first epitope on human CCL2 and a second antigen-binding site that (specifically) binds a second epitope on human CCL2, wherein A) i) said first antigen-binding site comprises a VH domain comprising the amino acid sequence of SEQ ID NO:71;

and a VL domain comprising the amino acid sequence of SEQ ID NO:75; and ii) said second antigen-binding site comprises a VH domain comprising the amino acid sequence of SEQ ID NO:90;

and a VL domain comprising the amino acid sequence of SEQ ID NO:93;

or

B) i) said first antigen-binding site comprises a VH domain comprising the amino acid sequence of SEQ ID NO:71;

and a VL domain comprising the amino acid sequence of SEQ ID NO:75; and ii) said second antigen-binding site comprises a VH domain comprising the amino acid sequence of SEQ ID NO:91;

and a VL domain comprising the amino acid sequence of SEQ ID NO:93;

or

C) i) said first antigen-binding site comprises
   a VH domain comprising the amino acid sequence of SEQ ID NO:71;
   and a VL domain comprising the amino acid sequence of SEQ ID NO:75; and
   ii) said second antigen-binding site comprises
   a VH domain comprising the amino acid sequence of SEQ ID NO:90;
   and a VL domain comprising the amino acid sequence of SEQ ID NO:94;
or
D) i) said first antigen-binding site comprises
   a VH domain comprising the amino acid sequence of SEQ ID NO:72;
   and a VL domain comprising the amino acid sequence of SEQ ID NO:75; and
   ii) said second antigen-binding site comprises
   a VH domain comprising the amino acid sequence of SEQ ID NO:90;
   and a VL domain comprising the amino acid sequence of SEQ ID NO:94;
or
E) i) said first antigen-binding site comprises
   a VH domain comprising the amino acid sequence of SEQ ID NO:73;
   and a VL domain comprising the amino acid sequence of SEQ ID NO:75; and
   ii) said second antigen-binding site comprises
   a VH domain comprising the amino acid sequence of SEQ ID NO:90;
   and a VL domain comprising the amino acid sequence of SEQ ID NO:93;
or
F) i) said first antigen-binding site comprises
   a VH domain comprising the amino acid sequence of SEQ ID NO:73;
   and a VL domain comprising the amino acid sequence of SEQ ID NO:75; and
   ii) said second antigen-binding site comprises
   a VH domain comprising the amino acid sequence of SEQ ID NO:90;
   and a VL domain comprising the amino acid sequence of SEQ ID NO:94;
or
G) i) said first antigen-binding site comprises
   a VH domain comprising the amino acid sequence of SEQ ID NO:73;
   and a VL domain comprising the amino acid sequence of SEQ ID NO:75; and
   ii) said second antigen-binding site comprises
   a VH domain comprising the amino acid sequence of SEQ ID NO:92;
   and a VL domain comprising the amino acid sequence of SEQ ID NO:93;
or
H) i) said first antigen-binding site comprises
   a VH domain comprising the amino acid sequence of SEQ ID NO:73;
   and a VL domain comprising the amino acid sequence of SEQ ID NO:75; and
   ii) said second antigen-binding site comprises
   a VH domain comprising the amino acid sequence of SEQ ID NO:91;
   and a VL domain comprising the amino acid sequence of SEQ ID NO:93;
or
I) i) said first antigen-binding site comprises
   a VH domain comprising the amino acid sequence of SEQ ID NO:72;
   and a VL domain comprising the amino acid sequence of SEQ ID NO:75; and
   ii) said second antigen-binding site comprises
   a VH domain comprising the amino acid sequence of SEQ ID NO:90;
   and a VL domain comprising the amino acid sequence of SEQ ID NO:93;
or
J) i) said first antigen-binding site comprises
   a VH domain comprising the amino acid sequence of SEQ ID NO:72;
   and a VL domain comprising the amino acid sequence of SEQ ID NO:75; and
   ii) said second antigen-binding site comprises
   a VH domain comprising the amino acid sequence of SEQ ID NO:92;
   and a VL domain comprising the amino acid sequence of SEQ ID NO:93;
or
K) i) said first antigen-binding site comprises
   a VH domain comprising the amino acid sequence of SEQ ID NO:72;
   and a VL domain comprising the amino acid sequence of SEQ ID NO:75; and
   ii) said second antigen-binding site comprises
   a VH domain comprising the amino acid sequence of SEQ ID NO:91;
   and a VL domain comprising the amino acid sequence of SEQ ID NO:93;
or
L) i) said first antigen-binding site comprises
   a VH domain comprising the amino acid sequence of SEQ ID NO:74;
   and a VL domain comprising the amino acid sequence of SEQ ID NO:75; and
   ii) said second antigen-binding site comprises
   a VH domain comprising the amino acid sequence of SEQ ID NO:90;
   and a VL domain comprising the amino acid sequence of SEQ ID NO:93;
or
M) i) said first antigen-binding site comprises
   a VH domain comprising the amino acid sequence of SEQ ID NO:74;
   and a VL domain comprising the amino acid sequence of SEQ ID NO:75; and
   ii) said second antigen-binding site comprises
   a VH domain comprising the amino acid sequence of SEQ ID NO:90;
   and a VL domain comprising the amino acid sequence of SEQ ID NO:94;
or
N) i) said first antigen-binding site comprises
   a VH domain comprising the amino acid sequence of SEQ ID NO:74;
   and a VL domain comprising the amino acid sequence of SEQ ID NO:75; and
   ii) said second antigen-binding site comprises
   a VH domain comprising the amino acid sequence of SEQ ID NO:92;
   and a VL domain comprising the amino acid sequence of SEQ ID NO:93;

or

O) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;

or

P) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93.

One embodiment of the invention is an (isolated) bispecific antibody comprising a first antigen-binding site that (specifically) binds to a first epitope on human CCL2 and a second antigen-binding site that (specifically) binds a second epitope on human CCL2, wherein A) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHY-GXS of SEQ ID NO: 57 wherein X is I, (b) a CDR-H2 comprising the amino acid sequence GX$^1$IX$^2$IFX$^3$TANYAQKFQG of SEQ ID NO: 58 wherein X$^1$ is V, X$^2$ is P, and X$^3$ is H, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D, and (c) a CDR-H3 comprising the amino acid sequences GVFGFFXH of SEQ ID NO:78 wherein X is D;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F and X$^2$ is R, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W;

or

B) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHY-GXS of SEQ ID NO: 57 wherein X is I, (b) a CDR-H2 comprising the amino acid sequence GX$^1$IX$^2$IFX$^3$TANYAQKFQG of SEQ ID NO: 58 wherein X$^1$ is V, X$^2$ is P, and X$^3$ is H, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D, and (c) a CDR-H3 comprising the amino acid sequences GVFGFFXH of SEQ ID NO:78 wherein X is E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F and X$^2$ is R, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W;

or

C) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

D) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

E) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

F) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

G) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

H) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

I) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

J) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

K) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

L) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

M) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

N) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

O) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

P) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

In one embodiment the bispecific antibody described herein
  i) blocks binding of CCL2 to its receptor CCR2 in vitro (reporter assay, IC$_{50}$=0.5 nM); and/or
  ii) inhibits CCL2-mediated chemotaxis of myeloid cells in vitro (IC$_{50}$=1.5 nM); and/or
  iii) is cross-reactive to cynomolgus and human CCL2.

In one embodiment the bispecific antibody described herein is not cross-reactive to other CCL homologs in particular it shows 100 time less binding to other CCL homologs (as e.g. CCL8) compared to the binding to CCL2

In one embodiment the bispecific antibody described herein binds to the first and second epitope on human CCL2 in ion-dependent manner.

In one embodiment the bispecific antibody described herein binds to human CCL2 in pH dependent manner and wherein the first antigen binding site and the second antigen binding site both bind to CCL2 with a higher affinity at neutral pH than at acidic pH.

In one embodiment the bispecific antibody described herein binds to human CCL2 with a 10 times higher affinity at pH 7.4, than at pH 5.8.

In one embodiment the bispecific antibody described herein comprises a IgG1 heavy chain constant domain (or the Fc domain thereof) comprising one or more of the following mutations (Kabat EU numbering)
  i) Q311R and/or P343R (suitable for increasing pI for enhancing uptake of antigen); and/or
  ii) L234Y, L235W, G236N, P238D, T250V, V264I, H268D, Q295L, T307P, K326T and/or A330K (suitable for increasing affinity to human FcgRIIb and decreasing affinity to other human FcgR); and/or
  iii) M428L, N434A and/or Y436T (suitable for increasing affinity to FcRn for longer plasma half-life); and/or
  iv) Q438R and/or S440E (suitable for suppressing rheumatoid factor binding).

In one embodiment the bispecific antibody described herein comprises a IgG1 heavy chain constant domain (or the Fc domain thereof) comprising one or more of the following mutations (Kabat EU numbering)
  i) Q311R, and/or P343R (suitable for increasing pI for enhancing uptake of antigen); and/or
  ii) L235W, G236N, H268D, Q295L, K326T and/or A330K (suitable for increasing affinity to human FcgRIIb and decreasing affinity to other human FcgR); and/or iii) N434A (suitable for increasing affinity to FcRn for longer plasma half-life); and/or
iv) Q438R and/or S440E (suitable for suppressing rheumatoid factor binding).

In one embodiment the bispecific antibody described herein comprises a IgG1 heavy chain constant domain (or the Fc domain thereof) comprising the following mutations (Kabat EU numbering)
i) Q311R and P343R (suitable for increasing pI for enhancing uptake of antigen); and
ii) L235W, G236N, H268D, Q295L, K326T and A330K (suitable for increasing affinity to human FcgRIIb and decreasing affinity to other human FcgR); and
iii) N434A (suitable for increasing affinity to FcRn for longer plasma half-life); and
iv) Q438R and/S440E (suitable for suppressing rheumatoid factor binding).

In one embodiment the bispecific antibody described herein comprises a IgG1 heavy chain constant domain (or the Fc domain thereof) comprising the following mutations (Kabat EU numbering)
i) Q311R and P343R (suitable for increasing pI for enhancing uptake of antigen); and
ii) N434A (suitable for increasing affinity to FcRn for longer plasma half-life); and
iii) Q438R and/S440E (suitable for suppressing rheumatoid factor binding).

In one embodiment the bispecific antibody described herein comprises a IgG1 heavy chain constant domain (or the Fc domain thereof) comprising the following mutations (Kabat EU numbering) Q311R and P343R (suitable for increasing pI for enhancing uptake of antigen).

In one embodiment the bispecific antibody described herein comprises a IgG1 heavy chain constant domain (or the Fc domain thereof) comprising one or more of the following mutations (Kabat EU numbering)
i) Q311R and/or P343R (suitable for increasing pI for enhancing uptake of antigen); and/or
ii) L234Y, P238D, T250V, V264I, T307P and/or A330K (suitable for increasing affinity to human FcgRIIb and decreasing affinity to other human FcgR); and/or
iii) M428L, N434A and/or Y436T (suitable for increasing affinity to FcRn for longer plasma half-life); and/or
iv) Q438R and/or S440E (suitable for suppressing rheumatoid factor binding).

In one embodiment the bispecific antibody described herein comprises a IgG1 heavy chain constant domain (or the Fc domain thereof) comprising one or more of the following mutations (Kabat EU numbering)
i) Q311R and P343R (suitable for increasing pI for enhancing uptake of antigen); and
ii) L234Y, P238D, T250V, V264I, T307P and A330K (suitable for increasing affinity to human FcgRIIb and decreasing affinity to other human FcgR); and iii) M428L, N434A and Y436T (suitable for increasing affinity to FcRn for longer plasma half-life); and
iv) Q438R and S440E (suitable for suppressing rheumatoid factor binding).

In one embodiment the bispecific antibody described herein comprises a IgG1 heavy chain constant domain (or the Fc domain thereof) comprising one or more of the following mutations (Kabat EU numbering)
i) Q311R and P343R (suitable for increasing pI for enhancing uptake of antigen); and
ii) L234Y, P238D, T250V, V264I, T307P and A330K (suitable for increasing affinity to human FcgRIIb and decreasing affinity to other human FcgR); and
iii) N434A and (suitable for increasing affinity to FcRn for longer plasma half-life); and
iv) Q438R and S440E (suitable for suppressing rheumatoid factor binding).

In one embodiment the bispecific antibody described herein comprises two IgG1 heavy chain constant domains (or the Fc domain thereof) comprising (independently or in addition to the above described mutations) the following mutations (EU numbering)
i) S354C and T366W in one of the heavy chain constant domains
ii) Y349C, T366S, L368A, Y407V in the other of the heavy chain constant domains One embodiment of the invention is an (isolated) (monospecific) antibody that (specifically) binds to a human CCL2, wherein the antibody comprises
A) a VH domain comprising (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
and
a VL domain comprising (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62;
or
B) a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E; and
a VL domain comprising (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

One embodiment of the invention is an (isolated) (monospecific) antibody that (specifically) binds to a human CCL2, wherein the antibody comprises
A) a VH domain comprising the amino acid sequence of SEQ ID NO:71;
and a VL domain comprising the amino acid sequence of SEQ ID NO:75;
or
B) a VH domain comprising the amino acid sequence of SEQ ID NO:72;
and a VL domain comprising the amino acid sequence of SEQ ID NO:75;
or
C) a VH domain comprising the amino acid sequence of SEQ ID NO:73;
and a VL domain comprising the amino acid sequence of SEQ ID NO:75;

or

D) a VH domain comprising the amino acid sequence of SEQ ID NO:74;
   and a VL domain comprising the amino acid sequence of SEQ ID NO:75;
or
E) a VH domain comprising the amino acid sequence of SEQ ID NO:90;
   and a VL domain comprising the amino acid sequence of SEQ ID NO:93;
or
F) a VH domain comprising the amino acid sequence of SEQ ID NO:91;
   and a VL domain comprising the amino acid sequence of SEQ ID NO:93;
or
G) a VH domain comprising the amino acid sequence of SEQ ID NO:92;
   and a VL domain comprising the amino acid sequence of SEQ ID NO:93;
or
H) a VH domain comprising the amino acid sequence of SEQ ID NO:90;
   and a VL domain comprising the amino acid sequence of SEQ ID NO:94;

One embodiment of the invention is an isolated nucleic acid encoding the (mono- or bispecific) antibody according to any one of the preceding embodiments.

One embodiment of the invention is a host cell comprising such nucleic acid.

One embodiment of the invention is a method of producing an antibody comprising culturing such host cell so that the antibody is produced.

In one embodiment of the invention such method further comprises the step of recovering the antibody from the host cell.

One embodiment of the invention is a pharmaceutical formulation comprising the bispecific antibody as described herein and a pharmaceutically acceptable carrier.

One embodiment of the invention is the bispecific antibody as described herein for use as a medicament.

One embodiment of the invention is the use of the bispecific antibody as described herein in the manufacture of a medicament.

In one embodiment such medicament is for the treatment of cancer.

In one embodiment such medicament is for the treatment of an inflammatory or autoimmune disease.

One embodiment of the invention is the bispecific antibody as described herein for use in treating cancer.

One embodiment of the invention is the bispecific antibody as described herein for use in treating an inflammatory or autoimmune disease.

One embodiment of the invention is a method of treating an individual having cancer comprising administering to the individual an effective amount of the antibody as described herein.

One embodiment of the invention is a method of treating an individual having an inflammatory or autoimmune disease comprising administering to the individual an effective amount of the antibody as described herein.

BRIEF DESCRIPTION OF THE DRAWINGS

FIG. 1, FIG. 1A, FIG. 1B, and FIG. 1C: Surface plasmon resonance (Biacore®) sensorgrams showing binding of monospecific anti-CCL2 antibodies (CNTO888 (=CNTO), 1A5, 1G9 and humanized 11K2 (=11k2) to recombinant CCL2 and CCL2 homologs.

FIG. 8, left panel). Similarly, CCL2-0048, the parent unmodified bispecific antibody CNTO888/11k2k2 IgG1 of CKLO2, which is non-pH dependent, also shows an $IC_{50}$ of 0.2 µg/ml, since pH-dependency is critical for antigen sweeping, a phenomenon that does not take place in this assay.

Figure 8:
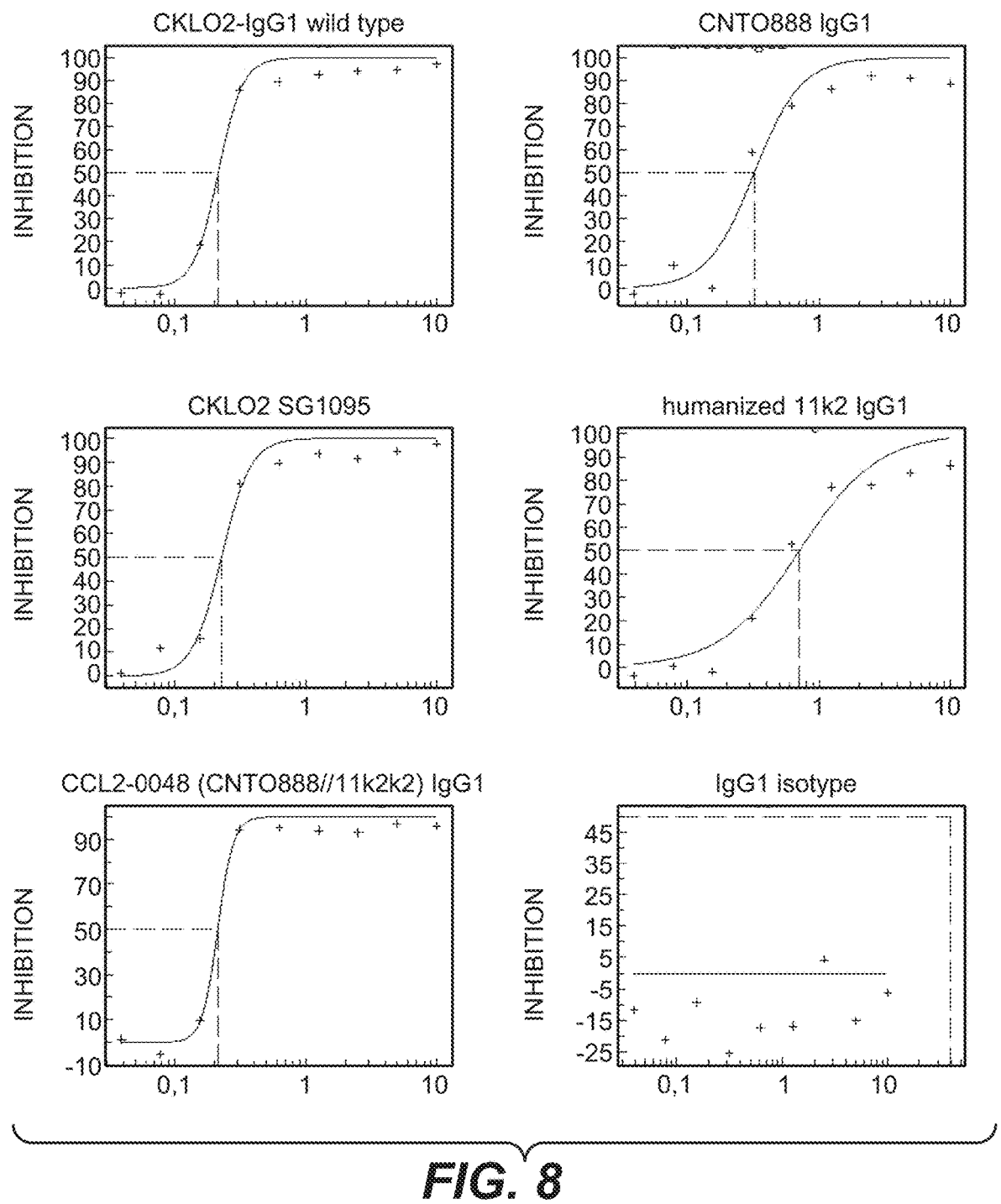
FIG. 8: Chemotaxis Assay: Bispecific anti-CCL2 antibodies with identical CDRs and variable regions VH/VL, namely CKLO2-IgG1 wild type and CKLO2-SG1095, but different Fc moieties, can inhibit the migration of THP-1 cells with identical potencies ($IC_{50}$=0.2 µg/ml.

The corresponding monospecific antibodies CNTO888 IgG1 and humanized 11k2 IgG1 display $IC_{50}$ values of 0.3 and 0.7 µg/ml, respectively, while the huIgG1 isotype control shows no inhibition (FIG. 8, right panel).

Figure 9:
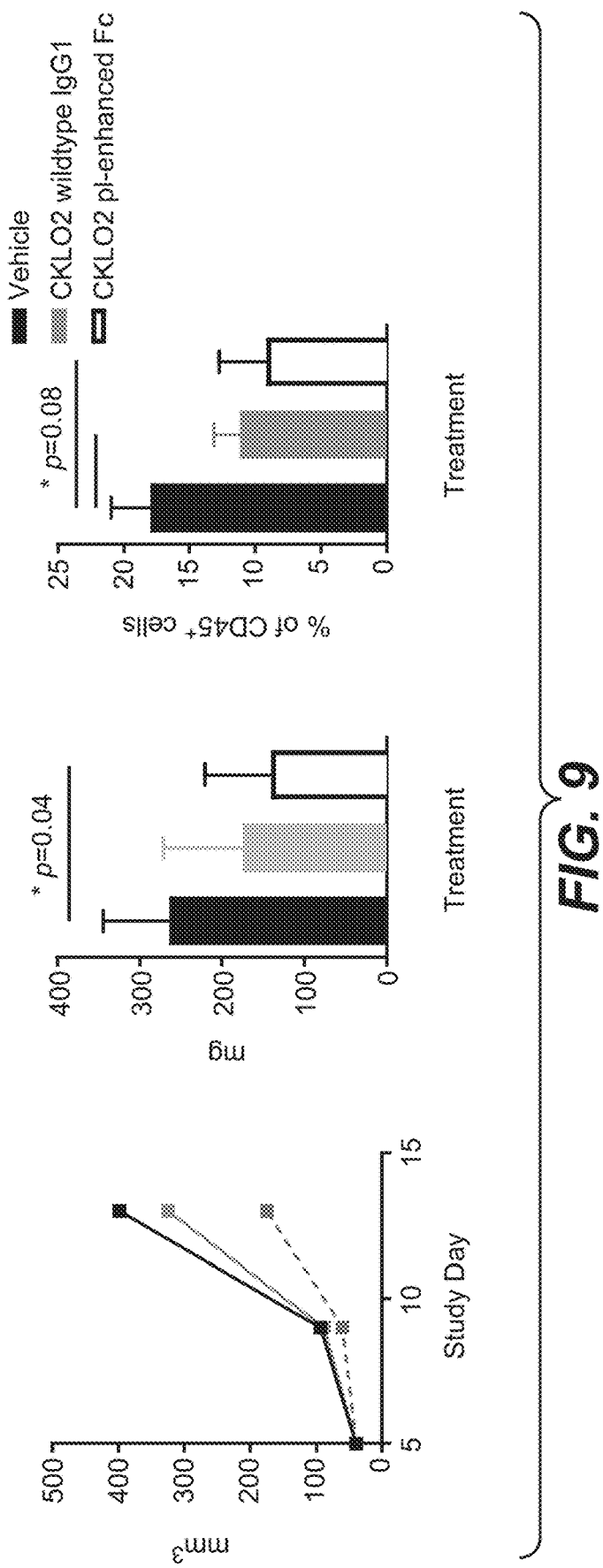

FIG. 9: In vivo anti-tumor activity in a genetically-modified mouse model. Treatment of mouse tumor model with Mab CKLO2-IgG1 (Fc wild type IgG1) and CKLO2-SG1099 ((=CKLO2 pI-enhanced). Tumor volumes (left), tumor weights (middle), and M-MDSC infiltrate (right) at end of study. (vehicle in black, CKLO2 wild type IgG1 in grey, and CKLO2pI-enhanced Fc (CKLO2-SG1099) in white bars/dotted line)

Figure 10:
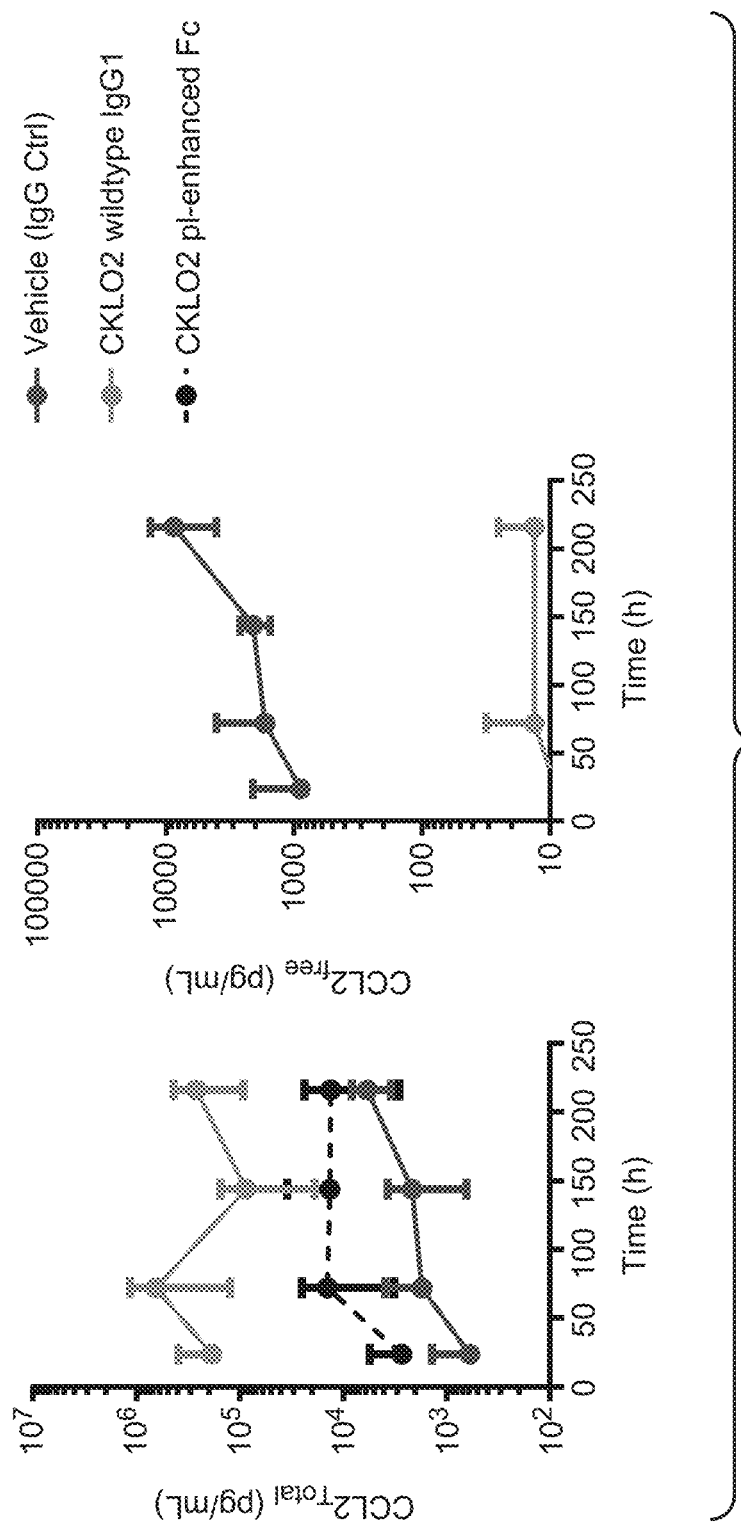

FIG. 10: Serum total (left) and free (right) CCL2 levels during the in vivo anti-tumor activity study (see efficacy in FIG. 9) under treatment with bispecific anti-CCL2 antibodies (vehicle in black, CKLO2 wild type IgG1 in grey, and pI-enhanced Fc (CKLO2-SG1099) in white bars/dotted line).

Figure 11:
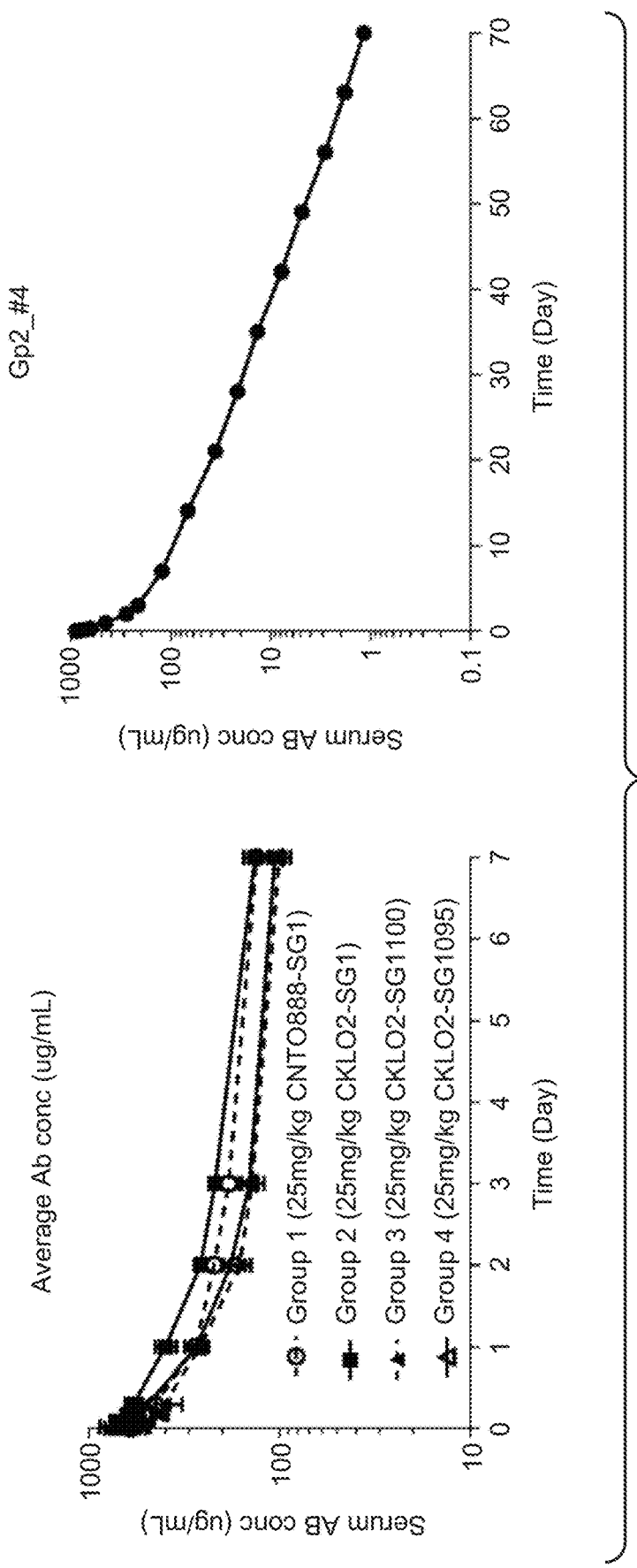

FIG. 11: Proof of concept study of CCL2 sweeping efficiency in cynomolgus monkeys. Total antibody concentration-time profiles in serum of cynomolgus monkeys; left panel: average concentration-time profiles of the four antibodies is presented over seven days; Group 1: monospecific CNTO888-SG1 (=IgG1 wild type) anti-CCL2 antibody (n=3 animals) as control of maximal total CCL2 accumulation; group 2: a biparatopic anti-CCL2 antibody CKLO2-SG1 (IgG1 wild type) with pH dependent target binding but no Fc-modifications (n=3); group 3: a biparatopic anti-CCL2 antibody CKLO2-SG1100 with pH dependent target binding and Fc-pI and further modifications (n=4) and group 4: biparatopic anti-CCL2 antibody CKLO2-SG1095 with pH dependent target binding, Fc-pI and FcγRIIb affinity enhanced and further modifications (n=4); right panel: individual concentration-time profile of individual 4 (group 2) is presented over the duration of the PK study (70 days).

Figure 12:
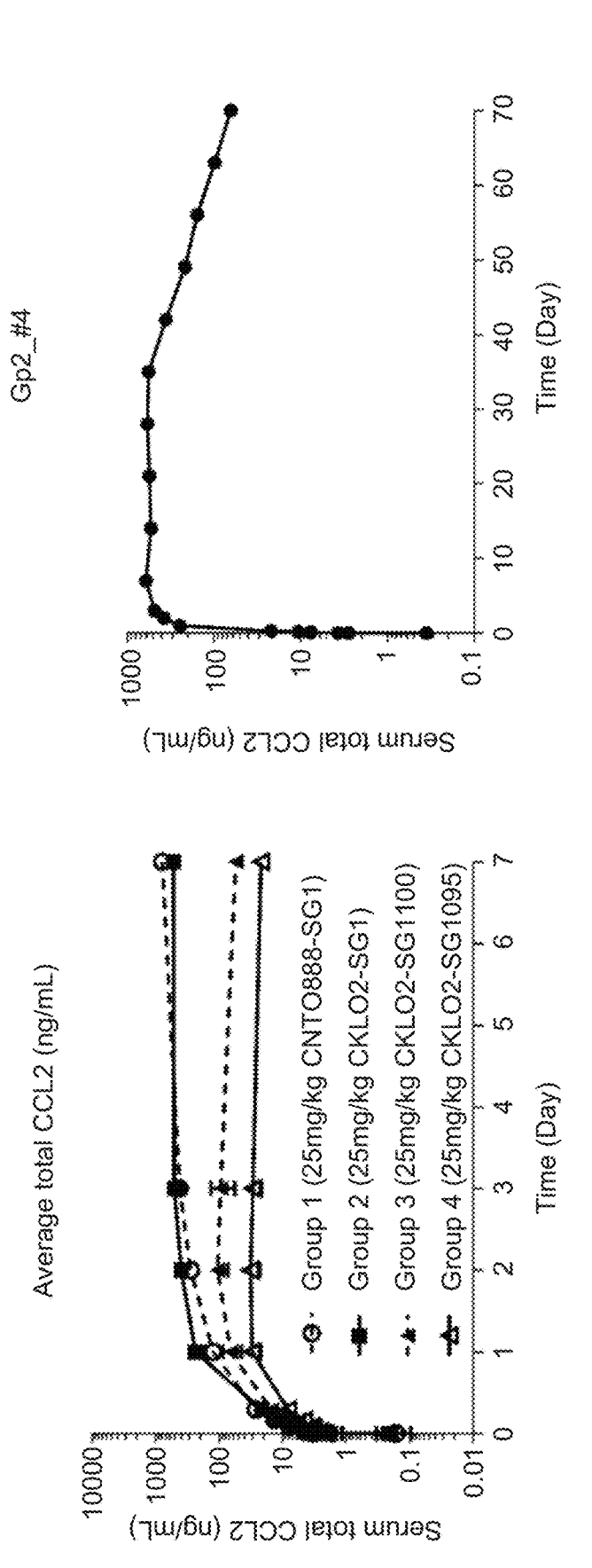

FIG. 12: Proof of concept study of CCL2 sweeping efficiency in cynomolgus monkeys. Total CCL2 concentration-time profiles in serum of cynomolgus monkeys; left panel: average total CCL2 concentration-time profiles of the four antibodies is presented over seven days; right panel: individual total CCL2 concentration-time profile of individual 4 (group 2) is presented over the duration of the PK study (70 days).

Figure 13:
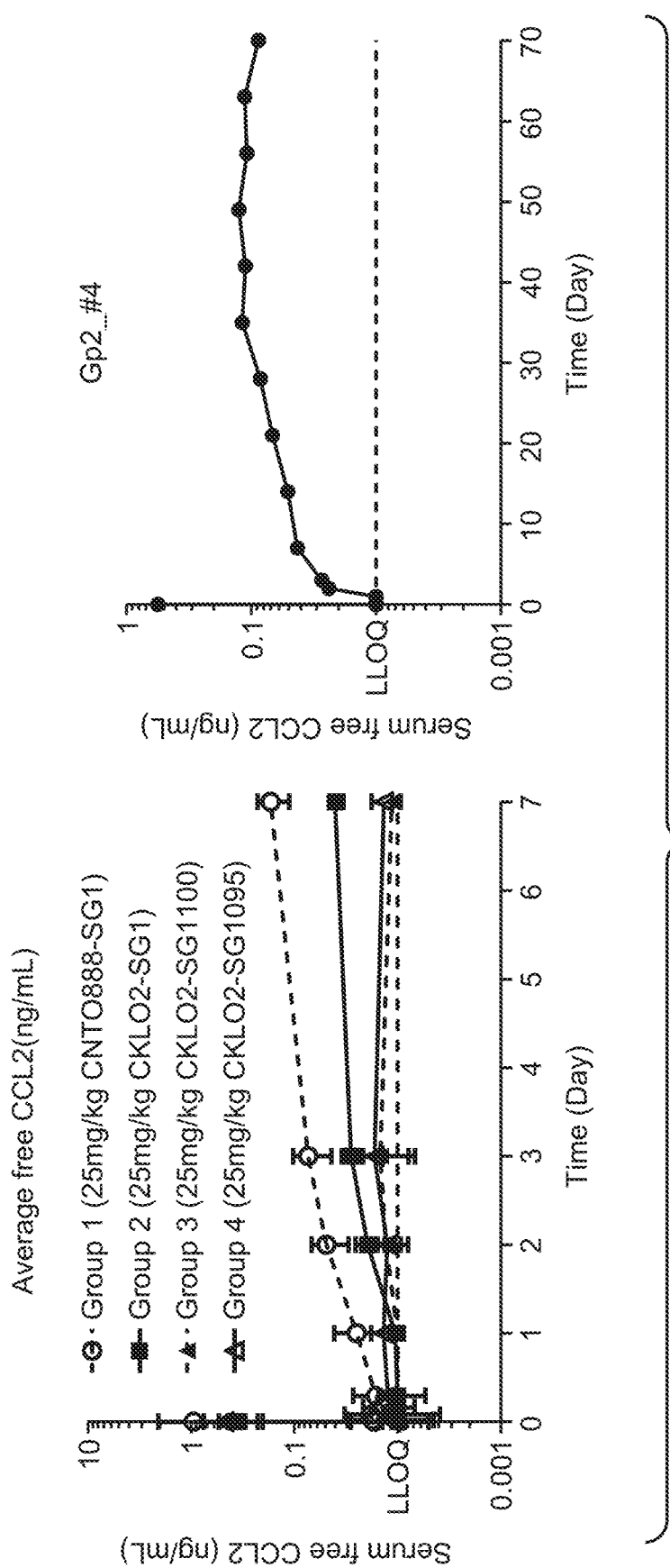

FIG. 13: Free CCL2 concentration-time profiles in serum of cynomolgus monkeys; left panel: average free CCL2 concentration-time profiles of the four antibodies is presented over seven days; right panel: individual free CCL2 concentration-time profile of individual 4 (group 2) is presented over the duration of the PK study (70 days); average profiles were calculated using a value of 0.01 ng/mL (lower limit of quantification) for samples that were below detection limit.

Figure 14:
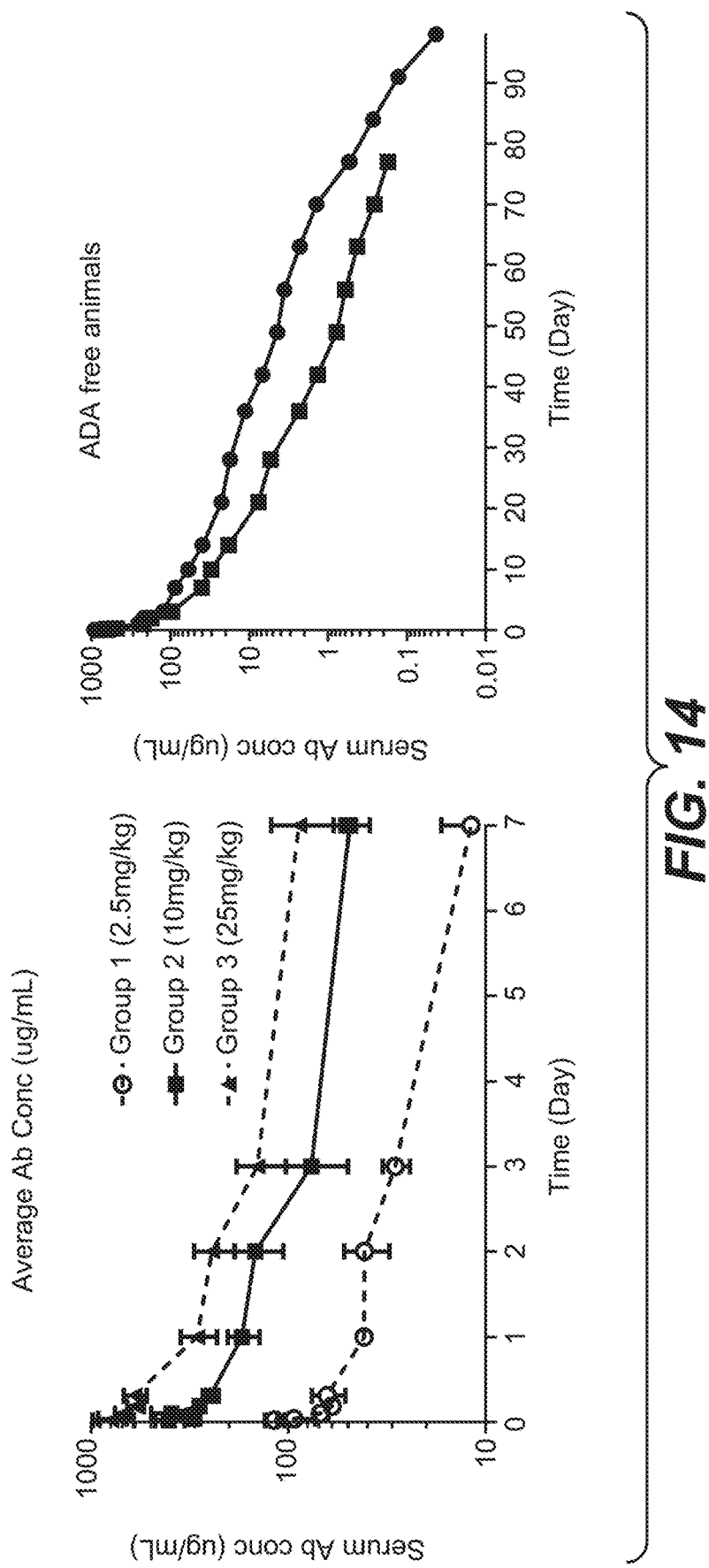

FIG. 14: PK/PD study of CCL2 sweeping efficiency in cynomolgus monkeys. Total CKL02-SG1095 concentration-time profiles in serum of cynomolgus monkeys (CKL02-SG1095 treatment with different concentrations (group 1-3)); left panel: average concentration-time profiles (n=4) for the three dose levels are presented over seven days; right panel: individual concentration-time profiles of two ADA-negative individual animals (25 mg/kg dose group) are presented over the duration of the study (98 days).

Figure 15:
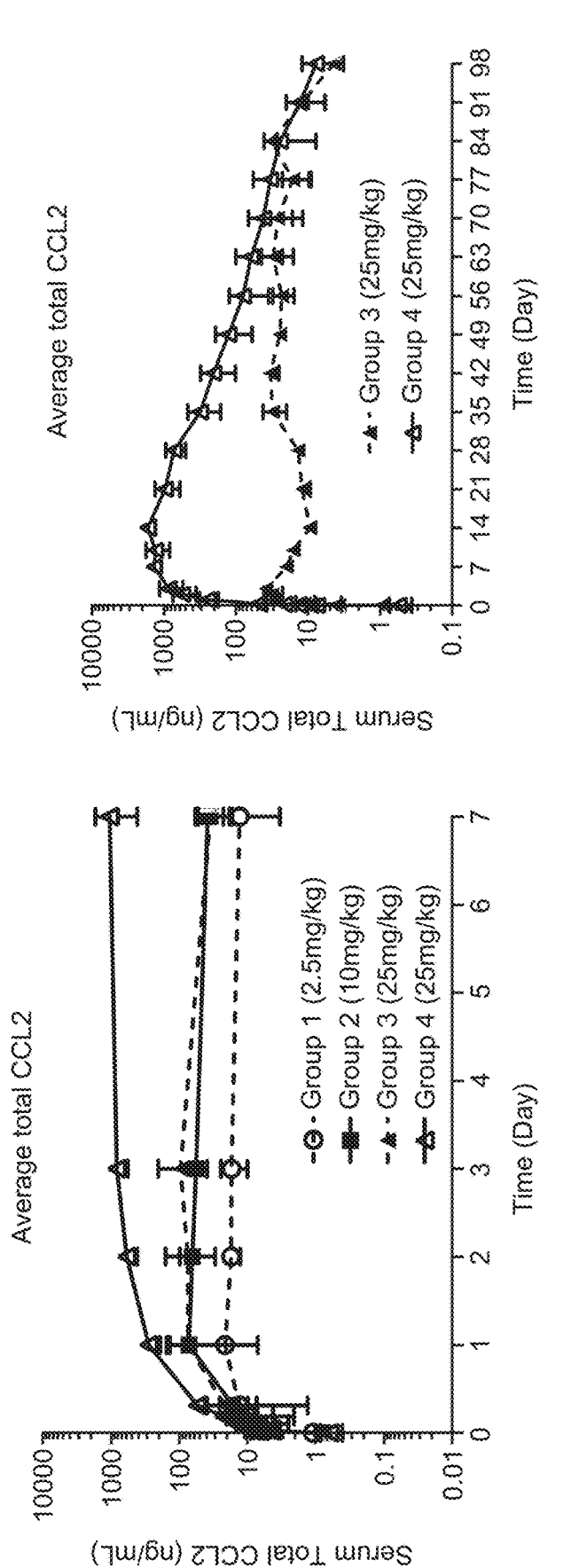

FIG. 15: PK/PD study of CCL2 sweeping efficiency in cynomolgus monkeys. Total CCL2 concentration-time profiles in serum of cynomolgus monkeys under CKL02-SG1095 treatment with different concentrations (group 1-3) and in comparison with CNTO888-SG1 treatment (group 4); left panel: average total CCL2 concentration-time profiles (error bars indicate SD) of the four study groups is presented over seven days; right panel: individual total CCL2 concentration-time profiles of ADA-negative animals from groups 3 (n=2, error bars indicate range) and 4 (n=3, error bars indicate SD) are presented over the duration of the PK study (98 days).

Figure 16:
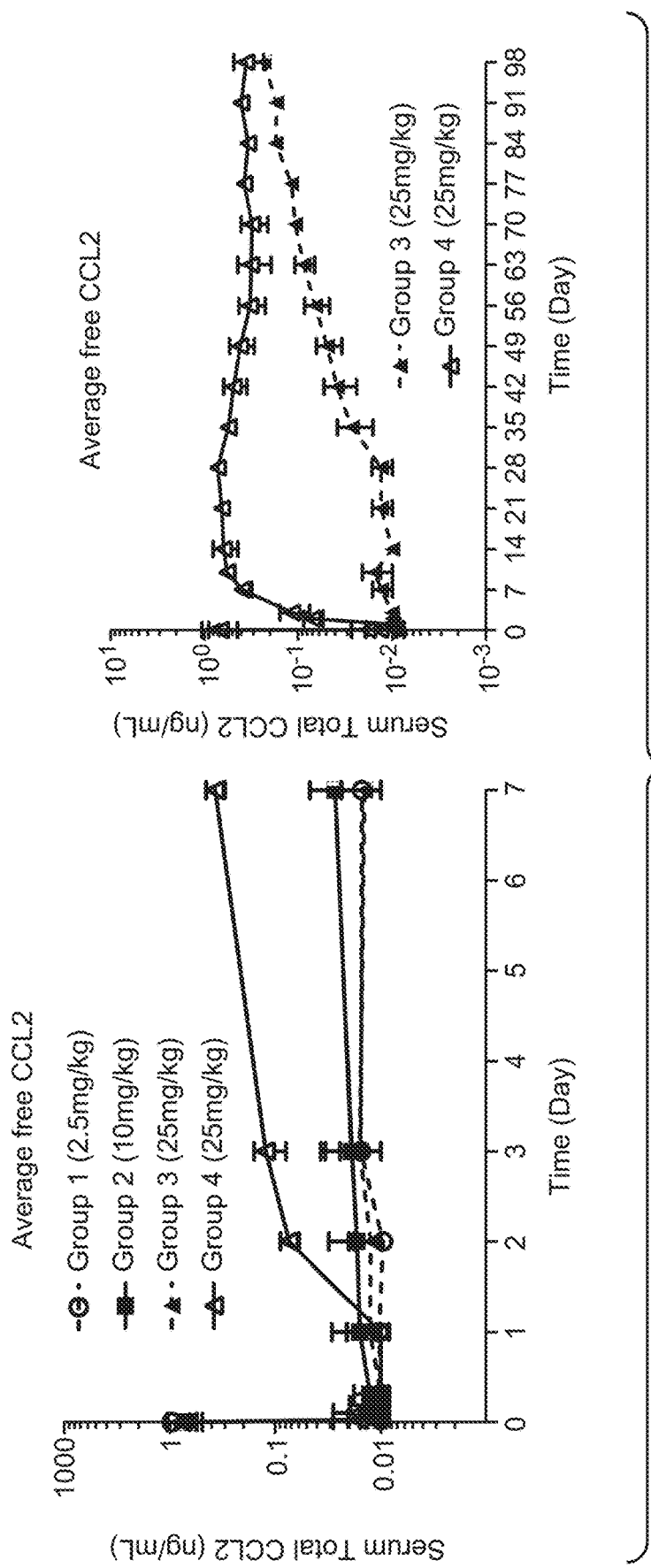

FIG. 16: PK/PD study of CCL2 sweeping efficiency in cynomolgus monkeys. Free CCL2 concentration-time profiles in serum of cynomolgus monkeys; left panel: average free CCL2 concentration-time profiles (error bars indicate SD) of the four study groups is presented over seven days (CKL02-SG1095 treatment with different concentrations (group 1-3) and in comparison with CNTO888-SG1 treatment (group 4)); right panel: average free CCL2 concentration-time profiles of ADA-negative animals from groups 3 (n=2, error bars indicate range) and 4 (n=3, error bars indicate SD) are presented over the duration of the PK study (70 days); average profiles were calculated using a value of 0.01 ng/mL (lower limit of quantification) for samples that were below detection limit.

DETAILED DESCRIPTION OF THE INVENTION

The present invention relates to bispecific anti-CCL2 antibodies binding to two different epitopes on human CCL2, pharmaceutical compositions thereof, their manufacture, and use as medicaments for the treatment of cancers, inflammatory, autoimmune and ophthalmologic diseases. So the antibody comprises a first antigen-binding site that (specifically) binds to a first epitope on human CC2 and a second different antigen-binding site that (specifically) binds a different second epitope.

The present invention includes bispecific antibodies comprising a first antigen-binding site that (specifically) binds to a first epitope on human CCL2 and a second antigen-binding site that (specifically) binds a second epitope on human CCL2, wherein
i) said first antigen-binding site binds to same epitope on CCL2 as an antibody comprising
a VH domain comprising the amino acid sequence of SEQ ID NO:39 wherein the VH domain comprises
(a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
and a VL domain comprising the amino acid sequence of SEQ ID NO:40 wherein the VL domain comprises
(d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
ii) said second antigen-binding site binds to same epitope on CCL2 as an antibody comprising
a VH domain comprising the amino acid sequence of SEQ ID NO:47 wherein the VH domain comprises
(a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;
and a VL domain comprising the amino acid sequence of SEQ ID NO:48 wherein the VL domain comprises
(d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46.

In one embodiment the in vivo clearance rate for human CCL2 (ml/day/kg) after administration of the bispecific antibody comprising a constant heavy chain domain of human wild type IgG1 isotype (or the Fc domain thereof) is at least 15 fold higher, in particular at least 20 fold higher, compared to the in vivo clearance rate for human CCL2 (ml/day/kg) after administration of a bispecific antibody comprising a Fc gamma receptor silenced constant heavy chain domain of human IgG1 isotype (or the Fc domain thereof) comprising the mutations L234A, L235A, P329G (Kabat EU numbering), when a pre-formed immune complex consisting of 20 mg/kg of each bispecific antibody and 0.1 mg/kg human CCL2 was administered at a single dose of 10 ml/kg into FcRn transgenic mice.

The term "epitope" includes any polypeptide determinant capable of specific binding to an antibody. In certain embodiments, epitope determinant includes chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. The present invention relates to bispecific anti-CCL2 antibodies binding to two different epitopes on human CCL2. The terms first and second epitope refer to two different epitopes on humans CCL2. So the second epitope is different from the first epitope. One can easily determine whether an antibody binds to the same epitope as, or competes for binding with, a reference anti-CCL2 antigen binding site by using routine methods known in the art. For example, to determine if a test antibody binds to the same epitope as a reference anti-CCL2 antigen binding site of the invention, the reference antibody is allowed to bind to CCL2 domain thereof under saturating conditions. Next, the ability of a test antibody to bind to human CCL2 is assessed. If the test antibody is able to bind to human CCL2 following saturation binding with the reference anti-CCL2 antigen binding site, it can be concluded that the test antibody binds to a different epitope than the reference anti-CCL2 antigen binding site. On the other hand, if the test antibody is not able to bind to human CCL2 following saturation binding with the reference anti-CCL2 antibody, then the test antibody may bind to the same epitope as the epitope bound by the reference anti-CCL2 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance (e.g. Biacore), flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502).

Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-CCL2 antibody, the above-described binding methodology is performed in two orientations: In a first orientation, the reference antibody is allowed to bind to CCL2 under saturating conditions followed by assessment of binding of the test antibody to human CCL2. In a second orientation, the test antibody is allowed to bind to an CCL2 molecule under saturating conditions followed by assessment of binding of the reference antibody to humans CCL2. If, in both orientations, only the first (saturating) antibody is capable of binding to the CCL2 molecule, then it is concluded that the test antibody and the reference antibody compete for binding to CCL2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

When used herein, the term "CCL2", "human CCL2", which also called "MCP-1" is meant the 76 amino acid sequence referenced in NCBI record accession No. NP_002973 and variously known as CCL2, MCP-1 (monocyte chemotactic protein 1), SMC-CF (smooth muscle cell chemotactic factor), LDCF (lymphocyte-derived chemotactic factor), GDCF (glioma-derived monocyte chemotactic factor), TDCF (tumor-derived chemotactic factors), HC11 (human cytokine 11), MCAF (monocyte chemotactic and activating factor). The gene symbol is SCYA2, the JE gene on human chromosome 17, and the new designation is CCL2 (Zlotnik, Yoshie 2000. Immunity 12: 121-127). JE is the mouse homolog of human MCP-1/CCL2.

Handel and others (Biochemistry. 1996; 35:6569-6584) determined the solution structure of a CCL2 dimer. These studies indicated that the secondary structure of CCL2 consists of four β-sheets. Additionally, the residues responsible for the dimerization interface of CCL2 were described by Zhang and Rollins (Mol Cell Biol. 1995; 15:4851-4855). The protein complex appears elongated with the two monomers oriented in such a way that they form a large pocket. Structures of monomeric and dimeric CCL2 in two crystal forms, the so-called I and P forms, have also been determined (Lubkowski et al., Nat Struct Biol. 1997; 4:64-69). Paolini et al, (J Immunol. 1994 Sep. 15; 153(6):2704-17), described that MCP1/CCL2 exists as a monomer at physiologically relevant concentrations: By analysing rec. CCL2 protein (purchased from Peprotech) with size exclusion HPLC, sedimentation equilibrium ultracentrifugation and chemical cross-linking, they could show that the weight fraction of monomeric and dimeric forms of MCP-1 depends on the concertation in vitro. Finally, Seo and colleagues (J Am Chem Soc. 2013 Mar. 20; 135(11):4325-32) could show by ion mobility mass spectrometry the presence of injected CCL2 in both monomeric and dimeric forms under physiological conditions.

Thus "wild type CCL-2" (wt CCL2) can exist as monomer but actually can also form dimers at physiological concentrations. This monomer-dimer equilibrium is certainly different and has to be carefully taken into account for all in vitro experiments described where different concentrations might be used. To avoid any uncertainties, we generated point mutated CCL2 variants: The "P8A" variant of CCL2 carries a mutation in the dimerization interface resulting in an inability to form a dimer leading to a defined, pure CCL2 monomer. In contrast, the "T10C" variant of CCL2 results in a fixed dimer of CCL2 (J Am Chem Soc. 2013 Mar. 20; 135(11):4325-32).

The CCL2/CCR2 axis is the main mediator of immature myeloid cell recruitment into the tumor. CCL2 is overexpressed by malignant cells and binds to the extracellular matrix (ECM) building up a chemoattractant gradient. Once they reach the tumor, myeloid-derived suppressive cells (MDSCs) contribute to the pro-tumorigenic milieu by secreting/up-regulating anti-inflammatory cytokines/receptors that in turn inhibit the initiation of an anti-tumor T cell response. In this way, MDSCs may reduce or even impair the efficacy of any T cell-activating therapy (Meyer et al, 2014). Therefore, the specific inhibition of the recruitment of these immature myeloid cells will boost the efficacy of checkpoint inhibitors, T cell bispecific and cancer immune therapies. In addition, CCL2 has also been implicated in the promotion of angiogenesis, metastasis and tumor growth, suggesting that neutralizing CCL2 might contribute to several lines of anti-tumor intervention.

Targeting CCL2—as opposed to its receptor—will specifically inhibit the undesired CCL2-mediated effects, sparing those that might signal through the same receptor (CCR2) but different ligands (e.g. CCL7, CCL8, CCL13) which are involved in the recruitment of other immune cell populations, like Th1 and NK cells.

Clinically, CCL2 has been a preferred antibody-target in several studies aiming at neutralizing its elevated levels caused by different inflammatory diseases, such as rheumatoid arthritis (Haringman et al, 2006), idiopathic pulmonary fibrosis (Raghu et al, 2015), diabetic nephropathy (Menne et al, 2017) and cancer (Sandhu et al, 2013). However, its high synthesis rate together with the observed high in vivo antibody-antigen dissociation constants (KD) have proven to be the main obstacles hindering the suppression of free CCL2 by conventional antibodies at clinically viable doses (Fetterly et al, 2013).

CCL2 neutralization appears to be more obviously relevant in patients with elevated serum levels of CCL2, which has been observed in several types of cancers like breast cancer (BC), ovarian cancer (OvCa), colorectal cancer (CRC), pancreatic cancer and prostate cancer. However, even patients within these indications who do not present this serology but whose tumors are highly infiltrated with immune cells of the myeloid lineage might very well profit from this novel therapy due to the many roles that CCL2 plays in the tumor context as mentioned above.

As used herein, an antibody "binding to human CCL2", "specifically binding to human CCL2", "that binds to human CCL2" or "anti-CCL2 antibody" refers to an antibody specifically binding to the human CCL2 antigen with a binding affinity of a $K_D$-value of $5.0 \times 10^{-8}$ mol/l or lower, in one embodiment of a $K_D$-value of $1.0 \times 10^{-9}$ mol/l or lower, in one embodiment of a $K_D$-value of $5.0 \times 10^{-8}$ mol/l to $1.0 \times 10^{-13}$ mol/l.

The binding affinity is determined with a standard binding assay, such as surface plasmon resonance technique (BIAcore®, GE-Healthcare Uppsala, Sweden) e.g. using constructs comprising CCL2 extracellular domain (e.g. in its natural occurring 3 dimensional structure). In one embodiment binding affinity is determined with a standard binding assay using exemplary soluble CCL2.

Antibody specificity refers to selective recognition of the antibody for a particular epitope of an antigen. Natural antibodies, for example, are monospecific.

The term "monospecific" antibody as used herein denotes an antibody that has one or more binding sites each of which bind to the same epitope of the same antigen.

The term "bispecific antibody that binds to (human) CCL2", "biparatopic antibody that binds to (human) CCL2", "bispecific anti-CCL2 antibody", "biparatopic anti-CCL2 antibody" as used herein means that the antibody is able to specifically bind to at least two different epitopes on (human) CCL2. Typically, such bispecific antibody comprises two different antigen binding sites (two different paratopes), each of which is specific for a different epitope of (human) CCL2. In certain embodiments the bispecific antibody is capable of binding two different and non-overlapping epitopes on CCL2, which means that the two different antigen binding sites do not compete for binding to CCL2.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "valent" as used herein denotes the presence of a specified number of antigen binding sites in an antibody. As such, the term "monovalent binding to an antigen" denotes the presence of one (and not more than one) antigen binding site specific for the antigen in the antibody.

The terms "antigen binding site" refers to the site or region, i.e. one or several amino acid residues, of an antibody which provides interaction with the antigen. For example, the antigen binding site of an antibody comprises amino acid residues from the complementarity determining regions (CDRs). In one embodiment the antigen binding site of an antibody comprises the comprises amino acid residues from the VH and VL. A native immunoglobulin molecule typically has two antigen binding sites; a Fab molecule typically has a single antigen binding site. "Antigen binding moiety" refers to a polypeptide molecule comprising an antigen binding site that specifically binds to an antigenic determinant. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" or "antigen" refers to a site on a polypeptide macromolecule to which an antigen binding moiety/site binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively. Preferably the bispecific antibodies of the invention are of human IgG isotype, more preferably of humans IgG1 isotype. The terms IgG isotype and IgG1 isotype as used herein refer to the human IgG isotype and human IgG1 isotype. Typically the different IgG isotypes exist in the form of slightly different allotypes based on allelic variation among the IgG subclasses (see Vidarsson et al.; Front Immunol 5 (2014) Article 520, 1-17). An "effective amount" of an agent, e.g., a pharmaceutical formulation, refers to an amount effective, at dosages and for periods of time necessary, to achieve the desired therapeutic or prophylactic result.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Amino acid sequences of heavy chains including Fc domains (or a subunit of an Fc domain as defined herein) are denoted herein without C-terminal glycine-lysine dipeptide if not indicated otherwise. In one embodiment of the invention, a heavy chain including a subunit of an Fc domain as specified herein, comprised in an antibody or bispecific antibody according to the invention, comprises an additional C-terminal glycine-lysine dipeptide (G446 and K447, numbering according to EU index of Kabat). In one embodiment of the invention, a heavy chain including a subunit of an Fc domain as specified herein, comprised in an antibody or bispecific antibody according to the invention, comprises an additional C-terminal glycine residue (G446, numbering according to EU index of Kabat). Compositions of the invention, such as the pharmaceutical compositions described herein, comprise a population of antibodies or bispecific antibodies of the invention. The population of antibodies or bispecific antibodies may comprise molecules having a full-length heavy chain and molecules having a cleaved variant heavy chain. The population of antibodies or bispecific antibodies may consist of a mixture of molecules having a full-length heavy chain and molecules having a cleaved variant heavy chain, wherein at least 50%, at least 60%, at least 70%, at least 80% or at least 90% of the antibodies or bispecific antibodies have a cleaved variant heavy chain. In one embodiment of the invention a composition comprising a population of antibodies or bispecific antibodies of the invention comprises an antibody or bispecific antibody comprising a heavy chain including a subunit of an Fc domain as specified herein with an additional C-terminal glycine-lysine dipeptide (G446 and K447, numbering according to EU index of Kabat). In one embodiment of the invention a composition comprising a population of antibodies or bispecific antibodies of the invention comprises an antibody or bispecific antibody comprising a heavy chain including a subunit of an Fc domain as specified herein with an additional C-terminal glycine residue (G446, numbering according to EU index of Kabat). In one embodiment of the invention such a composition comprises a population of antibodies or bispecific antibodies comprised of molecules comprising a heavy chain including a subunit of an Fc domain as specified herein; molecules comprising a heavy chain including a subunit of a Fc domain as specified herein with an additional C-terminal glycine residue (G446, numbering according to EU index of Kabat); and molecules comprising a heavy chain including a subunit of an Fc domain as specified herein with an additional C-terminal glycine-lysine dipeptide (G446 and K447, numbering according to EU index of Kabat). Unless otherwise specified herein, numbering of amino acid residues in the Fc region or constant region is "according to the EU numbering system", also called "numbering according to the EU index of Kabat" or "Kabat EU numbering", as described in Kabat et al., Sequences of Proteins of Immunological Interest, 5th Ed. Public Health Service, National Institutes of Health, Bethesda, Md., 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

"Framework" or "FR" refers to variable domain residues other than hypervariable region (HVR) residues. The FR of a variable domain generally consists of four FR domains: FR1, FR2, FR3, and FR4. Accordingly, the CDR and FR sequences generally appear in the following sequence in VH (or VL): FR-HT(L1)-CDR-H1(L1)-FR-H2(L2)-CDR-H2(L2)-FR-H3(L3)-CDR-H3(L3)-FR-H4(L4).

The terms "full length antibody", "intact antibody", and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human CDRs and amino acid residues from human FRs. In certain embodiments, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "complementarity determining regions" or "CDRs" as used herein refers to each of the regions of an antibody variable domain which are hypervariable in sequence and/or form structurally defined loops ("hypervariable loops") and/or contain the antigen-contacting residues ("antigen contacts"). Generally, antibodies comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (CDR-L1), 50-52 (CDR-L2), 91-96 (CDR-L3), 26-32 (CDR-H1), 53-55 (CDR-H2), and 96-101 (CDR-H3) (Chothia and Lesk, *J. Mol. Biol.* 196:901-917 (1987));
(b) CDRs occurring at amino acid residues 24-34 (CDR-L1), 50-56 (CDR-L2), 89-97 (CDR-L3), 31-35b (CDR-H1), 50-65 (CDR-H2), and 95-102 (CDR-H3) (Kabat et al., *Sequences of Proteins of Immunological Interest,* 5th Ed. Public Health Service, National Institutes of Health, Bethesda, Md. (1991));
(c) antigen contacts occurring at amino acid residues 27c-36 (CDR-L1), 46-55 (CDR-L2), 89-96 (CDR-L3), 30-35b (CDR-H1), 47-58 (CDR-H2), and 93-101 (CDR-H3) (MacCallum et al. *J. Mol. Biol.* 262: 732-745 (1996)); and
(d) combinations of (a), (b), and/or (c), including CDR amino acid residues 24-34 (CDR-L1), 50-56 (CDR-L2), 89-97 (vL3), 31-35 (CDR-H1), 50-63 (CDR-H2), and 95-102 (CDR-H3).

Unless otherwise indicated, CDR-residues and other residues in the variable domain (e.g., FR residues) are numbered herein according to Kabat et al., Kabat et al., *Sequences of Proteins of Immunological Interest,* 5th Ed. Public Health Service, National Institutes of Health, Bethesda, Md. (1991).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a mono- or bispecific anti-CCL2 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (CDRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See e.g., Portolano, S. et al., J. Immunol. 150 (1993) 880-887; Clackson, T. et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

I. Compositions and Methods

In one aspect, the invention is based, in part, on the finding that the bispecific antibodies as described herein use different anti-CCL2 antigen binding sites as first and second antigen binding site/moiety. These anti-CCL2 antibodies bind to certain epitopes of CCL2 with high specificity, and have ability to specifically inhibit binding of CCL2 to its receptor CCR2. They show improved immune complex formation compared to monospecific antibodies and improved CCL2 abrogation in vivo.

Bispecific-Anti-CCL2 Antibodies

Bispecific Antibodies

Bispecific antibodies as described herein are monoclonal antibodies that have binding specificities for at least two different epitopes on CCL2.

Techniques for making multi- and bispecific antibodies include, but are not limited to, recombinant co-expression of two immunoglobulin heavy chain-light chain pairs having different specificities (see Milstein and Cuello, Nature 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J Immunol., 152:5368 (1994)); and preparing trispecific antibodies as described, e.g., in Tutt et al. J Immunol. 147: 60 (1991).

Engineered antibodies with three or more antigen binding sites, including for example, "Octopus antibodies," or DVD-Ig are also included herein (see, e.g. WO 2001/77342 and WO 2008/024715). Other examples of multispecific antibodies with three or more antigen binding sites can be found in WO 2010/115589, WO 2010/112193, WO 2010/136172, WO2010/145792, and WO 2013/026831. The bispecific antibody or antigen binding fragment thereof also includes a "Dual Acting FAb" or "DAF" comprising an antigen binding site that binds to CCL2 as well as another different antigen, or two different epitopes of CCL2 (see, e.g., US 2008/0069820 and WO 2015/095539).

Multi-specific antibodies may also be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20), also called CrossMabs. Asymmetrical binding arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

Preferred Bispecific Antibody Formats.

According to particular embodiments of the invention, the bispecific antibody described herein with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20).

Charge modifications in such bispecific antibodies especially those with an exchange of the VH/VL domains (see WO 2015/150447): The bispecific antibodies of the invention may comprise amino acid substitutions in Fab molecules comprised therein which are particularly efficient in reducing mispairing of light chains with non-matching heavy chains (Bence-Jones-type side products), which can occur in the production of Fab-based bi-/antibodies with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired bispecific antibody compared to undesired side products, in particular Bence Jones-type side products occurring in bispecific antibodies with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some embodiments wherein the first and the second antigen binding moiety of the bispecific antibody are both Fab molecules, and in one of the antigen binding moieties (particularly the second antigen binding moiety) the variable domains VL and VH of the Fab light chain and the Fab heavy chain are replaced by each other,
i) in the constant domain CL of the first antigen binding moiety the amino acid at position 124 is substituted by a positively charged amino acid (numbering according to Kabat), and wherein in the constant domain CH1 of the first antigen binding moiety the amino acid at position 147 or the amino acid at position 213 is substituted by a negatively charged amino acid (numbering according to Kabat EU index); or
ii) in the constant domain CL of the second antigen binding moiety the amino acid at position 124 is substituted by a positively charged amino acid (numbering according to Kabat), and wherein in the constant domain CH1 of the second antigen binding moiety the amino acid at position 147 or the amino acid at position 213 is substituted by a negatively charged amino acid (numbering according to Kabat EU index).

The bispecific antibody does not comprise both modifications mentioned under i) and ii). The constant domains CL and CH1 of the antigen binding moiety having the VH/VL exchange are not replaced by each other (i.e. remain unexchanged).

In a more specific embodiment,
i) in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index); or
ii) in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In one such embodiment, in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index).

In a further embodiment, in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 is substituted independently by glutamic acid (E), or aspartic acid (D) (numbering according to Kabat EU index).

In a particular embodiment, in the constant domain CL of the first antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first antigen binding moiety the amino acid at position 124 is substituted by lysine (K) (numbering according to Kabat) and the amino acid at position 123 is substituted by lysine (K) (numbering according to Kabat), and in the constant domain CH1 of the first antigen binding moiety the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first antigen binding moiety the amino acid at position 124 is substituted by lysine (K) (numbering according to Kabat) and the amino acid at position 123 is substituted by arginine (R) (numbering according to Kabat), and in the constant domain CH1 of the first antigen binding moiety the amino acid at position 147 is substituted by glutamic acid (E) (numbering according to Kabat EU index) and the amino acid at position 213 is substituted by glutamic acid (E) (numbering according to Kabat EU index).

In particular embodiments, if amino acid substitutions according to the above embodiments are made in the constant domain CL and the constant domain CH1 of the first antigen binding moiety, the constant domain CL of the first antigen binding moiety is of kappa isotype.

Alternatively, the amino acid substitutions according to the above embodiments may be made in the constant domain CL and the constant domain CH1 of the second antigen binding moiety instead of in the constant domain CL and the constant domain CH1 of the first antigen binding moiety. In particular, such embodiments, the constant domain CL of the second antigen binding moiety is of kappa isotype.

Accordingly, in one embodiment, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In a further embodiment, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index).

In still another embodiment, in the constant domain CL of the second antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one embodiment, in the constant domain CL of the second antigen binding moiety the amino acid at position 124 is substituted by lysine (K) (numbering according to Kabat) and the amino acid at position 123 is substituted by lysine (K) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In another embodiment, in the constant domain CL of the second antigen binding moiety the amino acid at position 124 is substituted by lysine (K) (numbering according to Kabat) and the amino acid at position 123 is substituted by arginine (R) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

To improve heterodimerization of the Fc domain of these asymmetric (heterodimeric) proteins, in one embodiment according to these aspects of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further embodiment according to these aspects of the invention, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index).

Alternative heterodimerization techniques are described below under "Fc domains" and are also contemplated as further embodiments of the invention.

In still a further embodiment according to these aspects of the invention, the Fc domain is a human $IgG_1$ Fc domain.

Fc Domains and Modifications

In particular embodiments, the bispecific antibody of the invention comprises an Fc domain composed of a first and a second subunit. It is understood, that the features of the Fc domain described herein in relation to the bispecific antibody can equally apply to an Fc domain comprised in an antibody of the invention.

The Fc domain of the bispecific antibody consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment, the bispecific antibody of the invention comprises not more than one Fc domain.

In one embodiment, the Fc domain of the bispecific antibody is an IgG Fc domain. In a particular embodiment, the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat EU numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular embodiment, the Fc domain is a human Fc domain. In an even more particular embodiment, the Fc domain is a human $IgG_1$ Fc domain.

The Fc domains of IgG isotype are characterized bay various properties based e.g. on their interaction with the Fc gamma Receptors or with the neonatal Fc receptor (FcRn) (see e.g. see Vidarsson et al.; Front Immunol 5 (2014) Article 520, 1-17).

Fc Domain Modifications Promoting Heterodimerization

Bispecific antibodies according to the invention comprise different antigen binding moieties, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of bispecific antibodies in recombinant production, it will thus be advantageous to introduce in the Fc domain of the bispecific antibody a modification promoting the association of the desired polypeptides.

Accordingly, in particular embodiments, the Fc domain of the bispecific antibody according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the bispecific antibody which reduce heavy/light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the bispecific antibody an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In a particular embodiment the antigen binding moiety that binds to the second antigen is fused (optionally via the first antigen binding moiety, which binds to CCL2, and/or a peptide linker) to the first subunit of the Fc domain (comprising the "knob" modification). Without wishing to be bound by theory, fusion of the antigen binding moiety that binds a second antigen, such as an activating T cell antigen, to the knob-containing subunit of the Fc domain will (further) minimize the generation of antibodies comprising two antigen binding moieties that bind to an activating T cell antigen (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment, the heterodimerization approach described in EP 1870459, is used alternatively. This approach is based on the introduction of charged amino acids with opposite charges at specific amino acid positions in the CH3/CH3 domain interface between the two subunits of the Fc domain. One preferred embodiment for the bispecific antibody of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment, the bispecific antibody of the invention comprises amino acid mutation T366W in the CH3 domain of the first subunit of the Fc domain and amino acid mutations T366S, L368A, Y407V in the CH3 domain of the second subunit of the Fe domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment, the bispecific antibody of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said bispecific antibody comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one embodiment, the heterodimerization approach described in WO 2013/157953 is used alternatively. In one embodiment, a first CH3 domain comprises amino acid mutation T366K and a second CH3 domain comprises amino acid mutation L351D (numberings according to Kabat EU index). In a further embodiment, the first CH3 domain comprises further amino acid mutation L351K. In a further embodiment, the second CH3 domain comprises further an amino acid mutation selected from Y349E, Y349D and L368E (preferably L368E) (numberings according to Kabat EU index).

In one embodiment, the heterodimerization approach described in WO 2012/058768 is used alternatively. In one embodiment a first CH3 domain comprises amino acid mutations L351Y, Y407A and a second CH3 domain comprises amino acid mutations T366A, K409F. In a further embodiment the second CH3 domain comprises a further amino acid mutation at position T411, D399, S400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further embodiment a first CH3 domain comprises amino acid mutations L351Y, Y407A and a second CH3 domain comprises amino acid mutations T366V, K409F. In a further embodiment, a first CH3 domain comprises amino acid mutation Y407A and a second CH3 domain comprises amino acid mutations T366A, K409F. In a further embodiment, the second CH3 domain further comprises amino acid mutations K392E, T411E, D399R and S400R (numberings according to Kabat EU index).

In one embodiment, the heterodimerization approach described in WO 2011/143545 is used alternatively, e.g. with the amino acid modification at a position selected from the group consisting of 368 and 409 (numbering according to Kabat EU index).

In one embodiment, the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment, a first CH3 domain comprises amino acid mutation T366Y and a second CH3 domain comprises amino acid mutation Y407T (numberings according to Kabat EU index).

In one embodiment, the bispecific antibody or its Fc domain is of $IgG_2$ subclass and the heterodimerization approach described in WO 2010/129304 is used alternatively.

In an alternative embodiment, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment, a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment, the first CH3 domain further comprises amino acid substitution of K409 or R409 with a negatively charged amino acid (e.g. glutamic acid (E), or aspartic acid (D), preferably K409D or R409D). In a further embodiment the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment, the heterodimerization approach described in WO 2007/147901 is used alternatively. In one embodiment, a first CH3 domain comprises amino acid mutations K253E, D282K, and K322D and a second CH3 domain comprises amino acid mutations D239K, E240K, and K292D (numberings according to Kabat EU index).

In still another embodiment, the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

The term "wild type (WT) IgG or IgG1" as used herein for the bispecific anti-CCL2 antibodies refers to a bispecific antibody which comprises an IgG or IgG1 constant heavy chain which may comprise the above described modifications/mutations promoting heterodimerization but which does not comprise further Fc domain modifications/mutations increasing or reducing Fc receptor binding and/or effector function as described below.

Fc Domain Modifications/Mutations Increasing or Reducing Fc Receptor Binding and/or Effector Function:

Modification of the Bispecific Anti-CCL2 Antibodies Via Sweeping Technology

The bispecific anti-CCL2 antibodies were modified using the sweeping technology to enable the bispecific anti-CCL2 antibodies to abrogate free CCl2 over longer time periods to enable sustained a biological effect like anti-cancer efficacy in vivo.

The Sweeping concept is described e.g. in Igawa et al, Immunological Reviews 270 (2016) 132-151, WO2012/122011, WO2016/098357, and WO2013/081143 which are incorporated herein by reference.

The present invention provides methods for facilitating antibody mediated antigen uptake into cells, by reducing the antigen-binding activity (binding ability) in the acidic pH range of the above-described antibody to less than its antigen-binding activity in the neutral pH range; and this facilitates antigen uptake into cells. The present invention also provides methods for facilitating antibody-mediated antigen uptake into cells, which are based on altering at least one amino acid in the antigen-binding domain of the above-described antibody which facilitates antigen uptake into cells. The present invention also provides methods for facilitating antibody-mediated antigen uptake into cells, which are based on substituting histidine for at least one amino acid or inserting at least one histidine into the antigen-binding domain of the above-described antibody which facilitates antigen uptake into cells.

Herein, "antigen uptake into cells" mediated by an antibody means that antigens are taken up into cells by endocytosis. Meanwhile, herein, "facilitate the uptake into cells" means that the rate of intracellular uptake of antibody bound to an antigen in plasma is enhanced, and/or the quantity of recycling of uptaken antigen to the plasma is reduced. This means that the rate of uptake into cells is facilitated as compared to the antibody before increasing the human FcRn-binding activity of the antibody in the neutral pH range, or before increasing the human FcRn-binding activity and reducing the antigen-binding activity (binding ability) of the antibody in the acidic pH range to less than its antigen-binding activity in the neutral pH range. The rate is improved preferably as compared to intact human IgG, and more preferably as compared to intact human IgG. Thus, in the present invention, whether antigen uptake into cells is facilitated by an antibody can be assessed based on an increase in the rate of antigen uptake into cells. The rate of antigen uptake into cells can be calculated, for example, by monitoring over time reduction in the antigen concentration in the culture medium containing human FcRn-expressing cells after adding the antigen and antibody to the medium, or monitoring over time the amount of antigen uptake into human FcRn-expressing cells. Using methods of the present invention for facilitating the rate of antibody-mediated antigen uptake into cells, for example, the rate of antigen elimination from the plasma can be enhanced by administering antibodies. Thus, whether antibody-mediated antigen uptake into cells is facilitated can also be assessed, for example, by testing whether the rate of antigen elimination from the plasma is accelerated or whether the total antigen concentration in plasma is reduced by administering an antibody.

Herein, "total antigen concentration in plasma" means the sum of antibody bound antigen and non-bound antigen concentration, or "free antigen concentration in plasma" which is antibody non-bound antigen concentration. Various methods to measure "total antigen concentration in plasma" or "free antigen concentration in plasma" is well known in the art as described hereinafter.

"Intact human IgG" (or "wild type (WT) human IgG) as used herein is meant an unmodified (except with respect to the potential modifications for heterodimerization above) human IgG and is not limited to a specific class of IgG. This means that human IgG1, IgG2, IgG3 or IgG4 can be used as "intact human IgG" as long as it can bind to the human FcRn in the acidic pH range. Preferably, "intact human IgG" can be human IgG1.

The present invention also provides methods for increasing the number of antigens to which a single antibody can bind. More specifically, the present invention provides methods for increasing the number of antigens to which a single antibody having human FcRn-binding activity in the acidic pH range can bind, by increasing the human FcRn-binding activity of the antibody in the neutral pH range. The present invention also provides methods for increasing the number of antigens to which a single antibody having human FcRn-binding activity in the acidic pH range can bind, by altering at least one amino acid in the human FcRn-binding domain of the antibody.

The present invention provides methods for facilitating antibody-mediated antigen uptake into cells. More specifically, the present invention provides methods for facilitating the antigen uptake into cells by an antibody having human FcRn-binding activity in the acidic pH range, which are based on increasing the human FcRn-binding activity of the antibody in the neutral pH range. The present invention also provides methods for improving antigen uptake into cells by an antibody having human FcRn-binding activity in the acidic pH range, which are based on altering at least one amino acid in the human FcRn-binding domain of the antibody.

The present invention also provides methods for facilitating antigen uptake into cells by an antibody having human FcRn-binding activity in the acidic pH range, which are based on using a human FcRn-binding domain comprising an amino acid sequence with a substitution of a different amino acid for at least one amino acid selected from those of positions 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, and 436 (EU numbering) in the parent IgG Fc domain of the human FcRn-binding domain comprising the Fc domain of parent IgG.

The present invention also provides methods for facilitating antibody-mediated antigen uptake into cells, by reducing the antigen-binding activity (binding ability) in the acidic pH range of the above-described antibody to less than its antigen-binding activity in the neutral pH range; and this facilitates antigen uptake into cells. The present invention also provides methods for facilitating antibody-mediated antigen uptake into cells, which are based on altering at least one amino acid in the antigen-binding domain of the above-described antibody which facilitates antigen uptake into cells. The present invention also provides methods for facilitating antibody-mediated antigen uptake into cells, which are based on substituting histidine for at least one amino acid or inserting at least one histidine into the antigen-binding domain of the above-described antibody which facilitates antigen uptake into cells.

Herein, "antigen uptake into cells" mediated by an antibody means that antigens are taken up into cells by endocytosis. Meanwhile, herein, "facilitate the uptake into cells" means that the rate of intracellular uptake of antibody bound to an antigen in plasma is enhanced, and/or the quantity of recycling of uptaken antigen to the plasma is reduced. This means that the rate of uptake into cells is facilitated as compared to the antibody before increasing the human FcRn-binding activity of the antibody in the neutral pH range, or before increasing the human FcRn-binding activity and reducing the antigen-binding activity (binding ability) of the antibody in the acidic pH range to less than its antigen-binding activity in the neutral pH range. The rate is improved preferably as compared to intact human IgG, and more preferably as compared to intact human IgG. Thus, in the present invention, whether antigen uptake into cells is facilitated by an antibody can be assessed based on an increase in the rate of antigen uptake into cells. The rate of antigen uptake into cells can be calculated, for example, by monitoring over time reduction in the antigen concentration in the culture medium containing human FcRn-expressing cells after adding the antigen and antibody to the medium, or monitoring over time the amount of antigen uptake into human FcRn-expressing cells. Using methods of the present invention for facilitating the rate of antibody-mediated antigen uptake into cells, for example, the rate of antigen elimination from the plasma can be enhanced by administering antibodies. Thus, whether antibody-mediated antigen uptake into cells is facilitated can also be assessed, for example, by testing whether the rate of antigen elimination from the plasma is accelerated or whether the total antigen concentration in plasma is reduced by administering an antibody.

Herein, "total antigen concentration in plasma" means the sum of antibody bound antigen and non-bound antigen concentration, or "free antigen concentration in plasma" which is antibody non-bound antigen concentration. Various methods to measure "total antigen concentration in plasma" or "free antigen concentration in plasma" is well known in the art as described hereinafter.

"Intact human IgG" (or "wild type IgG") as used herein is meant an unmodified human IgG ((except with respect to the potential modifications for heterodimerization above) and is not limited to a specific class of IgG. This means that human IgG1, IgG2, IgG3 or IgG4 can be used as "intact human IgG" as long as it can bind to the human FcRn in the acidic pH range. Preferably, "intact human IgG" can be human IgG1.

"Parent IgG" as used herein means an unmodified IgG that is subsequently modified to generate a variant as long as a modified variant of parent IgG can bind to human FcRn in the acidic pH range (therefore, parent IgG does not necessary requires binding activity to human FcRn in the acidic condition). The parent IgG may be a naturally occurring IgG, or a variant or engineered version of a naturally occurring IgG. Parent IgG may refer to the polypeptide itself, compositions that comprise the parent IgG, or the amino acid sequence that encodes it. It should be noted that "parent IgG" includes known commercial, recombinantly produced IgG as outlined below. The origin of "parent IgG" is not limited and may be obtained from any organisms of non-human animals or human. Preferably, organism is selected from mouse, rat, guinea pig, hamster, gerbil, cat, rabbit, dog, goat, sheep, cow, horse, camel, and non-human primate. In another embodiment, "parent IgG" can also be obtained from cynomolgus, marmoset, rhesus, chimpanzee or human. Preferably, "parent IgG" is obtained from human IgG1 but not limited to a specific class of IgG. This means that human IgG1, IgG2, IgG3, or IgG4 can be appropriately used as "parent IgG". In the similar manner, any class or subclass of IgGs from any organisms hereinbefore can be preferably used as "parent IgG". Example of variant or engineered version of a naturally occurring IgG is described in Curr Opin Biotechnol. 2009 December; 20(6): 685-91, Curr Opin Immunol. 2008 August; 20(4): 460-70, Protein Eng Des Sel. 2010 April; 23(4): 195-202, WO 2009/086320, WO 2008/092117, WO 2007/041635 and WO 2006/105338, but not limited thereto.

The present invention also provides methods for increasing the ability to eliminate plasma antigen by administering antibodies. In the present invention, "methods for increasing the ability to eliminate plasma antigen" is synonymous to "methods for augmenting the ability of an antibody to eliminate antigen from plasma". More specifically, the present invention provides methods for increasing the ability to eliminate plasma antigen by an antibody having human FcRn-binding activity in the acidic pH range, by increasing the human FcRn-binding activity of the antibody in the neutral pH range. The present invention also provides methods for increasing the ability to eliminate plasma antigen by an antibody having human FcRn-binding activity in the acidic pH range, which are based on altering at least one amino acid in the human FcRn-binding domain of the antibody.

The present invention also provides methods for increasing the ability to eliminate plasma antigen by an antibody having human FcRn-binding activity in the acidic pH range, by using a human FcRn-binding domain comprising an amino acid sequence with a substitution of at least one amino acid selected from those of positions 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, and 436 (EU numbering) in the parent IgG Fc domain of the human FcRn-binding domain comprising the Fc domain of parent IgG with a different amino acid.

The present invention also provides methods for increasing the ability to eliminate plasma antigen by an antibody, by reducing the antigen-binding activity in the acidic pH range of the above-described antibody with improved ability to eliminate plasma antigen as compared to the antigen-binding activity in the neutral pH range. The present invention also provides methods for increasing the ability to eliminate plasma antigen by an antibody, by altering at least one amino acid in the antigen-binding domain of the above-described antibody with improved ability to eliminate plasma antigen. The present invention also provides methods for increasing the ability to eliminate plasma antigen by administering an antibody, by substituting histidine for at least one amino acid or inserting at least one histidine into the antigen-binding domain of the above-described antibody with improved ability to eliminate plasma antigen.

Herein, the "ability to eliminate plasma antigen" means the ability to eliminate antigen from the plasma when antibodies are administered or secreted in vivo. Thus, "increase in the ability of antibody to eliminate plasma antigen" herein means that the rate of antigen elimination from the plasma is accelerated upon administration of the antibody as compared to before increasing the human FcRn-binding activity of the antibody in the neutral pH range or before increasing the human FcRn-binding activity and simultaneously reducing its antigen-binding activity in the acidic pH range to less than that in the neutral pH range. Increase in the activity of an antibody to eliminate antigen from the plasma can be assessed, for example, by administering a soluble antigen and an antibody in vivo, and measuring the concentration of the soluble antigen in plasma after administration. When the concentration of soluble antigen in plasma after administration of the soluble antigen and antibody is reduced by increasing the human FcRn-binding activity of the antibody in the neutral pH range, or by increasing its human FcRn-binding activity and simultaneously reducing its antigen-binding activity in the acidic pH range to less than that in the neutral pH range, the ability of antibody to eliminate plasma antigen can be judged to be increased. A form of soluble antigen can be antibody bound antigen or antibody non-bound antigen whose concentration can be determined as "antibody bound antigen concentration in plasma" and "antibody non-bound antigen concentration in plasma" respectively (The latter is synonymous to "free antigen concentration in plasma". Since "total antigen concentration in plasma" means the sum of antibody bound antigen and non-bound antigen concentration, or "free antigen concentration in plasma" which is antibody non-bound antigen concentration, the concentration of soluble antigen can be determined as "total antigen concentration in plasma". Various methods for measuring "total antigen concentration in plasma" or "free antigen concentration in plasma" are well known in the art as described hereinafter.

The present invention also provides methods for improving the pharmacokinetics of antibodies. More specifically, the present invention provides methods for improving the pharmacokinetics of the antibody having human FcRn-binding activity in the acidic pH range by increasing the human FcRn-binding activity of the antibody in the neutral pH range. Furthermore, the present invention provides methods for improving the pharmacokinetics of an antibody having human FcRn-binding activity in the acidic pH range by altering at least one amino acid in the human FcRn-binding domain of the antibody.

The present invention also provides methods for improving the pharmacokinetics of an antibody having human FcRn-binding activity in the acidic pH range by using a human FcRn-binding domain comprising an amino acid sequence with a substitution of different amino acid for at least one amino acid selected from those of positions 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, and 436 (EU numbering) in the parent IgG Fc domain of the human FcRn-binding domain comprising the Fc domain of IgG.

The plasma concentration of free antigen not bound to the antibody or the ratio of free antigen concentration to the total concentration can be determined by methods known to those skilled in the art, for example, by the method described in Pharm Res. 2006 January; 23 (1): 95-103. Alternatively, when an antigen exhibits a particular function in vivo, whether the antigen is bound to an antibody that neutralizes the antigen function (antagonistic molecule) can be assessed by testing whether the antigen function is neutralized. Whether the antigen function is neutralized can be assessed by assaying an in vivo marker that reflects the antigen function. Whether the antigen is bound to an antibody that activates the antigen function (agonistic molecule) can be assessed by assaying an in vivo marker that reflects the antigen function.

Determination of the plasma concentration of free antigen and ratio of the amount of free antigen in plasma to the amount of total antigen in plasma, in vivo marker assay, and such measurements are not particularly limited; however, the assays are preferably carried out after a certain period of time has passed after administration of the antibody. In the present invention, the period after administration of the antibody is not particularly limited; those skilled in the art can determine the appropriate period depending on the properties and the like of the administered antibody. Such periods include, for example, one day after administration of the antibody, three days after administration of the antibody, seven days after administration of the antibody, 14 days after administration of the antibody, and 28 days after administration of the antibody. Herein, "plasma antigen concentration" means either "total antigen concentration in plasma" which is the sum of antibody bound antigen and non-bound antigen concentration or "free antigen concentration in plasma" which is antibody non-bound antigen concentration.

Total antigen concentration in plasma can be lowered by administration of antibody of the present invention by 2-fold, 5-fold, 10-fold, 20-fold, 50-fold, 100-fold, 200-fold, 500-fold, 1,000-fold, or even higher compared to the administration of a reference antibody comprising the intact human IgG Fc domain as a human FcRn-binding domain or compared to when antigen-binding domain molecule of the present invention is not administered.

In another aspect, the invention provides bispecific anti-CCL2 antibodies that exhibit pH-dependent binding characteristics. As used herein, the expression "pH-dependent binding" means that the antibody exhibits "reduced binding to CCL2 at acidic pH as compared to its binding at neutral pH" (for purposes of the present disclosure, both expressions may be used interchangeably). For example, antibodies "with pH-dependent binding characteristics" include antibodies that bind to CCL2 with higher affinity at neutral pH than at acidic pH. In certain embodiments, the bispecific antibodies of the present invention bind to CCL2 with at least 2, 3, 5, 10, 15, 20, 25, 30, 35, 40, 45, 50, 55, 60, 65, 70, 75, 80, 85, 90, 95, 100, 200, 400, 1000, 10000, or more times higher affinity at neutral pH than at acidic pH. In some embodiments, the antibodies bind to CCL2 with higher affinity at pH7.4 than at pH5.8. In further embodiments, the antibodies bind to CCL2 with at least 2, 3, 5, 10, 15, 20, 25, 30, 35, 40, 45, 50, 55, 60, 65, 70, 75, 80, 85, 90, 95, 100, 200, 400, 1000, 10000, or more times higher affinity at pH7.4 than at pH5.8.

When an antigen is a soluble protein, the binding of an antibody to the antigen can result in an extended half-life of the antigen in plasma (i.e., reduced clearance of the antigen from plasma), since the antibody can have a longer half-life in plasma than the antigen itself and may serve as a carrier for the antigen. This is due to the recycling of the antigen-antibody complex by FcRn through the endosomal pathway in cell (Roopenian, Nat. Rev. Immunol. 7(9): 715-725 (2007)). However, an antibody with pH-dependent binding characteristics, which binds to its antigen in neutral extracellular environment while releasing the antigen into acidic endosomal compartments following its entry into cells, is expected to have superior properties in terms of antigen neutralization and clearance relative to its counterpart that binds in a pH-independent manner (Igawa et al., Nature Biotechnol. 28(11):1203-1207 (2010); Devanaboyina et al., mAbs 5(6):851-859 (2013); WO 2009/125825).

The "affinity" of an antibody for CCL2, for purposes of the present disclosure, is expressed in terms of the KD of the antibody. The KD of an antibody refers to the equilibrium dissociation constant of an antibody-antigen interaction. The greater the KD value is for an antibody binding to its antigen, the weaker its binding affinity is for that particular antigen. Accordingly, as used herein, the expression "higher affinity at neutral pH than at acidic pH" (or the equivalent expression "pH-dependent binding") means that the KD of the antibody binding to CCL2 at acidic pH is greater than the KD of the antibody binding to CCL2 at neutral pH. For example, in the context of the present invention, an antibody is considered to bind to CCL2 with higher affinity at neutral pH than at acidic pH if the KD of the antibody binding to CCL2 at acidic pH is at least 2 times greater than the KD of the antibody binding to CCL2 at neutral pH. Thus, the present invention includes antibodies that bind to CCL2 at acidic pH with a KD that is at least 2, 3, 5, 10, 15, 20, 25, 30, 35, 40, 45, 50, 55, 60, 65, 70, 75, 80, 85, 90, 95, 100, 200, 400, 1000, 10000, or more times greater than the KD of the antibody binding to CCL2 at neutral pH. In another embodiment, the KD value of the antibody at neutral pH can be $10^{-7}$ M, $10^{-8}$ M, $10^{-9}$ M, $10^{-10}$ M, $10^{-11}$ M, $10^{-12}$ M, or less.

In another embodiment, the KD value of the antibody at acidic pH can be 10-9 M, 10-8 M, 10-7 M, 10-6 M, or greater.

In further embodiments an antibody is considered to bind to with a higher affinity at neutral pH than at acidic pH if the KD of the antibody binding to CCL2 at pH5.8 is at least 2 times greater than the KD of the antibody binding to CCL2 at pH7.4. In some embodiments the provided antibodies bind to CCL2 at pH5.8 with a KD that is at least 3, 5, 10, 15, 20, 25, 30, 35, 40, 45, 50, 55, 60, 65, 70, 75, 80, 85, 90, 95, 100, 200, 400, 1000, 10000, or more times greater than the KD of the antibody binding to CCL2 at pH7.4. In another embodiment, the KD value of the antibody at pH7.4 can be 10-7 M, 10-8 M, 10-9 M, 10-10 M, 10-11 M, 10-12 M, or less. In another embodiment, the KD value of the antibody at pH5.8 can be 10-9 M, 10-8 M, 10-7 M, 10-6 M, or greater.

The binding properties of an antibody for a particular antigen may also be expressed in terms of the kd of the antibody. The kd of an antibody refers to the dissociation rate constant of the antibody with respect to a particular antigen and is expressed in terms of reciprocal seconds (i.e., sec-1). An increase in kd value signifies weaker binding of an antibody to its antigen. The present invention therefore includes antibodies that bind to CCL2 with a higher kd value at acidic pH than at neutral pH. The present invention includes antibodies that bind to CCL2 at acidic pH with a kd that is at least 2, 3, 5, 10, 15, 20, 25, 30, 35, 40, 45, 50, 55, 60, 65, 70, 75, 80, 85, 90, 95, 100, 200, 400, 1000, 10000, or more times greater than the kd of the antibody binding to CCL2 at neutral pH. In another embodiment, the kd value of the antibody at neutral pH can be 10-2 1/s, 10-3 1/s, 10-4 1/s, 10-5 1/s, 10-6 1/s, or less. In another embodiment, the kd value of the antibody at acidic pH can be 10-3 1/s, 10-2 1/s, 10-1 1/s, or greater. The invention also includes antibodies that bind to CCL2 with a higher kd value at pH5.8 than at pH7.4. The invention includes antibodies that bind to CCL2 at pH5.8 with a kd that is at least 3, 5, 10, 15, 20, 25, 30, 35, 40, 45, 50, 55, 60, 65, 70, 75, 80, 85, 90, 95, 100, 200, 400, 1000, 10000, or more times greater than the kd of the antibody binding to CCL2 at pH7.4. In another embodiment, the kd value of the antibody at pH7.4 can be 10-2 1/s, 10-3 1/s, 10-4 1/s, 10-5 1/s, 10-6 1/s, or less. In another embodiment, the kd value of the antibody at pH5.8 can be 10-3 1/s, 10-2 1/s, 10-1 1/s, or greater.

In certain instances, a "reduced binding to CCL2 at acidic pH as compared to its binding at neutral pH" is expressed in terms of the ratio of the KD value of the antibody binding to CCL2 at acidic pH to the KD value of the antibody binding to CCL2 at neutral pH (or vice versa). For example, an antibody may be regarded as exhibiting "reduced binding to CCL2 at acidic pH as compared to its binding at neutral pH", for purposes of the present invention, if the antibody exhibits an acidic/neutral KD ratio of 2 or greater. In certain embodiments, the pH5.8/pH7.4 KD ratio for an anti-CCL2 antibody of the present invention is 2 or greater. In certain exemplary embodiments, the acidic/neutral KD ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the KD value of the antibody at neutral pH can be 10-7 M, 10-8 M, 10-9 M, 10-10 M, 10-11 M, 10-12 M, or less. In another embodiment, the KD value of the antibody at acidic pH can be 10-9 M, 10-8 M, 10-7 M, 10-6 M, or greater. In further instances an antibody may be regarded as exhibiting "reduced binding to CCL2 at acidic pH as compared to its binding at neutral pH", if the antibody exhibits an pH5.8/pH7.4 KD ratio of 2 or greater. In certain exemplary embodiments, the pH5.8/pH7.4 KD ratio for the antibody can be 3, 5, 10, 15, 20, 25, 30, 35, 40, 45, 50, 55, 60, 65, 70, 75, 80, 85, 90, 95, 100, 200, 400, 1000, 10000, or greater. In another embodiment, the KD value of the antibody at pH7.4 can be 10-7 M, 10-8 M, 10-9 M, 10-10 M, 10-11 M, 10-12 M, or less. In another embodiment, the KD value of the antibody at pH5.8 can be 10-9 M, 10-8 M, 10-7 M, 10-6 M, or greater.

In certain instances, a "reduced binding to CCL2 at acidic pH as compared to its binding at neutral pH" is expressed in terms of the ratio of the kd value of the antibody binding to CCL2 at acidic pH to the kd value of the antibody binding to CCL2 at neutral pH (or vice versa). For example, an antibody may be regarded as exhibiting "reduced binding to CCL2 at acidic pH as compared to its binding at neutral pH", for purposes of the present invention, if the antibody exhibits an acidic/neutral kd ratio of 2 or greater. In certain exemplary embodiments, the pH5.8/pH7.4 kd ratio for an antibody of the present invention is 2 or greater. In certain exemplary embodiments, the acidic/neutral kd ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the kd value of the antibody at neutral pH can be 10-2 1/s, 10-3 1/s, 10-4 1/s, 10-5 1/s, 10-6 1/s, or less. In another embodiment, the kd value of the antibody at acidic pH can be 10-3 1/s, 10-2 1/s, 10-1 1/s, or greater. In certain exemplary embodiments, the pH5.8/pH7.4 kd ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the kd value of the antibody at pH7.4 can be 10-2 1/s, 10-3 1/s, 10-4 1/s, 10-5 1/s, 10-6 1/s, or less. In another embodiment, the kd value of the antibody at pH5.8 can be 10-3 1/s, 10-2 1/s, 10-1 1/s, or greater.

As used herein, the expression "acidic pH" means a pH of 4.0 to 6.5. The expression "acidic pH" includes pH values of any one of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, and 6.5. In particular aspects, the "acidic pH" is 5.8.

As used herein, the expression "neutral pH" means a pH of 6.7 to about 10.0. The expression "neutral pH" includes pH values of any one of 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0. In particular aspects, the "neutral pH" is 7.4.

KD values, and kd values, as expressed herein, may be determined using a surface plasmon resonance-based biosensor to characterize antibody-antigen interactions. KD values, and kd values can be determined at 25 degrees C. or 37 degrees C.

In a further aspect, the invention provides a bispecific anti-CCL2 antibody that forms an immune complex (i.e. antigen-antibody complex) with CCL2. In certain embodiments, two or more bispecific anti-CCL2 antibodies bind to two or more CCL2 molecules to form an immune complex. This is possible because CCL2 exists as a homodimer containing two CCL2 molecules while an antibody has two antigen-binding sites.

Generally speaking, when two or more antibodies form an immune complex with two or more antigens, the resulting immune complex can strongly bind to Fc receptors existing on cell surfaces due to avidity effects through the Fc regions of the antibodies in the complex and can then be taken up into the cell with high efficiency. Thus, the above-mentioned anti-CCL2 antibody capable of forming an immune complex containing two or more anti-CCL2 antibodies and two or more CCL2 molecules can lead to a rapid clearance of CCL2 from plasma in a living body, via the strong binding to Fc receptors due to avidity effects.

Furthermore, an antibody with pH-dependent binding characteristics is thought to have superior properties in terms of antigen neutralization and clearance relative to its counterpart that binds in a pH-independent manner (Igawa et al., Nature Biotech. 28(11):1203-1207 (2010); Devanaboyina et al. mAbs 5(6):851-859 (2013); WO 2009/125825). Therefore, an antibody having both properties above, that is, an antibody which has pH-dependent binding characteristics and which forms an immune complex containing two or more antibodies with two or more antigens, is expected to have even more superior properties for highly accelerated elimination of antigens from plasma (WO 2013/081143).

In one aspect, the invention provides polypeptides comprising variant Fc regions with enhanced FcgammaRIIb-binding activity comprising at least two amino acid alterations comprising: (a) one amino acid alteration at position 236, and (b) at least one amino acid alteration of at least one position selected from the group consisting of: 231, 232, 233, 234, 235, 237, 238, 239, 264, 266, 267, 268, 271, 295, 298, 325, 326, 327, 328, 330, 331, 332, 334, and 396, according to EU numbering.

In one aspect, the invention provides polypeptides comprising a variant Fc region with enhanced FcgammaRIIb-binding activity comprising an amino acid alteration at position 236 according to EU numbering.

In one aspect, the invention provides polypeptides comprising a variant Fc region with enhanced FcgammaRIIb-binding activity comprising at least two amino acid alterations comprising: (a) one amino acid alteration at position 236, and (b) at least one amino acid alteration of at least one position selected from the group consisting of: 231, 232, 235, 239, 268, 295, 298, 326, 330, and 396, according to EU numbering. In a further embodiment, the variant Fc region comprises an amino acid alteration of at least one position selected from the group consisting of: 231, 232, 235, 239, 268, 295, 298, 326, 330, and 396, according to EU numbering. In a further embodiment, the variant Fc region comprises an amino acid alteration of at least one position selected from the group consisting of: 268, 295, 326, and 330, according to EU numbering.

In another aspect, the invention provides polypeptides comprising variant Fc regions with enhanced FcgammaRIIb-binding activity comprising amino acid alterations of any one of the following (1)-(37): (1) positions 231, 236, 239, 268 and 330; (2) positions 231, 236, 239, 268, 295 and 330; (3) positions 231, 236, 268 and 330; (4) positions 231, 236, 268, 295 and 330; (5) positions 232, 236, 239, 268, 295 and 330; (6) positions 232, 236, 268, 295 and 330; (7) positions 232, 236, 268 and 330; (8) positions 235, 236, 268, 295, 326 and 330; (9) positions 235, 236, 268, 295 and 330; (10) positions 235, 236, 268 and 330; (11) positions 235, 236, 268, 330 and 396; (12) positions 235, 236, 268 and 396; (13) positions 236, 239, 268, 295, 298 and 330; (14) positions 236, 239, 268, 295, 326 and 330; (15) positions 236, 239, 268, 295 and 330; (16) positions 236, 239, 268, 298 and 330; (17) positions 236, 239, 268, 326 and 330; (18) positions 236, 239, 268 and 330; (19) positions 236, 239, 268, 330 and 396; (20) positions 236, 239, 268 and 396; (21) positions 236 and 268; (22) positions 236, 268 and 295; (23) positions 236, 268, 295, 298 and 330; (24) positions 236, 268, 295, 326 and 330; (25) positions 236, 268, 295, 326, 330 and 396; (26) positions 236, 268, 295 and 330; (27) positions 236, 268, 295, 330 and 396; (28) positions 236, 268, 295 and 396; (29) positions 236, 268, 298 and 330; (30) positions 236, 268, 326 and 330; (31) positions 236, 268, 326, 330 and 396; (32) positions 236, 268 and 330; (33) positions 236, 268, 330 and 396; (34) positions 236, 268 and 396; (35) positions 236 and 295; (36) positions 236, 330 and 396; and (37) positions 236 and 396, according to EU numbering.

In a further embodiment, the variant Fc region with enhanced FcgammaRIIb-binding activity comprises at least one amino acid selected from the group consisting of: (a) Asp, Glu, Phe, Gly, His, Ile, Lys, Leu, Met, Asn, Pro, Gln, Arg, Ser, Thr, Val, Trp, Tyr at position 231; (b) Ala, Asp, Glu, Phe, Gly, His, Ile, Lys, Leu, Met, Asn, Gln, Arg, Ser, Thr, Val, Trp, Tyr at position 232; (c) Asp at position 233; (d) Trp, Tyr at position 234; (e) Trp at position 235; (f) Ala, Asp, Glu, His, Ile, Leu, Met, Asn, Gln, Ser, Thr, Val at position 236; (g) Asp, Tyr at position 237; (h) Glu, Ile, Met, Gln, Tyr at position 238; (i) Ile, Leu, Asn, Pro, Val at position 239; (j) Ile at position 264; (k) Phe at position 266; (l) Ala, His, Leu at position 267; (m) Asp, Glu at position 268; (n) Asp, Glu, Gly at position 271; (o) Leu at position 295; (p) Leu at position 298; (q) Glu, Phe, Ile, Leu at position 325; (r) Thr at position 326; (s) Ile, Asn at position 327; (t) Thr at position 328; (u) Lys, Arg at position 330; (v) Glu at position 331; (w) Asp at position 332; (x) Asp, Ile, Met, Val, Tyr at position 334; and (y) Ala, Asp, Glu, Phe, Gly, His, Ile, Lys, Leu, Met, Asn, Gln, Arg, Ser, Thr, Val, Trp, Tyr at position 396; according to EU numbering.

In a further embodiment, the variant Fc region with enhanced FcgammaRIIb-binding activity comprises at least one amino acid alteration (e.g., substitution) selected from the group consisting of: (a) Gly, Thr at position 231; (b) Asp at position 232; (c) Trp at position 235; (d) Asn, Thr at position 236; (e) Val at position 239; (f) Asp, Glu at position 268; (g) Leu at position 295; (h) Leu at position 298; (i) Thr at position 326; (j) Lys, Arg at position 330; and (k) Lys, Met at position 396; according to EU numbering. In a further embodiment, the variant Fc region with enhanced FcgammaRIIb-binding activity comprises amino acid alterations (e.g., substitutions) of: Asn at position 236, Glu at position 268, Lys at position 330, and Met at position 396; according to EU numbering. In a further embodiment, the variant Fc region with enhanced FcgammaRIIb-binding activity comprises amino acid alterations (e.g., substitutions) of: Asn at position 236, Asp at position 268, and Lys at position 330; according to EU numbering. In a further embodiment, the variant Fc region with enhanced FcgammaRIIb-binding activity comprises amino acid alterations (e.g., substitutions) of Asn at position 236, Asp at position 268, Leu at position 295, and Lys at position 330; according to EU numbering. In a further embodiment, the variant Fc region with enhanced FcgammaRIIb-binding activity comprises amino acid alterations (e.g., substitutions) of Thr at position 236, Asp at position 268, and Lys at position 330; according to EU numbering. In a further embodiment, the variant Fc region with enhanced FcgammaRIIb-binding activity comprises amino acid alterations (e.g., substitutions) of: Asn at position 236, Asp at position 268, Leu at position 295, Thr at position 326, and Lys at position 330; according to EU numbering. In a further embodiment, the variant Fc region with enhanced FcgammaRIIb-binding activity comprises amino acid alterations (e.g., substitutions) of Trp at position 235, Asn at position 236, Asp at position 268, Leu at position 295, Thr at position 326, and Lys at position 330; according to EU numbering.

In another aspect, the invention provides isolated polypeptides comprising variant Fc regions with increased isoelectric point (pI). In certain embodiments, a variant Fc region described herein comprises at least two amino acid alterations in a parent Fc region. In certain embodiments, each of the amino acid alterations increases the isoelectric point (pI) of the variant Fc region compared with that of the parent Fc region. They are based on the findings that antigen elimination from plasma can be promoted with an antibody whose pI has been increased by modification of at least two amino acid residues, for example when the antibody is administered in vivo.

In the present invention, pI may be either a theoretical or an experimentally determined pI. The value of pI can be determined, for example, by isoelectric focusing known to those skilled in the art. The value of a theoretical pI can be calculated, for example, using gene and amino acid sequence analysis software (Genetyx, etc.).

In one embodiment, the pI value may be increased, for example, at least by 0.01, 0.03, 0.05, 0.1, 0.2, 0.3, 0.4, 0.5, or more, at least by 0.6, 0.7, 0.8, 0.9, or more, at least by 1.0, 1.1, 1.2, 1.3, 1.4, 1.5, or more, or at least by 1.6, 1.7, 1.8, 1.9, 2.0, 2.1, 2.2, 2.3, 2.4, 2.5, 3.0 or more, as compared to before modification.

In certain embodiments, the amino acid for increased pI can be exposed on the surface of the variant Fc region. In the present invention, an amino acid that can be exposed on the surface generally refers to an amino acid residue located on the surface of a polypeptide constituting a variant Fc region. An amino acid residue located on the surface of a polypeptide refers to an amino acid residue whose side chain can be in contact with solvent molecules (which in general are mostly water molecules). However, the side chain does not necessarily have to be wholly in contact with solvent molecules, and when even a portion of the side chain is in contact with the solvent molecules, the amino acid is defined as an "amino acid residue located on the surface". The amino acid residues located on the surface of a polypeptide also include amino acid residues located close to the surface and thereby can have an electric charge influence from another amino acid residue whose side chain, even partly, is in contact with the solvent molecules. Those skilled in the art can prepare a homology model of a polypeptide for example, using commercially available softwares. Alternatively, it is possible to use methods known to those skilled in the art, such as X-ray crystallography. The amino acid residues that can be exposed on the surface are determined, for example, using coordinates from a three-dimensional model using a computer program such as InsightII program (Accelrys). Surface-exposable sites may be determined using algorithms known in the technical field (for example, Lee and Richards (J. Mol. Biol. 55:379-400 (1971)); Connolly (J. Appl. Cryst. 16:548-558 (1983)). Surface-exposable sites can be determined using software suitable for protein modeling and three-dimensional structure information. Software available for such purposes includes, for example, the SYBYL Biopolymer Module software (Tripos Associates). When an algorithm requires a user input size parameter, the "size" of a probe which is used in the calculation may be set to about 1.4 Angstrom or less in radius. Furthermore, methods for determining surface-exposable regions using software for personal computers have been described by Pacios (Comput. Chem. 18(4):377-386 (1994); J. Mol. Model. 1:46-53 (1995)). Based on such information as described above, appropriate amino acid residues located on the surface of a polypeptide that constitutes a variant Fc region can be selected.

In certain embodiments, a polypeptide comprises both the variant Fc region and an antigen-binding domain. In further embodiments, the antigen is a soluble antigen. In one embodiment, the antigen is present in biological fluids (for example, plasma, interstitial fluid, lymphatic fluid, ascitic fluid, and pleural fluid) of subjects. The antigen may also be a membrane antigen.

In further embodiments, antigen-binding activity of the antigen-binding domain changes according to ion concentration conditions. In one embodiment, ion concentration is not particularly limited and refers to hydrogen ion concentration (pH) or metal ion concentration. Herein, metal ions refer to ions of group I elements except hydrogen, such as alkaline metals and the copper group elements, group II elements such as alkaline earth metals and zinc group elements, group III elements except boron, group IV elements except carbon and silicon, group VIII elements such as iron group and platinum group elements, elements belonging to subgroup A of groups V, VI, and VII, and metal elements such as antimony, bismuth, and polonium. In the present invention, metal ions include, for example, calcium ion, as described in WO 2012/073992 and WO 2013/125667. In one embodiment, "ion concentration condition" may be a condition that focuses on differences in the biological behavior of an antigen-binding domain between a low ion concentration and a high ion concentration. Furthermore, "antigen-binding activity of an antigen-binding domain changes according to ion concentration conditions" means that the antigen-binding activity of an antigen-binding domain changes between a low ion concentration and a high ion concentration (such an antigen-binding domain is referred to herein as "ion concentration-dependent antigen-binding domain"). The antigen-binding activity of an antigen-binding domain under a high ion concentration condition may be higher (stronger) or lower (weaker) than that under a low ion concentration condition. In one embodiment, ion concentration-dependent antigen-binding domains (such as pH-dependent antigen-binding domains or calcium ion concentration-dependent antigen-binding domains) can be obtained by known methods, for example, described in WO 2009/125825, WO 2012/073992, and WO 2013/046722.

In the present invention, the antigen-binding activity of an antigen-binding domain under a high calcium ion concentration condition may be higher than under a low calcium ion concentration condition. The high calcium ion concentration is not particularly limited to but may be a concentration selected between 100 micro M and 10 mM, between 200 micro M and 5 mM, between 400 micro M and 3 mM, between 200 micro M and 2 mM, between 400 micro M and 1 mM, or between 500 micro M and 2.5 mM, which is preferable to be close to the plasma (blood) concentration of calcium ion in vivo. Meanwhile, the low calcium ion concentration is not particularly limited to but may be a concentration selected between 0.1 micro M and 30 micro M, between 0.2 micro M and 20 micro M, between 0.5 micro M and 10 micro M, between 1 micro M and 5 micro M, or between 2 micro M and 4 micro M, which is preferable to be close to the concentration of calcium ion in early endosomes in vivo.

In one embodiment, the ratio between the antigen-binding activities under a low calcium ion concentration condition and a high calcium ion concentration condition is not limited but the ratio of the dissociation constant (KD) under a low calcium ion concentration condition to the KD under a high calcium ion concentration condition, i.e., KD (low calcium ion concentration condition)/KD (high calcium ion concentration condition), is 2 or more, 10 or more, or 40 or more. The upper limit of the ratio may be 400, 1000, or 10000, as long as such an antigen-binding domain can be produced by techniques known to those skilled in the art. Alternatively, for example, the dissociation rate constant (kd) can be used instead of the KD. In this case, the ratio of the kd under a low calcium ion concentration condition to the kd under a high calcium ion concentration condition, i.e., kd (low calcium ion concentration condition)/kd (high calcium ion concentration condition), is 2 or more, 5 or more, 10 or more, or 30 or more. The upper limit of the ratio may be 50, 100, or 200, as long as the antigen-binding domain can be produced based on the common technical knowledge of those skilled in the art.

In the present invention, the antigen-binding activity of an antigen-binding domain under a low hydrogen ion concentration (neutral pH) may be higher than under a high hydrogen ion concentration (acidic pH). The acidic pH may be, for example, a pH selected from pH4.0 to pH6.5, selected from pH4.5 to pH6.5, selected from pH5.0 to pH6.5, or selected from pH5.5 to pH6.5, which is preferable to be close to the in vivo pH in early endosomes. The acidic pH may also be, for example, pH5.8 or pH6.0. In particular embodiments, the acidic pH is pH5.8. Meanwhile, the neutral pH may be, for example, a pH selected from pH6.7 to pH10.0, selected from pH6.7 to pH9.5, selected from pH7.0 to pH9.0, or selected from pH7.0 to pH8.0, which is preferable to be close to the in vivo pH in plasma (blood). The neutral pH may also be, for example, pH7.4 or pH7.0. In particular embodiments, the neutral pH is pH7.4.

In one embodiment, the ratio between the antigen-binding activities under an acidic pH condition and a neutral pH condition is not limited but the ratio of the dissociation constant (KD) under an acidic pH condition to the KD under a neutral pH condition, i.e., KD (acidic pH condition)/KD (neutral pH condition), is 2 or more, 10 or more, or 40 or more. The upper limit of the ratio may be 400, 1000, or 10000, as long as such an antigen-binding domain can be produced by techniques known to those skilled in the art. Alternatively, for example, the dissociation rate constant (kd) can be used instead of the KD. In this case, the ratio of the kd under an acidic pH condition to the kd under a neutral pH condition, i.e., kd (acidic pH condition)/kd (neutral pH condition) is 2 or more, 5 or more, 10 or more, or 30 or more. The upper limit of the ratio may be 50, 100, or 200, as long as the antigen-binding domain can be produced based on the common technical knowledge of those skilled in the art.

In one embodiment, for example, at least one amino acid residue is substituted with an amino acid residue with a side-chain pKa of 4.0-8.0, and/or at least one amino acid with a side-chain pKa of 4.0-8.0 is inserted in the antigen-binding domain, as described in WO 2009/125825. The amino acid may be substituted and/or inserted at any site as long as the antigen-binding activity of the antigen-binding domain becomes weaker under an acidic pH condition than under a neutral pH condition as compared to before the substitution or insertion. When the antigen-binding domain has a variable region or CDR, the site may be within the variable region or CDR. The number of amino acids that are substituted or inserted can be appropriately determined by those skilled in the art; and the number may be one or more. Amino acids with a side-chain pKa of 4.0-8.0 can be used to change the antigen-binding activity of the antigen-binding domain according to the hydrogen ion concentration condition. Such amino acids include, for example, natural amino acids such as His (H) and Glu (E), and unnatural amino acids such as histidine analogs (US2009/0035836), m-N02-Tyr (pKa 7.45), 3,5-Br2-Tyr (pKa 7.21), and 3,5-12-Tyr (pKa7.38) (Heyl et al., Bioorg. Med. Chem. 11(17):3761-3768 (2003)). Amino acids with a side-chain pKa of 6.0-7.0 can also be used, which include, e.g., His (H).

In another embodiment, preferable antigen-binding domains for the variant Fc region with increased pI are described and can be obtained by methods described in WO2016/125495 and WO2017/046994.

In certain embodiments, the variant Fc region with increased pI comprises at least two amino acid alterations of at least two positions selected from the group consisting of: 285, 311, 312, 315, 318, 333, 335, 337, 341, 342, 343, 384, 385, 388, 390, 399, 400, 401, 402, 413, 420, 422, and 431, according to EU numbering.

In further embodiments, the variant Fc region with increased pI comprises at least two amino acid alterations of at least two positions selected from the group consisting of: 311, 341, 343, 384, 399, 400, 401, 402, and 413, according to EU numbering.

In another aspect, the invention provides polypeptides comprising variant Fc regions with increased pI comprising amino acid alterations of any one of the following (1)-(10): (1) positions 311 and 341; (2) positions 311 and 343; (3) positions 311, 343 and 413; (4) positions 311, 384 and 413; (5) positions 311 and 399; (6) positions 311 and 401; (7) positions 311 and 413; (8) positions 400 and 413; (9) positions 401 and 413; and (10) positions 402 and 413; according to EU numbering.

In one aspect, the invention provides polypeptides comprising variant Fc regions with enhanced FcgammaRIIb-binding activity and increased pI comprising at least three amino acid alterations comprising: (a) at least one amino acid alteration of at least one position selected from the group consisting of: 231, 232, 233, 234, 235, 236, 237, 238, 239, 264, 266, 267,268, 271, 295, 298, 325, 326, 327, 328, 330, 331, 332, 334, and 396, according to EU numbering, and (b) at least two amino acid alterations of at least two positions selected from the group consisting of: 285, 311, 312, 315, 318, 333, 335, 337, 341, 342, 343, 384, 385, 388, 390, 399, 400, 401, 402, 413, 420, 422, and 431, according to EU numbering.

In one aspect, the invention provides polypeptides comprising variant Fc regions with enhanced FcgammaRIIb-binding activity and increased pI, and that comprise at least three amino acid alterations comprising: (a) at least one amino acid alteration of at least one position selected from the group consisting of: 231, 232, 235, 236, 239, 268, 295, 298, 326, 330, and 396, according to EU numbering, and (b) at least two amino acid alterations of at least two positions selected from the group consisting of: 311, 341, 343, 384, 399, 400, 401, 402, and 413, according to EU numbering.

In another aspect, the invention provides polypeptides comprising variant Fc regions with enhanced FcgammaRIIb-binding activity and increased pI comprising amino acid alterations of any one of the following (1)-(9): (1) positions 235, 236, 268, 295, 311, 326, 330 and 343; (2) positions 236, 268, 295, 311, 326, 330 and 343; (3) positions 236, 268, 295, 311, 330 and 413; (4) positions 236, 268, 311, 330, 396 and 399; (5) positions 236, 268, 311, 330 and 343; (6) positions 236, 268, 311, 330, 343 and 413; (7) positions 236, 268, 311, 330, 384 and 413; (8) positions 236, 268, 311, 330 and 413; and (9) positions 236, 268, 330, 396, 400 and 413; according to EU numbering.

In one aspect, the invention provides polypeptides comprising variant Fc regions with enhanced FcgammaRIIb-binding activity and increased pI comprising at least three amino acid alterations comprising: (a) at least one amino acid alteration of at least one position selected from the group consisting of: 234, 238, 250, 264, 267, 307, and 330, and (b) at least two amino acid alterations of at least two positions selected from the group consisting of: 285, 311, 312, 315, 318, 333, 335, 337, 341, 342, 343, 384, 385, 388, 390, 399, 400, 401, 402, 413, 420, 422, and 431, according to EU numbering. In further embodiments, the polypeptides comprise at least two amino acid alterations of at least two positions selected from the group consisting of: 311, 341, 343, 384, 399, 400, 401, 402, and 413, according to EU numbering.

In another aspect, the invention provides polypeptides comprising variant Fc regions with enhanced FcgammaRIIb-binding activity and increased pI comprising amino acid alterations of any one of the following (1)-(16): (1) positions 234, 238, 250, 264, 307, 311, 330 and 343; (2) positions 234, 238, 250, 264, 307, 311, 330 and 413; (3) positions 234, 238, 250, 264, 267, 307, 311, 330 and 343; (4) positions 234, 238, 250, 264, 267, 307, 311, 330 and 413; (5) positions 234, 238, 250, 267, 307, 311, 330 and 343; (6) positions 234, 238, 250, 267, 307, 311, 330 and 413; (7) positions 234, 238, 250, 307, 311, 330 and 343; (8) positions 234, 238, 250, 307, 311, 330 and 413; (9) positions 238, 250, 264, 267, 307, 311, 330 and 343; (10) positions 238, 250, 264, 267, 307, 311, 330 and 413; (11) positions 238, 250, 264, 307, 311, 330 and 343; (12) positions 238, 250, 264, 307, 311, 330 and 413; (13) positions 238, 250, 267, 307, 311, 330 and 343; (14) positions 238, 250, 267, 307, 311, 330 and 413; (15) positions 238, 250, 307, 311, 330 and 343; and (16) positions 238, 250, 307, 311, 330 and 413; according to EU numbering.

In addition, amino acid alterations performed for other purpose(s) can be combined in a variant Fc region described herein. For example, amino acid substitutions that improve FcRn-binding activity (Hinton et al., J. Immunol. 176(1): 346-356 (2006); Dall'Acqua et al., J. Biol. Chem. 281(33): 23514-23524 (2006); Petkova et al., Intl. Immunol. 18(12): 1759-1769 (2006); Zalevsky et al., Nat. Biotechnol. 28(2): 157-159 (2010); WO 2006/019447; WO 2006/053301; and WO 2009/086320), and amino acid substitutions for improving antibody heterogeneity or stability (WO 2009/041613) may be added. Alternatively, polypeptides with the property of promoting antigen clearance, which are described in WO 2011/122011, WO 2012/132067, WO 2013/046704 or WO 2013/180201, polypeptides with the property of specific binding to a target tissue, which are described in WO 2013/180200, polypeptides with the property for repeated binding to a plurality of antigen molecules, which are described in WO 2009/125825, WO 2012/073992 or WO 2013/047752, can be combined with a variant Fc region described herein. Alternatively, with the objective of conferring binding ability to other antigens, the amino acid alterations disclosed in EP1752471 and EP1772465 may be combined in CH3 of a variant Fc region described herein. Alternatively, with the objective of increasing plasma retention, amino acid alterations that decrease the pI of the constant region (WO 2012/016227) may be combined in a variant Fc region described herein. Alternatively, with the objective of promoting uptake into cells, amino acid alterations that increase the pI of the constant region (WO 2014/145159) may be combined in a variant Fc region described herein. Alternatively, with the objective of promoting elimination of a target molecule from plasma, amino acid alterations that increase the pI of the constant region (WO2016/125495) may be combined in a variant Fc region described herein. In one embodiment, such alteration may include, for example, substitution at al least one position selected from the group consisting of 311, 343, 384, 399, 400, and 413 according to EU numbering. In a further embodiment, such substitution may be a replacement of an amino acid with Lys or Arg at each position.

Amino acid alterations of enhancing human FcRn-binding activity under acidic pH can also be combined in a variant Fc region described herein. Specifically, such alterations may include, for example, substitution of Leu for Met at position 428 and substitution of Ser for Asn at position 434, according to EU numbering (Zalevsky et al., Nat. Biotechnol. 28:157-159 (2010)); substitution of Ala for Asn at position 434 (Deng et al., Metab. Dispos. 38(4):600-605 (2010)); substitution of Tyr for Met at position 252, substitution of Thr for Ser at position 254 and substitution of Glu for Thr at position 256 (Dall'Acqua et al., J. Biol. Chem. 281:23514-23524 (2006)); substitution of Gln for Thr at position 250 and substitution of Leu for Met at position 428 (Hinton et al., J. Immunol. 176(1):346-356 (2006)); substitution of His for Asn at position 434 (Zheng et al., Clin. Pharmacol. Ther. 89(2):283-290 (2011), and alterations described in WO 2010/106180, WO 2010/045193, WO 2009/058492, WO 2008/022152, WO 2006/050166, WO 2006/053301, WO 2006/031370, WO 2005/123780, WO 2005/047327, WO 2005/037867, WO 2004/035752, or WO 2002/060919. Such alterations may include, for example, at least one alteration selected from the group consisting of substitution of Leu for Met at position 428, substitution of Ala for Asn at position 434 and substitution of Thr for Tyr at position 436. Those alterations may further include substitution of Arg for Gln at position 438 and/or substitution of Glu for Ser at position 440 (WO2016/125495).

Exemplary Bispecific-Anti-CCL2 Antibodies

One embodiment of the invention is a bispecific antibody comprising a first antigen-binding site that (specifically) binds to a first epitope on human CCL2 and a second different antigen-binding site that (specifically) binds a second different epitope on human CCL2, wherein A) i) said first antigen-binding site comprises
   a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
   and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
   ii) said second antigen-binding site comprises
   a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;
   and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;
   or B) i) said first antigen-binding site comprises
   a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
   and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
ii) said second antigen-binding site comprises
a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;
and a VL domain comprising (d) a CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22;
or
C) i) said first antigen-binding site comprises
a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
ii) said second antigen-binding site comprises
a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;
and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14;
or
D) i) said first antigen-binding site comprises
a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;
and a VL domain comprising (d) a CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22; and
ii) said second antigen-binding site comprises
a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;
and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;
or
E) i) said first antigen-binding site comprises
a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;
and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30; and
ii) said second antigen-binding site comprises
a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43; and
a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;
or
F) i) said first antigen-binding site comprises
a VH domain comprising (a) a CDR-H1 comprising the amino acid sequence of SEQ ID NO: 49, (b) a CDR-H2 comprising the amino acid sequence of SEQ ID NO: 50, and (c) a CDR-H3 comprising the amino acid sequence of SEQ ID NO: 51;
and a VL domain comprising (d) a CDR-L1 comprising the amino acid sequence of SEQ ID NO: 52; (e) a CDR-L2 comprising the amino acid sequence of SEQ ID NO: 53, and (f) a CDR-L3 comprising the amino acid sequence of SEQ ID NO: 54; and
ii) said second antigen-binding site comprises
a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43; and
a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;
or
G) i) said first antigen-binding site comprises
a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;
and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14; and
ii) said second antigen-binding site comprises
a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;
and a VL domain comprising a (d) CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22;
or
H) i) said first antigen-binding site comprises
a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;

and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14; and ii) said second antigen-binding site comprises a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;

and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30;

or

I) i) said first antigen-binding site comprises a VH domain comprising (a) a CDR-H1 comprising the amino acid sequence of SEQ ID NO: 1, (b) a CDR-H2 comprising the amino acid sequence of SEQ ID NO: 2, and (c) a CDR-H3 comprising the amino acid sequence of SEQ ID NO: 3;

and a VL domain comprising (d) a CDR-L1 comprising the amino acid sequence of SEQ ID NO: 4; (e) a CDR-L2 comprising the amino acid sequence of SEQ ID NO: 5, and (f) a CDR-L3 comprising the amino acid sequence of SEQ ID NO: 6; and ii) said second antigen-binding site comprises a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;

and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30.

In one embodiment the bispecific antibody comprises a Fc domain of human IgG1 isotype.

In one embodiment the bispecific antibody comprises constant heavy chain domain of human IgG1 isotype.

In one embodiment the in vivo clearance rate for human CCL2 (ml/day/kg) after administration of the bispecific antibody comprising a constant heavy chain domain of human wild type IgG1 isotype (or the Fc domain thereof) is at least two fold higher (in one embodiment at least 5 fold higher, in one embodiment at least 10 fold higher, in one embodiment at least 20 fold higher) compared to the in vivo clearance rate for human CCL2 (ml/day/kg) after administration of a bispecific antibody comprising a Fc gamma receptor silenced constant heavy chain domain of human IgG1 isotype (or the Fc domain thereof) comprising the mutations L234A, L235A, P329G, when a pre-formed immune complex consisting of 20 mg/kg of each bispecific antibody and 0.1 mg/kg human CCL2 was administered at a single dose of 10 ml/kg into FcRn transgenic mice.

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein i) said first antigen-binding site binds to same epitope on CCL2 as an antibody comprising a VH domain comprising the amino acid sequence of SEQ ID NO:39 wherein the VH domain comprises (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;

and a VL domain comprising the amino acid sequence of SEQ ID NO:40 wherein the VL domain comprises (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and ii) said second antigen-binding site binds to same epitope on CCL2 as an antibody comprising a VH domain comprising the amino acid sequence of SEQ ID NO:47 wherein the VH domain comprises (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;

and a VL domain comprising the amino acid sequence of SEQ ID NO:48 wherein the VL domain comprises (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46.

In one embodiment the bispecific antibody comprises a Fc domain of human IgG1 isotype.

In one embodiment the bispecific antibody comprises constant heavy chain domain of human IgG1 isotype.

In one embodiment the in vivo clearance rate for human CCL2 (ml/day/kg) after administration of the bispecific antibody comprising a constant heavy chain domain of human wild type IgG1 isotype (or the Fc domain thereof). is at least 15 fold higher, in particular at least 20 fold higher, compared to the in vivo clearance rate for human CCL2 (ml/day/kg) after administration of a bispecific antibody comprising a Fc gamma receptor silenced constant heavy chain domain of human IgG1 isotype (or the Fc domain thereof) comprising the mutations L234A, L235A, P329G, when a pre-formed immune complex consisting of 20 mg/kg of each bispecific antibody and 0.1 mg/kg human CCL2 was administered at a single dose of 10 ml/kg into FcRn transgenic mice.

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein i) said first antigen-binding site comprises a VH domain comprising (a) a CDR-H1 comprising the amino acid sequence SHYGXS of SEQ ID NO: 57 wherein X is I or T, (b) a CDR-H2 comprising the amino acid sequence $GX^1IX^2IFX^3TANYAQKFQG$ of SEQ ID NO: 58 wherein $X^1$ is V, I, or H, $X^2$ is P or H, and $X^3$ is H or G, and (c) a CDR-H3 comprising the amino acid sequence YDAHYGELDF of SEQ ID NO: 59;

and a VL domain comprising (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E; and
a VL domain comprising (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
i) said first antigen-binding site comprises
a VH domain comprising (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, (c) a CDR-H3 comprising the amino acid sequence YDAHYGELDF of SEQ ID NO: 59, (d) a FR-H1 comprising the amino acid sequence QVQLVQSGAEVKKPGSSVKVSCKASGGTF of SEQ ID NO:63, (e) a FR-H2 comprising the amino acid sequence WVRQAPGQGLEWMG of SEQ ID NO:64, (f) a FR-H3 comprising the amino acid sequence RVTITADESTSTAYMELSSLRSEDTAVY YCAR of SEQ ID NO:65, and (g) a FR-H4 comprising the amino acid sequence WGQGTLVTVSS of SEQ ID NO:66; and
a VL domain comprising (h) a CDR-L1 comprising the amino acid sequence RASQHVSDAYLA of SEQ ID NO: 60; (i) a CDR-L2 comprising the amino acid sequence DASDRAE of SEQ ID NO: 61, and (j) a CDR-L3 comprising the amino acid sequence HQYIHLHSFT of SEQ ID NO: 62, (k) a FR-L1 comprising the amino acid sequence EIVLTQSPATLSLSPGERATLSC of SEQ ID NO:67, (l) a FR-L2 comprising the amino acid sequence WYQQKPGQAPRLLIY of SEQ ID NO:68, (m) a FR-L3 comprising the amino acid sequence GVPARFSGSGSGTDFTLTISSLEPEDFAVYYC of SEQ ID NO:69, and (n) a FR-L4 comprising the amino acid sequence GQGTKVEIK of SEQ ID NO:70;
and ii) said second antigen-binding site comprises
a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, (c) a CDR-H3 comprising the amino acid sequences GVFGFFXH of SEQ ID NO:78 wherein X is D or E, (d) a FR-H1 comprising the amino acid sequence QVQLVQSGAEVKKPGSSVKVSCKASGLTIS of SEQ ID NO:82, (e) a FR-H2 comprising the amino acid sequence WVRQAPGQGLEWMG of SEQ ID NO:83, (f) a FR-H3 comprising the amino acid sequence RVTITADTSTSTAYMELSSLRSEDTAVYYCAR of SEQ ID NO:84, and (g) a FR-H4 comprising the amino acid sequence WGQGTTVTVSS of SEQ ID NO:85;
and
a VL domain comprising (h) a CDR-L1 comprising the amino acid sequence KAX$^1$EDIYNRX$^2$A of SEQ ID NO: 79 wherein X$^1$ is F or T and X$^2$ is R or L, (i) a CDR-L2 comprising the amino acid sequence GATSLEH of SEQ ID NO: 80, (j) a CDR-L3 comprising the amino acid sequence QQFXSAPYT of SEQ ID NO: 81 wherein X is W or R, (k) a FR-L1 comprising the amino acid sequence DIQMTQSPSSLSASVGDRVTITC of SEQ ID NO:86, (l) a FR-L2 comprising the amino acid sequence WYQQKPGKAPKLLIH of SEQ ID NO:87, (m) a FR-L3 comprising the amino acid sequence GVPSRFSGSGSGTDYTLTISSLQPEDFATYYC of SEQ ID NO:88, and (n) a FR-L4 comprising the amino acid sequence FGGGTKVEIK of SEQ ID NO:89.

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
A) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;
or
B) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID or
C) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;
or
D) i) said first antigen-binding site comprises
a VH domain comprising the amino acid sequence of SEQ ID NO:72;

and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;
or
E) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;
or
F) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;
or
G) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93;
or
H) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;
or
I) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;
or
J) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93;
or
K) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;
or
L) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;
or
M) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;
or
N) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93;
or
O) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;
or
P) i) said first antigen-binding site comprises
a VH domain comprising the amino acid sequence of SEQ ID NO:71;

and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93.

In one embodiment the bispecific antibody comprises a Fc domain of human IgG1 isotype.

In one embodiment the bispecific antibody comprises constant heavy chain domain of human IgG1 isotype.

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93.

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94.

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
i) said first antigen-binding site comprises
a VH domain comprising the amino acid sequence of SEQ ID NO:72;

and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94.

In one embodiment the bispecific antibody comprises a Fc domain of human IgG1 isotype.

In one embodiment the bispecific antibody comprises constant heavy chain domain of human IgG1 isotype. One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
A) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHYGXS of SEQ ID NO: 57 wherein X is I, (b) a CDR-H2 comprising the amino acid sequence $GX^1IX^2IFX^3TANYAQKFQG$ of SEQ ID NO: 58 wherein $X^1$ is V, $X^2$ is P, and $X^3$ is H, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D, and (c) a CDR-H3 comprising the amino acid sequences GVFGFFXH of SEQ ID NO:78 wherein X is D;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence $KAX^1EDIYNRX^2A$ of SEQ ID NO: 79 wherein $X^1$ is F and $X^2$ is R, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W;
or
B) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHY- GXS of SEQ ID NO: 57 wherein X is I, (b) a CDR-H2 comprising the amino acid sequence GX$^1$IX$^2$IFX$^3$TANYAQKFQG of SEQ ID NO: 58 wherein X$^1$ is V, X$^2$ is P, and X$^3$ is H, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D, and (c) a CDR-H3 comprising the amino acid sequences GVFGFFXH of SEQ ID NO:78 wherein X is E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F and X$^2$ is R, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W;

or

C) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

D) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

E) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

F) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

G) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO:

80, and (f) a CDR-L3 comprising the amino acid sequence QQFXSAPYT of SEQ ID NO: 81 wherein X is W or R;

or

H) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

I) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

J) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX¹EDIYNRX²A of SEQ ID NO: 79 wherein X¹ is F or T and X² is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

K) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX¹IX²IFX³TANYAQKFQG of SEQ ID NO: 58 wherein X¹ is V, I, or H, X² is P or H, and X³ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX¹EDIYNRX²A of SEQ ID NO: 79 wherein X¹ is F or T and X² is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

L) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHYGXS of SEQ ID NO: 57 wherein X is I or T, (b) a CDR-H2 comprising the amino acid sequence GX¹IX²IFX³TANYAQKFQG of SEQ ID NO: 58 wherein X¹ is V, I, or H, X² is P or H, and X³ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX¹EDIYNRX²A of SEQ ID NO: 79 wherein X¹ is F or T and X² is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

M) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHYGXS of SEQ ID NO: 57 wherein X is I or T, (b) a CDR-H2 comprising the amino acid sequence GX¹IX²IFX³TANYAQKFQG of SEQ ID NO: 58 wherein X¹ is V, I, or H, X² is P or H, and X³ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

N) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

O) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

P) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

In one embodiment the bispecific antibody comprises a Fc domain of human IgG1 isotype.

In one embodiment the bispecific antibody comprises constant heavy chain domain of human IgG1 isotype.

In one embodiment the bispecific antibody described herein
  i) blocks binding of CCL2 to its receptor CCR2 in vitro (reporter assay, IC$_{50}$=0.5 nM); and/or
  ii) inhibits CCL2-mediated chemotaxis of myeloid cells in vitro (IC$_{50}$=1.5 nM); and/or
  iii) is cross-reactive to cynomolgus and human CCL2.

In one embodiment the bispecific antibody described herein is not cross-reactive to other human CCL homologs in particular it shows 100 time less binding to other CCL homologs (selected from the group of CCL8, CCL7, and CCL13) compared to the binding to CCL2

In one embodiment the bispecific antibody described herein binds to the first and second epitope on human CCL2 in ion-dependent manner.

In one embodiment the bispecific antibody described herein binds to human CCL2 in pH dependent manner and wherein the first antigen binding site and the second antigen binding site both bind to CCL2 with a higher affinity at neutral pH than at acidic pH.

In one embodiment the bispecific antibody described herein binds to human CCL2 with a 10 times higher affinity at pH 7.4, than at pH 5.8

In one embodiment the bispecific antibody described herein comprises two IgG1 heavy chain constant domains (or the Fc domain thereof) comprising (independently or in addition to the above described mutations) the following mutations (EU numbering)
  i) S354C and T366W in one of the heavy chain constant domains
  ii) Y349C, T366S, L368A, Y407V in the other of the heavy chain constant domains In one embodiment the bispecific antibody comprises a Fc domain of human IgG1 isotype.

In one embodiment the bispecific antibody comprises constant heavy chain domain of human IgG1 isotype. In one embodiment the bispecific antibody described herein comprises a human IgG1 heavy chain constant domain (or the Fc domain thereof) comprising one or more of the following mutations (Kabat EU numbering)
  i) Q311R and/or P343R (suitable for increasing pI for enhancing uptake of antigen); and/or
  ii) L234Y, L235W, G236N, P238D, T250V, V264I, H268D, Q295L, T307P, K326T and/or A330K (suitable for increasing affinity to human FcgRIIb and decreasing affinity to other human FcgR); and/or
  iii) M428L, N434A and/or Y436T (suitable for increasing affinity to FcRn for longer plasma half-life); and/or
  iv) Q438R and/or S440E (suitable for suppressing rheumatoid factor binding).

In one embodiment the bispecific antibody described herein comprises a human IgG1 heavy chain constant domain (or the Fc domain thereof) comprising one or more of the following mutations (Kabat EU numbering)
  i) Q311R, and/or P343R (suitable for increasing pI for enhancing uptake of antigen); and/or
  ii) L235W, G236N, H268D, Q295L, K326T and/or A330K (suitable for increasing affinity to human FcgRIIb and decreasing affinity to other human FcgR); and/or
  iii) N434A (suitable for increasing affinity to FcRn for longer plasma half-life); and/or
  iv) Q438R and/or S440E (suitable for suppressing rheumatoid factor binding).

In one embodiment the bispecific antibody described herein comprises a human IgG1 heavy chain constant domain (or the Fc domain thereof) comprising the following mutations (Kabat EU numbering)
  i) Q311R and P343R (suitable for increasing pI for enhancing uptake of antigen); and
  ii) L235W, G236N, H268D, Q295L, K326T and A330K (suitable for increasing affinity to human FcgRIIb and decreasing affinity to other human FcgR); and
  iii) N434A (suitable for increasing affinity to FcRn for longer plasma half-life); and
  iv) Q438R and S440E (suitable for suppressing rheumatoid factor binding).

In one embodiment the bispecific antibody described herein comprises a human IgG1 heavy chain constant domain (or the Fc domain thereof) comprising the following mutations (Kabat EU numbering)
  i) Q311R and P343R (suitable for increasing pI for enhancing uptake of antigen); and
  ii) N434A (suitable for increasing affinity to FcRn for longer plasma half-life); and
  iii) Q438R and S440E (suitable for suppressing rheumatoid factor binding).

In one embodiment the bispecific antibody described herein comprises a human IgG1 heavy chain constant domain (or the Fc domain thereof) comprising the following mutations (Kabat EU numbering) Q311R and P343R (suitable for increasing pI for enhancing uptake of antigen).

In one embodiment the bispecific antibody described herein comprises a human IgG1 heavy chain constant domain (or the Fc domain thereof) comprising one or more of the following mutations (Kabat EU numbering)
  i) Q311R and/or P343R (suitable for increasing pI for enhancing uptake of antigen); and/or
  ii) L234Y, P238D, T250V, V264I, T307P and/or A330K (suitable for increasing affinity to human FcgRIIb and decreasing affinity to other human FcgR); and/or
  iii) M428L, N434A and/or Y436T (suitable for increasing affinity to FcRn for longer plasma half-life); and/or
  iv) Q438R and/or S440E (suitable for suppressing rheumatoid factor binding).

In one embodiment the bispecific antibody described herein comprises a human IgG1 heavy chain constant domain (or the Fc domain thereof) comprising one or more of the following mutations (Kabat EU numbering)
  i) Q311R and P343R (suitable for increasing pI for enhancing uptake of antigen); and
  ii) L234Y, P238D, T250V, V264I, T307P and A330K (suitable for increasing affinity to human FcgRIIb and decreasing affinity to other human FcgR); and iii) M428L, N434A and Y436T (suitable for increasing affinity to FcRn for longer plasma half-life); and
iv) Q438R and S440E (suitable for suppressing rheumatoid factor binding).

In one embodiment the bispecific antibody described herein comprises a human IgG1 heavy chain constant domain (or the Fc domain thereof) comprising one or more of the following mutations (Kabat EU numbering)
i) Q311R and P343R (suitable for increasing pI for enhancing uptake of antigen); and
ii) L234Y, P238D, T250V, V264I, T307P and A330K (suitable for increasing affinity to human FcgRIIb and decreasing affinity to other human FcgR); and
iii) N434A and (suitable for increasing affinity to FcRn for longer plasma half-life); and
iv) Q438R and S440E (suitable for suppressing rheumatoid factor binding).

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
A) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;
or
B) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;
or
C) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;
or
D) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;

wherein said bispecific antibody is a full length antibody of human IgG isotype (preferably of human IgG1 isotype) with
a) a first light chain and a first heavy chain of a first antibody comprising said first antigen binding site under the respective i); and
b) a second light chain and a second heavy chain of a second antibody comprising said second antigen binding site under the respective ii), and wherein the variable domains VL and VH in the second light chain and second heavy chain of the second antibody are replaced by each other; and
wherein in the constant domain CL of the first light chain under a) the amino acid at position 124 is substituted by lysine (K) (numbering according to Kabat) and the amino acid at position 123 is substituted by lysine (K) (numbering according to Kabat),
and wherein in the constant domain CH1 of the first heavy chain under a) the amino acid at position 147 is substituted by glutamic acid (E) (numbering according to Kabat EU index) and the amino acid at position 213 is substituted by glutamic acid (E) (numbering according to Kabat EU index).

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;
wherein said bispecific antibody is a (full length) antibody with
a) a first kappa or lambda light chain of and a first heavy chain of IgG1 isotype comprising said first antigen binding site under i); and
b) a second kappa or lambda light chain and a second IgG1 heavy chain IgG1 isotype comprising said second antigen binding site under ii), and wherein the variable domains VL and VH in the second light chain and second heavy chain of the second antibody are replaced by each other; and
wherein in the constant domain CL of the first light chain under a) the amino acid at position 124 is substituted by lysine (K) (numbering according to Kabat) and the amino acid at position 123 is substituted by lysine (K) (numbering according to Kabat),
and wherein in the constant domain CH1 of the first heavy chain under a) the amino acid at position 147 is substituted by glutamic acid (E) (numbering according to Kabat EU index) and the amino acid at position 213 is substituted by glutamic acid (E) (numbering according to Kabat EU index).

In one embodiment such bispecific antibody comprises the following mutations (Kabat EU numbering)
i) S354C and T366W in one of the heavy chain constant domains
ii) Y349C, T366S, L368A, Y407V in the other of the heavy chain constant domains In one embodiment such bispecific antibody comprises in addition the following mutations (Kabat EU numbering):
i) Q311R and P343R (suitable for increasing pI for enhancing uptake of antigen); and
ii) L235W, G236N, H268D, Q295L, K326T and A330K (suitable for increasing affinity to human FcgRIIb and decreasing affinity to other human FcgR); and
iii) N434A (suitable for increasing affinity to FcRn for longer plasma half-life); and
iv) Q438R and S440E (suitable for suppressing rheumatoid factor binding).

In one alternative embodiment such bispecific antibody comprises in addition the following mutations (Kabat EU numbering):
i) Q311R and P343R (suitable for increasing pI for enhancing uptake of antigen); and
ii) N434A (suitable for increasing affinity to FcRn for longer plasma half-life); and
iii) Q438R and S440E (suitable for suppressing rheumatoid factor binding).

In one alternative embodiment such bispecific antibody comprises in addition the following mutations (Kabat EU numbering):
Q311R and P343R (suitable for increasing pI for enhancing uptake of antigen).

In one alternative embodiment such bispecific antibody comprises in addition the following mutations (Kabat EU numbering):
i) Q311R and P343R (suitable for increasing pI for enhancing uptake of antigen); and
ii) L234Y, P238D, T250V, V264I, T307P and A330K (suitable for increasing affinity to human FcgRIIb and decreasing affinity to other human FcgR); and
iii) M428L, N434A and Y436T (suitable for increasing affinity to FcRn for longer plasma half-life); and
iv) Q438R and S440E (suitable for suppressing rheumatoid factor binding.

In one alternative embodiment such bispecific antibody comprises in addition the following mutations (Kabat EU numbering):
i) Q311R and P343R (suitable for increasing pI for enhancing uptake of antigen); and
ii) L234Y, P238D, T250V, V264I, T307P and A330K (suitable for increasing affinity to human FcgRIIb and decreasing affinity to other human FcgR); and
iii) N434A and (suitable for increasing affinity to FcRn for longer plasma half-life); and
iv) Q438R and S440E (suitable for suppressing rheumatoid factor binding).

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 112, a polypeptide comprising an amino acid sequence that is at least 98%, or 99% identical to the sequence of SEQ ID NO: 113, a polypeptide comprising an amino acid sequence that is at least 98%, or 99% identical to the sequence of SEQ ID NO: 114, and a polypeptide comprising an amino acid sequence that is at least 98%, or 99% identical to the sequence of SEQ ID NO: 115.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 112, a polypeptide comprising the amino acid sequence of SEQ ID NO: 113, a polypeptide comprising the amino acid sequence of SEQ ID NO: 114 and a polypeptide comprising the amino acid sequence of SEQ ID NO: 115.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 116, a polypeptide comprising an amino acid sequence that is at least 98%, or 99% identical to the sequence of SEQ ID NO: 117, a polypeptide comprising an amino acid sequence that is at least 98%, or 99% identical to the sequence of SEQ ID NO: 118, and a polypeptide comprising an amino acid sequence that is at least 98%, or 99% identical to the sequence of SEQ ID NO: 119.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 116, a polypeptide comprising the amino acid sequence of SEQ ID NO: 117, a polypeptide comprising the amino acid sequence of SEQ ID NO: 118 and a polypeptide comprising the amino acid sequence of SEQ ID NO: 119.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 120, a polypeptide comprising an amino acid sequence that is at least 98%, or 99% identical to the sequence of SEQ ID NO: 121, a polypeptide comprising an amino acid sequence that is at least 98%, or 99% identical to the sequence of SEQ ID NO: 122, and a polypeptide comprising an amino acid sequence that is at least 98%, or 99% identical to the sequence of SEQ ID NO: 123.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 120, a polypeptide comprising the amino acid sequence of SEQ ID NO: 121, a polypeptide comprising the amino acid sequence of SEQ ID NO: 122 and a polypeptide comprising the amino acid sequence of SEQ ID NO: 123.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 120, a polypeptide comprising an amino acid sequence that is at least 98%, or 99% identical to the sequence of SEQ ID NO: 121, a polypeptide comprising an amino acid sequence that is at least 98%, or 99% identical to the sequence of SEQ ID NO: 122, and a polypeptide comprising an amino acid sequence that is at least 98%, or 99% identical to the sequence of SEQ ID NO: 123.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 120, a polypeptide comprising the amino acid sequence of SEQ ID NO: 121, a polypeptide comprising the amino acid sequence of SEQ ID NO: 122 and a polypeptide comprising the amino acid sequence of SEQ ID NO: 123.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 155, a polypeptide comprising an amino acid sequence that is at least 98%, or 99% identical to the sequence of SEQ ID NO: 156, a polypeptide comprising an amino acid sequence that is at least 98%, or 99% identical to the sequence of SEQ ID NO: 157, and a polypeptide comprising an amino acid sequence that is at least 98%, or 99% identical to the sequence of SEQ ID NO: 158.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 155, a polypeptide comprising the amino acid sequence of SEQ ID NO: 156, a polypeptide comprising the amino acid sequence of SEQ ID NO: 157 and a polypeptide comprising the amino acid sequence of SEQ ID NO: 158.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 159, a polypeptide comprising an amino acid sequence that is at least 98%, or 99% identical to the sequence of SEQ ID NO: 160, a polypeptide comprising an amino acid sequence that is at least 98%, or 99% identical to the sequence of SEQ ID NO: 161, and a polypeptide comprising an amino acid sequence that is at least 98%, or 99% identical to the sequence of SEQ ID NO: 162.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 159, a polypeptide comprising the amino acid sequence of SEQ ID NO: 160, a polypeptide comprising the amino acid sequence of SEQ ID NO: 161 and a polypeptide comprising the amino acid sequence of SEQ ID NO: 162.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 163, a polypeptide comprising an amino acid sequence that is at least 98%, or 99% identical to the sequence of SEQ ID NO: 164, a polypeptide comprising an amino acid sequence that is at least 98%, or 99% identical to the sequence of SEQ ID NO: 165, and a polypeptide comprising an amino acid sequence that is at least 98%, or 99% identical to the sequence of SEQ ID NO: 166.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 163, a polypeptide comprising the amino acid sequence of SEQ ID NO: 164, a polypeptide comprising the amino acid sequence of SEQ ID NO: 165 and a polypeptide comprising the amino acid sequence of SEQ ID NO: 166.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 167, a polypeptide comprising an amino acid sequence that is at least 98%, or 99% identical to the sequence of SEQ ID NO: 168, a polypeptide comprising an amino acid sequence that is at least 98%, or 99% identical to the sequence of SEQ ID NO: 169, and a polypeptide comprising an amino acid sequence that is at least 98%, or 99% identical to the sequence of SEQ ID NO: 170.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 167, a polypeptide comprising the amino acid sequence of SEQ ID NO: 168, a polypeptide comprising the amino acid sequence of SEQ ID NO: 169 and a polypeptide comprising the amino acid sequence of SEQ ID NO: 170.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 171, a polypeptide comprising an amino acid sequence that is at least 98%, or 99% identical to the sequence of SEQ ID NO: 172, a polypeptide comprising an amino acid sequence that is at least 98%, or 99% identical to the sequence of SEQ ID NO: 173, and a polypeptide comprising an amino acid sequence that is at least 98%, or 99% identical to the sequence of SEQ ID NO: 174.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 171, a polypeptide comprising the amino acid sequence of SEQ ID NO: 172, a polypeptide comprising the amino acid sequence of SEQ ID NO: 173 and a polypeptide comprising the amino acid sequence of SEQ ID NO: 174.

One embodiment of the invention is an (isolated) bispecific antibody comprising a first antigen-binding site that (specifically) binds to a first epitope on human CCL2 and a second antigen-binding site that (specifically) binds a second different epitope on human CCL2, wherein
  i) said first antigen-binding site comprises
    a VH domain comprising the amino acid sequence of SEQ ID NO:71;
    and a VL domain comprising the amino acid sequence of SEQ ID NO:75; and
  ii) said second antigen-binding site comprises
    a VH domain comprising the amino acid sequence of SEQ ID NO:90;
    and a VL domain comprising the amino acid sequence of SEQ ID NO:94;
  wherein said bispecific antibody is a (full length) antibody of human IgG1 isotype with
  a) a first kappa or lambda light chain of and a first heavy chain of IgG1 isotype comprising said first antigen binding site under i); and
  b) a second kappa or lambda light chain and a second IgG1 heavy chain IgG1 isotype comprising said second antigen binding site under ii), and wherein the variable domains VL and VH in the second light chain and second heavy chain of the second antibody are replaced by each other; and
  wherein in the constant domain CL of the first light chain under a) the amino acid at position 124 is substituted by lysine (K) (numbering according to Kabat) and the amino acid at position 123 is substituted by lysine (K) (numbering according to Kabat),
  and wherein in the constant domain CH1 of the first heavy chain under a) the amino acid at position 147 is substituted by glutamic acid (E) (numbering according to Kabat EU index) and the amino acid at position 213 is substituted by glutamic acid (E) (numbering according to Kabat EU index).

In one embodiment such bispecific antibody comprises the following mutations (Kabat EU numbering)
  i) S354C and T366W in one of the heavy chain constant domains
  ii) Y349C, T366S, L368A, Y407V in the other of the heavy chain constant domains In one embodiment such bispecific antibody comprises in addition the following mutations (Kabat EU numbering):
  i) Q311R and P343R (suitable for increasing pI for enhancing uptake of antigen); and
  ii) L235W, G236N, H268D, Q295L, K326T and A330K (suitable for increasing affinity to human FcgRIIb and decreasing affinity to other human FcgR); and
  iii) N434A (suitable for increasing affinity to FcRn for longer plasma half-life); and
  iv) Q438R and S440E (suitable for suppressing rheumatoid factor binding).

In one embodiment the bispecific antibody described herein comprises a IgG1 heavy chain constant domain (or the Fc domain thereof) comprising the following mutations (Kabat EU numbering)
  i) Q311R and P343R (suitable for increasing pI for enhancing uptake of antigen); and
  ii) N434A (suitable for increasing affinity to FcRn for longer plasma half-life); and
  iii) Q438R and S440E (suitable for suppressing rheumatoid factor binding).

In one embodiment the bispecific antibody described herein comprises a IgG1 heavy chain constant domain (or the Fc domain thereof) comprising the following mutations (Kabat EU numbering) Q311R and P343R (suitable for increasing pI for enhancing uptake of antigen).

In one alternative embodiment such bispecific antibody comprises in addition the following mutations (Kabat EU numbering):
  i) Q311R and P343R (suitable for increasing pI for enhancing uptake of antigen); and
  ii) L234Y, P238D, T250V, V264I, T307P and A330K (suitable for increasing affinity to human FcgRIIb and decreasing affinity to other human FcgR); and
  iii) M428L, N434A and Y436T (suitable for increasing affinity to FcRn for longer plasma half-life); and
  iv) Q438R and S440E (suitable for suppressing rheumatoid factor binding).

In one alternative embodiment such bispecific antibody comprises in addition the following mutations (Kabat EU numbering):
  i) Q311R and P343R (suitable for increasing pI for enhancing uptake of antigen); and
  ii) L234Y, P238D, T250V, V264I, T307P and A330K (suitable for increasing affinity to human FcgRIIb and decreasing affinity to other human FcgR); and
  iii) N434A and (suitable for increasing affinity to FcRn for longer plasma half-life); and
  iv) Q438R and S440E (suitable for suppressing rheumatoid factor binding).

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 124, a polypeptide comprising an amino acid sequence that is at least 98%, or 99% identical to the sequence of SEQ ID NO: 125, a polypeptide comprising an amino acid sequence that is at least 98%, or 99% identical to the sequence of SEQ ID NO: 126, and a polypeptide comprising an amino acid sequence that is at least 98%, or 99% identical to the sequence of SEQ ID NO: 127.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 124, a polypeptide comprising the amino acid sequence of SEQ ID NO: 125, a polypeptide comprising the amino acid sequence of SEQ ID NO: 126 and a polypeptide comprising the amino acid sequence of SEQ ID NO: 127.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 128, a polypeptide comprising an amino acid sequence that is at least 98%, or 99% identical to the sequence of SEQ ID NO: 129, a polypeptide comprising an amino acid sequence that is at least 98%, or 99% identical to the sequence of SEQ ID NO: 130, and a polypeptide comprising an amino acid sequence that is at least 98%, or 99% identical to the sequence of SEQ ID NO: 131.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 128, a polypeptide comprising the amino acid sequence of SEQ ID NO: 129, a polypeptide comprising the amino acid sequence of SEQ ID NO: 130 and a polypeptide comprising the amino acid sequence of SEQ ID NO: 131.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein the bispecific antibody comprises a polypeptide comprising an amino acid sequence that is at least 98%, or 99% identical to the sequence of SEQ ID NO: 132, a polypeptide comprising an amino acid sequence that is at least 98%, or 99% identical to the sequence of SEQ ID NO: 133, a polypeptide comprising an amino acid sequence that is at least 98%, or 99% identical to the sequence of SEQ ID NO: 134, and a polypeptide comprising an amino acid sequence that is at least 98%, or 99% identical to the sequence of SEQ ID NO: 135.

A specific embodiment of the invention is an (isolated) bispecific antibody comprising a first antigen-binding site that (specifically) binds to a first epitope on human CCL2 and a second antigen-binding site that (specifically) binds a second epitope on human CCL2 wherein bispecific antibody comprises a polypeptide comprising the amino acid sequence of SEQ ID NO: 132, a polypeptide comprising the amino acid sequence of SEQ ID NO: 133, a polypeptide comprising the amino acid sequence of SEQ ID NO: 134 and a polypeptide comprising the amino acid sequence of SEQ ID NO: 135.

Recombinant Methods and Compositions

Antibodies may be produced using recombinant methods and compositions, e.g., as described in U.S. Pat. No. 4,816,567. In one embodiment, isolated nucleic acid encoding an anti-CCL2 antibody (either bispecific or monospecific) as described herein is provided. Such nucleic acid may encode an amino acid sequence comprising one or all VL and/or an amino acid sequence comprising one or all VH of the mono- or bispecific antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell, a HEK293 cell or lymphoid cell (e.g., Y0, NS0, Sp20 cell). In one embodiment, a method of making an anti-CCL2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CCL2 cell, such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68;

MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

In another aspect, the invention is based, in part, on the finding that the modified monospecific antibodies as described herein show improved pH dependent binding properties and re therefore especially useful for the generation of the bispecific antibodies of the invention Monospecific Anti-CCL2 Antibodies with pH Dependent Binding Properties One embodiment of the invention is an (isolated) (monospecific) antibody that (specifically) binds to a human CCL2, wherein the antibody comprises
- A) a VH domain comprising (a) a CDR-H1 comprising the amino acid sequence SHYGXS of SEQ ID NO: 57 wherein X is I or T, (b) a CDR-H2 comprising the amino acid sequence $GX^1IX^2IFX^3TANYAQKFQG$ of SEQ ID NO: 58 wherein $X^1$ is V, I, or H, $X^2$ is P or H, and $X^3$ is H or G, and (c) a CDR-H3 comprising the amino acid sequence YDAHYGELDF of SEQ ID NO: 59;
  and
  a VL domain comprising (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62;
  or
- B) a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
  and
  a VL domain comprising (d) a CDR-L1 comprising the amino acid sequence $KAX^1EDIYNRX^2A$ of SEQ ID NO: 79 wherein $X^1$ is F or T and $X^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

One embodiment of the invention is an (isolated) (monospecific) antibody that (specifically) binds to a human CCL2, wherein the antibody comprises
- A) a VH domain comprising the amino acid sequence of SEQ ID NO:71;
  and a VL domain comprising the amino acid sequence of SEQ ID NO:75;
  or
- B) a VH domain comprising the amino acid sequence of SEQ ID NO:72;
  and a VL domain comprising the amino acid sequence of SEQ ID NO:75;
  or
- C) a VH domain comprising the amino acid sequence of SEQ ID NO:73;
  and a VL domain comprising the amino acid sequence of SEQ ID NO:75;
  or
- D) a VH domain comprising the amino acid sequence of SEQ ID NO:74;
  and a VL domain comprising the amino acid sequence of SEQ ID NO:75;
  or
- E) a VH domain comprising the amino acid sequence of SEQ ID NO:90;
  and a VL domain comprising the amino acid sequence of SEQ ID NO:93;
  or
- F) a VH domain comprising the amino acid sequence of SEQ ID NO:91;
  and a VL domain comprising the amino acid sequence of SEQ ID NO:93;
  or
- G) a VH domain comprising the amino acid sequence of SEQ ID NO:92;
  and a VL domain comprising the amino acid sequence of SEQ ID NO:93;
  or
- H) a VH domain comprising the amino acid sequence of SEQ ID NO:90;
  and a VL domain comprising the amino acid sequence of SEQ ID NO:94;

Methods and Compositions for Diagnostics and Detection

In certain embodiments, any of the mono- or bispecific anti-CCL2 antibodies provided herein is useful for detecting the presence of CCL2 in a biological sample. The term "detecting" as used herein encompasses quantitative or qualitative detection. In certain embodiments, a biological sample comprises a cell or tissue, such as immune cell or T cell infiltrates and or tumor cells.

In one embodiment, a mono- or bispecific anti-CCL2 antibody for use in a method of diagnosis or detection is provided. In a further aspect, a method of detecting the presence of CCL2 in a biological sample is provided. In certain embodiments, the method comprises contacting the biological sample with a mono- or bispecific anti-CCL2 antibody as described herein under conditions permissive for binding of the mono- or bispecific anti-CCL2 antibody to CCL2, and detecting whether a complex is formed between the mono- or bispecific anti-CCL2 antibody and CCL2. Such method may be an in vitro or in vivo method. In one embodiment, a mono- or bispecific anti-CCL2 antibody is used to select subjects eligible for therapy with a mono- or bispecific anti-CCL2 antibody, e.g. where CCL2 is a biomarker for selection of patients.

In certain embodiments, labeled mono- or bispecific anti-CCL2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, p-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Formulations

Pharmaceutical formulations of a mono- or bispecific anti-CCL2 antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

F. Therapeutic Methods and Compositions

Any of the mono- or bispecific anti-CCL2 antibodies provided herein may be used in therapeutic methods.

In one aspect, a mono- or bispecific anti-CCL2 antibody for use as a medicament is provided. In further aspects, a mono- or bispecific anti-CCL2 antibody or use in treating cancer is provided. In certain embodiments, a mono- or bispecific anti-CCL2antibody for use in a method of treatment is provided. In certain embodiments, the invention provides a mono- or bispecific anti-CCL2 antibody for use in a method of treating an individual having cancer comprising administering to the individual an effective amount of the mono- or bispecific anti-CCL2 antibody.

In further embodiments, the invention provides a mono- or bispecific anti-CCL2 antibody inhibits immunosuppression in tumors and thus makes tumor susceptible for immuno stimulatory agents like anti-PD1, anti-PDL-1 antagonists and the like.

Therefore one aspect of the is the combination of the mono- or bispecific anti-CCL2 antibodies described here with a cancer immunotherapy like anti-PD1, anti-PDL-1 antagonists and the like.

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers.

An "individual" according to any of the above embodiments is preferably a human. In a further aspect, the invention provides for the use of a mono- or bispecific anti-CCL2 antibody in the manufacture or preparation of a medicament. In one embodiment, the medicament is for treatment of cancer. In a further embodiment, the medicament is for use in a method of treating cancer comprising administering to an individual having cancer an effective amount of the medicament. In a further embodiment, the medicament is for inducing cell mediated lysis of cancer cells In a further embodiment, the medicament is for use in a method of inducing cell mediated lysis of cancer cells in an individual suffering from cancer comprising administering to the individual an amount effective of the medicament to induce apoptosis in a cancer cell/or to inhibit cancer cell proliferation. An "individual" according to any of the above embodiments may be a human.

In a further aspect, the invention provides a method for treating cancer. In one embodiment, the method comprises administering to an individual having cancer an effective amount of mono- or bispecific anti-CCL2 antibody. An "individual" according to any of the above embodiments may be a human.

In a further aspect, the invention provides a method for inducing cell mediated lysis of cancer cells in an individual suffering from cancer. In one embodiment, the method comprises administering to the individual an effective amount of a mono- or bispecific anti-CCL2 antibody to induce cell mediated lysis of cancer cells in the individual suffering from cancer. In one embodiment, an "individual" is a human.

In another aspect of the invention, a mono- or bispecific anti-CCL2 antibody for use in treating inflammatory diseases or autoimmune diseases is provided. In certain embodiments, the invention provides a mono- or bispecific anti-CCL2 antibody for use in a method of treating an individual having an inflammatory disease or autoimmune disease comprising administering to the individual an effective amount of the mono- or bispecific anti-CCL2 antibody.

In a further aspect, the invention provides pharmaceutical formulations comprising any of the mono- or bispecific anti-CCL2 antibodies provided herein, e.g., for use in any of the above therapeutic methods. In one embodiment, a pharmaceutical formulation comprises any of the mono- or bispecific anti-CCL2 antibodies provided herein and a pharmaceutically acceptable carrier.

In some embodiments, the inflammatory diseases or autoimmune disease is an autoimmune disorder, inflammatory disorder, fibrotic disorder, granulocytic (neutrophilic or eosinophilic) disorder, monocytic disorder, or lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder. In some embodiments the pulmonary disorder is associated with granulocytic (eosinophilic and/or neutrophilic) pulmonary inflammation, infection-induced pulmonary conditions (including those associated with viral (e.g., influenza, parainfluenza, rhinovirus, human metapneumovirus, and respiratory syncytial virus), bacterial, or fungal (e.g., *Aspergillus*) triggers. In some embodiments, the disorder is an allergen-induced pulmonary condition, a toxic environmental pollutant-induced pulmonary condition (e.g., asbestosis, silicosis, or berylliosis), a gastric aspiration-induced pulmonary condition, or associated with immune dysregulation or an inflammatory condition with genetic predisposition such as cystic fibrosis. In some embodiments, the disorder is a physical trauma-induced pulmonary condition (e.g., ventilator injury), emphysema, cigarette-induced emphysema, bronchitis, sarcoidosis, histiocytosis, lymphangiomyomatosis, acute lung injury, acute respiratory distress syndrome, chronic lung disease, bronchopulmonary dysplasia, pneumonia (e.g., community-acquired pneumonia, nosocomial pneumonia, ventilator-associated pneumonia, viral pneumonia, bacterial pneumonia, and severe pneumonia), airway exacerbations, and acute respiratory distress syndrome (ARDS)). In some embodiments, the inflammatory pulmonary disorder is COPD.

In some embodiments, the inflammatory pulmonary disorder is asthma. In some embodiments, the asthma is persistent chronic severe asthma with acute events of worsening symptoms (exacerbations or flares) that can be life threatening. In some embodiments, the asthma is atopic (also known as allergic) asthma, non-allergic asthma (e.g., often triggered by infection with a respiratory virus (e.g., influenza, parainfluenza, rhinovirus, human metapneumovirus, and respiratory syncytial virus) or inhaled irritant (air pollutants, smog, diesel particles, volatile chemicals and gases indoors or outdoors, or even by cold dry air), In some embodiments, the asthma is intermittent or exercise-induced, asthma due to acute or chronic primary or second-hand exposure to "smoke" (typically cigarettes, cigars, pipes), inhaling or "vaping" (tobacco, marijuana or other such substances), or asthma triggered by recent ingestion of aspirin or related NSAIDS. In some embodiments, the asthma is mild, or corticosteroid naïve asthma, newly diagnosed and untreated asthma, or not previously requiring chronic use of inhaled topical or systemic steroids to control the symptoms (cough, wheeze, shortness of breath/breathlessness, or chest pain). IN some embodiments, the asthma is chronic, corticosteroid resistant asthma, corticosteroid refractory asthma, asthma uncontrolled on corticosteroids or other chronic asthma controller medications. In some embodiments, the autoimmune disorder, inflammatory disorder, fibrotic disorder, neutrophilic disorder, or eosinophilic disorder is pulmonary fibrosis. In some embodiments, the pulmonary fibrosis is idiopathic pulmonary fibrosis (IPF). In some embodiments, the autoimmune disorder, inflammatory disorder, fibrotic disorder, granulocytic (neutrophilic or eosinophilic) disorder, monocytic disorder, or lymphocytic disorder is esophogitis, allergic rhinitis, non-allergic rhinitis, rhinosinusitis with polyps, nasal polyposis, bronchitis, chronic pneumonia, allergic bronchopulmonary aspergillosis, airway inflammation, allergic rhinitis, bronchiectasis, and/or chronic bronchitis.

In some embodiments, the autoimmune disorder, inflammatory disorder, fibrotic disorder, granulocytic (neutrophilic or eosinophilic) disorder, monocytic disorder, or lymphocytic disorder, is arthritis. In some embodiments, the arthritis is rheumatoid arthritis. In some embodiments, the arthritis is osteoarthritis, rheumatoid arthritis, juvenile arthritis, juvenile rheumatoid arthritis, early arthritis, polyarticular rheumatoid arthritis, systemic-onset rheumatoid arthritis, enteropathic arthritis, reactive arthritis, psoriatic arthritis, and/or arthritis as a result of injury.

In some embodiments, the autoimmune disorder, inflammatory disorder, fibrotic disorder, granulocytic (neutrophilic or eosinophilic) disorder, monocytic disorder, or lymphocytic disorder is a gastrointestinal inflammatory condition. In some embodiments, the gastrointestinal inflammatory condition is IBD (inflammatory bowel disease), ulcerative colitis (UC), Crohn's disease (CD), colitis (e.g., colitis caused by environmental insults (e.g., caused by or associated with a therapeutic regimen, such as chemotherapy, radiation therapy, etc.), infectious colitis, ischemic colitis, collagenous or lymphocytic colitis, necrotizing enterocolitis, colitis in conditions such as chronic granulomatous disease or celiac disease, food allergies, gastritis, gastroenteritis, infectious gastritis or enterocolitis (e.g., *Helicobacter pylori*-infected chronic active gastritis), and other forms of gastrointestinal inflammation caused by an infectious agent, or indeterminate colitis.

In some embodiments, the autoimmune disorder, inflammatory disorder, fibrotic disorder, granulocytic (neutrophilic or eosinophilic) disorder, monocytic disorder, or lymphocytic disorder, or disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia) is lupus or Systemic Lupus Erythematosus (SLE), or one or more organ-specific manifestations of lupus (e.g., lupus nephritis (LN) affecting the kidney, or extra-renal lupus (ERL) affecting the blood and/or lymphoid organs (lymph nodes, spleen, thymus, and associated lymphatic vessels), and/or joints and/or other organs, but not necessarily the kidney). In some embodiments, the autoimmune disorder, inflammatory disorder, or fibrotic disorder is related to sepsis and/or trauma, HIV infection, or idiopathic (of unknown etiology) such as ANCA-associated vaculitides (AAV), granulomatosis with polyangiitis (formerly known as Wegener's granulomatosis), Behcet's disease, cardiovascular disease, eosinophilic bronchitis, Reiter's Syndrome, SEA Syndrome (Seronegativity, Enthesopathy, Arthropathy Syndrome), ankylosing spondylitis, dermatomyositis, scleroderma, e.g., systemic scleroderma also called systemic sclerosis, vasculitis (e.g., Giant Cell Arteritis (GCA), also called temporal arteritis, cranial arteritis or Horton disease), myositis, polymyositis, dermatomyositis, polyarteritis nodosa, arteritis, polymyalgia rheumatica, sarcoidosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, pemphigus, e.g., pemphigus vulgaris, atherosclerosis, lupus, Still's disease, myasthenia gravis, celiac disease, multiple sclerosis (MS) of the relapsing-remitting (RRMS) or primary progressive (PPMS) or secondary progressive (SPMS) subtypes, Guillain-Barre disease, Type I diabetes mellitus (T1DM) or insulin-dependent (IDDM) or juvenile onset DM type, thyroiditis (e.g., Graves' disease), coeliac disease, Churg-Strauss syndrome, myalgia syndrome, hypereosinophilic syndrome, oedematous reactions including episodic angioedema, helminth infections, onchocercal dermatitis eosinophilic oesophagitis, eosinophilic enteritis, eosinophilic colitis, obstructive sleep apnea, endomyocardial fibrosis, Addison's disease, Raynaud's disease or phenomenon, autoimmune hepatitis, graft versus host disease (GVHD), or organ transplant rejection.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

II. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third)

container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In the following specific embodiments of the invention are listed:

1. A bispecific antibody comprising a first antigen-binding site that (specifically) binds to a first epitope on human CCL2 and a second different antigen-binding site that (specifically) binds a second different epitope on human CCL2, wherein the bispecific antibody comprises a Fc domain of human IgG isotype, preferably of IgG1 isotype.

2. The bispecific antibody according to embodiment 1, wherein

A) i) said first antigen-binding site comprises
   a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
   and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
   ii) said second antigen-binding site comprises
   a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;
   and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

or

B) i) said first antigen-binding site comprises
   a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
   and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
   ii) said second antigen-binding site comprises
   a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;
   and a VL domain comprising (d) a CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22;

or

C) i) said first antigen-binding site comprises
   a VH domain comprising (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;
   and a VL domain comprising (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and
   ii) said second antigen-binding site comprises
   a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;
   and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14;

or

D) i) said first antigen-binding site comprises
   a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;
   and a VL domain comprising (d) a CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22; and
   ii) said second antigen-binding site comprises
   a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;
   and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

or

E) i) said first antigen-binding site comprises
   a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;
   and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30; and
   ii) said second antigen-binding site comprises
   a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43; and
   a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

F) i) said first antigen-binding site comprises
   a VH domain comprising (a) a CDR-H1 comprising the amino acid sequence of SEQ ID NO: 49, (b) a CDR-H2 comprising the amino acid sequence of SEQ ID NO: 50, and (c) a CDR-H3 comprising the amino acid sequence of SEQ ID NO: 51;

and a VL domain comprising (d) a CDR-L1 comprising the amino acid sequence of SEQ ID NO: 52; (e) a CDR-L2 comprising the amino acid sequence of SEQ ID NO: 53, and (f) a CDR-L3 comprising the amino acid sequence of SEQ ID NO: 54; and ii) said second antigen-binding site comprises a VH domain comprising (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43; and a VL domain comprising (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

or

G) i) said first antigen-binding site comprises a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;

and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14; and ii) said second antigen-binding site comprises a VH domain comprising (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;

and a VL domain comprising a (d) CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22;

or

H) i) said first antigen-binding site comprises a VH domain comprising (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;

and a VL domain comprising (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14; and ii) said second antigen-binding site comprises a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;

and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30;

or

I) i) said first antigen-binding site comprises a VH domain comprising (a) a CDR-H1 comprising the amino acid sequence of SEQ ID NO: 1, (b) a CDR-H2 comprising the amino acid sequence of SEQ ID NO: 2, and (c) a CDR-H3 comprising the amino acid sequence of SEQ ID NO: 3;

and a VL domain comprising (d) a CDR-L1 comprising the amino acid sequence of SEQ ID NO: 4; (e) a CDR-L2 comprising the amino acid sequence of SEQ ID NO: 5, and (f) a CDR-L3 comprising the amino acid sequence of SEQ ID NO: 6; and ii) said second antigen-binding site comprises a VH domain comprising (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;

and a VL domain comprising (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30.

3. The bispecific antibody according to embodiment 2, wherein

A) i) said first antigen-binding site comprises a VH domain comprising the amino acid sequence of SEQ ID NO:39 wherein the VH domain comprises (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;

and a VL domain comprising the amino acid sequence of SEQ ID NO:40 wherein the VL domain comprises (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and ii) said second antigen-binding site comprises a VH domain comprising the amino acid sequence of SEQ ID NO:47 wherein the VH domain comprises (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;

and a VL domain comprising the amino acid sequence of SEQ ID NO:48 wherein the VL domain comprises (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

or

B) i) said first antigen-binding site comprises a VH domain comprising the amino acid sequence of SEQ ID NO:39 wherein the VH domain comprises (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;

and a VL domain comprising the amino acid sequence of SEQ ID NO:40 wherein the VL domain comprises (d) a CDR-L1 comprising the amino acid sequence of SEQ ID NO: 36; (e) a CDR-L2 comprising the amino acid sequence of SEQ ID NO: 37, and (f) a
CDR-L3 comprising the amino acid sequence of
SEQ ID NO: 38; and
ii) said second antigen-binding site comprises
a VH domain comprising the amino acid sequence of
SEQ ID NO:23 wherein the VH domain comprises
(a) a CDR-H1 comprising the amino acid sequence
of SEQ ID NO: 17, (b) a CDR-H2 comprising the
amino acid sequence of SEQ ID NO: 18, and (c) a
CDR-H3 comprising the amino acid sequence of
SEQ ID NO: 19;
and a VL domain comprising the amino acid sequence
of SEQ ID NO:24 wherein the VL domain comprises
(d) a CDR-L1 comprising the amino acid sequence
of SEQ ID NO: 20; (e) a CDR-L2 comprising the
amino acid sequence of SEQ ID NO: 21, and (f) a
CDR-L3 comprising the amino acid sequence of
SEQ ID NO: 22;
or
C) i) said first antigen-binding site comprises
a VH domain comprising the amino acid sequence of
SEQ ID NO:39 wherein the VH domain comprises
(a) a CDR-H1 comprising the amino acid sequence
of SEQ ID NO: 33, (b) a CDR-H2 comprising the
amino acid sequence of SEQ ID NO: 34, and (c) a
CDR-H3 comprising the amino acid sequence of
SEQ ID NO: 35;
and a VL domain comprising the amino acid sequence
of SEQ ID NO:40 wherein the VL domain comprises
(d) a CDR-L1 comprising the amino acid sequence
of SEQ ID NO: 36; (e) a CDR-L2 comprising the
amino acid sequence of SEQ ID NO: 37, and (f) a
CDR-L3 comprising the amino acid sequence of
SEQ ID NO: 38; and
ii) said second antigen-binding site comprises
a VH domain comprising the amino acid sequence of
SEQ ID NO:15 wherein the VH domain comprises
(a) a CDR-H1 comprising the amino acid sequence
of SEQ ID NO: 9, (b) a CDR-H2 comprising the
amino acid sequence of SEQ ID NO: 10, and (c) a
CDR-H3 comprising the amino acid sequence of
SEQ ID NO: 11;
and a VL domain comprising the amino acid sequence
of SEQ ID NO:16 wherein the VL domain comprises
(d) a CDR-L1 comprising the amino acid sequence
of SEQ ID NO: 12; (e) a CDR-L2 comprising the
amino acid sequence of SEQ ID NO: 13, and (f) a
CDR-L3 comprising the amino acid sequence of
SEQ ID NO: 14;
or
D) i) said first antigen-binding site comprises
a VH domain comprising the amino acid sequence of
SEQ ID NO:23 wherein the VH domain comprises
(a) a CDR-H1 comprising the amino acid sequence
of SEQ ID NO: 17, (b) a CDR-H2 comprising the
amino acid sequence of SEQ ID NO: 18, and (c) a
CDR-H3 comprising the amino acid sequence of
SEQ ID NO: 19;
and a VL domain comprising the amino acid sequence
of SEQ ID NO:24 wherein the VL domain comprises
(d) a CDR-L1 comprising the amino acid sequence
of SEQ ID NO: 20; (e) a CDR-L2 comprising the
amino acid sequence of SEQ ID NO: 21, and (f) a
CDR-L3 comprising the amino acid sequence of
SEQ ID NO: 22; and ii) said second antigen-binding site comprises
a VH domain comprising the amino acid sequence of
SEQ ID NO:47 wherein the VH domain comprises
(a) a CDR-H1 comprising the amino acid sequence
of SEQ ID NO: 41, (b) a CDR-H2 comprising the
amino acid sequence of SEQ ID NO: 42, and (c) a
CDR-H3 comprising the amino acid sequence of
SEQ ID NO: 43;
and a VL domain comprising the amino acid sequence
of SEQ ID NO:48 wherein the VL domain comprises
(d) a CDR-L1 comprising the amino acid sequence
of SEQ ID NO: 44; (e) a CDR-L2 comprising the
amino acid sequence of SEQ ID NO: 45, and (f) a
CDR-L3 comprising the amino acid sequence of
SEQ ID NO: 46;
or
E) i) said first antigen-binding site comprises
a VH domain comprising the amino acid sequence of
SEQ ID NO:31 wherein the VH domain comprises
(a) a CDR-H1 comprising the amino acid sequence
of SEQ ID NO: 25, (b) a CDR-H2 comprising the
amino acid sequence of SEQ ID NO: 26, and (c) a
CDR-H3 comprising the amino acid sequence of
SEQ ID NO: 27;
and a VL domain comprising the amino acid sequence
of SEQ ID NO:32 wherein the VL domain comprises
(d) a CDR-L1 comprising the amino acid sequence
of SEQ ID NO: 28; (e) a CDR-L2 comprising the
amino acid sequence of SEQ ID NO: 29, and (f) a
CDR-L3 comprising the amino acid sequence of
SEQ ID NO: 30; and
ii) said second antigen-binding site comprises
a VH domain comprising the amino acid sequence of
SEQ ID NO:47 wherein the VH domain comprises
(a) a CDR-H1 comprising the amino acid sequence
of SEQ ID NO: 41, (b) a CDR-H2 comprising the
amino acid sequence of SEQ ID NO: 42, and (c) a
CDR-H3 comprising the amino acid sequence of
SEQ ID NO: 43;
and a VL domain comprising the amino acid sequence
of SEQ ID NO:48 wherein the VL domain comprises
(d) a CDR-L1 comprising the amino acid sequence
of SEQ ID NO: 44; (e) a CDR-L2 comprising the
amino acid sequence of SEQ ID NO: 45, and (f) a
CDR-L3 comprising the amino acid sequence of
SEQ ID NO: 46;
F) i) said first antigen-binding site comprises
a VH domain comprising the amino acid sequence of
SEQ ID NO:55 wherein the VH domain comprises
(a) a CDR-H1 comprising the amino acid sequence
of SEQ ID NO: 49, (b) a CDR-H2 comprising the
amino acid sequence of SEQ ID NO: 50, and (c) a
CDR-H3 comprising the amino acid sequence of
SEQ ID NO: 51;
and a VL domain comprising the amino acid sequence
of SEQ ID NO:56 wherein the VL domain comprises
(d) a CDR-L1 comprising the amino acid sequence
of SEQ ID NO: 52; (e) a CDR-L2 comprising the
amino acid sequence of SEQ ID NO: 53, and (f) a
CDR-L3 comprising the amino acid sequence of
SEQ ID NO: 54; and
ii) said second antigen-binding site comprises
a VH domain comprising the amino acid sequence of
SEQ ID NO:47 wherein the VH domain comprises
(a) a CDR-H1 comprising the amino acid sequence
of SEQ ID NO: 41, (b) a CDR-H2 comprising the amino acid sequence of SEQ ID NO: 42, and (c) a CDR-H3 comprising the amino acid sequence of SEQ ID NO: 43;

and a VL domain comprising the amino acid sequence of SEQ ID NO:48 wherein the VL domain comprises (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46;

or

G) i) said first antigen-binding site comprises a VH domain comprising the amino acid sequence of SEQ ID NO:15 wherein the VH domain comprises (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;

and a VL domain comprising the amino acid sequence of SEQ ID NO:16 wherein the VL domain comprises (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14; and ii) said second antigen-binding site comprises a VH domain comprising the amino acid sequence of SEQ ID NO:23 wherein the VH domain comprises (a) a CDR-H1 comprising the amino acid sequence of SEQ ID NO: 17, (b) a CDR-H2 comprising the amino acid sequence of SEQ ID NO: 18, and (c) a CDR-H3 comprising the amino acid sequence of SEQ ID NO: 19;

and a VL domain comprising the amino acid sequence of SEQ ID NO:24 wherein the VL domain comprises a (d) CDR-L1 comprising the amino acid sequence of SEQ ID NO: 20; (e) a CDR-L2 comprising the amino acid sequence of SEQ ID NO: 21, and (f) a CDR-L3 comprising the amino acid sequence of SEQ ID NO: 22;

or

H) i) said first antigen-binding site comprises a VH domain comprising the amino acid sequence of SEQ ID NO:15 wherein the VH domain comprises (a) a CDR-H1 comprising the amino acid sequence of SEQ ID NO: 9, (b) a CDR-H2 comprising the amino acid sequence of SEQ ID NO: 10, and (c) a CDR-H3 comprising the amino acid sequence of SEQ ID NO: 11;

and a VL domain comprising the amino acid sequence of SEQ ID NO:16 wherein the VL domain comprises (d) a CDR-L1 comprising the amino acid sequence of SEQ ID NO: 12; (e) a CDR-L2 comprising the amino acid sequence of SEQ ID NO: 13, and (f) a CDR-L3 comprising the amino acid sequence of SEQ ID NO: 14; and ii) said second antigen-binding site comprises a VH domain comprising the amino acid sequence of SEQ ID NO:31 wherein the VH domain comprises (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;

and a VL domain comprising the amino acid sequence of SEQ ID NO:32 wherein the VL domain comprises (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30;

or

I) i) said first antigen-binding site comprises a VH domain comprising the amino acid sequence of SEQ ID NO:7 wherein the VH domain comprises (a) a CDR-H1 comprising the amino acid sequence of SEQ ID NO: 1, (b) a CDR-H2 comprising the amino acid sequence of SEQ ID NO: 2, and (c) a CDR-H3 comprising the amino acid sequence of SEQ ID NO: 3;

and a VL domain comprising the amino acid sequence of SEQ ID NO:8 wherein the VL domain comprises (d) a CDR-L1 comprising the amino acid sequence of SEQ ID NO: 4; (e) a CDR-L2 comprising the amino acid sequence of SEQ ID NO: 5, and (f) a CDR-L3 comprising the amino acid sequence of SEQ ID NO: 6; and ii) said second antigen-binding site comprises a VH domain comprising the amino acid sequence of SEQ ID NO:31 wherein the VH domain comprises (a) a CDR-H1 comprising the amino acid sequence of SEQ ID NO: 25, (b) a CDR-H2 comprising the amino acid sequence of SEQ ID NO: 26, and (c) a CDR-H3 comprising the amino acid sequence of SEQ ID NO: 27;

and a VL domain comprising the amino acid sequence of SEQ ID NO:32 wherein the VL domain comprises (d) a CDR-L1 comprising the amino acid sequence of SEQ ID NO: 28; (e) a CDR-L2 comprising the amino acid sequence of SEQ ID NO: 29, and (f) a CDR-L3 comprising the amino acid sequence of SEQ ID NO: 30.

4. The bispecific antibody according to any one of claims 1 to 3, wherein the bispecific antibody comprising a Fc domain of human IgG isotype is a bispecific antibody comprising a constant heavy chain domain of human IgG1 isotype.

5. The bispecific antibody according to embodiment 4, wherein the in vivo clearance rate for human CCL2 (ml/day/kg) after administration of the bispecific antibody comprising a constant heavy chain domain of human wild type IgG1 isotype is at least two fold higher (in one embodiment at least 5 fold higher, in one embodiment at least 10 fold higher, in one embodiment at least 20 fold higher) compared to the in vivo clearance rate for human CCL2 (ml/day/kg) after administration of a bispecific antibody comprising a Fc gamma receptor silenced constant heavy chain domain of human IgG1 isotype comprising the mutations L234A, L235A, P329G (Kabat EU numbering), when a pre-formed immune complex consisting of 20 mg/kg of each bispecific antibody and 0.1 mg/kg human CCL2 was administered at a single dose of 10 ml/kg into FcRn transgenic mice.

6. An (isolated) bispecific antibody comprising a first antigen-binding site that (specifically) binds to a first epitope on human CCL2 and a second antigen-binding site that (specifically) binds a second different epitope on human CCL2, wherein the bispecific antibody comprises a Fc domain of human IgG isotype and wherein i) said first antigen-binding site binds to same epitope on CCL2 as an antibody comprising a VH domain comprising the amino acid sequence of SEQ ID NO:39 wherein the VH domain comprises (a) a CDR-H1 comprising the amino acid sequence of SEQ ID NO: 33, (b) a CDR-H2 comprising the amino acid sequence of SEQ ID NO: 34, and (c) a CDR-H3 comprising the amino acid sequence of SEQ ID NO: 35;

and a VL domain comprising the amino acid sequence of SEQ ID NO:40 wherein the VL domain comprises (d) a CDR-L1 comprising the amino acid sequence of SEQ ID NO: 36; (e) a CDR-L2 comprising the amino acid sequence of SEQ ID NO: 37, and (f) a CDR-L3 comprising the amino acid sequence of SEQ ID NO: 38; and ii) said second antigen-binding site binds to same epitope on CCL2 as an antibody comprising a VH domain comprising the amino acid sequence of SEQ ID NO:47 wherein the VH domain comprises (a) a CDR-H1 comprising the amino acid sequence of SEQ ID NO: 41, (b) a CDR-H2 comprising the amino acid sequence of SEQ ID NO: 42, and (c) a CDR-H3 comprising the amino acid sequence of SEQ ID NO: 43;

and a VL domain comprising the amino acid sequence of SEQ ID NO:48 wherein the VL domain comprises (d) a CDR-L1 comprising the amino acid sequence of SEQ ID NO: 44; (e) a CDR-L2 comprising the amino acid sequence of SEQ ID NO: 45, and (f) a CDR-L3 comprising the amino acid sequence of SEQ ID NO: 46.

7. The bispecific antibody according to embodiment 6, wherein the in vivo clearance rate for human CCL2 (ml/day/kg) after administration of the bispecific antibody comprising a constant heavy chain domain of human wild type IgG1 isotype is at least 15 fold higher, in particular at least 20 fold higher, compared to the in vivo clearance rate for human CCL2 (ml/day/kg) after administration of a bispecific antibody comprising a Fc gamma receptor silenced constant heavy chain domain of human IgG1 isotype comprising the mutations L234A, L235A, P329G (Kabat EU numbering), when a pre-formed immune complex consisting of 20 mg/kg of each bispecific antibody and 0.1 mg/kg human CCL2 was administered at a single dose of 10 ml/kg into FcRn transgenic mice.

8. An (isolated) bispecific antibody comprising a first antigen-binding site that (specifically) binds to a first epitope on human CCL2 and a second antigen-binding site that (specifically) binds a second epitope on human CCL2, wherein i) said first antigen-binding site comprises a VH domain comprising (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
and a VL domain comprising (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62;
and ii) said second antigen-binding site comprises a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain comprising (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

9. An (isolated) bispecific antibody comprising a first antigen-binding site that (specifically) binds to a first epitope on human CCL2 and a second antigen-binding site that (specifically) binds a second epitope on human CCL2, wherein i) said first antigen-binding site comprises a VH domain comprising (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, (c) a CDR-H3 comprising the amino acid sequence YDAHYGELDF of SEQ ID NO: 59, (d) a FR-H1 comprising the amino acid sequence QVQLVQSGAEVKKPGSSVKVSCKASGGTF of SEQ ID NO:63, (e) a FR-H2 comprising the amino acid sequence WVRQAPGQGLEWMG of SEQ ID NO:64, (f) a FR-H3 comprising the amino acid sequence RVTITADESTSTAYMELSSLRSEDTAVY YCAR of SEQ ID NO:65, and (g) a FR-H4 comprising the amino acid sequence WGQGTLVTVSS of SEQ ID NO:66;
and a VL domain comprising (h) a CDR-L1 comprising the amino acid sequence RASQHVSDAYLA of SEQ ID NO: 60; (i) a CDR-L2 comprising the amino acid sequence DASDRAE of SEQ ID NO: 61, and (j) a CDR-L3 comprising the amino acid sequence HQYIHLHSFT of SEQ ID NO: 62, (k) a FR-L1 comprising the amino acid sequence EIVLTQSPATLSLSPGERATLSC of SEQ ID NO:67, (l) a FR-L2 comprising the amino acid sequence WYQQKPGQAPRLLIY of SEQ ID NO:68, (m) a FR-L3 comprising the amino acid sequence GVPARFSGSGSGTDFTLTISSLEPEDFAVYYC of SEQ ID NO:69, and (n) a FR-L4 comprising the amino acid sequence GQGTKVEIK of SEQ ID NO:70;
and ii) said second antigen-binding site comprises a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, (c) a CDR-H3 comprising the amino acid sequences GVFGFFXH of SEQ ID NO:78 wherein X is D or E, (d) a FR-H1 comprising the amino acid sequence QVQLVQS- GAEVKKPGSSVKVSCKASGLTIS of SEQ ID NO:82, (e) a FR-H2 comprising the amino acid sequence WVRQAPGQGLEWMG of SEQ ID NO:83, (f) a FR-H3 comprising the amino acid sequence RVTITADTSTSTAYMELSSLRSED-TAVYYCAR of SEQ ID NO:84, and (g) a FR-H4 comprising the amino acid sequence WGQGTTVTVSS of SEQ ID NO:85;

and a VL domain comprising (h) a CDR-L1 comprising the amino acid sequence KAX$^1$EDIYNRX$^2$A of SEQ ID NO: 79 wherein X$^1$ is F or T and X$^2$ is R or L, (i) a CDR-L2 comprising the amino acid sequence GATSLEH of SEQ ID NO: 80, (j) a CDR-L3 comprising the amino acid sequence QQFXSAPYT of SEQ ID NO: 81 wherein X is W or R, (k) a FR-L1 comprising the amino acid sequence DIQMTQSPSSLSASVGDRVTITC of SEQ ID NO:86, (1) a FR-L2 comprising the amino acid sequence WYQQKPGKAPKLLIH of SEQ ID NO:87, (m) a FR-L3 comprising the amino acid sequence GVPSRFSGSGSGTDYTLTISSLQPEDFATYYC of SEQ ID NO:88, and (n) a FR-L4 comprising the amino acid sequence FGGGTKVEIK of SEQ ID NO:89.

10. An (isolated) bispecific antibody comprising a first antigen-binding site that (specifically) binds to a first epitope on human CCL2 and a second antigen-binding site that (specifically) binds a second epitope on human CCL2, wherein A) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;

or

B) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;

or

C) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;

or

D) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;

or

E) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;

or

F) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;

or

G) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93;

or

H) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;

or

I) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;

or

J) i) said first antigen-binding site comprises
a VH domain comprising the amino acid sequence of SEQ ID NO:72;

and a VL domain comprising the amino acid sequence of SEQ ID NO:75; and ii) said second antigen-binding site comprises
a VH domain comprising the amino acid sequence of SEQ ID NO:92;
and a VL domain comprising the amino acid sequence of SEQ ID NO:93;

or

K) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;

or

L) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;

or

M) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;

or

N) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93;

or

O) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;

or

P) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93.

11. An (isolated) bispecific antibody comprising a first antigen-binding site that (specifically) binds to a first epitope on human CCL2 and a second antigen-binding site that (specifically) binds a second epitope on human CCL2, wherein A) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHYGXS of SEQ ID NO: 57 wherein X is I, (b) a CDR-H2 comprising the amino acid sequence $GX^1IX^2IFX^3TANYAQKFQG$ of SEQ ID NO: 58 wherein $X^1$ is V, $X^2$ is P, and $X^3$ is H, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D, and (c) a CDR-H3 comprising the amino acid sequences GVFGFFXH of SEQ ID NO:78 wherein X is D;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence $KAX^1EDIYNRX^2A$ of SEQ ID NO: 79 wherein $X^1$ is F and $X^2$ is R, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W;

or

B) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHYGXS of SEQ ID NO: 57 wherein X is I, (b) a CDR-H2 comprising the amino acid sequence $GX^1IX^2IFX^3TANYAQKFQG$ of SEQ ID NO: 58 wherein $X^1$ is V, $X^2$ is P, and $X^3$ is H, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D, and (c) a CDR-H3 comprising the amino acid sequences GVFGFFXH of SEQ ID NO:78 wherein X is E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F and X$^2$ is R, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W;

or

C) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

D) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

E) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

F) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

G) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

H) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:73 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

I) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

J) i) said first antigen-binding site comprises a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;

and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and ii) said second antigen-binding site comprises a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO:

80, and (f) a CDR-L3 comprising the amino acid sequence QQFXSAPYT of SEQ ID NO: 81 wherein X is W or R;

or

K) i) said first antigen-binding site comprises
   a VH domain sequence having at least 90%, 91%, 92%, 93%, 94%, 95%, 96%, 97%, 98%, 99%, or 100% sequence identity to the amino acid sequence of SEQ ID NO:72 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
   and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
   ii) said second antigen-binding site comprises
   a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
   and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

L) i) said first antigen-binding site comprises
   a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
   and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
   ii) said second antigen-binding site comprises
   a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
   and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

M) i) said first antigen-binding site comprises
   a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHY-GXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
   and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
   ii) said second antigen-binding site comprises
   a VH domain sequence having at least 90%, 91%, 92%, 93%, 94%, 95%, 96%, 97%, 98%, 99%, or 100% sequence identity to the amino acid sequence of SEQ ID NO:90 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
   and a VL domain sequence having at least 90%, 91%, 92%, 93%, 94%, 95%, 96%, 97%, 98%, 99%, or 100% sequence identity to the amino acid sequence of SEQ ID NO:94 wherein the VL domain comprises (d) a CDR-L1 comprising the amino acid sequence KAX¹EDIYNRX²A of SEQ ID NO: 79 wherein X¹ is F or T and X² is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

N) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHY-GXS of SEQ ID NO: 57 wherein X is I or T, (b) a CDR-H2 comprising the amino acid sequence GX¹IX²IFX³TANYAQKFQG of SEQ ID NO: 58 wherein X¹ is V, I, or H, X² is P or H, and X³ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX¹EDIYNRX²A of SEQ ID NO: 79 wherein X¹ is F or T and X² is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

O) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:74 wherein the VH domain comprises (a) a CDR-H1 comprising the amino acid sequence SHY-GXS of SEQ ID NO: 57 wherein X is I or T, (b) a CDR-H2 comprising the amino acid sequence GX¹IX²IFX³TANYAQKFQG of SEQ ID NO: 58 wherein X¹ is V, I, or H, X² is P or H, and X³ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:91 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;
and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX¹EDIYNRX²A of SEQ ID NO: 79 wherein X¹ is F or T and X² is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R;

or

P) i) said first antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:71 wherein the VH domain comprises (a) a CDR-H1 comprising the amino acid sequence SHY-GXS of SEQ ID NO: 57 wherein X is I or T, (b) a CDR-H2 comprising the amino acid sequence GX¹IX²IFX³TANYAQKFQG of SEQ ID NO: 58 wherein X¹ is V, I, or H, X² is P or H, and X³ is H or G, and (c) a CDR-H3 comprising the amino acid sequence YDAHYGELDF of SEQ ID NO: 59;
and a VL domain sequence having at least 90%, 91%, 92%, 93%, 94%, 95%, 96%, 97%, 98%, 99%, or 100% sequence identity to the amino acid sequence of SEQ ID NO:75 wherein the VL domain comprises (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62; and
ii) said second antigen-binding site comprises
a VH domain sequence having at least 90%, 91%, 92%, 93%, 94%, 95%, 96%, 97%, 98%, 99%, or 100% sequence identity to the amino acid sequence of SEQ ID NO:92 wherein the VH domain comprises (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E;

and a VL domain sequence having at least 90%, 91%, 92%, 93%, 94%, 95%, 96%, 97%, 98%, 99%, or 100% sequence identity to the amino acid sequence of SEQ ID NO:93 wherein the VL domain comprises (d) a CDR-L1 comprising the amino acid sequence KAX¹EDIYNRX²A of SEQ ID NO: 79 wherein X¹ is F or T and X² is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

12. The bispecific antibody according to anyone of the embodiments 8 to 11, wherein the bispecific antibody a Fc domain of human IgG isotype, preferably of human IgG1 isotype.

13. The bispecific antibody according to anyone of the embodiments 8 to 11, wherein the bispecific wherein the bispecific antibody comprises a constant domain of human IgG isotype, preferably of human IgG1 isotype.

14. The bispecific antibody according to anyone of the preceding embodiments, wherein the bispecific antibody
   i) blocks binding of CCL2 to its receptor CCR2 in vitro (reporter assay, IC$_{50}$=0.5 nM); and/or
   ii) inhibits CCL2-mediated chemotaxis of myeloid cells in vitro (IC$_{50}$=1.5 nM); and/or
   iii) is cross-reactive to cyno and human CCL2.

15. The bispecific antibody according to anyone of the preceding embodiments, wherein the bispecific antibody is not cross-reactive to other CCL homologs, (shows 100 time less binding to other CCL homologs (selected from the group of CCL8, CCL7, and CCL13) compared to the binding to CCL2

16. The bispecific antibody according to anyone of the preceding embodiments, wherein the bispecific antibody binds to the first and second epitope on human CCL2 in ion-dependent manner.

17. The bispecific antibody according to anyone of the preceding embodiments, wherein the bispecific antibody binds to human CCL2 in pH dependent manner and wherein the first antigen binding site and the second antigen binding site both bind to CCL2 with a higher affinity at neutral pH than at acidic pH.

18. The bispecific antibody according to anyone of the preceding embodiments, wherein the bispecific antibody binds to human CCL2 with a 10 times higher affinity at pH 7.4, than at pH 5.8.

19. The bispecific antibody according to anyone of the preceding claims, wherein the bispecific antibody, comprises a human IgG1 heavy chain constant domain comprising one or more of the following mutations (Kabat EU numbering)
   i) Q311R and/or P343R (suitable for increasing pI for enhancing uptake of antigen); and/or
   ii) L234Y, L235W, G236N, P238D, T250V, V264I, T307PH268D, Q295L, K326T and/or A330K (suitable for increasing affinity to human FcgRIIb and decreasing affinity to other human FcgR); and/or
   iii) M428L, N434A and/or Y436T (suitable for increasing affinity to FcRn for longer plasma half-life); and/or
   iv) Q438R and/or S440E (suitable for suppressing rheumatoid factor binding).

20. The bispecific antibody according to anyone of the preceding embodiments, wherein the bispecific antibody, comprises a human IgG1 heavy chain constant domain comprising one or more of the following mutations (Kabat EU numbering)
   i) Q311R, and/or P343R (suitable for increasing pI for enhancing uptake of antigen); and/or
   ii) L235W, G236N, H268D, Q295L, K326T and/or A330K (suitable for increasing affinity to human FcgRIIb and decreasing affinity to other human FcgR); and/or
   iii) N434A (suitable for increasing affinity to FcRn for longer plasma half-life); and/or
   iv) Q438R and/or S440E (suitable for suppressing rheumatoid factor binding).

21. The bispecific antibody according to anyone of the preceding embodiments, wherein the bispecific antibody, comprises a human IgG1 heavy chain constant domain comprising the following mutations (Kabat EU numbering)
   i) Q311R and P343R (suitable for increasing pI for enhancing uptake of antigen); and
   ii) L235W, G236N, H268D, Q295L, K326T and A330K (suitable for increasing affinity to human FcgRIIb and decreasing affinity to other human FcgR); and
   iii) N434A (suitable for increasing affinity to FcRn for longer plasma half-life); and
   iv) Q438R and S440E (suitable for suppressing rheumatoid factor binding).

22. The bispecific antibody according to anyone of the preceding claims, wherein the bispecific antibody, comprises a human IgG1 heavy chain constant domain comprising one or more of the following mutations (Kabat EU numbering)
   i) Q311R and/or P343R (suitable for increasing pI for enhancing uptake of antigen); and/or
   ii) L234Y, P238D, T250V, V264I, T307V and/or A330K (suitable for increasing affinity to human FcgRIIb and decreasing affinity to other human FcgR); and/or
   iii) M428L, N434A and/or Y436T (suitable for increasing affinity to FcRn for longer plasma half-life); and/or
   iv) Q438R and/or S440E (suitable for suppressing rheumatoid factor binding).

23. The bispecific antibody according to anyone of the preceding claims, wherein the bispecific antibody, comprises a human IgG1 heavy chain constant domain comprising one or more of the following mutations (Kabat EU numbering)
   i) Q311R and/P343R (suitable for increasing pI for enhancing uptake of antigen); and
   ii) L234Y, P238D, T250V, V264I, T307V and A330K (suitable for increasing affinity to human FcgRIIb and decreasing affinity to other human FcgR); and
   iii) M428L, N434A and Y436T (suitable for increasing affinity to FcRn for longer plasma half-life); and/
   iv) Q438R and S440E (suitable for suppressing rheumatoid factor binding).

24. The bispecific antibody according to anyone of the preceding claims, wherein the bispecific antibody, comprises a human IgG1 heavy chain constant domain comprising one or more of the following mutations (Kabat EU numbering)
   i) Q311R and/P343R (suitable for increasing pI for enhancing uptake of antigen); and
   ii) L234Y, P238D, T250V, V264I, T307V and A330K (suitable for increasing affinity to human FcgRIIb and decreasing affinity to other human FcgR); and
   iii) N434A (suitable for increasing affinity to FcRn for longer plasma half-life); and/ iv) Q438R and S440E (suitable for suppressing rheumatoid factor binding).

25. The bispecific antibody according to anyone of the preceding embodiments, wherein the bispecific antibody comprises two human IgG1 heavy chain constant domains comprising the following mutations (EU numbering)
   i) S354C and T366W in one of the heavy chain constant domains
   ii) Y349C, T366S, L368A, Y407V in the other of the heavy chain constant domains 26. An (isolated) antibody that (specifically) binds to a human CCL2, wherein the antibody comprises
   A) a VH domain comprising (a) a CDR-H1 comprising the amino acid sequence SHYGXS of SEQ ID NO: 57 wherein X is I or T, (b) a CDR-H2 comprising the amino acid sequence GX$^1$IX$^2$IFX$^3$TANYAQKFQG of SEQ ID NO: 58 wherein X$^1$ is V, I, or H, X$^2$ is P or H, and X$^3$ is H or G, and (c) a CDR-H3 comprising the amino acid sequence YDAHYGELDF of SEQ ID NO: 59;
   and
      a VL domain comprising (d) a CDR-L1 comprising the amino acid sequence RASQHVSDAYLA of SEQ ID NO: 60; (e) a CDR-L2 comprising the amino acid sequence DASDRAE of SEQ ID NO: 61, and (f) a CDR-L3 comprising the amino acid sequence HQYIHLHSFT of SEQ ID NO: 62;
   or
   B) a VH domain comprising (a) a CDR-H1 comprising the amino acid sequence HTYMH of SEQ ID NO: 76, (b) a CDR-H2 comprising the amino acid sequence RIDPXNHNTKFDPKFQG of SEQ ID NO: 77 wherein X is D or E, and (c) a CDR-H3 comprising the amino acid sequences GVFGFFXH of SEQ ID NO:78 wherein X is D or E; and
      a VL domain comprising (d) a CDR-L1 comprising the amino acid sequence KAX$^1$EDIYNRX$^2$A of SEQ ID NO: 79 wherein X$^1$ is F or T and X$^2$ is R or L, (e) a CDR-L2 comprising the amino acid sequence GATSLEH of SEQ ID NO: 80, and (f) a CDR-L3 comprising the amino acid sequence QQFXSAPYT of SEQ ID NO: 81 wherein X is W or R.

27. An (isolated) antibody that (specifically) binds to a human CCL2, wherein the antibody comprises
   A) a VH domain comprising the amino acid sequence of SEQ ID NO:71;
      and a VL domain comprising the amino acid sequence of SEQ ID NO:75;
   or
   B) a VH domain comprising the amino acid sequence of SEQ ID NO:72;
      and a VL domain comprising the amino acid sequence of SEQ ID NO:75;
   or
   C) a VH domain comprising the amino acid sequence of SEQ ID NO:73;
      and a VL domain comprising the amino acid sequence of SEQ ID NO:75;
   or
   D) a VH domain comprising the amino acid sequence of SEQ ID NO:74;
      and a VL domain comprising the amino acid sequence of SEQ ID NO:75;
   or
   E) a VH domain comprising the amino acid sequence of SEQ ID NO:90;
      and a VL domain comprising the amino acid sequence of SEQ ID NO:93;
   or
   F) a VH domain comprising the amino acid sequence of SEQ ID NO:91;
      and a VL domain comprising the amino acid sequence of SEQ ID NO:93;
   or
   G) a VH domain comprising the amino acid sequence of SEQ ID NO:92;
      and a VL domain comprising the amino acid sequence of SEQ ID or
   H) a VH domain comprising the amino acid sequence of SEQ ID NO:90;
      and a VL domain comprising the amino acid sequence of SEQ ID NO:94;

28. Isolated nucleic acid encoding the antibody according to any one of the preceding embodiments.

29. A host cell comprising the nucleic acid of embodiment 28.

30. A method of producing an antibody comprising culturing the host cell of embodiment 29 so that the antibody is produced.

31. The method of embodiment 30, further comprising recovering the antibody from the host cell.

32. A pharmaceutical formulation comprising the bispecific antibody according any one of embodiments 1 to 25 and a pharmaceutically acceptable carrier.

33. The bispecific antibody according any one of embodiments 1 to 25 for use as a medicament.

34. The bispecific antibody according any one of embodiments 1 to 25 for use in treating cancer.

35. The bispecific antibody according any one of embodiments 1 to 25 for use in treating an inflammatory or autoimmune disease.

36. Use of the bispecific antibody according any one of embodiments 1 to 25 in the manufacture of a medicament.

37. The use of embodiment 36, wherein the medicament is for treatment of cancer.

38. The use of embodiment 36, wherein the medicament is for treatment of an inflammatory or autoimmune disease.

39. A method of treating an individual having cancer comprising administering to the individual an effective amount of the bispecific antibody according any one of embodiments 1 to 25.

40. A method of treating an individual having an inflammatory or autoimmune disease comprising administering to the individual an effective amount of the bispecific antibody according any one of embodiments 1 to 25.

The following examples and figures are provided to aid the understanding of the present invention, the true scope of which is set forth in the appended claims. It is understood that modifications can be made in the procedures set forth without departing from the spirit of the invention.

Description of the Amino Acid Sequences Anti-CCL2 Antigen Binding Moieties (Variable Regions and Hypervariable Regions (CDRs)) Binding to Different Epitopes:

| SEQ ID NO: | 1 | heavy chain CDR-H1 | 1A4 | WIC |
|---|---|---|---|---|

| SEQ ID NO: | 2 | heavy chain CDR-H2 | 1A4 | CIGAGSSGSTYYASWAKG |
|---|---|---|---|---|
| SEQ ID NO: | 3 | heavy chain CDR-H3 | 1A4 | TGTEFTYYSL |
| SEQ ID NO: | 4 | light chain CDR-L1 | 1A4 | QASQSVYNNNMA |
| SEQ ID NO: | 5 | light chain CDR-L2 | 1A4 | TASSLAS |
| SEQ ID NO: | 6 | light chain CDR-L3 | 1A4 | AGYKSYSNDEYG |
| SEQ ID NO: | 7 | heavy chain variable domain VH | 1A4 | QSLEESGGDLVKPGASLTLTCTASELDFYWICWVRQAPGKGLEWIACIGAGSSGSTYYASWAKGRFTVSKTSSTTVTLQMTSLTAADTATYFCARTGTEFTYYSLWGPGTLVTVSS |
| SEQ ID NO: | 8 | light chain variable domain VL | 1A4 | ALVMTQTPSSVSAAVGGTVTINCQASQSVYNNNMAWYQQKPGQPPKLLIYTASSLASGVPSHFRGSGSGTQFTLTISDLESDDAATYYCAGYKSYSNDEYGFGGGTEVVVK |
| SEQ ID NO: | 9 | heavy chain CDR-H1 | 1A5 | TSYWMC |
| SEQ ID NO: | 10 | heavy chain CDR-H2 | 1A5 | CISSSIGVTYYASWAEG |
| SEQ ID NO: | 11 | heavy chain CDR-H3 | 1A5 | TTDDNWNVGFNL |
| SEQ ID NO: | 12 | light chain CDR-L1 | 1A5 | QASQSIGNRYLS |
| SEQ ID NO: | 13 | light chain CDR-L2 | 1A5 | GTSTLAS |
| SEQ ID NO: | 14 | light chain CDR-L3 | 1A5 | QQGATISYLDNA |
| SEQ ID NO: | 15 | heavy chain variable domain VH | 1A5 | QEQLVESGGDLVKPEGSLTLTCTASGFSFSTSYWMCWVRQAPGKGLELIACISSSIGVTYYASWAEGRFTISKTSSTTVTLQMTSLTVADTATYFCARTTDDNWNVGFNLWGPGTLVTVSS |
| SEQ ID NO: | 16 | light chain variable domain VL | 1A5 | AYDMTQTPASVEVGVGGTVTIKCQASQSIGNRYLSWYQQKPGQPPKLLIYGTSTLASGVSSRFKGSGSGTQFTLTISGVESADSATYYCQQGATISYLDNAFGGGTEVWK |
| SEQ ID NO: | 17 | heavy chain CDR-H1 | 1G9 | LYSYMC |
| SEQ ID NO: | 18 | heavy chain CDR-H2 | 1G9 | CVDAGASGSTYYASWAKG |

-continued

| SEQ ID NO: | 19 | heavy chain CDR-H3 | 1G9 | GILYYTWPYPAGAIDAFDS |
|---|---|---|---|---|
| SEQ ID NO: | 20 | light chain CDR-L1 | 1G9 | QASESISNYLS |
| SEQ ID NO: | 21 | light chain CDR-L2 | 1G9 | KASTLAS |
| SEQ ID NO: | 22 | light chain CDR-L3 | 1G9 | QQSYSSSNVFNT |
| SEQ ID NO: | 23 | heavy chain variable domain VH | 1G9 | QSLEESGGDLVKPGASLTLTCKASGIDF SLYSYMCWVRQAPGKGLEWIACVDAG ASGSTYYASWAKGRFTISKTSSTTVTL QMTSLTAADTATYFCARGILYYTWPYP AGAIDAFDSWGPGTLVTVSS |
| SEQ ID NO: | 24 | light chain variable domain VL | 1G9 | AYDMTQTPASVSEPVGGTVTIKCQASE SISNYLSWYQQKPGQPPKLLIYKASTLA SGVPSRFKGSGSGTEYTVTISGVQSDD AATYYCQQSYSSSNVFNTFGGGTEVV VK |
| SEQ ID NO: | 25 | heavy chain CDR-H1 | 2F6 | NNYYMC |
| SEQ ID NO: | 26 | heavy chain CDR-H2 | 2F6 | CISTDDSNTHYASWAQG |
| SEQ ID NO: | 27 | heavy chain CDR-H3 | 2F6 | DAHFTSYGYGFDL |
| SEQ ID NO: | 28 | light chain CDR-L1 | 2F6 | RASEDIENLVA |
| SEQ ID NO: | 29 | light chain CDR-L2 | 2F6 | QASKLAS |
| SEQ ID NO: | 30 | light chain CDR-L3 | 2F6 | QGDYGSGWIMYS |
| SEQ ID NO: | 31 | heavy chain variable domain VH | 2F6 | QSLEESGGGLVQPEGSLTLTCTASGFSF NNYYMCWVRQAPGKGLEWIGCISTD DSNTHYASWAQGRFTISKASSTALTLQ VAGLTVADMATYFCARDAHFTSYGYG FDLWGPGTLVTVSS |
| SEQ ID NO: | 32 | light chain variable domain VL | 2F6 | DIVMTQTPASVSAAVGGTVSINCRASE DIENLVAWYQQKPGQPPKLLIYQASKL ASGVPSRFKGSGSGAEFTLTIGDLESAD AATYYCQGDYGSGWIMYSFGGGTDLV VK |
| SEQ ID NO: | 33 | heavy chain CDR-H1 | CNTO888 | SYGIS |
| SEQ ID NO: | 34 | heavy chain CDR-H2 | CNTO888 | GIIPIFGTANYAQKFQG |
| SEQ ID NO: | 35 | heavy chain CDR-H3 | CNTO888 | YDGIYGELDF |

| | | | | |
|---|---|---|---|---|
| SEQ ID NO: | 36 | light chain CDR-L1 | CNTO888 | RASQSVSDAYLA |
| SEQ ID NO: | 37 | light chain CDR-L2 | CNTO888 | DASSRAT |
| SEQ ID NO: | 38 | light chain CDR-L3 | CNTO888 | HQYIQLHSFT |
| SEQ ID NO: | 39 | heavy chain variable domain VH | CNTO888 | QVQLVQSGAEVKKPGSSVKVSCKASG GTFSSYGISWVRQAPGQGLEWMGGIIPI FGTANYAQKFQGRVTITADESTSTAYM ELSSLRSEDTAVYYCARYDGIYGELDF WGQGTLVTVSS |
| SEQ ID NO: | 40 | light chain variable domain VL | CNTO888 | EIVLTQSPATLSLSPGERATLSCRASQS VSDAYLAWYQQKPGQAPRLLIYDASS RATGVPARFSGSGSGTDFTLTISSLEPE DFAVYYCHQYIQLHSFTFGQGTKVEIK |
| SEQ ID NO: | 41 | heavy chain CDR-H1 | Humanized 11K2 (=11K2) | DTYMH |
| SEQ ID NO: | 42 | heavy chain CDR-H2 | Humanized 11K2 (=11K2) | RIDPANGNTKFDPKFQG |
| SEQ ID NO: | 43 | heavy chain CDR-H3 | Humanized 11K2 (=11K2) | GVFGFFDY |
| SEQ ID NO: | 44 | light chain CDR-L1 | Humanized 11K2 (=11K2) | KATEDIYNRLA |
| SEQ ID NO: | 45 | light chain CDR-L2 | Humanized 11K2 (=11K2) | GATSLET |
| SEQ ID NO: | 46 | light chain CDR-L3 | Humanized 11K2 (=11K2) | QQFWSAPYT |
| SEQ ID NO: | 47 | heavy chain variable domain VH | Humanized 11K2 (=11K2) | QVQLVQSGAEVKKPGSSVKVSCKASG LTISDTYMHWVRQAPGQGLEWMGRID PANGNTKFDPKFQGRVTITADTSTSTA YMELSSLRSEDTAVYYCARGVFGFFDY WGQGTTVTVSS |
| SEQ ID NO: | 48 | light chain variable domain VL | Humanized 11K2 (=11K2) | DIQMTQSPSSLSASVGDRVTITCKATED IYNRLAWYQQKPGKAPKLLISGATSLE TGVPSRFSGSGSGTDYTLTISSLQPEDF ATYYCQQFWSAPYTFGGGTKVEIK |
| SEQ ID NO: | 49 | heavy chain CDR-H1 | ABN912 | HYWMS |
| SEQ ID NO: | 50 | heavy chain CDR-H2 | ABN912 | NIEQDGSEKYYVDSVKG |
| SEQ ID NO: | 51 | heavy chain CDR-H3 | ABN912 | DLEGLHGDGYFDL |
| SEQ ID NO: | 52 | light chain CDR-L1 | ABN912 | RASQGVSSALA |
| SEQ ID NO: | 53 | light chain CDR-L2 | ABN912 | DASSLES |

-continued

| | | | | |
|---|---|---|---|---|
| SEQ ID NO: | 54 | light chain CDR-L3 | ABN912 | QQFNSYPLT |
| SEQ ID NO: | 55 | heavy chain variable domain VH | ABN912 | EVQLVQSGGGLVQPGGSLRLSCAASGF TFSHYWMSWVRQAPGKGLEWLANIEQ DGSEKYYVDSVKGRFTISRDNAKNSLY LQMNSLRAEDTAVYFCARDLEGLHGD GYFDLWGRGTLVTVSS |
| SEQ ID NO: | 56 | light chain variable domain VL | ABN912 | AIQLTQSPSSLSASVGDRVILTCRASQG VSSALAWYQQKPGKAPKLLIYDASSLE SGVPSRFSGSGSGPDFTLTISSLQPEDFA TYFCQQFNSYPLTFGGGTKVEIK |

CDR Modified Anti-CCL2 Antigen Binding Moieties (Variable Regions and Hypervariable Regions (CDRs)):

| Modified CNTO888 | | | | |
|---|---|---|---|---|
| SEQ ID NO: | 57 | heavy chain CDR-H1 | mutated variant CNTO888 | SHYGXS wherein X is I or T |
| SEQ ID NO: | 58 | heavy chain CDR-H2 | mutated variant CNTO888 | GX$^1$IX$^2$IFX$^3$TANYAQKFQG wherein X$^1$ is V, I, or H, X$^2$ is P or H, and X$^3$ is H or G |
| SEQ ID NO: | 59 | heavy chain CDR-H3 | mutated variant CNTO888 | YDAHYGELDF |
| SEQ ID NO: | 60 | light chain CDR-L1 | mutated variant CNTO888 | RASQHVSDAYLA |
| SEQ ID NO: | 61 | light chain CDR-L2 | mutated variant CNTO888 | DASDRAE |
| SEQ ID NO: | 62 | light chain CDR-L3 | mutated variant CNTO888 | HQYIHLHSFT |
| SEQ ID NO: | 63 | heavy chain FR-H1 | mutated variant CNTO888 | QVQLVQSGAEVKKPGSSVKVSCKA SGGTF |
| SEQ ID NO: | 64 | heavy chain FR-H2 | mutated variant CNTO888 | WVRQAPGQGLEWMG |
| SEQ ID NO: | 65 | heavy chain FR-H3 | mutated variant CNTO888 | RVTITADESTSTAYMELSSLRSEDT AVYYCAR |
| SEQ ID NO: | 66 | heavy chain FR-H4 | mutated variant CNTO888 | WGQGTLVTVSS |
| SEQ ID NO: | 67 | light chain FR-L1 | mutated variant CNTO888 | EIVLTQSPATLSLSPGERATLSC |
| SEQ ID NO: | 68 | light chain FR-L2 | mutated variant CNTO888 | WYQQKPGQAPRLLIY |
| SEQ ID NO: | 69 | light chain FR-L3 | mutated variant CNTO888 | GVPARFSGSGSGTDFTLTISSLEPED FAVYYC |
| SEQ ID NO: | 70 | light chain FR-L4 | mutated variant CNTO888 | GQGTKVEIK |

-continued

| Modified CNTO888 | | | | |
|---|---|---|---|---|
| SEQ ID NO: | 71 | heavy chain variable domain VH | mutated variant CNTO888 H0695 | QVQLVQSGAEVKKPGSSVKVSCKASGGTFSHYGISWVRQAPGQGLEWMGGVIPIFHTANYAQKFQGRVTITADESTSTAYMELSSLRSEDTAVYYCARYDAHYGELDFWGQGTLVTVSS |
| SEQ ID NO: | 72 | heavy chain variable domain VH | mutated variant CNTO888 H0625 | QVQLVQSGAEVKKPGSSVKVSCKASGGTFSHYGISWVRQAPGQGLEWMGGIIHIFHTANYAQKFQGRVTITADESTSTAYMELSSLRSEDTAVYYCARYDAHYGELDFWGQGTLVTVSS |
| SEQ ID NO: | 73 | heavy chain variable domain VH | mutated variant CNTO888 H0634 | QVQLVQSGAEVKKPGSSVKVSCKASGGTFSHYGTSWVRQAPGQGLEWMGGIIHIFGTANYAQKFQGRVTITADESTSTAYMELSSLRSEDTAVYYCARYDAHYGELDFWGQGTLVTVSS |
| SEQ ID NO: | 74 | heavy chain variable domain VH | mutated variant CNTO888 H0635 | QVQLVQSGAEVKKPGSSVKVSCKASGGTFSHYGISWVRQAPGQGLEWMGGHIHIFGTANYAQKFQGRVTITADESTSTAYMELSSLRSEDTAVYYCARYDAHYGELDFWGQGTLVTVSS |
| SEQ ID NO: | 75 | light chain variable domain VL | mutated variant CNTO888 L0616 | EIVLTQSPATLSLSPGERATLSCRASQHVSDAYLAWYQQKPGQAPRLLIYDASDRAEGVPARFSGSGSGTDFTLTISSLEPEDFAVYYCHQYIHLHSFTFGQGTKVEIK |

Modified Humanized 11K2

| SEQ ID NO: | 76 | heavy chain CDR-H1 | mutated variant humanized 11K2 | HTYMH |
| SEQ ID NO: | 77 | heavy chain CDR-H2 | mutated variant humanized 11K2 | RIDPXNHNTKFDPKFQG wherein X is D or E |
| SEQ ID NO: | 78 | heavy chain CDR-H3 | mutated variant humanized 11K2 | GVFGFFXH wherein X is D or E |
| SEQ ID NO: | 79 | light chain CDR-L1 | mutated variant humanized 11K2 | KAX$^1$EDIYNRX$^2$A wherein X$^1$ is F or T and X$^2$ is R or L |
| SEQ ID NO: | 80 | light chain CDR-L2 | mutated variant humanized 11K2 | GATSLEH |
| SEQ ID NO: | 81 | light chain CDR-L3 | mutated variant humanized 11K2 | QQFXSAPYT wherein X is W or R |
| SEQ ID NO: | 82 | heavy chain FR-H1 | mutated variant humanized 11K2 | QVQLVQSGAEVKKPGSSVKVSCKASGLTIS |
| SEQ ID NO: | 83 | heavy chain FR-H2 | mutated variant humanized 11K2 | WVRQAPGQGLEWMG |

| SEQ ID NO: | 84 | heavy chain FR-H3 | mutated variant humanized 11K2 | RVTITADTSTSTAYMELSSLRSEDT AVYYCAR |
|---|---|---|---|---|
| SEQ ID NO: | 85 | heavy chain FR-H4 | mutated variant humanized 11K2 | WGQGTTVTVSS |
| SEQ ID NO: | 86 | light chain FR-L1 | mutated variant humanized 11K2 | DIQMTQSPSSLSASVGDRVTITC |
| SEQ ID NO: | 87 | light chain FR-L2 | mutated variant humanized 11K2 | WYQQKPGKAPKLLIH |
| SEQ ID NO: | 88 | light chain FR-L3 | mutated variant humanized 11K2 | GVPSRFSGSGSGTDYTLTISSLQPED FATYYC |
| SEQ ID NO: | 89 | light chain FR-L4 | mutated variant humanized 11K2 | FGGGTKVEIK |
| SEQ ID NO: | 90 | heavy chain variable domain VH | mutated variant humanized 11K2 H1503 | QVQLVQSGAEVKKPGSSVKVSCKA SGLTISHTYMHWVRQAPGQGLEW MGRIDPDNHNTKFDPKFQGRVTIT ADTSTSTAYMELSSLRSEDTAVYY CARGVFGFFDHWGQGTTVTVSS |
| SEQ ID NO: | 91 | heavy chain variable domain VH | mutated variant humanized 11K2 H1510 | QVQLVQSGAEVKKPGSSVKVSCKA SGLTISHTYMHWVRQAPGQGLEW MGRIDPDNHNTKFDPKFQGRVTIT ADTSTSTAYMELSSLRSEDTAVYY CARGVFGFFEHWGQGTTVTVSS |
| SEQ ID NO: | 92 | heavy chain variable domain VH | mutated variant humanized 11K2 H1514 | QVQLVQSGAEVKKPGSSVKVSCKA SGLTISHTYMHWVRQAPGQGLEW MGRIDPENHNTKFDPKFQGRVTITA DTSTSTAYMELSSLRSEDTAVYYC ARGVFGFFEHWGQGTTVTVSS |
| SEQ ID NO: | 93 | light chain variable domain VL | mutated variant humanized 11K2 L1338 | DIQMTQSPSSLSASVGDRVTITCKA FEDIYNRRAWYQQKPGKAPKLLIH GATSLEHGVPSRFSGSGSGTDYTLT ISSLQPEDFATYYCQQFWSAPYTFG GGTKVEIK |
| SEQ ID NO: | 94 | light chain variable domain VL | mutated variant humanized 11K2 L1201 | DIQMTQSPSSLSASVGDRVTITCKA TEDIYNRLAWYQQKPGKAPKLLIH GATSLEHGVPSRFSGSGSGTDYTLT ISSLQPEDFATYYCQQFRSAPYTFG GGTKVEIK |

Exemplary Constant Light Chain Regions:
SEQ ID NO: 95 exemplary human kappa light chain constant region
SEQ ID NO: 96 exemplary human lambda light chain constant region
Exemplary Constant Heavy Chain Regions:
SEQ ID NO: 97 exemplary human heavy chain constant region derived from IgG1
SEQ ID NO: 98 exemplary human heavy chain constant region derived from IgG1 with mutations L234A, L235A and P329G (Fcgamma receptor silenced)
SEQ ID NO: 99 exemplary human heavy chain constant region derived from IgG1 (SG1-IgG1 allotype) SEQ ID NO: 100 exemplary human heavy chain constant region derived from IgG1 with mutations (SG105-IgG1 allotype—Fcgamma receptor silenced)

SEQ ID NO: 101 SG1095-exemplary human heavy chain constant region derived from IgG1 including the mutations (Kabat EU numbering):
L235W/G236N/H268D/Q295L/A330K/K326T (suitable for increasing affinity to human FcgRIIb and decreasing affinity to other human FcgR);
Q311R/P343R (suitable for increasing isoelectric point (pI) for enhancing uptake of antigen;
N434A (suitable for increasing affinity to FcRn for longer plasma half-life of antibody; and
Q438R/S440E (suitable for suppressing rheumatoid factor binding
SEQ ID NO: 102 SG1099-exemplary human heavy chain constant region derived from IgG1 including mutations (Kabat EU numbering):

Q311R/P343R (suitable for increasing pI for enhancing uptake of antigen)
SEQ ID NO: 103 SG1100-exemplary human heavy chain constant region derived from IgG1 including the mutations (Kabat EU numbering):
  Q311R/P343R (suitable for increasing pI for enhancing uptake of antigen);
  N434A (suitable for increasing affinity to FcRn for longer plasma half-life of antibody); and
  Q438R/S440E (suitable for suppressing rheumatoid factor binding)
CNTO888/11K2-WT IgG1 (exemplary bispecific CNTO888/11K2-WT IgG1 Crossmab)
SEQ ID NO: 104 heavy chain 1-CNTO888/11K2-WT IgG1
SEQ ID NO: 105 heavy chain 2-CNTO888/11K2-WT IgG1
SEQ ID NO: 106 light chain 1-CNTO888/11K2-WT IgG1
SEQ ID NO: 107 light chain 2-CNTO888/11K2-WT IgG1
CKLO2-IgG1 (exemplary bispecific CKLO2 IgG1 Crossmab)
SEQ ID NO: 108 heavy chain 1-CKLO2 IgG1
SEQ ID NO: 109 heavy chain 2-CKLO2 IgG1
SEQ ID NO: 110 light chain 1-CKLO2 IgG1
SEQ ID NO: 111 light chain 2-CKLO2 IgG1
CKLO2-SG1095 (exemplary bispecific CLOK2 Crossmab including SG1095 Fc mutations)
SEQ ID NO: 112 heavy chain 1-CKLO2-SG1095
SEQ ID NO: 113 heavy chain 2-CKLO2-SG1095
SEQ ID NO: 114 light chain 1-CKLO2-SG1095
SEQ ID NO: 115 light chain 2-CKLO2-SG1095
CKLO2-SG1099 (exemplary bispecific CKLO2 Crossmab including SG1099 Fc mutations)
SEQ ID NO: 116 heavy chain 1-CKLO2-SG1099
SEQ ID NO: 117 heavy chain 2-CKLO2-SG1099
SEQ ID NO: 118 light chain 1-CKLO2-SG1099
SEQ ID NO: 119 light chain 2-CKLO2-SG1099
CKLO2-SG1100 (exemplary bispecific CKLO2 Crossmab including SG1100 Fc mutations)
SEQ ID NO: 120 heavy chain 1-CKLO2-SG1100
SEQ ID NO: 121 heavy chain 2-CKLO2-SG1100
SEQ ID NO: 122 light chain 1-CKLO2-SG1100
SEQ ID NO: 123 light chain 2-CKLO2-SG1100
CKLO3-SG1095 (exemplary bispecific CLOK3 Crossmab including SG1095 Fc mutations)
SEQ ID NO: 124 heavy chain 1-CKLO3-SG1095
SEQ ID NO: 125 heavy chain 2-CKLO3-SG1095
SEQ ID NO: 126 light chain 1-CKLO3-SG1095
SEQ ID NO: 127 light chain 2-CKLO3-SG1095
CKLO3-SG1099 (exemplary bispecific CKLO3 Crossmab including SG1099 Fc mutations)
SEQ ID NO: 128 heavy chain 1-CKLO3-SG1099
SEQ ID NO: 129 heavy chain 2-CKLO3-SG1099
SEQ ID NO: 130 light chain 1-CKLO3-SG1099
SEQ ID NO: 131 light chain 2-CKLO3-SG1099
CKLO3-SG1100 (exemplary bispecific CKLO3 Crossmab including SG1100 Fc mutations)
SEQ ID NO: 132 heavy chain 1-CKLO3-SG1100
SEQ ID NO: 133 heavy chain 2-CKLO3-SG1100
SEQ ID NO: 134 light chain 1-CKLO3-SG1100
SEQ ID NO: 135 light chain 2-CKLO3-SG1100
Further Anti-CCL2 Antigen Binding Moieties:
SEQ ID NO: 136 heavy chain variable domain VH 2F2
SEQ ID NO: 137 light chain variable domain VL 2F2
SEQ ID NO: 138 heavy chain variable domain VH murine 11K2 (=11K2m)
SEQ ID NO: 139 light chain variable domain VL murine 11K2 (=11K2m)
SEQ ID NO: 140 heavy chain variable domain VH 1H11
SEQ ID NO: 141 light chain variable domain VL 1H11
Exemplary CCL2 and Homologs (without Signal Peptide):
SEQ ID NO: 142 exemplary human CCL2 (MCP1)-wild type (wt)
SEQ ID NO: 143 exemplary human CCL2 (MCP1)-P8A variant
SEQ ID NO: 144 exemplary human CCL2 (MCP1)-T10C variant
SEQ ID NO: 145 exemplary human CCL8 (MCP2)-wild type (wt)
SEQ ID NO: 146 exemplary human CCL8 (MCP2)-P8A variant
SEQ ID NO: 147 exemplary human CCL7 (MCP3)-wild type (wt)
SEQ ID NO: 148 exemplary human CCL13 (MCP4)-wild type (wt)
SEQ ID NO: 149 exemplary cynomolgus CCL2-wild type (wt)
SEQ ID NO: 150 exemplary mouse CCL2-wild type (wt)
Further Exemplary Constant Heavy Chain Regions:
SEQ ID NO: 151 GG01—exemplary human heavy chain constant region derived from IgG1 including the mutations (Kabat EU numbering):
  L234Y/P238D/T250V/V264I/T307P/A330K (suitable for increasing affinity to human FcgRIIb and decreasing affinity to other human FcgR);
  Q311R/P343R (suitable for increasing isoelectric point (pI) for enhancing uptake of antigen);
  N434A (suitable for increasing affinity to FcRn for longer plasma half-life of antibody); and
  Q438R/S440E (suitable for suppressing rheumatoid factor binding)
SEQ ID NO: 152 GG02—exemplary human heavy chain constant region derived from IgG1 including mutations (Kabat EU numbering):
  L234Y/P238D/T250V/V264I/T307P/A330K (suitable for increasing affinity to human FcgRIIb and decreasing affinity to other human FcgR);
  Q311R/P343R (suitable for increasing isoelectric point (pI) for enhancing uptake of antigen);
  M428L/N434A/Y436T (suitable for increasing affinity to FcRn for longer plasma half-life of antibody); and
  Q438R/S440E (suitable for suppressing rheumatoid factor binding)
SEQ ID NO: 153 GG03—exemplary human heavy chain constant region derived from IgG1 (comprising-IgG1 allotype sequences) including the mutations (Kabat EU numbering):
  L234Y/P238D/T250V/V264I/T307P/A330K (suitable for increasing affinity to human FcgRIIb and decreasing affinity to other human FcgR);
  Q311R/P343R (suitable for increasing isoelectric point (pI) for enhancing uptake of antigen);
  N434A (suitable for increasing affinity to FcRn for longer plasma half-life of antibody); and
  Q438R/S440E (suitable for suppressing rheumatoid factor binding)
SEQ ID NO: 154 GG04—exemplary human heavy chain constant region derived from IgG1 (comprising-IgG1 allotype sequences) including mutations (Kabat EU numbering):
  L234Y/P238D/T250V/V264I/T307P/A330K (suitable for increasing affinity to human FcgRIIb and decreasing affinity to other human FcgR);
  Q311R/P343R (suitable for increasing isoelectric point (pI) for enhancing uptake of antigen);

M428L/N434A/Y436T (suitable for increasing affinity to FcRn for longer plasma half-life of antibody); and
Q438R/S440E (suitable for suppressing rheumatoid factor binding)
CKLO2-GG01 (exemplary bispecific CLOK2 Crossmab including GG01 Fc mutations)
SEQ ID NO: 155 heavy chain 1-CKLO2-GG01
SEQ ID NO: 156 heavy chain 2-CKLO2-GG01
SEQ ID NO: 157 light chain 1-CKLO2-GG01
SEQ ID NO: 158 light chain 2-CKLO2-GG01
CKLO2-GG02 (exemplary bispecific CLOK2 Crossmab including GG02 Fc mutations)
SEQ ID NO: 159 heavy chain 1-CKLO2 GG02
SEQ ID NO: 160 heavy chain 2-CKLO2 GG02
SEQ ID NO: 161 light chain 1-CKLO2 GG02
SEQ ID NO: 162 light chain 2-CKLO2 GG02
CKLO2-GG03 (exemplary bispecific CLOK2 Crossmab including GG03 Fc mutations)
SEQ ID NO: 163 heavy chain 1-CKLO2-GG03
SEQ ID NO: 164 heavy chain 2-CKLO2-GG03
SEQ ID NO: 165 light chain 1-CKLO2-GG03
SEQ ID NO: 166 light chain 2-CKLO2-GG03
CKLO2-GG04 (exemplary bispecific CKLO2 Crossmab including GG04 Fc mutations)
SEQ ID NO: 167 heavy chain 1-CKLO2-GG04
SEQ ID NO: 168 heavy chain 2-CKLO2-GG04
SEQ ID NO: 169 light chain 1-CKLO2-GG04
SEQ ID NO: 170 light chain 2-CKLO2-GG04
CKLO2-GG03/GG04 (exemplary bispecific CKLO2 Crossmab including GG03 Fc mutations in the Knob chain and including GG04 Fc mutations in Hole chain)
SEQ ID NO: 171 heavy chain 1-CKLO2-GG03/GG04
SEQ ID NO: 172 heavy chain 2-CKLO2-GG03/GG04
SEQ ID NO: 173 light chain 1-CKLO2-GG03/GG04
SEQ ID NO: 174 light chain 2-CKLO2-GG03/GG04
Designation Monospecific Unmodified Anti-CCL2 Antibodies/Antigen Binding Moieties which were Used for the Anti-CCL2 Bispecific Antibodies Described Herein

| Antibody/antigen binding site | Alias | VH/VL |
|---|---|---|
| 1A4 | CCL2-0008 | SEQ ID NO: 8/SEQ ID NO: 9 |
| 1A5 | CCL2-0009 | SEQ ID NO: 15/SEQ ID NO: 16 |
| 1G9 | CCL2-0010 | SEQ ID NO: 23/SEQ ID NO: 24 |
| 2F6 | CCL2-0014 | SEQ ID NO: 31/SEQ ID NO: 32 |
| CNTO888 | CCL2-0004 | SEQ ID NO: 39/SEQ ID NO: 40 |
| Humanized 11K2 (=11K2) | CCL2-0002 | SEQ ID NO: 47/SEQ ID NO: 48 |
| ABN912 | CCL2-0003 | SEQ ID NO: 55/SEQ ID NO: 56 |

Designation Bispecific Anti-CCL2 with Unmodified VH/VL as Crossmabs (See WO 2016/016299) with Either IgG1 or IgG1 Including Mutations L234A, L235A and P329G (PGLALA)

| Bispecific anti-CCL2 Antibodies | Alias |
|---|---|
| 11K2//1G9-WT IgG1 | CCL2-0049 |
| 11K2//1G9-PGLALA | CCL2-0043 |
| CNTO888//11K2-WT IgG1 | CCL2-0048 |
| CNTO888//11K2-PGLALA | CCL2-0042 |
| CNTO888//1G9-WT IgG1 | CCL2-0051 |
| CNTO888//1G9-PGLALA | CCL2-0045 |
| CNTO888//1A5-WT IgG1 | CCL2-0050 |
| CNTO888//1A5-PGLALA | CCL2-0044 |
| 1A5//1G9-WT IgG1 | CCL2-0052 |
| 1A5//1G9-PGLALA | CCL2-0046 |
| 11K2//2F6-WT IgG1 | CCL2-0056 |
| 11K2//2F6-PGLALA | CCL2-0053 |
| ABN912//11K2-WT IgG1 | CCL2-0047 |
| ABN912//11K2-PGLALA | CCL2-0041 |
| 1A4//2F6-WT IgG1 | CCL2-0057 |
| 1A4//2F6-PGLALA | CCL2-0054 |
| 1A5//2F6-WT IgG1 | CCL2-0058 |
| 1A5//2F6-PGLALA | CCL2-0055 |

Designation Bispecific Antibodies with Modified VH/VL as Crossmabs (See WO 2016/016299). Depending on the Heavy Chain Constant Domain Used (e.g. IgG1 Wild Type, PGLALA, SG1095, SG1099, 1100) the Suffixes IgG1 Wild Type, PGLALA, SG1095, SG1099, 1100 are Added

| Bispecific CCL2 antibody (and parental monospecific) | Name of variable region (VHs/VLs) | VH (SEQ ID NO) | VL (SEQ ID NO) | VH (SEQ ID NO) | VL (SEQ ID NO) |
|---|---|---|---|---|---|
| Humanized 11K2 parental | 11K2 VH/11K2 VL | 47 | 48 | — | — |
| CNTO888 parental | CNTO888 VH/CNTO888VL | | | 39 | 40 |
| CKLO01 | 11K2H1503/11K2L1338//CNTO888H0695/CNTO888L0616 | 90 | 93 | 71 | 75 |
| CKLO02 | 11K2H1510/11K2L1338//CNTO888H0695/CNTO888L0616 | 91 | 93 | 71 | 75 |
| CKLO03 | 11K2H1503/11K2L1201//CNTO888H0695/CNTO888L0616 | 90 | 94 | 71 | 75 |
| CKLO04 | 11K2H1503/11K2L1201//CNTO888H0625/CNTO888L0616 | 90 | 94 | 72 | 75 |
| CKLO05 | 11K2H1503/11K2L1338//CNTO888H0634/CNTO888L0616 | 90 | 93 | 73 | 75 |
| CKLO06 | 11K2H1503/11K2L1201//CNTO888H0634/CNTO888L0616 | 90 | 94 | 73 | 75 |
| CKLO07 | 11K2H1514/11K2L1338//CNTO888H0634/CNTO888L0616 | 92 | 93 | 73 | 75 |
| CKLO08 | 11K2H1510/11K2L1338//CNTO888H0634/CNTO888L0616 | 91 | 93 | 73 | 75 |
| CKLO09 | 11K2H1503/11K2L1338//CNTO888H0625/CNTO888L0616 | 90 | 93 | 72 | 75 |
| CKLO10 | 11K2H1514/11K2L1338//CNTO888H0625/CNTO888L0616 | 92 | 93 | 72 | 75 |
| CKLO11 | 11K2H1510/11K2L1338//CNTO888H0625/CNTO888L0616 | 91 | 93 | 72 | 75 |
| CKLO12 | 11K2H1503/11K2L1338//CNTO888H0635/CNTO888L0616 | 90 | 93 | 74 | 75 |
| CKLO13 | 11K2H1503/11K2L1201//CNTO888H0635/CNTO888L0616 | 90 | 94 | 74 | 75 |
| CKLO14 | 11K2H1514/11K2L1338//CNTO888H0635/CNTO888L0616 | 92 | 93 | 74 | 75 |
| CKLO15 | 11K2H1510/11K2L1338//CNTO888H0635/CNTO888L0616 | 91 | 93 | 74 | 75 |

-continued

| Bispecific CCL2 antibody (and parental monospecific) | Name of variable region (VHs/VLs) | VH (SEQ ID NO) | VL (SEQ ID NO) | VH (SEQ ID NO) | VL (SEQ ID NO) |
|---|---|---|---|---|---|
| CKLO16 | 11K2H1514/11K2L1338// CNTO888H0695/CNTO8 88L0616 | 92 | 93 | 71 | 75 |

EXAMPLES

Example A-1 Monospecific Anti-CCL2 Antibodies

Generation of monospecific anti-CCL2 antibodies and CCL2 antigen
Recombinant DNA Techniques
Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.
Gene and Oligonucleotide Synthesis
Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany)
Description of the Basic/Standard Mammalian Expression Plasmid
For the expression of a desired gene/protein (e.g. full length antibody heavy chain, full length antibody light chain, or a CCL-2 molecule, a transcription unit comprising the following functional elements is used:
 the immediate early enhancer and promoter from the human cytomegalovirus (P-CMV) including intron A,
 a human heavy chain immunoglobulin 5'-untranslated region (5'UTR),
 a murine immunoglobulin heavy chain signal sequence,
 a gene/protein to be expressed (e.g. full length antibody heavy chain or antibody light chain or CCL-2 molecule), and
 the bovine growth hormone polyadenylation sequence (BGH pA).
Beside the expression unit/cassette including the desired gene to be expressed the basic/standard mammalian expression plasmid contains
 an origin of replication from the vector pUC18 which allows replication of this plasmid in E. coli, and
 a beta-lactamase gene which confers ampicillin resistance in E. coli.
Generation of Expression Plasmids for Recombinant Monoclonal Antibodies and CCL-2 Molecules
The expression plasmids for the transient expression of monoclonal antibodies and CCL-2 antigens comprised besides the respective expression cassettes an origin of replication from the vector pUC18, which allows replication of this plasmid in E. coli, and a beta-lactamase gene which confers ampicillin resistance in E. coli.

The transcription unit of the respective immunoglobulin HC or LC or CCL-2 molecule comprised the following functional elements:
 the immediate early enhancer and promoter from the human cytomegalovirus (P-CMV) including intron A,
 a human heavy chain immunoglobulin 5'-untranslated region (5'UTR),
 a murine immunoglobulin heavy chain signal sequence, and
 the bovine growth hormone polyadenylation sequence (BGH pA).
The Respective Antibodies 1A4, 1A5, 1G9, 2F6, CNTO888, Murine and Humanized 11K2, ABN912, Based on their VH and VL were Generated as I2G1 Wild Type and as I2G1 PGLALA/Effector Silent Fc with Kappa Light Chain Transient Expression and Purification
The recombinant production was performed by transient transfection of HEK293 cells (human embryonic kidney cell line 293-derived) cultivated in F17 Medium (Invitrogen Corp.). For the production of monoclonal antibodies, cells were co-transfected with plasmids containing the respective immunoglobulin heavy- and light chain. For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).
General information regarding the recombinant expression of human immunoglobulins in e.g. HEK293 cells is given in: Meissner, P. et al., Biotechnol. Bioeng. 75 (2001) 197-203.
Antibodies were purified from cell culture supernatants by affinity chromatography using MabSelectSure-Sepharose™ (GE Healthcare, Sweden) and Superdex 200 size exclusion (GE Healthcare, Sweden) chromatography. Briefly, sterile filtered cell culture supernatants were captured on a MabSelect SuRe resin equilibrated with PBS buffer (10 mM Na2HPO4, 1 mM KH2PO4, 137 mM NaCl and 2.7 mM KCl, pH 7.4), washed with equilibration buffer and eluted with 25 mM sodium citrate at pH 3.0. The eluted protein fractions were pooled, neutralized with 2M Tris, pH 9.0 and further purified by size exclusion chromatography using a Superdex 200 26/60 GL (GE Healthcare, Sweden) column equilibrated with 20 mM histidine, 140 mM NaCl, pH 6.0. Size exclusion chromatography fractions were analysed by CE-SDS (Caliper Life Science, USA) and antibody containing fractions were pooled and stored at −80° C.
Generation of Recombinant CCL2
Wild type CCL2 can exist as monomer but actually can also form dimers at physiological concentrations. This monomer-dimer equilibrium might be different and has to be carefully taken into account for all in vitro experiments described where different concentrations might be used. To avoid any uncertainties, we generated point mutated CCL2 variants: The P8A variant of CCL2 carries a mutation in the dimerization interface resulting in an inability to form a dimer leading to a defined, pure CCL2 monomer. In contrast, the T10C variant of CCL2 results in a fixed dimer of CCL2 (J Am Chem Soc. 2013 Mar. 20; 135(11):4325-32).
The respective soluble CCL2 protein (wild type, P8A or T10C variants) was purified from cell culture supernatants by cation exchange chromatography using SP-Sepharose HP (GE Healthcare, Sweden) and Superdex 200 size exclusion (GE Healthcare, Sweden) chromatography. Briefly, sterile filtered cell culture supernatants were diluted with 10 mM KH2PO4, pH 5.0 to adjust conductivity <4 mS/cm. The diluted supernatant was loaded on SP-Sepharose resin equilibrated with 10 mM KH2PO4, pH 5.0, washed with equilibration buffer and eluted using a gradient to 10 mM KH2PO4, 1 M NaCl, pH 5.0. The eluted protein fractions were pooled and further purified by size exclusion chromatography using a Superdex 200 16/60 GL (GE Healthcare, Sweden) column equilibrated with 20 mM histidine, 140 mM NaCl, pH 6.0. Size exclusion chromatography fractions were analyzed by SDS-PAGE and analytical high performance size exclusion chromatography. CCL2 containing fractions were pooled and stored at −80° C.

Functional Characterization (Binding)

A T200 instrument was mounted with a Biacore Series S Sensor Chip CM5. The system buffer was HBS-ET (10 mM HEPES (pH 7.4), 150 mM NaCl, 1 mM EDTA, 0.05% (w/v) P20). The system was set to 37° C. For each measurement the sample buffer was the system buffer, additionally supplemented with 1 mg/ml CMD (Carboxymethyldextran, Fluka).

An antibody capture system was established. 14000 GARFcγ (goat anti rabbit Fcγ), 111-005-046, Jackson ImmunoResearch) were immobilized at 25° C. at 25 µg/ml in 10 mM sodium acetate buffer pH 5.0, by EDC/NHS coupling as described by the manufacturer. The capture system was regenerated at 20 µl/min by a 15 sec injection with HBS buffer (100 mM HEPES pH 7.4, 1.5 M NaCl, 0.05% (w/v) Tween 20), a 1 min injection with 10 mM glycine buffer pH 2.0 followed by two injections for 1 min with 10 mM glycine buffer pH 2.25. In another embodiment murine monoclonal antibodies were captured on the biosensor by immobilizing 12700 RU polyclonal rabbit anti mouse (RAMIgG, GE Healthcare) antibodies on a Biacore Series CM5 sensor like described above. The sensor was regenerated by a 3 min injection of 10 mM glycine buffer pH 1.7.

Antibody clone supernatants were diluted 1:2 in system buffer and were captured for 1 min at 5 µl/min. After antibody capturing the system was washed by 2.5-fold concentrated system buffer for 30 sec at 80 µl/min followed by 2 min baseline stabilization. Analyte kinetics were performed at 30 µl/min. As analyte in solution wt human CCL2 or monomeric CCL2 P8A variant CCL2 were used. Analytes were injected at 90 nM highest concentration. The analyte contact time was 3 min and the dissociation time was 10 min. The Biaevaluation software V.3.0 was used according to the instructions of the manufacturer GEHC. A 1:1 binding model with RMAX local was applied to apparently estimate kinetic rates.

Binding of Antibodies to Wild Type (Wt) Human CCL2 and Human CCL2 P8A Variant (Monomer)

| Antibody | alias | KD [nM] wt human CCL2 | T1/2 [min] | KD [nM] monomeric human CCL2 | T1/2 [min] |
|---|---|---|---|---|---|
| 1A4 | CCL2-0008 | 0.073 | 100 | 0.059 | 174 |
| 1A5 | CCL2-0009 | 0.024 | 160 | 0.046 | 137 |
| 1G9 | CCL2-0010 | 0.062 | 177 | 0.051 | 218 |
| 2F6 | CCL2-0014 | 0.059 | 52 | 0.091 | 47 |
| murine 11K2 | X-0048 | 0.35 | 19 | 0.011 | 518 |
| humanized 11K2 (=11K2) | CCL2-0002 | 0.028 | 118 | 0.035 | 116 |
| AB912 | CCL2-0003 | 0.036 | 33 | 0.046 | 25 |
| CNTO888 | CCL2-0004 | 0.026 | 94 | 0.054 | 44 |

Summary pH Dependent CCL2 Binding Kinetics Obtained from SPR Analysis I

A T200 instrument was mounted with a Biacore Series S Sensor Chip CM5. The system buffer was HBS-ET (10 mM HEPES (pH 7.4), 150 mM NaCl, 1 mM EDTA, 0.05% (w/v) P20). In other embodiments the pH of the system buffers was set to pH 8.3, pH 7.9, pH 7.4, pH 7.1, pH 6.7, pH 6.3, pH 5.9, pH 5.5. The system was set to 25° C. For each measurement the sample buffer was the system buffer, additionally supplemented with 1 mg/ml CMD (Carboxymethyldextran, Fluka).

An antibody capture system was established. 13000 MAb<h-Fc-pan>M-R10Z8E9-IgG (Roche) were immobilized at 25° C. at 18 µg/ml in 10 mM sodium acetate buffer pH 5.0, by EDC/NHS coupling as described by the manufacturer. The capture system was regenerated by an injection at 20 µl/min with HBS buffer (100 mM HEPES pH 7.4, 1.5 M NaCl, 0.05% (w/v) Tween 20), followed by a 1 min 15 sec injection with 10 mM NaOH and two 10 mM glycine buffer pH 2.5 injections for 1 min. Antibodies were captured were injected for 30 sec at 10 µl/min at 80 nM concentration diluted in the respective system buffer. After antibody capturing the system was washed by 2.5-fold concentrated system buffer for 30 sec at 50 µl/min followed by 2 min baseline stabilization. Concentration-dependent analyte series were injected in 1:3 dilution steps, from 0 nM (buffer control) 0.4 nM, 1.1 nM, two injections at 3.3 nM, 30 nM. The analyte contact time was 3 min and the dissociation time was 10 min. Analyte kinetics were performed at 50 µl/min.

Human antibodies were captured as ligands on the sensor surface:

Human normal IgG as positive control (H-N-IgG, Id.: 11717570, Roche),
anti-human CCL2 mAb (humanized 11k2: CCL2-0002),
anti-human CCL2 mAb (AB912, CCL2-0003), and
anti-human CCL2 mAb (CNTO888, CCL2-0004);
system buffer as negative control.

The Biaevaluation software V.3.0 was used according to the instructions of the manufacturer GEHC. A 1:1 binding model with $R_{MAX}$ local was applied to determine kinetic rates.

| | humanized 11K2 CCL2-0002 | | ABN912 CCL2-0003 | | CNTO888 CCL2-0004 | |
|---|---|---|---|---|---|---|
| pH | KD [nM] | t ½-diss. [min] | KD [nM] | t ½-diss. [min] | KD [nM] | t ½-diss. [min] |
| 8.3 | 0.003 | 1155 | 0.004 | 35 | 0.01 | 135 |
| 7.9 | 0.02 | 165 | 0.004 | 25 | 0.01 | 138 |
| 7.4 | 0.02 | 163 | 0.01 | 33 | 0.02 | 130 |
| 7.1 | 0.01 | 215 | 0.02 | 20 | 0.02 | 124 |
| 6.7 | 0.01 | 292 | 0.2 | 8 | 0.03 | 103 |
| 6.3 | 0.003 | 1155 | 1 | 3 | 0.02 | 128 |
| 5.9 | 0.01 | 287 | 13 | 1 | 0.04 | 61 |
| 5.5 | 0.01 | 118 | 2000 | 0.03 | 0.06 | 31 |

Crossreactivity CCL homologs

As CCL2 (MCP-1) has high homology to CCL7 (MCP-3), CCL8 (MCP-2), CCL13 (MCP-4), and these CCL chemokines are able to bind to CCR2, the binding of anti-CCL2 antibodies to these homologs was assessed. Results are shown in FIG. 1, FIG. 1A, FIG. 1B, and FIG. 1C. With the exception of CNTO888 which was described to have selectivity to CCL2 (Mol Immunol. 2012 June; 51(2): 227-33), the other antibodies tested bound to either CCL7 or CCL8 (showed cross-reactivity to either CCL7 or CCL8).

Biacore assay method: The binding of anti-CCL2 antibodies to the CCL homologs e.g. CCL2 (MCP-1), CCL8 (MCP-2), CCL7 (MCP-3), and CCL13 (MCP-4) were assessed at 25° C. using Biacore T200 instrument (GE Healthcare). Mouse anti-human IgG (Fc) (GE Healthcare)

was immobilized on each flow cells of a CM4 sensor chip using amine coupling kit (GE Healthcare) according to the recommended settings by the manufacturer. Antibodies and analytes were diluted into ACES pH 7.4 buffer (20 mM ACES, 150 mM NaCl, 1 mg/ml BSA, 0.05% Tween 20, 0.005% NaN3). Antibodies were captured onto the anti-Fc sensor surfaces, then recombinant human CCL homologs proteins was injected over the flow cell at 5 nM and 20 nM. Wild type CCL2 (MCP-1), CCL8 (MCP-2), CCL7 (MCP-3), and CCL13 (MCP-4) were commercially available from R&D Systems, whereas monomer CCL2 (P8A variant) was in-house generated antigen. Sensor surface was regenerated each cycle with 3M MgCl2. Binding sensorgram was processed using Biacore T200 Evaluation software, version 2.0 (GE Healthcare).

Functional Characterization (Biological)

CCR2 Signaling I—Calcium Flux Assay

THP-1 (human acute monocytic leukemia cell line; ATCC TIB-202) cells were cultivated in RPMI 1640, 10% FBS, 1 mM sodium pyruvate, 10 mM HEPES, 50 µM ß-mercaptoethanol (supplier Thermo Fisher Scientific). On the assay day the cell density was adjusted to $8.33 \times 10^5$ cells/ml in 25.8 ml assay medium (RPMI 1640 w/o FBS). FLIPR® Calcium Assay Kits (FLIPR Calcium 4 Assay Kit, Cat #R8142, Molecular Devices) were used for detecting intracellular calcium changes in a homogeneous assay format.

A dye loading solution was prepared by mixing two vials of component A with 20 ml component B (HBSS buffer plus 20 mM HEPES, pH 7.4) according to the instructions of the manufacturer Molecular Devices. 516 µl 1 M Hepes (final assay concentration: 10 mM) is added followed by 516 µl 250 mM probenecid (final assay concentration: 2.5 mM). For the stock solution dissolve 65.4 mg probenecid (Sigma P8761) in 465 µl 1 N NaOH and add 465 µl 1×HBSS (Thermo Fisher Scientific). 25.8 ml loading buffer was mixed with 25.8 ml assay medium with cells sufficient for e.g. four microtiter plates (52.6 ml volume is needed; $10^6$ THP-1/ml). 120 µl cell suspension in loading buffer was transferred to each well of a black F-bottom 96-well cell culture plate. The plates were incubated at room temperature for 3-4 hours.

In the meantime, the antibody and the ligand solution were prepared. Eight concentrations of each antibody from 30 µg/ml to 0.025 µg/ml (no serial dilution, final concentration in wells) have been tested. Each concentration was tested on two plates. All dilutions were prepared in assay medium as 10-fold concentrated solution. As reference antibody human CCL2/JE/MCP-1 Antibody (R&D Systems Cat #MAB279) was used. Ligand CCL2 (R&D Systems Cat #279-MC-10) was prepared by dissolving 50 µg CCL2 lyophilisate in 500 µl RPMI 1640 (100 µg/ml) and transferring 400 µl into 10 ml assay medium (4 µg/ml stock solution). As stimulation control ionomycin (Sigma Cat #I-0634) was used (1 mg ionomycin dissolved in 1340 µl DMSO (Sigma Cat #D-8779), 1 mM). 10 µl of the 1 mM stock solution was diluted in 1990 µl assay medium (5 µM, final assay concentration 500 nM). 100 µl was pipetted in the corresponding control wells of the polypropylene MTP.

The antibody dilutions and CCL2 were preincubated in two V-shape polypropylene 96 well plates. 50 µl of the 4 µg/ml stock solution CCL2 (final 400 ng/ml CCL2) and 50 µl of the 10-fold concentrated antibody dilution were pipetted into the well. Plates were incubated for 30-60 min at room temperature.

After incubation, the cell plate and the compound plate were transferred directly to the FlexStation® 3 (Molecular Devices) read position and the calcium assay was performed as described in the system manual (excitation 485 nm, emission 525 nm). The read out was done at several seconds interval.

Results:

TABLE 1

40 ng/ml PMA and 4 µM ionomycin were used as positive controls. The table includes mean of $EC_{50}$ of n = 2.

| Anti-CCL2 antibodies | | Inhibition of CCR2 signaling | |
|---|---|---|---|
| Antibody | Alias | EC50 [µg/ml] | EC50 [nM] |
| 1A4 | CCL2-0008 | 4.2 | 28.0 |
| 1A5 | CCL2-0009 | 2.2 | 14.6 |
| 1G9 | CCL2-0010 | 2.4 | 16 |
| 2F6 | CCL2-0014 | 8.7 | 3.9 |
| Mab279 (R&D) | Commercial reference | 2.6 | 17.4 |
| murine 11K2 (11K2m) | X-0048 | 4.5 | 30.0 |
| Humanized 11K2 (11K2) | CCL2-0002 | 2.1 | 14.0 |
| AB912 | CCL2-0003 | 1.9 | 12.7 |
| CNTO888 | CCL2-0004 | 2.7 | 18 |

Potency of Anti-CCL2 Antibodies to Inhibit CCL2-Induced Internalization of the CCR2 Receptor Expressed on Monocytes To prevent the ligand-induced CCR2 internalization on myeloid cells we set up an in vitro assay and characterized anti-CCL2 antibodies. Monocytes were isolated from peripheral blood of healthy donors by magnetic separation using a commercial kit (Stemcell, cat no. #15068). For blocking of FcγRs, monocytes were pre-incubated with normal human IgG (Privigen, CSL Behring) at a final concentration of 500 µg/ml on ice for 50 min in FACS buffer (PBS+0.2% BSA). Cells were then centrifuged for 10 min (300×g, 4° C.), washed one more time with FACS buffer and stored on ice. Anti-CCL2 antibody dilutions (50 µl each) were prepared (in parallel approaches at 4° C. and 37° C.) in 96 U-bottom wells (BD). Monocytes were split, resuspended in medium (RPMI 1640; 10% FCS; 2 mM L-Glutamine) and incubated at 4° C. and 37° C., respectively, until further usage. Recombinant CCL2 (50 µl; at a final concentration of 100 ng/ml) was added to the prepared antibody dilutions (at variable concentrations) both at 4° C. and 37° C. 100 µl monocyte suspension ($2 \times 10^5$ cells/well) was added to the CCL2/anti-CCL2 mixes at a total volume of 200 µl and cells were incubated at 4° C. and 37° C. for 1 h 30 min before centrifugation at 300×g, 4° C. From now on all steps were conducted with pre-cooled buffers: cells were washed with 250 µl FACS buffer and additionally, cells were stained against CCR2 receptor (using a commercial CCR2-APC conjugate or appropriate isotype ctrl-APC according standard FACS protocols: Aliquots were stained with 5 µl/$10^6$ cell with CD192 (CCR2) APC (BioLegend, #357208, clone K036C2/mIgG2a κ) as well as an appropriate isotype ctrl antibody: 20 µl/$10^6$ cell mIgG2a k APC BD Biosciences, #400222, clone MOPC-173).

Then the receptor expression was analyzed on a FACS Canto II and the CCR2 internalization was calculated as follows:

No internalization: Cells analyzed in the absence of ligand (rec. CCL2) incubation.

100% internalization: Maximally reduced CCR2 expression level on cells previously incubated with rec. CCL2

| Anti-CCL2 antibodies | | Inhibition of CCR2 internalization | |
|---|---|---|---|
| Antibody | Alias | EC50 [µg/ml] | EC50 [nM] |
| 1A4 | CCL2-0008 | 2.52 | 16.81 |
| 1A5 | CCL2-0009 | 2.37 | 15.77 |
| 1G9 | CCL2-0010 | 2.16 | 14.42 |
| 2F6 | CCL2-0014 | 2.41 | 1.09 |
| 11K2 (murine) | X-0048 | 1.98 | 13.19 |
| AB912 | CCL2-0003 | 1.99 | 13.25 |
| CNTO888 | CCL2-0004 | 2.00 | 13.36 |
| Mab279 (R&D) | Commercial reference | 1.98 | 13.22 |

Inhibition of CCL2-Mediated Chemotaxis on Human THP-1 Cells

The migration of CCR2+THP1 cells towards a CCL2 gradient was tested as follows. Monocytic THP1 cells (ATCC©G TIB-202™) were cultured in RPM1 1640 medium (PAN, cat. no. #P04-17500) supplemented with FCS and L-Glutamine. Cells were normally passaged two to three times prior to use in the migration assay and then starved overnight in media with reduced FSC content (1.5% instead of 10% FCS). Cells were counted and incubated with 10 µg/ml normal human IgG (Invitrogen, cat. no. #12000; to block FcgRs) for 15 minutes at room temperature.

In the meantime, anti-CCL2 antibodies (and/or controls) were added to the lower chamber of a HTS Transwell 96 well plate system (Corning, cat. no. #3386; 3 µm pore size) containing serum-free media with 25 ng/ml rhCCL-2 (R&D Systems, cat. no. #279-MC). Then the insert-plates were stuck into the lower-chamber-plate and 75 µl ($1.5 \times 10^5$ cells) of the above mentioned cell-suspension (including the IgG-block) were added with or without 5 µg/ml antibody/isotype into each insert. Plates were covered and incubated over night at 37° C. in an CO2 incubator (5% CO2).

The insert-plate was removed and Cell-titer-glo substrate (Promega, cat. no. #G758) was added to each well of lower-chamber-plate to measure viability of migrated cells. After incubation for 1 hour on a shaker with 300 rpm (cover plate sealed), 200 µl of each well were transferred to a Microfluor black 96 well-plate (VWR, cat. no. #735-0527) and luminescence was measured (luminescence-reader e.g. Bio-Tek, Tecan). Fold change was calculated as the ratio between number of migrated cells (Cell Titer Glo, RLU) with IgG control antibody and anti-CCL2 antibodies. Shown in the following Table 2 are the results of 5-10 replicates per condition:

TABLE 2

| Antibody | Alias | THP1 chemotaxis [fold change compared to IgG control] |
|---|---|---|
| 1A4 | CCL2-0008 | 4.5 |
| 1A5 | CCL2-0009 | 3.6 |
| 1G9 | CCL2-0010 | 0.9 |
| 2F6 | CCL2-0014 | 6.7 |
| Mab279 (R&D) | — | 3.7 |
| Murine 11K2 (11K2m) | X-0048 | 6.9 |
| Humanized 11K2 (11K2) | CCL2-0002 | 7.2 |
| ABN912 | CCL2-0003 | 6.5 |
| CNTO888 | CCL2-0004 | 4.9 |

Evaluation of Human CCL2 Immune Complex Sweeping with Monospecific (Monoparatopic) Anti-CCL2 Antibodies in Mice To evaluate the ability of monoparatopic antibodies to form immune complex with wild type human CCL2, pre-formed immune complexes consisting of anti-CCL2 monoparatopic antibody (20 mg/kg) and wild type human CCL2 (0.1 mg/kg) were administered at a single dose of 10 ml/kg into the caudal vein of human FcRn transgenic mice (B6.Cg-Fcgrt$^{tm1Dcr}$Tg(FCGRT)32Dcr/DcrJ, Jackson Laboratory). Blood was collected 5 minutes, 7 hours, 1 day, 2 days, 3 days and 7 days after administration. Serum was prepared by centrifuging the blood immediately at 14,000 rpm for 10 minutes in 4° C. The serum was stored at or below −80° C. until measurement. The monoparatopic antibodies tested are listed in the Table 3 below. Antibodies with SG1 Fc have Fc gamma receptor binding similar to wild-type while antibodies with SG105 Fc are Fc gamma receptor binding silent.

The effect of immune complex sweeping of each anti-CCL2 monoparatopic antibody on hCCL2 clearance in vivo were assessed by comparing anti-CCL2 antibody with Fc gamma receptor binding (SG1, =IgG1 wild type with intact Fc gamma receptor binding; solid line) and anti-CCL2 antibody with Fc gamma receptor binding silent (SG105, =IgG1 with no Fc gamma receptor binding; dotted line), as shown in FIG. 2a-FIG. 2g. The respective FIG. 2a-FIG. 2g show the serum concentration of hCCL2 over time after injection of the pre-formed immune complexes consisting of hCCL2 and the respective anti-CCL2 antibody (with the two different Fc parts: SG1=IgG1 wild type with intact Fc gamma receptor binding and SG105=IgG1 with no Fc gamma receptor binding) into FcRn transgenic mice. The antibody profiles were analyzed by non-compartmental analysis using Phoenix 64 (Pharsight/Certara). The AUCinf was estimated by linear-log trapezoidal rule extrapolated to infinity. Clearance values are defined as Dose/AUCinf. This difference in clearance was also expressed as fold change, which is calculated by dividing the hCCL2 clearance of antibodies with Fc gamma receptor binding (SG1) by the hCCL2 clearance of antibodies with Fc gamma receptor binding silent (SG105) (Table 3 below). The data in the Table 3 below indicates that the clearance of human CCL2 by Fc gamma receptor binding antibodies (SG1=IgG1 wild type with intact Fc gamma receptor binding) was similar to that by Fc gamma receptor binding silent antibodies (SG105, with no Fc gamma receptor binding) for all the monoparatopic antibodies tested. This suggests that immune complex-mediated sweeping of CCL2 by the tested monoparatopic antibodies was not efficient.

TABLE 3

Clearance values of wild type CCL2 after administration of pre-formed immune complex of anti-CCL2 monospecific antibody (20 mg/kg) and wild type human CCL2 (0.1 mg/kg) (either IgG1 wild type (SG1) or IgG1 Fc receptor silenced (SG105)

| | Clearance (ml/day/kg) | Fold Change (wild type IgG1 (SG1) vs Fc receptor silenced IgG1 (SG105)) |
|---|---|---|
| CNTO888-SG1 | 14.05 | 1.60 |
| CNTO888-SG105 | 8.80 | |
| 11K2-SG1 | 80.60 | 1.69 |
| 11K2-SG105 | 47.83 | |

TABLE 3-continued

Clearance values of wild type CCL2 after administration of pre-formed immune complex of anti-CCL2 monospecific antibody (20 mg/kg) and wild type human CCL2 (0.1 mg/kg) (either IgG1 wild type (SG1) or IgG1 Fc receptor silenced (SG105)

| | Clearance (ml/day/kg) | Fold Change (wild type IgG1 (SG1) vs Fc receptor silenced IgG1 (SG105)) |
|---|---|---|
| ABN912-SG1 | 67.06 | 0.99 |
| ABN912-SG105 | 67.84 | |
| 1A4-SG1 | 38.93 | 1.66 |
| 1A4-SG105 | 23.39 | |
| 1A5-SG1 | 20.08 | 0.95 |
| 1A5-SG105 | 21.14 | |
| 1G9-SG1 | 14.02 | 0.87 |
| 1G9-SG105 | 16.07 | |
| 2F6-SG1 | 21.49 | 1.03 |
| 2F6-SG105 | 20.94 | |

Measurement of Total Human CCL2 Concentration in Serum by Electrochemiluminescence (ECL)

The concentration of total human CCL2 in mouse serum was measured by ECL. 3 ug/mL of anti-CCL2 antibody (F7 (Biolegend) or clone MAB679 (R&D Systems)) was immobilized onto a MULTI-ARRAY 96-well plate (Meso Scale Discovery) overnight before incubating in blocking buffer for 2 hours at 30° C. Anti-CCL2 MAB679 was used as capture antibody for samples containing humanized 11K2, 1A4 or 1A5 antibodies. Anti-CCL2 clone 5D3-F7 was used for samples containing ABN912, CNTO888, 1G9, 2F6H antibodies. Human CCL2 calibration curve samples, quality control samples and mouse serum samples were prepared by diluting in dilution buffer and incubating with excess drug for 30 minutes at 37° C. After that, the samples were added onto anti-CCL2-immobilized plate, and allowed to bind for 1 hour at 30° C. before washing. Next, SULFO TAG NHS-ester (Meso Scale Discovery) labelled anti-human Fc (clone: JDC-10, SouthernBiotech) was added and the plate was incubated for 1 hour at 30° C. before washing. Read Buffer T (×4) (Meso Scale Discovery) was immediately added to the plate and signal was detected by SECTOR Imager 2400 (Meso Scale Discovery). The human CCL2 concentration was calculated based on the response of the calibration curve using the analytical software SOFTmax PRO (Molecular Devices).

Measurement of Anti-CCL2 Antibody Concentration in Serum by Enzyme-Linked Immunosorbent Assay (ELISA)

The concentration of anti-CCL2 antibody in mouse serum was measured by ELISA. Anti-human IgG kappa-chain (Antibody Solutions) was dispensed onto a Nunc MaxiSorp plate (Thermofisher) and allowed to stand overnight at 4 degrees C. to prepare anti-human IgG-immobilized plates. Calibration curve and samples were prepared with 1% pooled mouse serum. Then, the samples were dispensed onto the anti-human IgG-immobilized plates, and allowed to stand for 1 hour at 30 degrees C. Subsequently, goat anti-human IgG (gamma-chain specific) with HRP conjugate (Southern Biotech) was added to react for 1 hour at 30 degrees C. Chromogenic reaction was carried out using TMB substrate (Life Technologies) as a substrate. After stopping the reaction with 1 N sulfuric acid (Wako), the absorbance at 450 nm was measured by a microplate reader. The concentration in mouse plasma was calculated from the absorbance of the calibration curve using the analytical software SOFTmax PRO (Molecular Devices).

Evaluation of Endogenous Mouse CCL2 Immune Complex Sweeping with Monoparatopic Antibody in Mice In addition to the results above (which suggests that immune complex-mediated sweeping of CCL2 by the tested monoparatopic antibodies was not efficient) a further evaluation was conducted.

To evaluate the ability of monoparatopic antibodies to form and clear immune complex with endogenous mouse CCL2, mouse cross-reactive 11K2 anti-CCL2 monoparatopic antibodies was administered to mice. Humanized 11K2H2-SG1 (IgG1 wild type=Fc gamma receptor binding) or humanized 11K2-SG105 (Fc gamma receptor binding silent) antibodies were intravenously administered at a single dose of 20 mg/kg at a single dose of 10 ml/kg into the caudal vein of Balb/c mice. Blood was collected pre-administration, 5 minutes, 7 hours, 1 day, 2 days, 3 days and 7 days after administration. Serum was prepared by centrifuging the blood immediately at 14,000 rpm for 10 minutes in 4° C. The serum was stored at or below −80° C. until measurement.

Figure 1A:
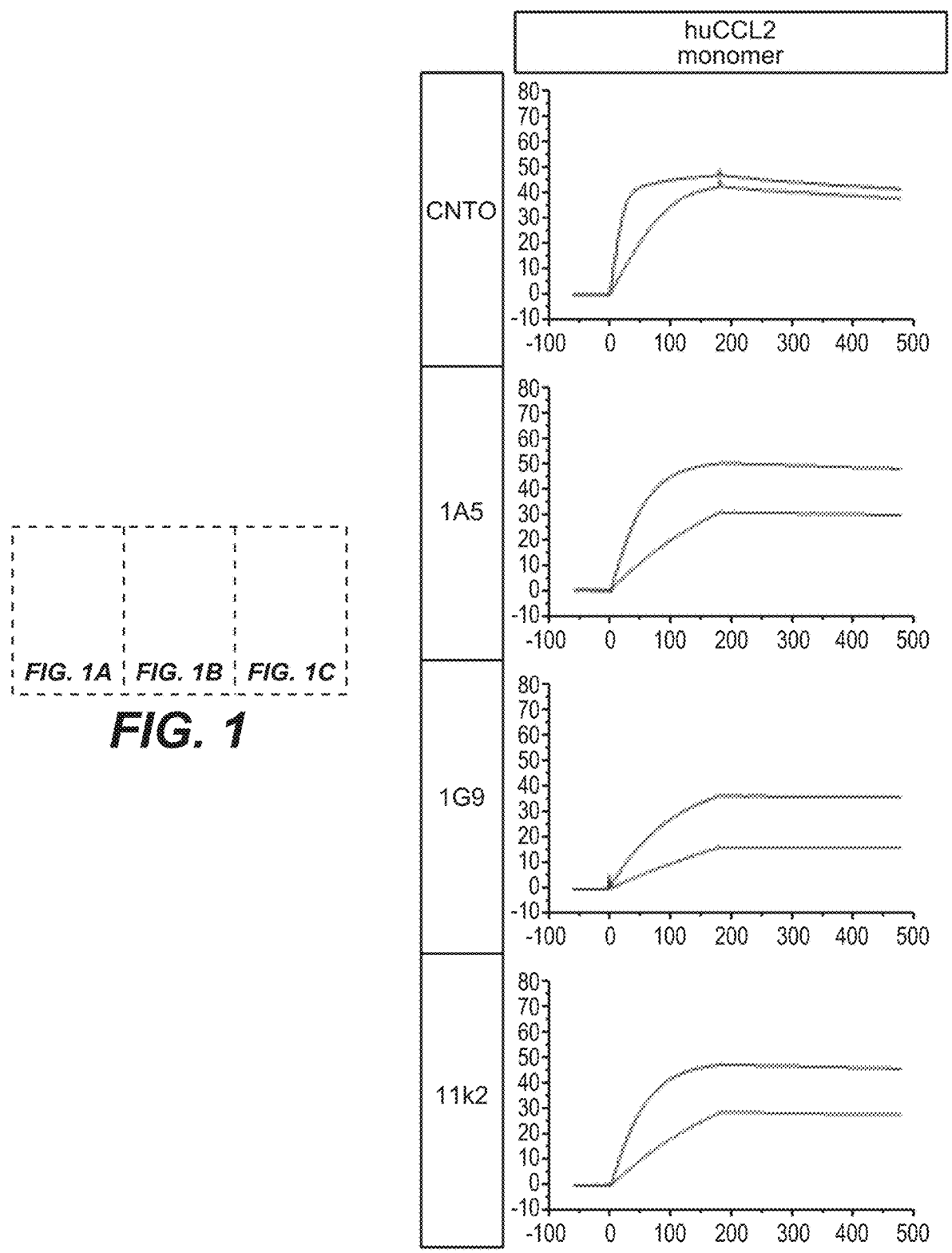
Figure 1B:
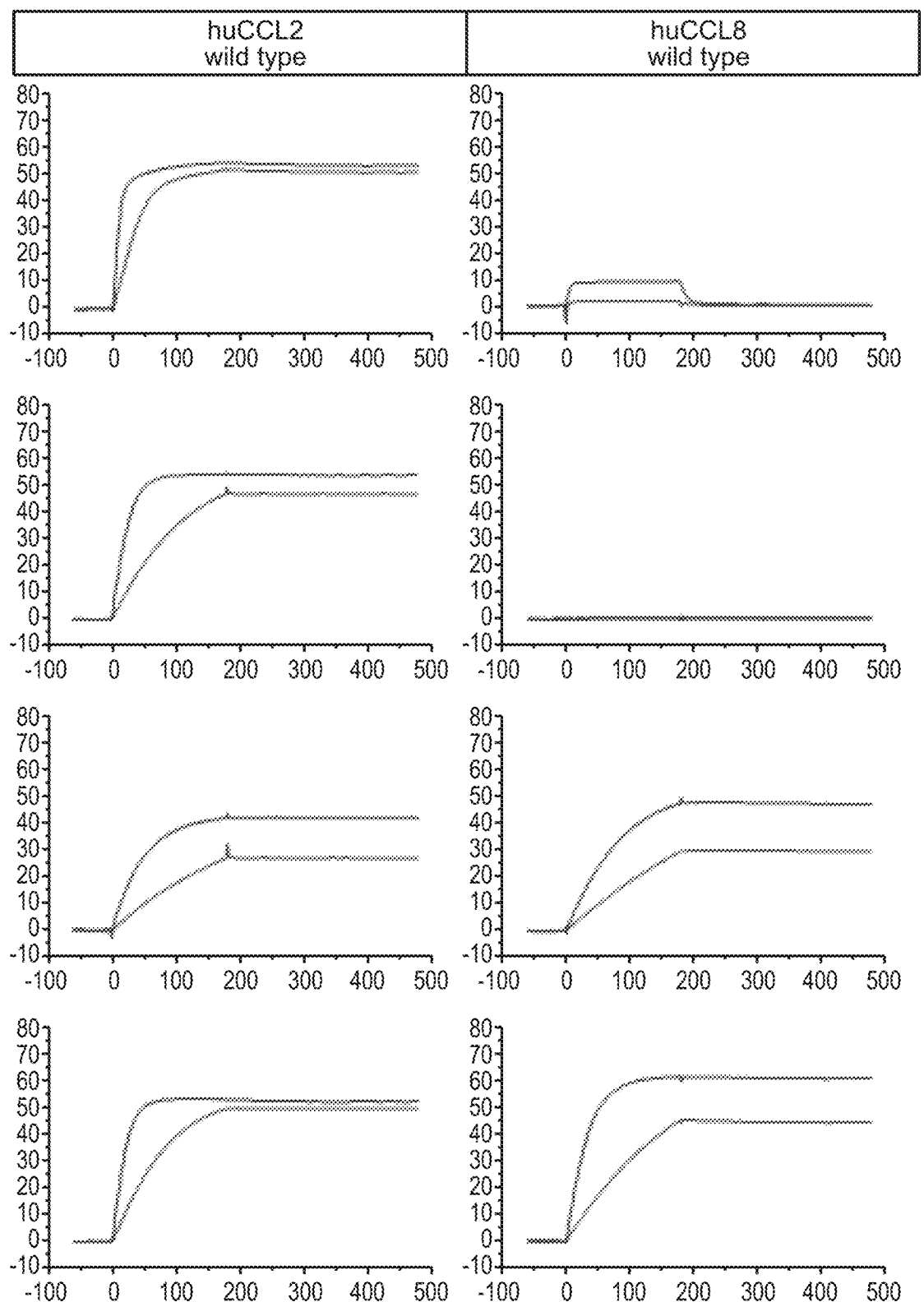
Figure 1C:
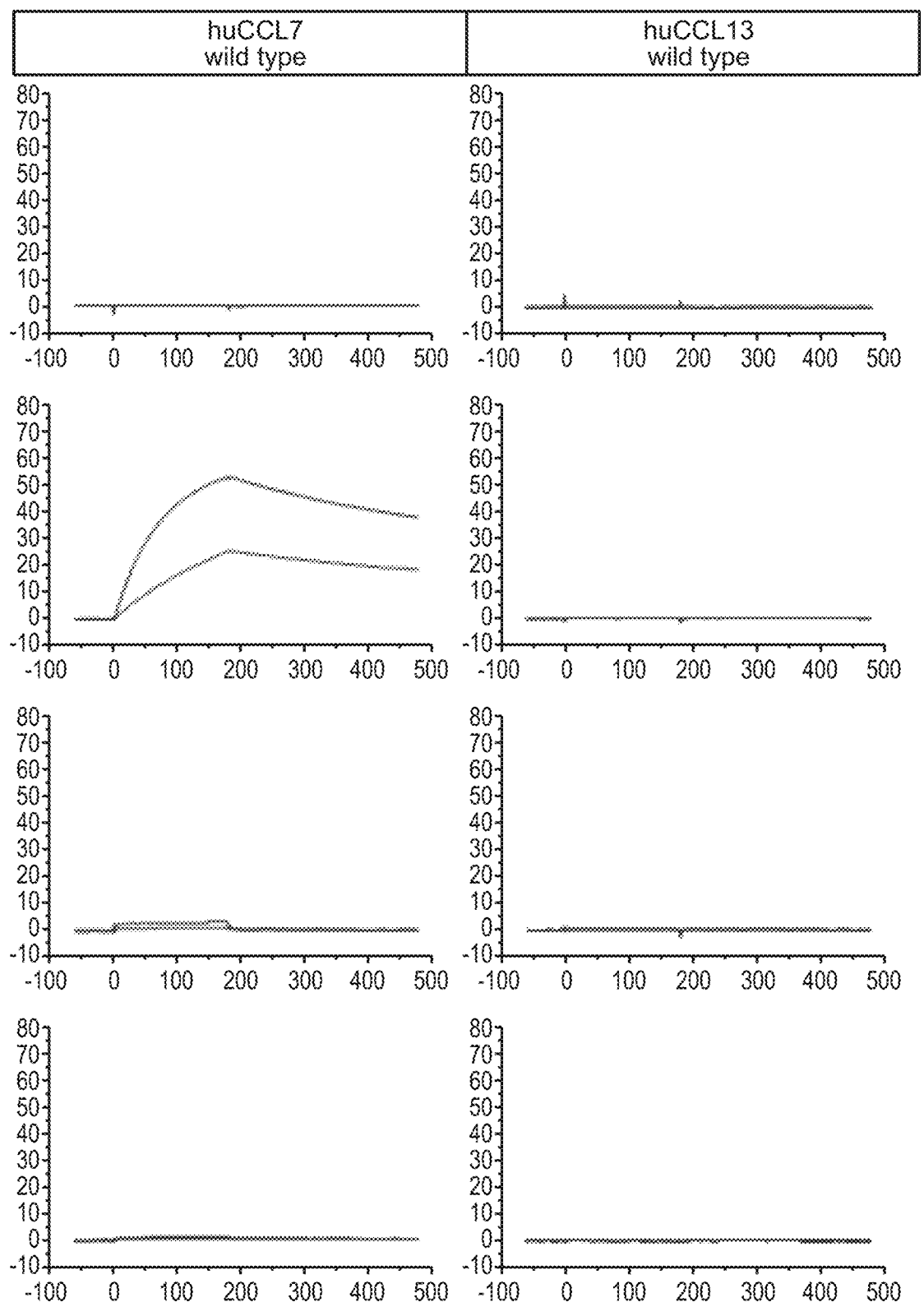
Figure 2A:
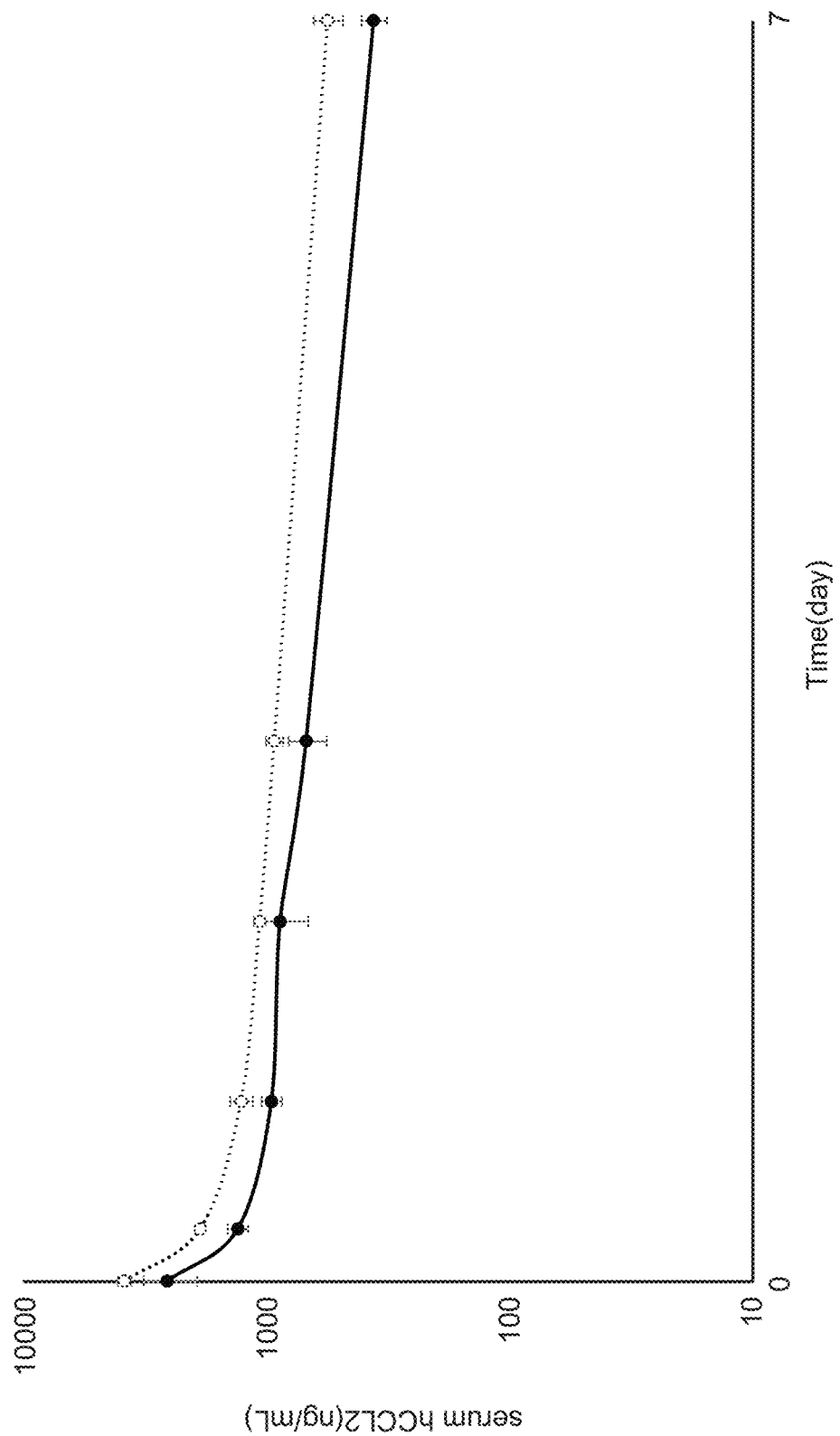
FIG. 2a: Serum concentration of hCCL2 over time after i.v. injection of pre-formed immune complex consisting of a) solid line: 0.1 mg/kg human CCL2 (hCCL2) and 20 mg/kg monospecific anti-CCL2 antibody CNTO888-SG1 (wild type IgG1) or b) dotted line: 0.1 mg/kg human CCL2 (hCCL2) and 20 mg/kg monospecific anti-CCL2 antibody CNTO888-SG105 (Fc receptor binding silenced IgG1) into FcRn transgenic mice.
Figure 2B:
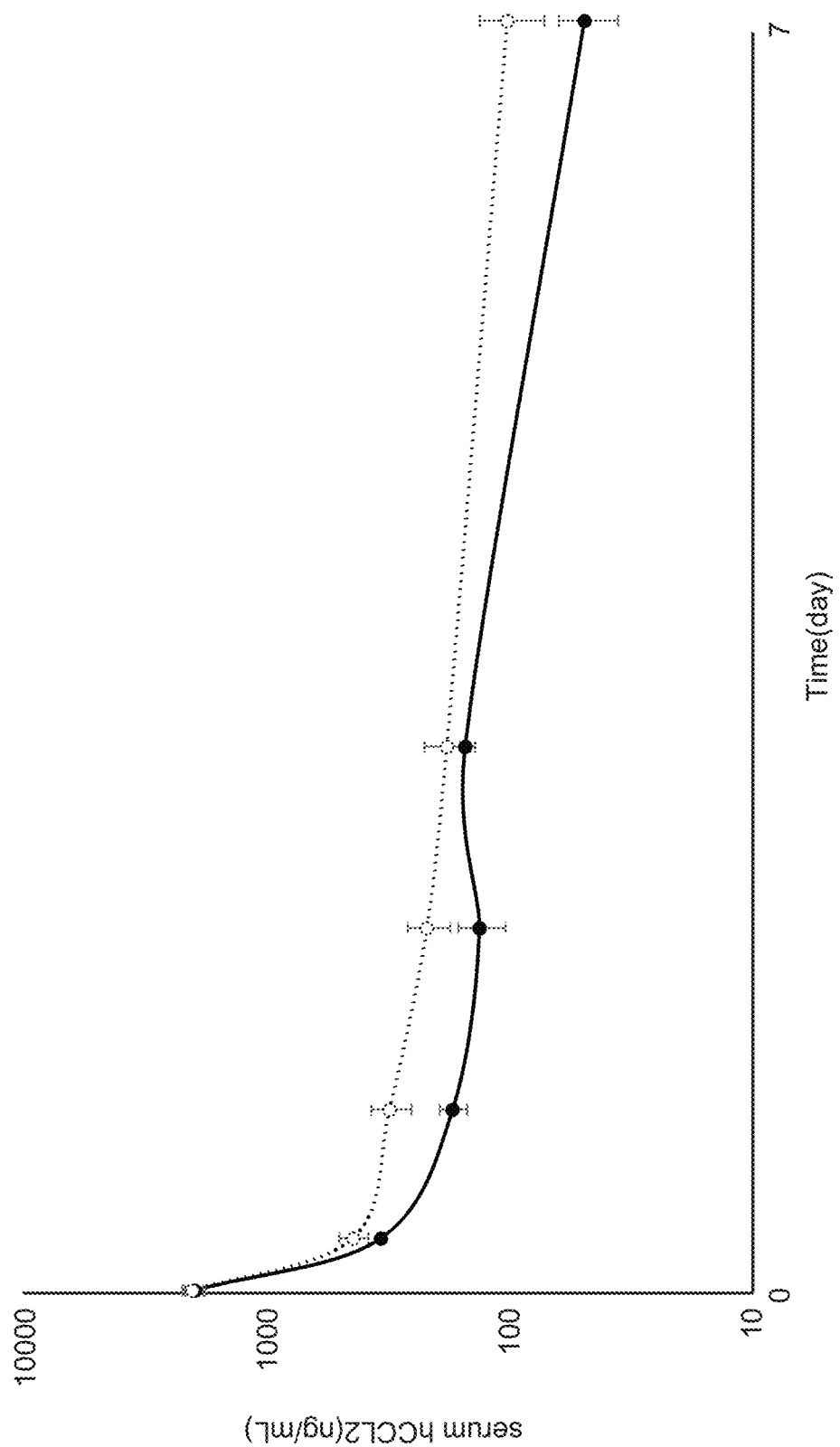
FIG. 2b: Serum concentration of hCCL2 over time after i.v. injection of pre-formed immune complex consisting of a) solid line: 0.1 mg/kg human CCL2 (hCCL2) and 20 mg/kg monospecific anti-CCL2 antibody 11K2-SG1 (wild type IgG1) or b) dotted line: 0.1 mg/kg human CCL2 (hCCL2) and 20 mg/kg monospecific anti-CCL2 antibody 11K2-SG105 (Fc receptor binding silenced IgG1) into FcRn transgenic mice.
Figure 2C:
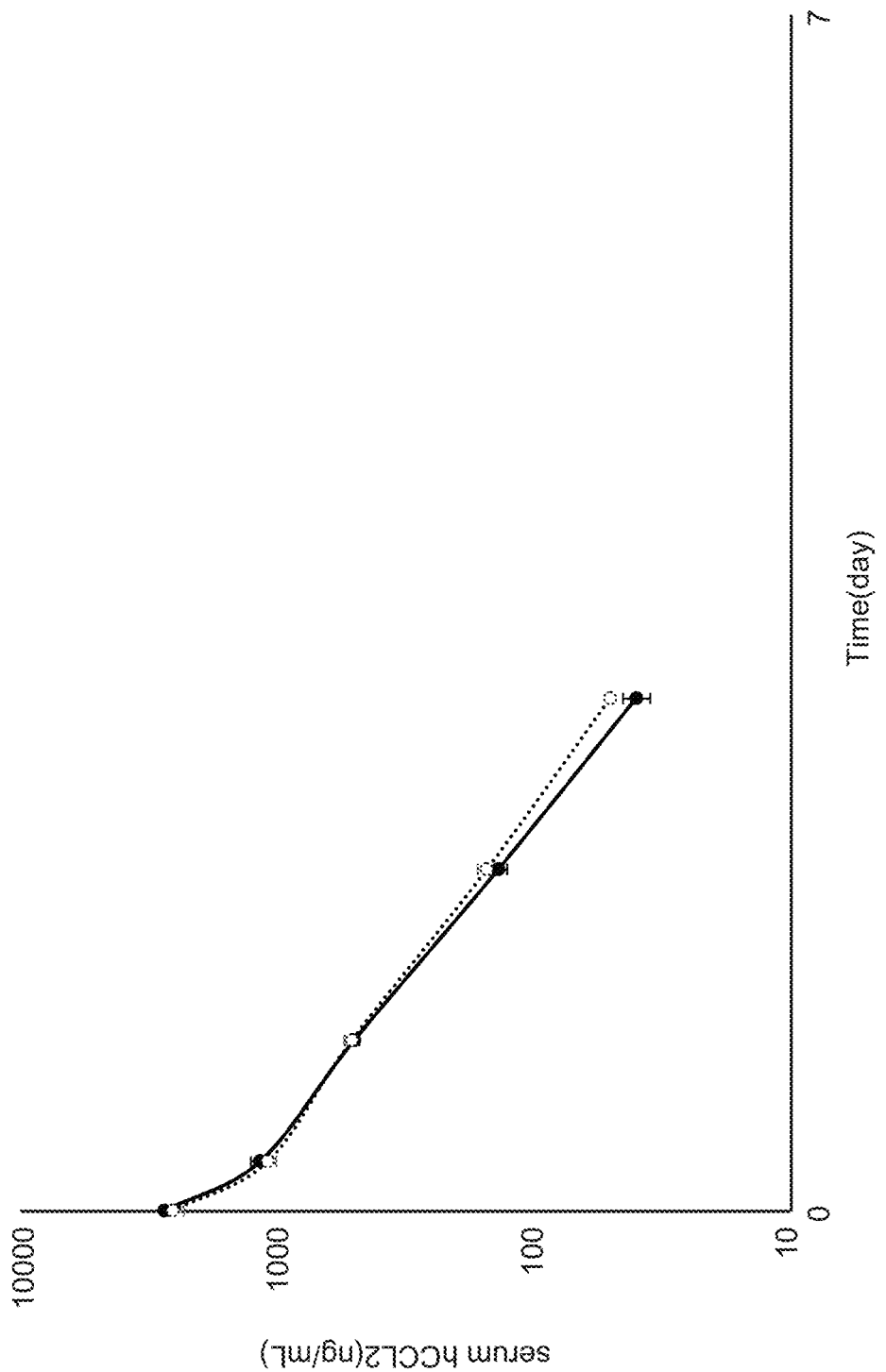
FIG. 2c: Serum concentration of hCCL2 over time after i.v. injection of pre-formed immune complex consisting of a) solid line: 0.1 mg/kg human CCL2 (hCCL2) and 20 mg/kg monospecific anti-CCL2 antibody ABN912-SG1 (wild type IgG1) or b) dotted line: 0.1 mg/kg human CCL2 (hCCL2) and 20 mg/kg monospecific anti-CCL2 antibody ABN912-SG105 (Fc receptor binding silenced IgG1) into FcRn transgenic mice.
Figure 2D:
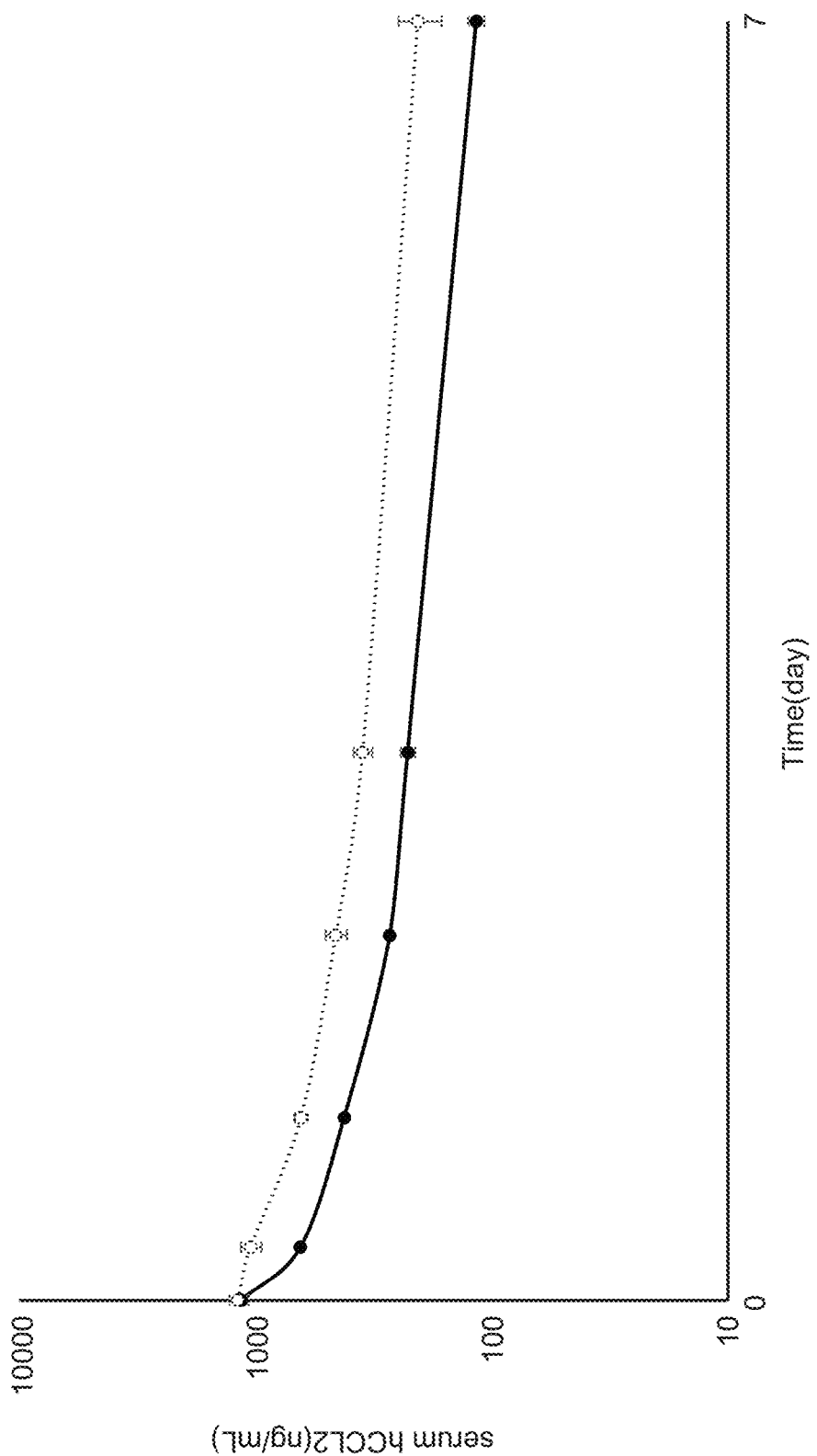
FIG. 2d: Serum concentration of hCCL2 over time after i.v. injection of pre-formed immune complex consisting of a) solid line: 0.1 mg/kg human CCL2 (hCCL2) and 20 mg/kg monospecific anti-CCL2 antibody 1A4-SG1 (wild type IgG1) or b) dotted line: 0.1 mg/kg human CCL2 (hCCL2) and 20 mg/kg monospecific anti-CCL2 antibody 1A4-SG105 (Fc receptor binding silenced IgG1) into FcRn transgenic mice.
Figure 2E:
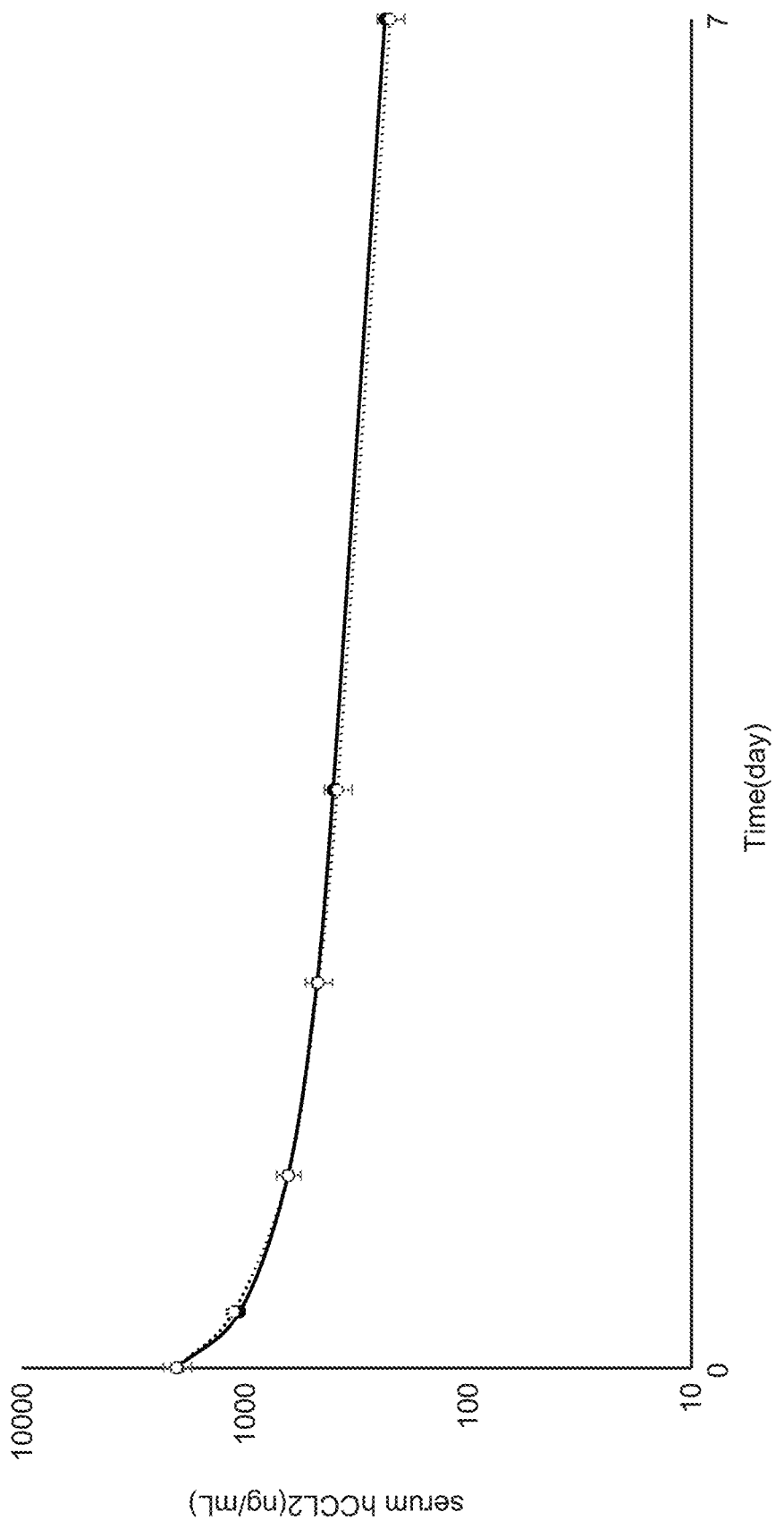
FIG. 2e: Serum concentration of hCCL2 over time after i.v. injection of pre-formed immune complex consisting of a) solid line: 0.1 mg/kg human CCL2 (hCCL2) and 20 mg/kg monospecific anti-CCL2 antibody 1A5-SG1 (wild type IgG1) or b) dotted line: 0.1 mg/kg human CCL2 (hCCL2) and 20 mg/kg monospecific anti-CCL2 antibody 1A5-SG105 (Fc receptor binding silenced IgG1) into FcRn transgenic mice.
Figure 2F:
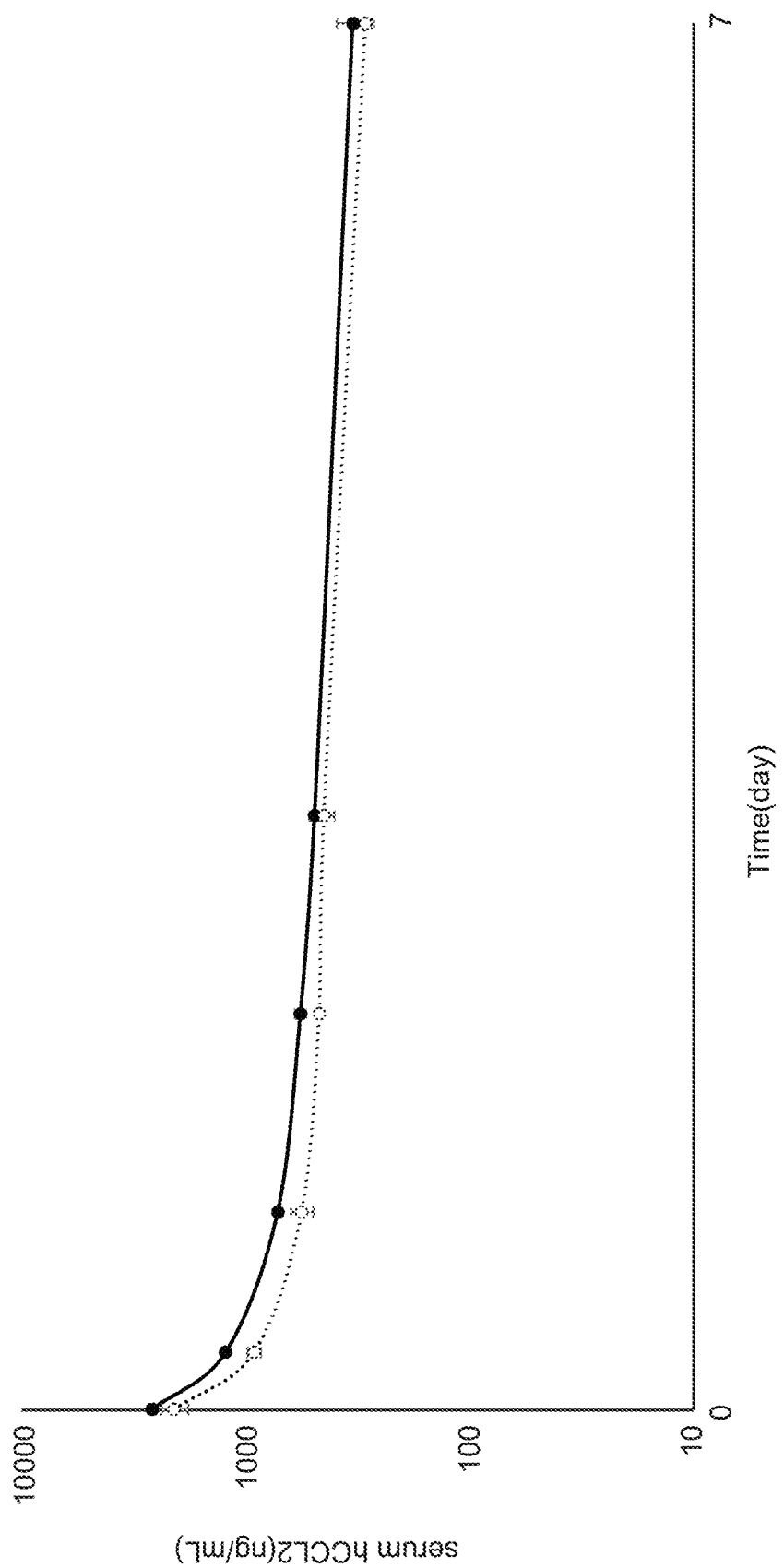
FIG. 2f: Serum concentration of hCCL2 over time after i.v. injection of pre-formed immune complex consisting of a) solid line: 0.1 mg/kg human CCL2 (hCCL2) and 20 mg/kg monospecific anti-CCL2 antibody 1G9-SG1 (wild type IgG1) or b) dotted line: 0.1 mg/kg human CCL2 (hCCL2) and 20 mg/kg monospecific anti-CCL2 antibody 1G9-SG105 (Fc receptor binding silenced IgG1) into FcRn transgenic mice.
Figure 2G:
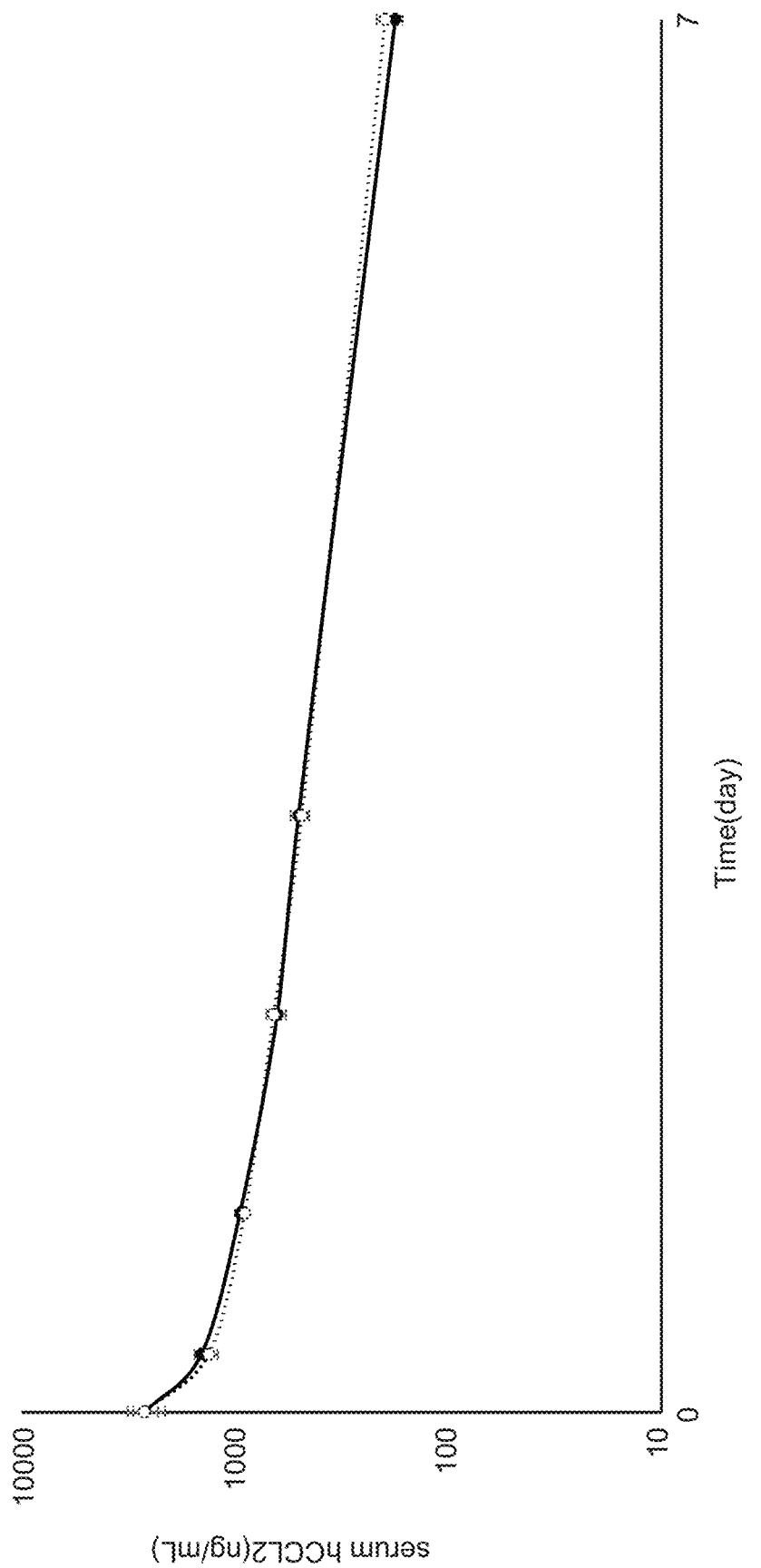
FIG. 2g: Serum concentration of hCCL2 over time after i.v. injection of pre-formed immune complex consisting of a) solid line: 0.1 mg/kg human CCL2 (hCCL2) and 20 mg/kg monospecific anti-CCL2 antibody 2F6-SG1 (wild type IgG1) or b) dotted line: 0.1 mg/kg human CCL2 (hCCL2) and monospecific anti-CCL2 antibody 20 mg/kg 2F6-SG105 (Fc receptor binding silenced IgG1) into FcRn transgenic mice.
Figure 3A:
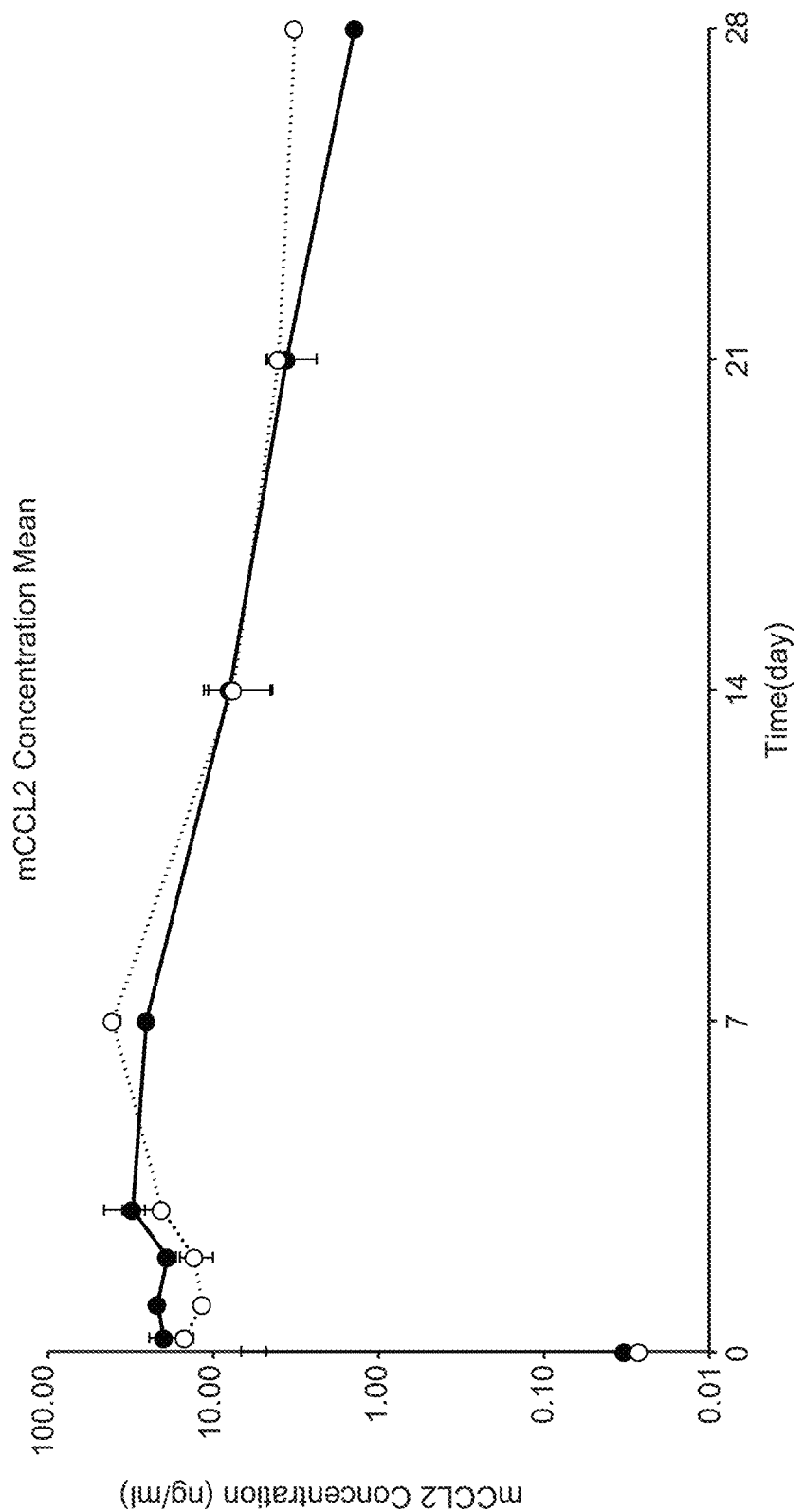
FIG. 3a and FIG. 3b: Shows the time course of serum total mouse CCL2 concentration (FIG. 3a) and antibody-time profile (FIG. 3b) after i.v. injection of a) solid line: 20 mg/kg monospecific anti-CCL2 antibodies 11K2-SG1 (wild type IgG1) and b) dotted line: 20 mg/kg monospecific anti-CCL2 antibodies 11K2-SG105 (Fc receptor binding silenced IgG1) in mice.
Figure 3B:
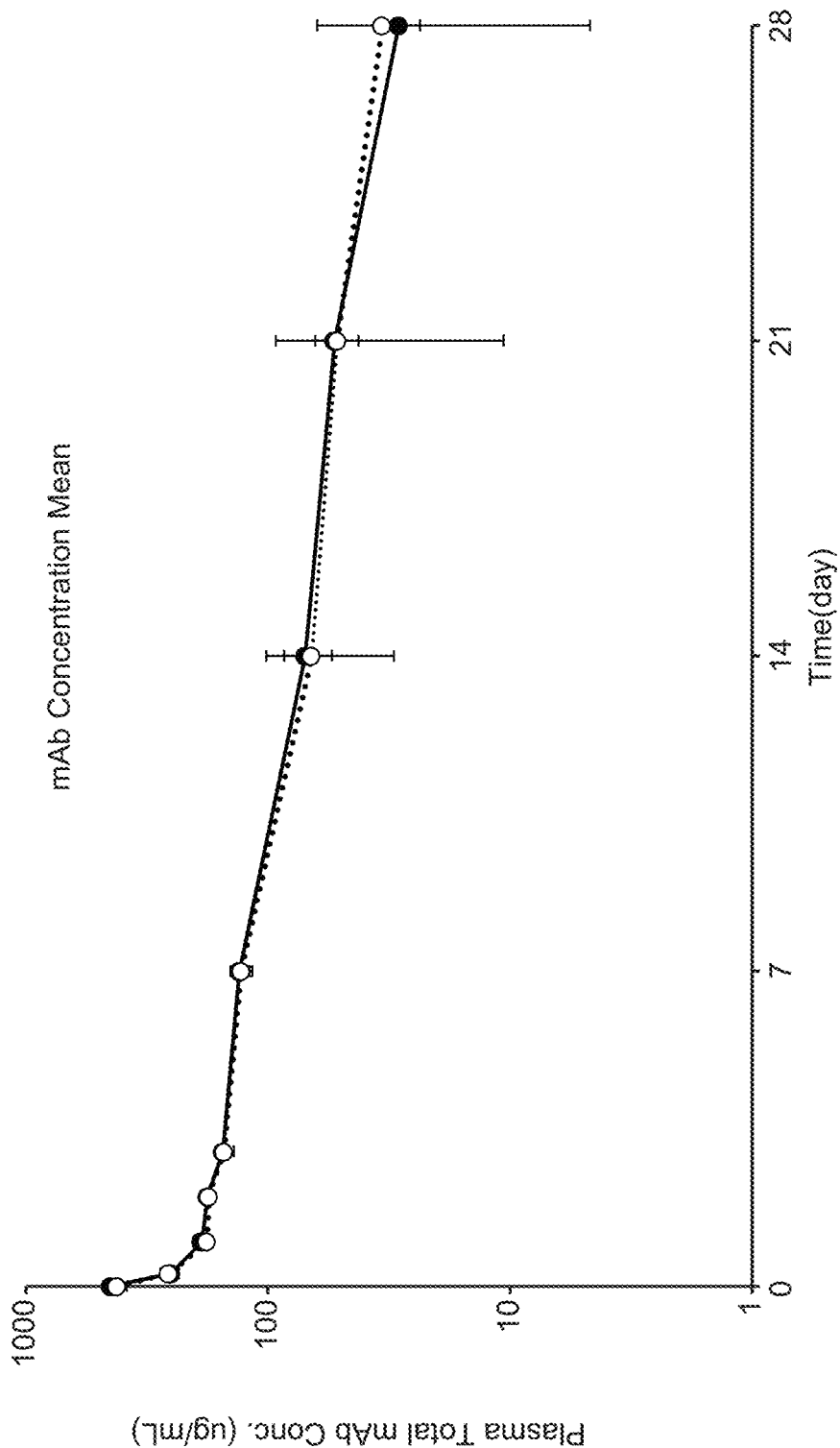
Figure 4A:
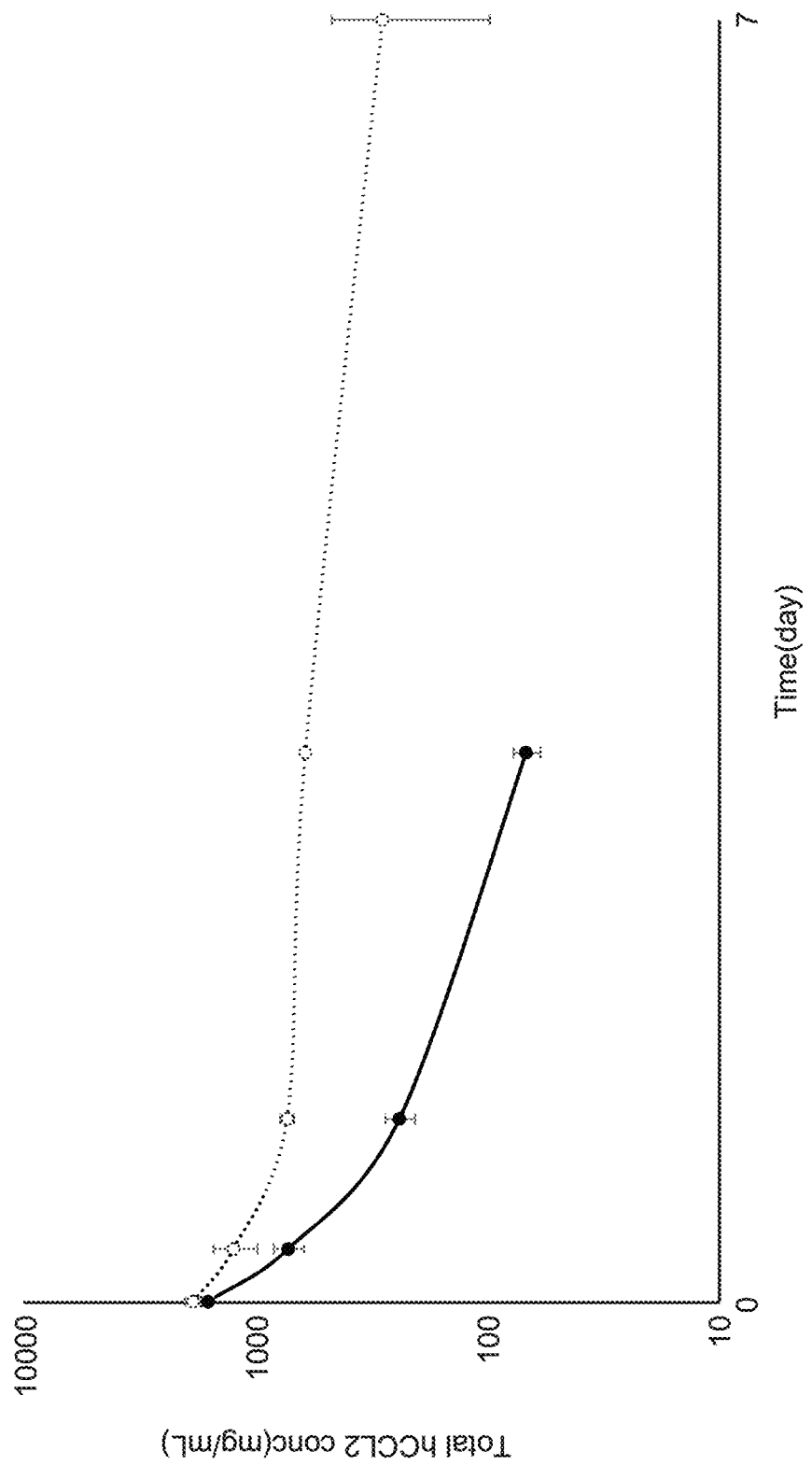
FIG. 4a: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody 11K2/1G9-WT IgG1 (wild type IgG1 with intact Fc receptor binding) or b) dotted line: 0.1 mg/kg human CCL2 (hCCL2) and 20 mg/kg bispecific anti-CCL2 antibody 11K2/1G9-PGLALA (Fc receptor binding silenced IgG1) into Balb/c mice.
Figure 4B:
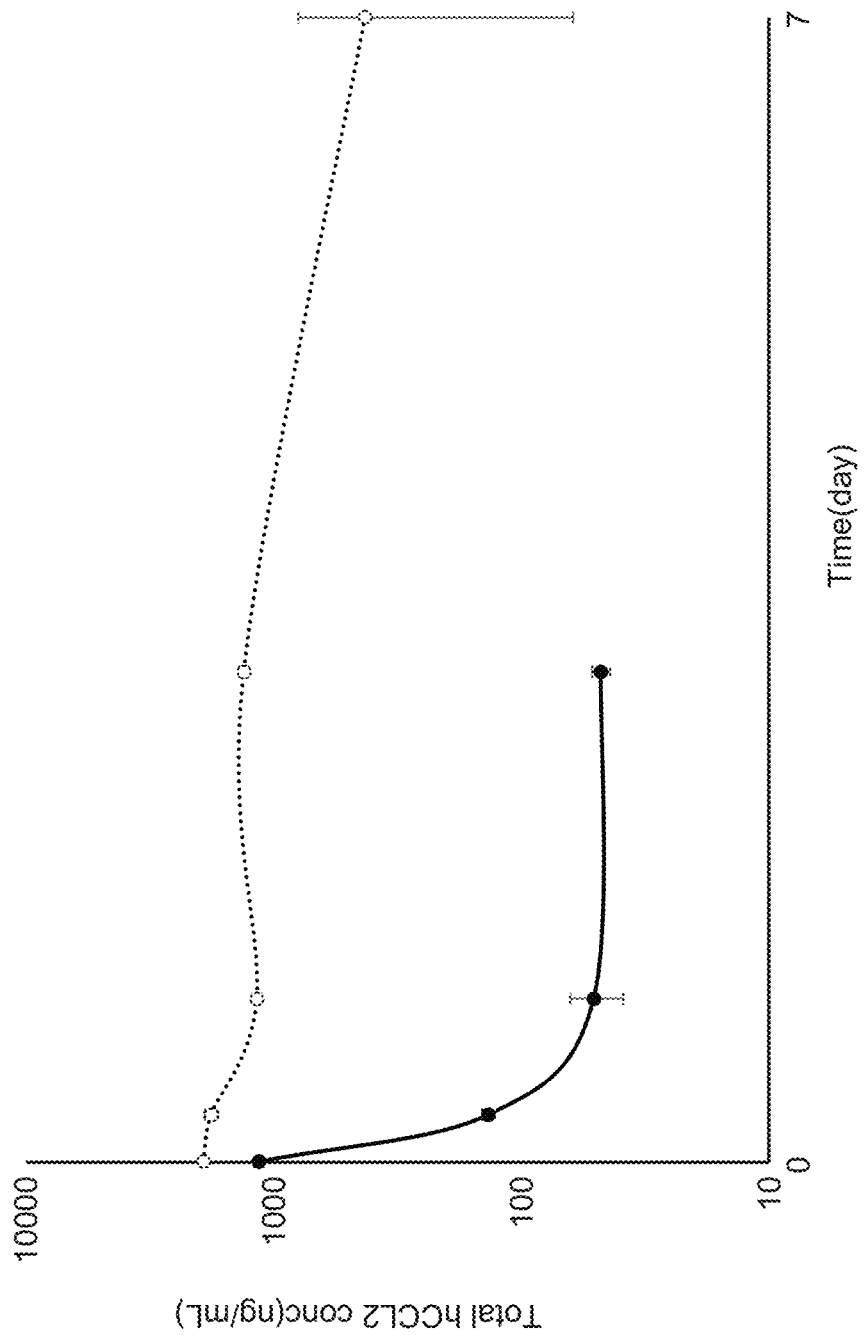
FIG. 4b: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody CNTO888/11K2-WT IgG1 (wild type IgG1 with intact Fc receptor binding) or b) dotted line: 0.1 mg/kg human CCL2 (hCCL2) and 20 mg/kg bispecific anti-CCL2 antibody CNTO888/11K2-PGLALA (Fc receptor binding silenced IgG1) into Balb/c mice.
Figure 4C:
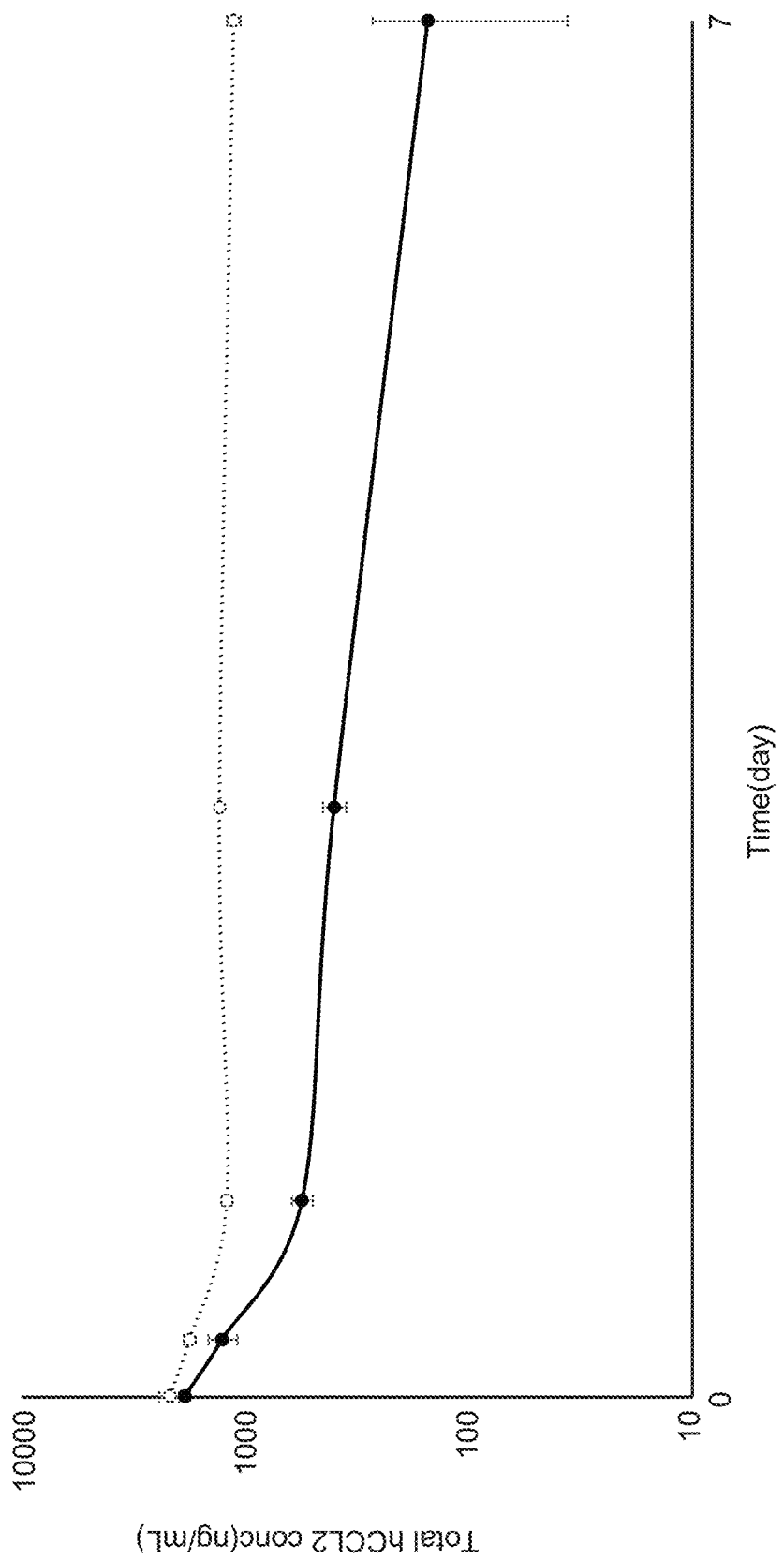
FIG. 4c: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody CNTO888/1G9-WT IgG1 (wild type IgG1 with intact Fc receptor binding) or b) dotted line: 0.1 mg/kg human CCL2 (hCCL2) and 20 mg/kg bispecific anti-CCL2 antibody 11K2/1G9-PGLALA (Fc receptor binding silenced IgG1) into Balb/c mice.
Figure 4D:
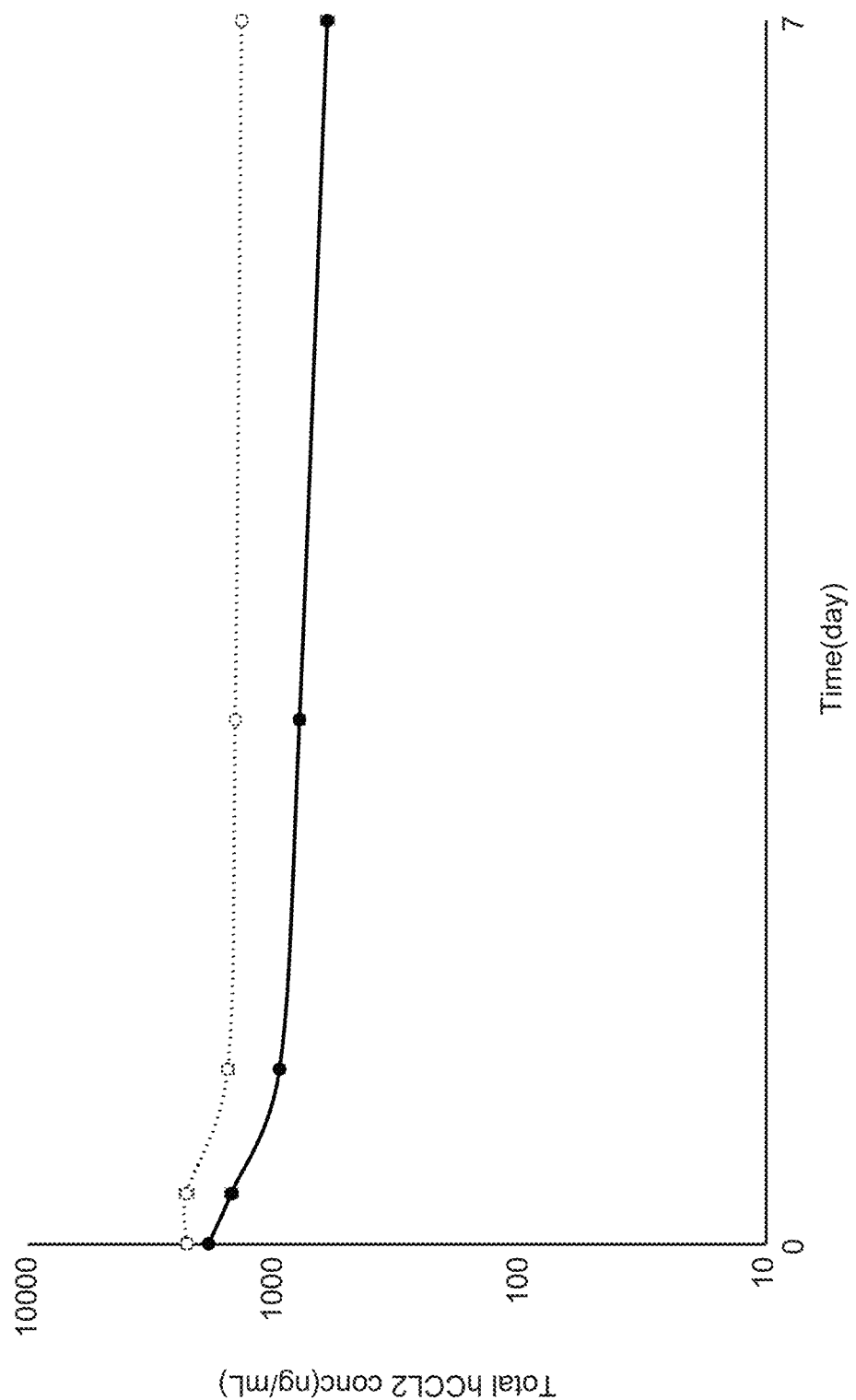
FIG. 4d: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody CNTO888/1A5-WT IgG1 (wild type IgG1 with intact Fc receptor binding) orb) dotted line: 0.1 mg/kg human CCL2 (hCCL2) and 20 mg/kg bispecific anti-CCL2 antibody CNTO888/1A5-PGLALA (Fc receptor binding silenced IgG1) into Balb/c mice.
Figure 4E:
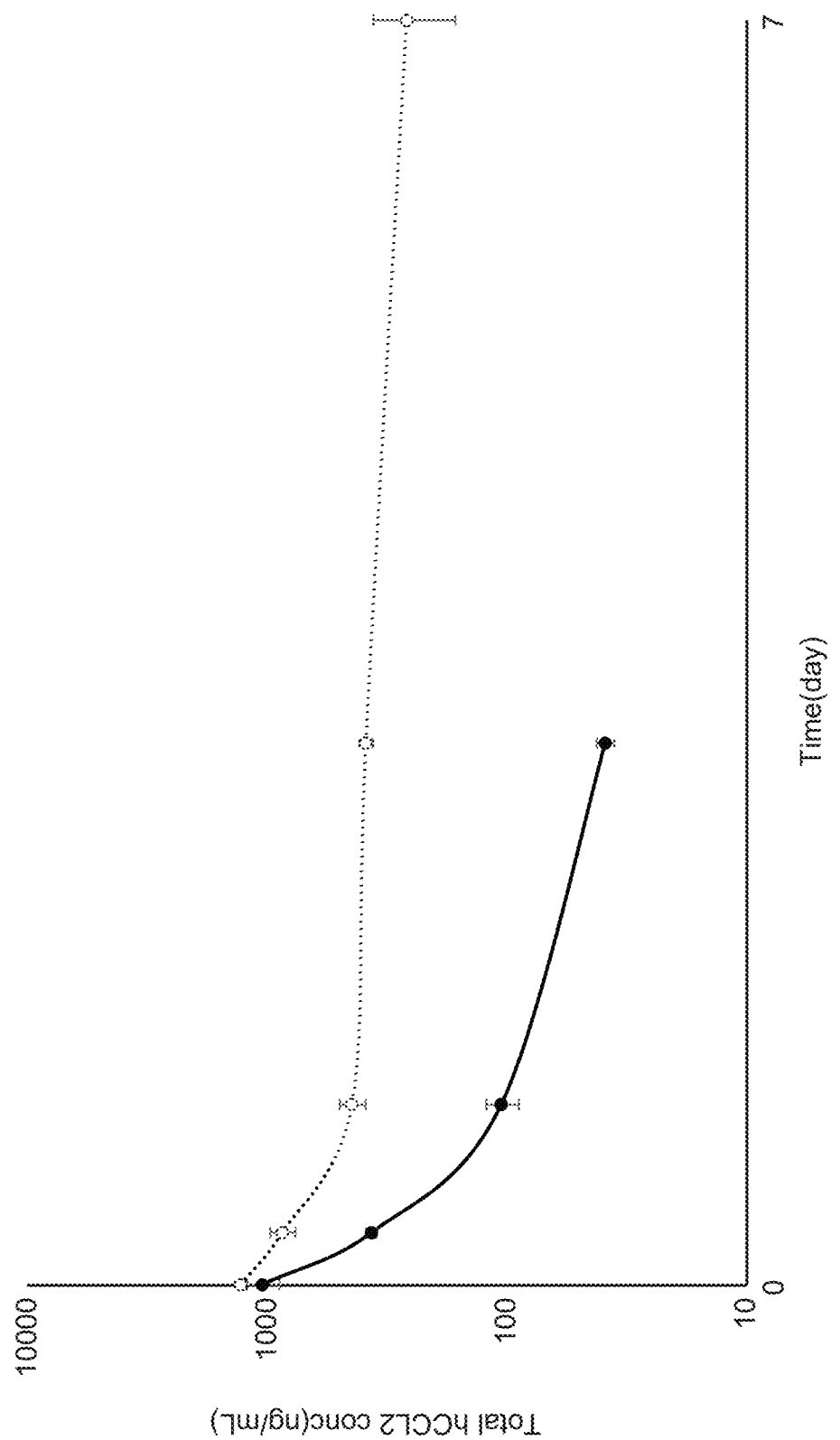
FIG. 4e: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody 1A5/1G9-WT IgG1 (wild type IgG1 with intact Fc receptor binding) or b) dotted line: 0.1 mg/kg human CCL2 (hCCL2) and 20 mg/kg bispecific anti-CCL2 antibody 1A5/1G9-PGLALA (Fc receptor binding silenced IgG1) into Balb/c mice.
Figure 4F:
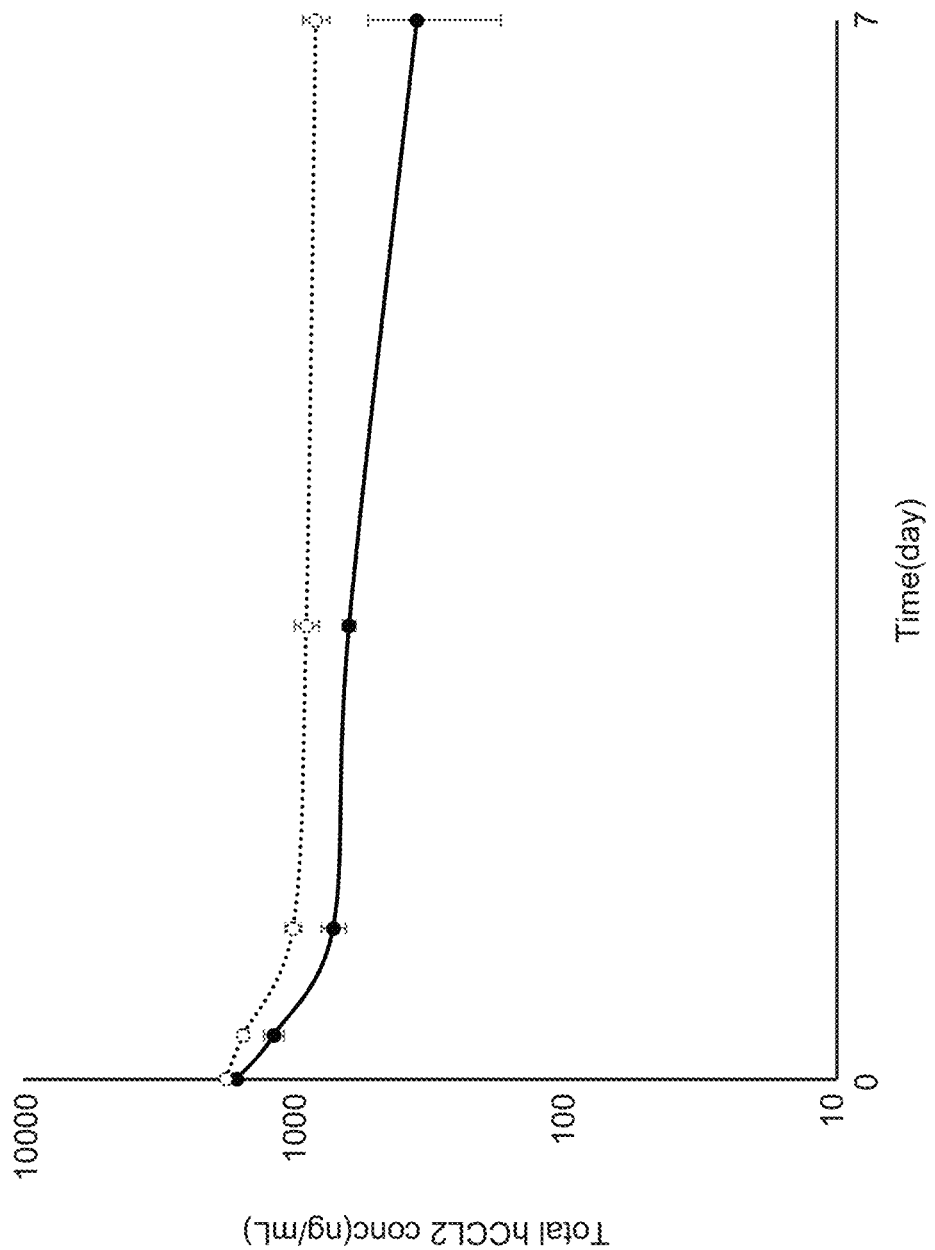
FIG. 4f: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody 11K2/2F6-WT IgG1 (wild type IgG1 with intact Fc receptor binding) or b) dotted line: 0.1 mg/kg human CCL2 (hCCL2) and 20 mg/kg bispecific anti-CCL2 antibody 11K2/2F6-PGLALA (Fc receptor binding silenced IgG1) into Balb/c mice.
Figure 4G:
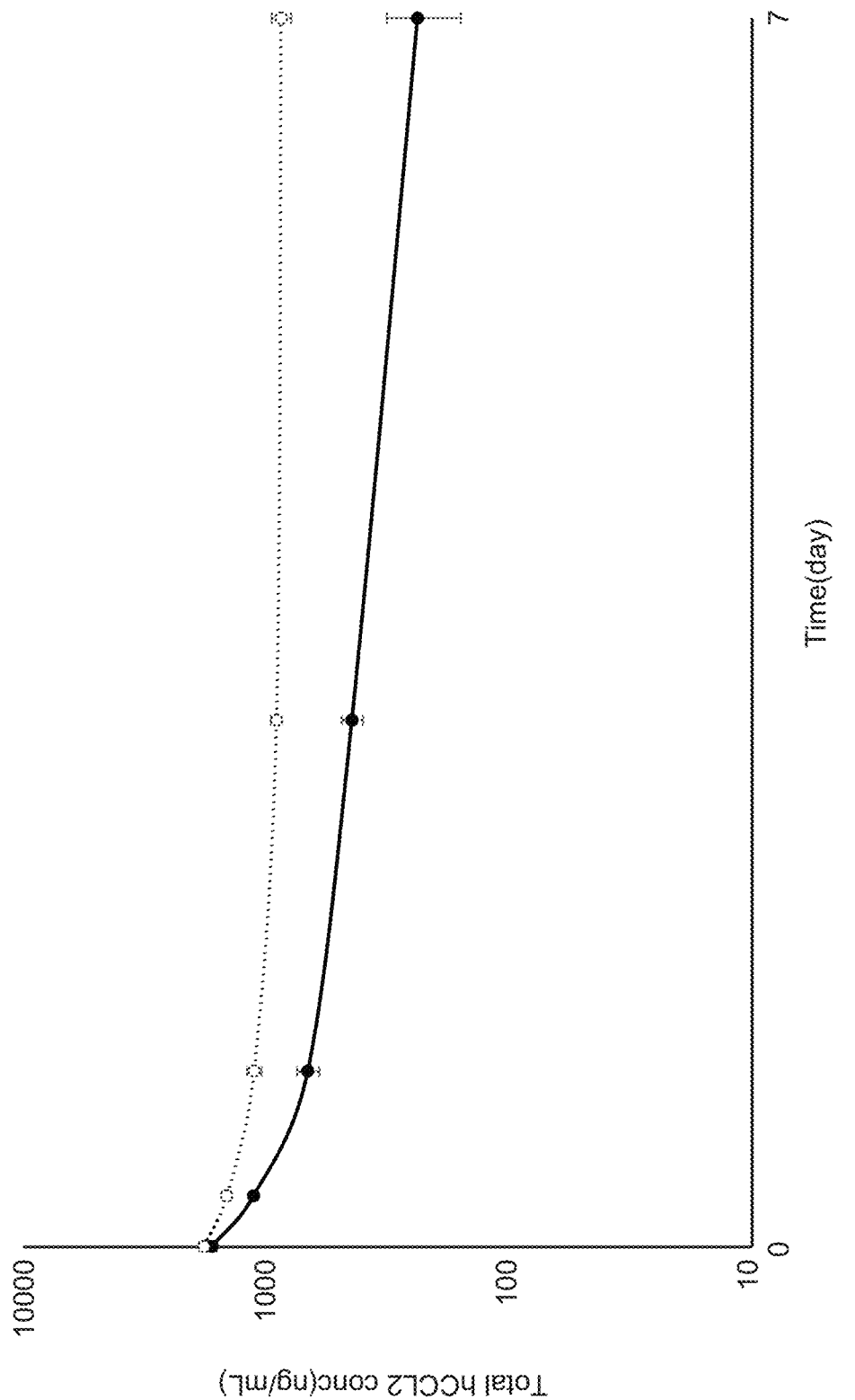
FIG. 4g: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody ABN912/11K2-WT IgG1 (wild type IgG1 with intact Fc receptor binding) orb) dotted line: 0.1 mg/kg human CCL2 (hCCL2) and 20 mg/kg bispecific anti-CCL2 antibody ABN912/11K2-PGLALA (Fc receptor binding silenced IgG1) into Balb/c mice.
Figure 4H:
FIG. 4h: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody 1A4/2F6-WT IgG1 (wild type IgG1 with intact Fc receptor binding) or b) dotted line: 0.1 mg/kg human CCL2 (hCCL2) and 20 mg/kg bispecific anti-CCL2 antibody 1A4/2F6-PGLALA (Fc receptor binding silenced IgG1) into Balb/c mice.
Figure 4I:
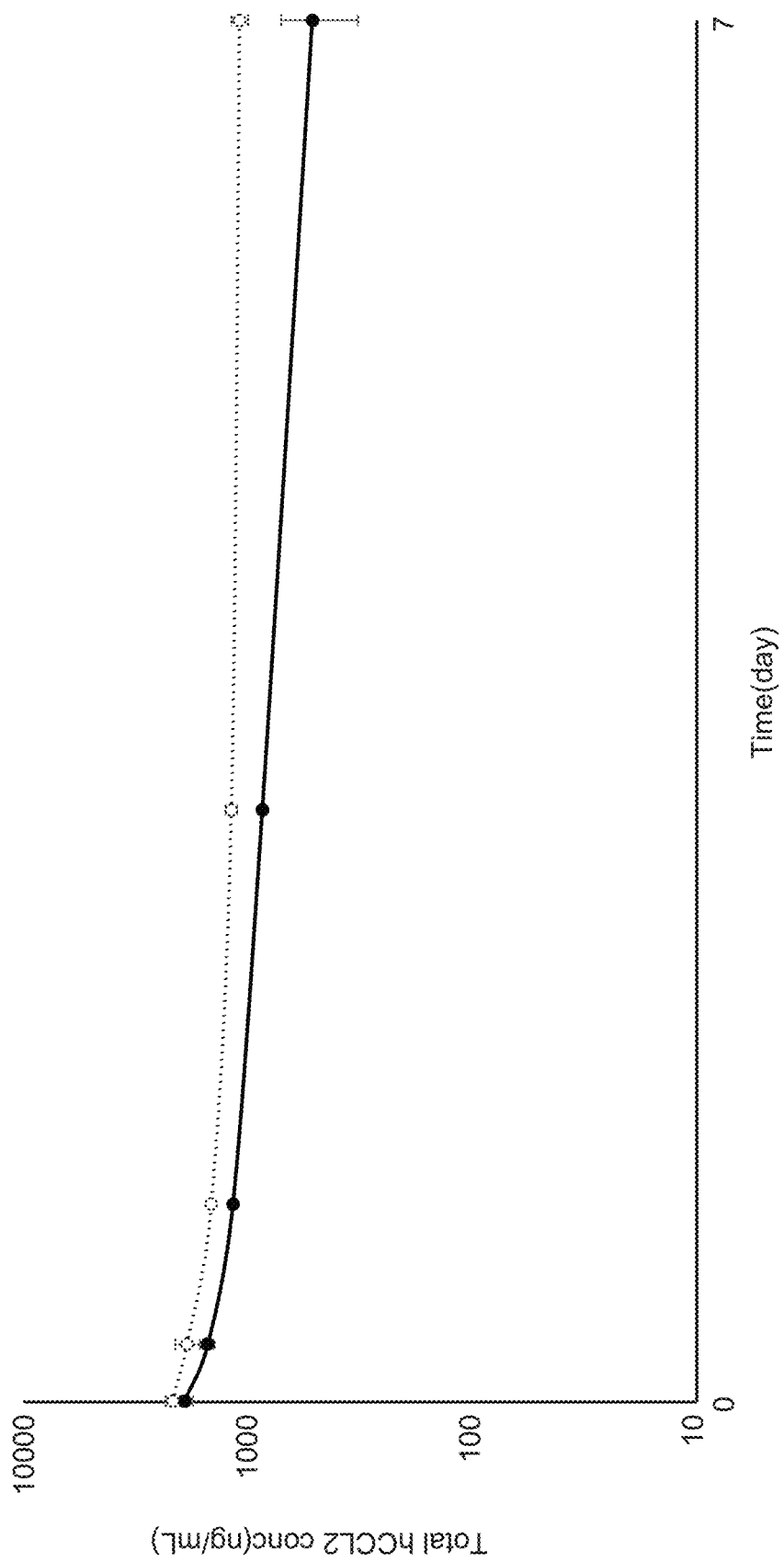
FIG. 4i: Serum concentration of hCCL2 over time after i.v. injection of pre-formed immune complex consisting of a) solid line: 0.1 mg/kg human CCL2 (hCCL2) and 20 mg/kg bispecific anti-CCL2 antibody 1A5/2F6-WT IgG1 (wild type IgG1 with intact Fc receptor binding) or b) dotted line: 0.1 mg/kg human CCL2 (hCCL2) and 20 mg/kg bispecific anti-CCL2 antibody 1A5/2F6-PGLALA (Fc receptor binding silenced IgG1) into Balb/c mice.
Figure 5A:
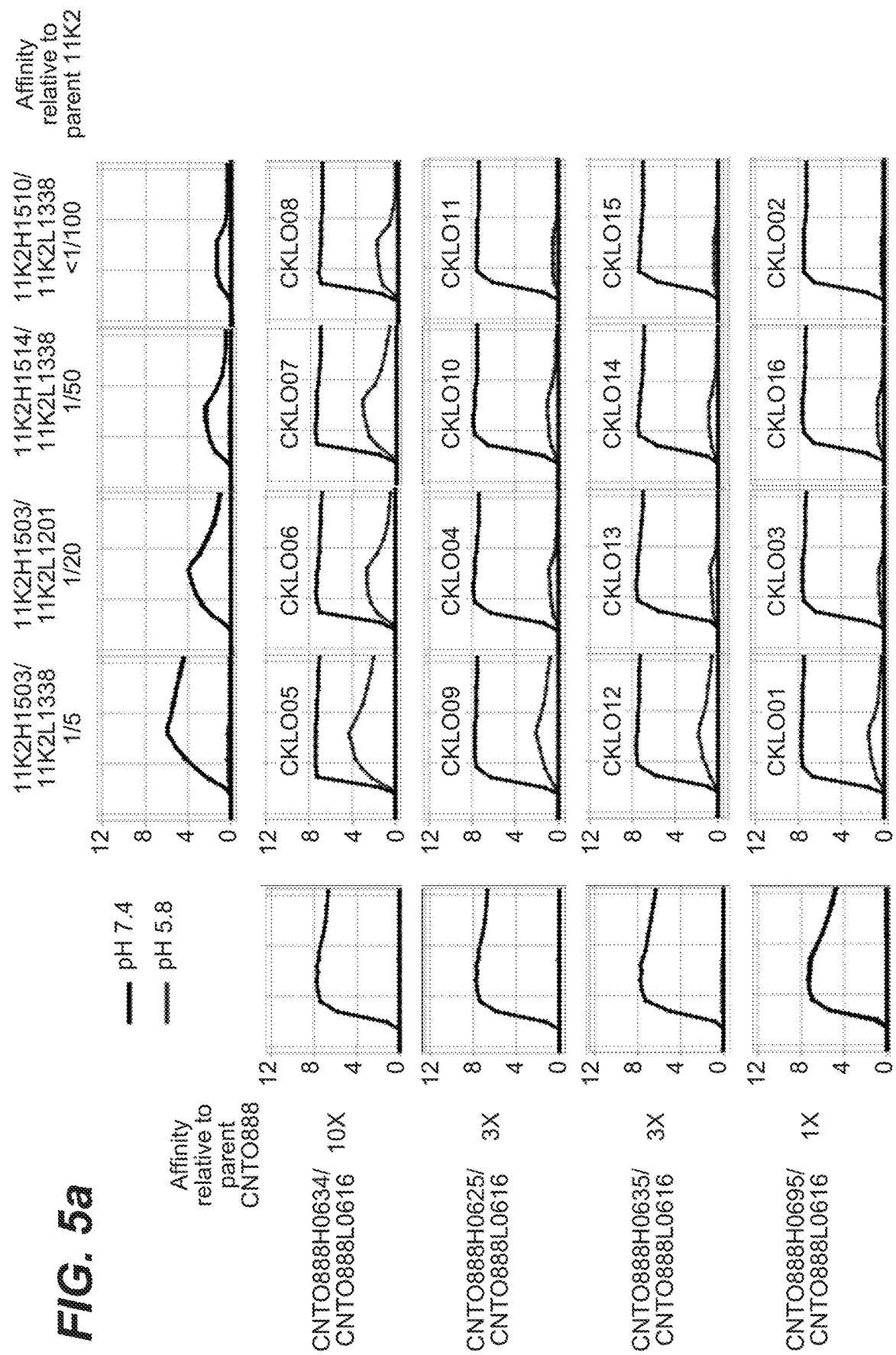
FIG. 5a: Biacore® sensorgrams showing binding profile to monomeric CCL2 at pH7.4 (black line) and pH5.8 (grey line) of the four modified 111K2 and four CNTO888 variants, and the 16 bispecific anti-CCL2 antibodies CKLO01 to CKLO16 resulting of the respective combination antigen binding moieties of the four modified 111K2 and four CNTO888 variants.
Figure 5B:
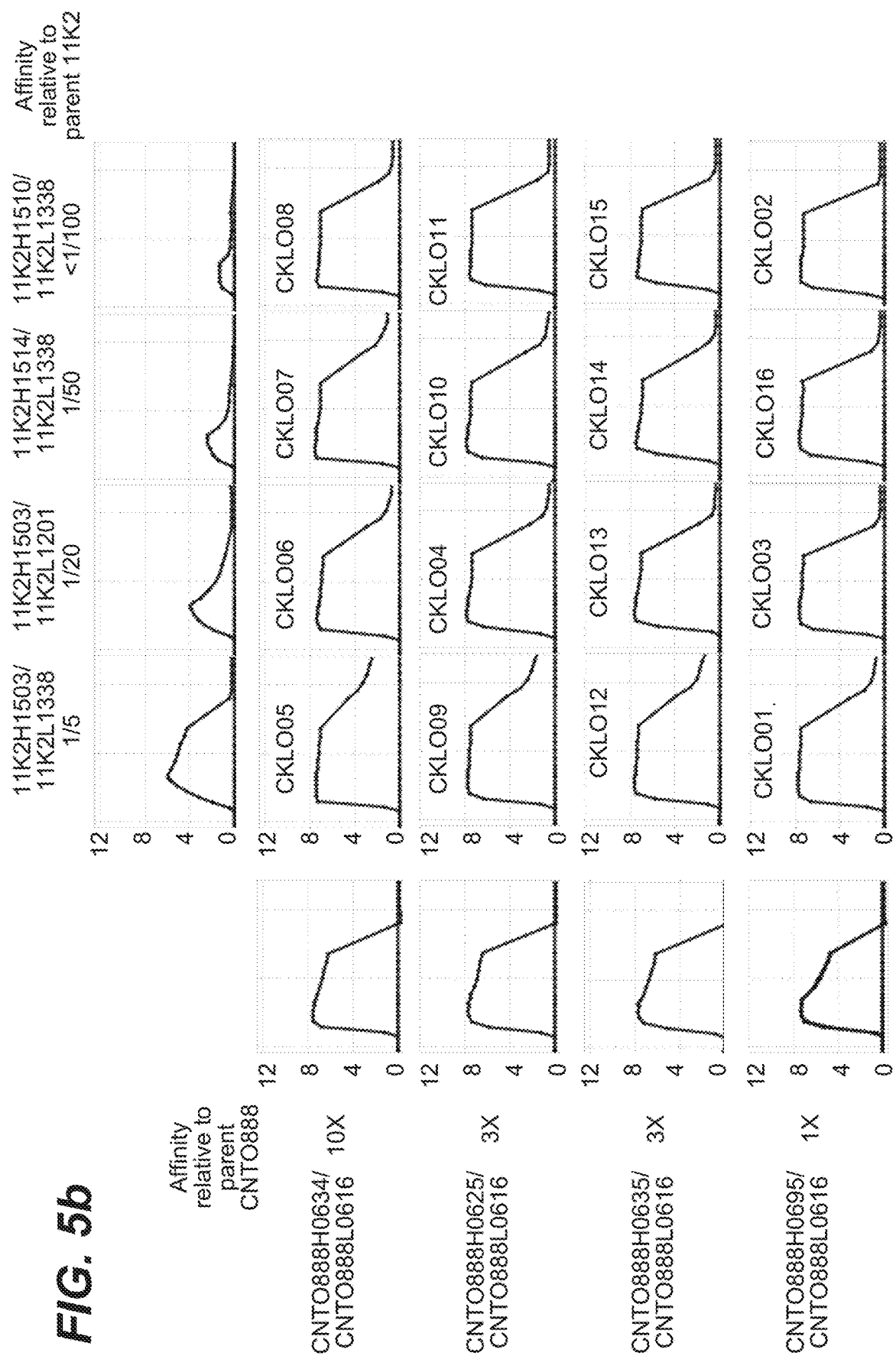
FIG. 5b: Biacore® sensorgrams showing binding profile to monomeric CCL2, of the four modified 11K2 and four CNTO888 variants, and the 16 bispecific anti-CCL2 antibodies CKLO01 to CKLO16 resulting of the respective combination antigen binding moieties of the four modified 11K2 and four CNTO888 variants. An additional dissociation phase at pH5.8 was integrated into the BIACORE® assay immediately after the dissociation phase at pH 7.4.

FIG. 3a and FIG. 3b show the time course of serum total mouse CCL2 concentration and antibody-time profile for humanized 11K2-SG1 and 11K2-SG105 in mice.

As seen in FIG. 3a and FIG. 3b, the levels of accumulated mouse CCL2 was not different between 11K2-SG105 (Fc gamma receptor binding silent Fc) and 11K2-SG1 (IgG1 wild type=Fc gamma receptor binding Fc). This indicates that there was no or little Fc gamma receptor-mediated clearance of endogenous mouse CCL2 by the injected antibodies. As antigens in immune complexes are cleared more rapidly than uncomplexed antigens via multimeric engagement of Fc gamma receptors, this suggests that the 11K2 antibody was not able to form immune-complexes with endogenous mouse CCL2.

Measurement of Mouse CCL2 Concentration in Mouse Serum by Enzyme-Linked Immunosorbent Assay (ELISA)

The concentration of mouse CCL2 in mouse serum was measured by adapting the reagents from a commercially available mouse CCL2 ELISA kit (R&D Systems). The manufacturer's protocol was followed except for preparation of calibration curve samples. Purified recombinant mouse CCL2 was substituted as the standard instead of the manufacturer's protein. For samples taken after antibody was injected, calibration curve samples and samples were prepared with 2.5% mouse serum injected antibody spiked in at a concentration of 40 microgram/ml, and incubated for 30 minutes at 37 degrees C. Subsequently, the samples were dispensed onto the anti-human CCL2-immobilized plates, and incubated at 30 degrees C. for 2 hours. Detection by adding mouse MCP-1 conjugate and incubating for 30 degrees C. for 2 hours, followed by substrate and stop solution.

For samples taken before antibody was injected, Mouse MCP-1 Ultra-Sensitive Kit (Meso Scale Discovery) was used according to the manufacturer's instructions. No antibody was spiked into the sample before addition to the plate.

Measurement of Anti-CCL2 Antibody Concentration in Serum by Enzyme-Linked Immunosorbent Assay (ELISA)

The concentration of anti-CCL2 antibody in mouse serum was measured by ELISA. Anti-human IgG kappa-chain (Antibody Solutions) was dispensed onto a Nunc MaxiSorp plate (Thermofisher) and allowed to stand overnight at 4 degrees C. to prepare anti-human IgG-immobilized plates. Calibration curve and samples were prepared with 1% pooled mouse serum. Then, the samples were dispensed onto the anti-human IgG-immobilized plates, and allowed to stand for 1 hour at room temperature. Subsequently, mouse anti-human IgG HRP (clone JDC-10, Southern Biotech) was added to react for 30 minutes at room temperature. Chromogenic reaction was carried out using ABTS substrate (KPL) as a substrate and the absorbance at 405 nm was measured by a microplate reader. The concentration in mouse plasma was calculated from the absorbance of the calibration curve using the analytical software SOFTmax PRO (Molecular Devices)

Conclusion of the Different Mouse PK Studies with Monospecific (Monoparatopic) Anti-CCL2 Antibodies To summarize the results of the mouse PK studies, none of the monoparatopic antibodies tested did show efficient clearance of CCL2 from the circulation. These data suggest that monoparatopic antibodies are not able to form immune complexes with CCL2 to efficiently clear it from the circulation.

In contrast, as described below, bispecific anti-CCL2 antibodies with two different antigen binding moieties/sites Sandwich ELISA was performed to identify antibody pairs that do not compete for binding to human CCL2. 384-well MAXISORP (NUNC) plates were coated with 1 µg/mL of the 7 indicated capture antibodies (Arm 1) and blocked with 2% BSA. Biotinylated (NHS-PEO$_4$-Biotin, Pierce) WT human CCL2 (20 ng/mL) was incubated with excess amount of the same 7 antibodies (Arm 2) at 1 µg/mL or block buffer for 1 hour at 37 degrees Celsius. After incubation, the mixtures were added to the blocked ELISA plate and incubated for 1 hour at room temperature. Detection of plate bound CCL2 was performed using streptavidin HRP followed by TMB One Component substrate (Lifetech). Signal development was stopped by 1N HCl acid (Wako). The O.D. of wells with no competing antibody was set as 100% signal for each capture antibody. The O.D. of blank wells with no CCL2 added was set as 0% signal. Nine antibody pairs that did not show strong competition for CCL2 binding in both directions were selected as candidates for generation of bispecific Crossmab antibodies.

|  |  | Antibody Arm 2 | | | | | | |
| --- | --- | --- | --- | --- | --- | --- | --- | --- |
|  |  | ABN 912 | CNTO 888 | 11K2 | 1A4 | 1A5 | 1G9 | 2F6 |
| Antibody Arm 1 | ABN912 |  |  | selected |  | selected |  |  |
|  | CNTO888 |  |  | selected |  |  | selected |  |
|  | 11K2 |  |  |  |  |  | selected | selected |
|  | 1A4 |  |  |  |  |  |  | selected |
|  | 1A5 |  |  |  |  |  | selected | selected |
|  | 1G9 |  |  |  |  |  |  |  |
|  | 2F6 |  |  |  |  |  |  |  |

(biparatopic anti-CCL2 antibodies) were able to efficiently form immune complexes with CCL2 and clear it from the circulation.

Example B-1

Bispecific (Biparatopic) Anti-CCL2 Antibodies
Several Bispecific Anti-CCL2 Antibodies with Two Different Antigen Bindings Moieties (Paratopes) Binding to Two Different Specific Epitopes on Human CCL2 were Generated Introduction To test whether single binding or cross-linking of the antigen has a significant impact on the in vivo CCL2 clearance, we generated bispecific anti-CCL2 antibodies with 2 different antigen-binding moieties/sites that bind to 2 different epitopes on CCL2 using the bispecific CrossMab Technology (see e.g., WO 2009/080252, WO 2015/150447), WO 2009/080253, WO 2009/080251, WO 2016/016299, Schaefer et al, PNAS, 108 (2011) 1187-1191, and Klein at al., MAbs 8 (2016) 1010-20) (bispecific (=biparatopic) CrossMabs). These molecules were first characterized in vitro for their biochemical and functional properties but they also served as tools for an in vivo CCL2 clearance evaluation in a mouse co-injection study. To evaluate the clearance potential based on Fcgamma Receptor (FcgR) binding mediated sweeping (e.g. in Igawa et al, Immunological Reviews 270 (2016) 132-151, WO2012/122011 and WO2016/098357 and WO2013/081143) we generated all Crossmabs as wild type huIgG1 which bind to FcgR and with modified human IgG1 constant chain which have reduced/abolished binding to FcgR effector silent molecules (e.g. IgG1 with mutations L234A, L235A, P329G (Kabat EU numbering).
Identification of Suitable Anti-CCL2 Antibody Pairs—Selection of Biparatopic Antibody Arms by Sandwich ELISA.

Generation and Characterization of Biparatopic Anti-CCL2 Antibodies and Immune Complexes
Generation of Biparatopic Anti-CCL2 Antibodies in Bispecific CrossMab Format Recombinant DNA Techniques Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany)

Description of the Basic/Standard Mammalian Expression Plasmid

For the expression of a desired gene/protein (e.g. antibody heavy chain or antibody light chain) a transcription unit comprising the following functional elements is used:
  the immediate early enhancer and promoter from the human cytomegalovirus (P-CMV) including intron A,
  a human heavy chain immunoglobulin 5'-untranslated region (5'UTR),
  a murine immunoglobulin heavy chain signal sequence,
  a gene/protein to be expressed (e.g. full length antibody heavy chain or MHC class I molecule), and the bovine growth hormone polyadenylation sequence (BGH pA).

Beside the expression unit/cassette including the desired gene to be expressed the basic/standard mammalian expression plasmid contains an origin of replication from the vector pUC18 which allows replication of this plasmid in E. coli, and a beta-lactamase gene which confers ampicillin resistance in E. coli.

Generation of Expression Plasmids for Recombinant Monoclonal Antibodies

The recombinant monoclonal antibody genes encode the respective immunoglobulin heavy and light chains.

The expression plasmids for the transient expression monoclonal antibody molecules comprised besides the immunoglobulin heavy or light chain expression cassette an origin of replication from the vector pUC18, which allows replication of this plasmid in E. coli, and a beta-lactamase gene which confers ampicillin resistance in E. coli.

The transcription unit of a respective antibody heavy or light chain comprised the following functional elements:

the immediate early enhancer and promoter from the human cytomegalovirus (P-CMV) including intron A, a human heavy chain immunoglobulin 5'-untranslated region (5'UTR), a murine immunoglobulin heavy chain signal sequence, the respective antibody heavy or light chain cDNA sequence and the bovine growth hormone polyadenylation sequence (BGH pA).

Transient Expression and Analytical Characterization

The recombinant production was performed by transient transfection of HEK293 cells (human embryonic kidney cell line 293-derived) cultivated in F17 Medium (Invitrogen Corp.). For the production of monoclonal antibodies, cells were co-transfected with plasmids containing the respective immunoglobulin heavy and light chain. For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).

General information regarding the recombinant expression of human immunoglobulins in e.g. HEK293 cells is given in: Meissner, P. et al., Biotechnol. Bioeng. 75 (2001) 197-203. To generate the following bispecific antibodies, the CrossMab technology described in WO 2016/016299 was used, in which VH/VL have been exchanged in one antibody arm and the CH1/CL interface of the other antibody arm has been modified by charge modifications, in combination with the knobs-into-holes technology in the CH3/CH3 interface to foster heterodimerization. An exemplary sequence for all four antibody chains where this technology was applied is given for CNTO888/11K2-WT IgG1 (see SEQ ID NO: 104 to SEQ ID NO:107)

List of Generated Bispecific (Biparatopic) Anti-CCL2 Crossmab Antibodies with Wild Type IgG1 (WT IgG1) (Wild Type IgG1 Means without Modifications/Mutations which Influence Fc Receptor Binding, However Heterodimerization Technology Like Knobs into Holes is Included)

| Bispecific antibody IgG1 | Alias 1 | Alias 2 | First antigen binding site VH/VL_crossed | Second antigen binding site VH/VL normal structure (non-crossed) |
|---|---|---|---|---|
| ABN912//11K2-WT IgG1 | CCL2-0047 | P1AA3447 | humanized 11K2 | ABN912 |
| CNTO888//11K2-WT IgG1 | CCL2-0048 | P1AA3429 | humanized 11K2 | CNTO888 |
| 11K2//1G9-WT IgG1 | CCL2-0049 | P1AA3461 | humanized 11K2 | 1G9 |
| 11K2//2F6-WT IgG1 | CCL2-0056 | P1AA3392 | humanized 11K2 | 2F6 |
| CNTO888//1A5-WT IgG1 | CCL2-0050 | P1AA3419 | CNTO888 | 1A5 |
| CNTO888//1G9-WT IgG1 | CCL2-0051 | P1AA3439 | CNTO888 | 1G9 |
| 1A4//2F6-WT IgG1 | CCL2-0057 | P1AA3400 | 1A4 | 2F6 |
| 1A5//2F6-WT IgG1 | CCL2-0058 | P1AA3427 | 1A5 | 2F6 |
| 1A5//1G9-WT IgG1 | CCL2-0052 | P1AA3446 | 1A5 | 1G9 |

List of Bispecific (Biparatopic) Anti-CCL2 Crossmab Antibodies with IgG1 Including the Fc Gamma Receptor Silencing Mutations L234A, L235A, P329G (Kabat EU Numbering) (IgG1-PGLALA)

| Bispecific antibody IgG1 PGLALA | Alias 1 | Alias 2 | First antigen binding site VH/VL_crossed | Second antigen binding site VH/VL normal structure (non-crossed) |
|---|---|---|---|---|
| ABN912//11K2-PGLALA | CCL2-0041 | P1AA3411 | humanized 11K2 | ABN912 |
| CNTO888//11K2-PGLALA | CCL2-0042 | P1AA3452 | humanized 11K2 | CNTO888 |
| 11K2//1G9-PGLALA | CCL2-0043 | P1AA3463 | humanized 11K2 | 1G9 |
| 11K2//2F6-PGLALA | CCL2-0053 | P1AA3450 | humanized 11K2 | 2F6 |
| CNTO888//1A5-PGLALA | CCL2-0044 | P1AA3448 | CNTO888 | 1A5 |
| CNTO888//1G9-PGLALA | CCL2-0045 | P1AA3455 | CNTO888 | 1G9 |
| 1A4//2F6-PGLALA | CCL2-0054 | P1AA3459 | 1A4 | 2F6 |
| 1A5//2F6-PGLALA | CCL2-0055 | P1AA3402 | 1A5 | 2F6 |
| 1A5//1G9-PGLALA | CCL2-0046 | P1AA3444 | 1A5 | 1G9 |

Purification of the Biparatopic Anti-CCL2 Antibodies

Biparatopic anti-CCL2 antibodies containing cell culture supernatants were filtered and purified by up to three chromatographic steps. Depending on the purity of the capture step eluate an ion exchange chromatography step was optionally implemented between capture and polishing step.

Biparatopic anti-CCL2 antibodies were purified from cell culture supernatants by affinity chromatography using MabSelectSure-Sepharose™ (GE Healthcare, Sweden), POROS 50 HS (Thermofisher Scientific) and Superdex 200 size exclusion (GE Healthcare, Sweden) chromatography. Briefly, sterile filtered cell culture supernatants were captured on a MabSelect SuRe resin equilibrated with PBS buffer (10 mM Na2HPO4, 1 mM KH2PO4, 137 mM NaCl and 2.7 mM KCl, pH 7.4), washed with equilibration buffer and eluted with 25 mM sodium citrate at pH 3.0. The eluted protein fractions were pooled and neutralized with 2M Tris, pH 9.0. Ion exchange chromatography as optional second purification step was performed with POROS 50 HS (Thermofisher Scientific), equilibration and wash with 20 mM histidine pH 5.6 and load of diluted capture step eluate a gradient chromatography was done with 20 mM histidine, 0.5M NaCl at pH 5.6. ion exchange chromatography fractions were analyzed by CE-SDS LabChip GX II (PerkinElmer) and Crossmab containing fractions were pooled.

Size exclusion chromatography on Superdex 200 (GE Healthcare) was used as second or third purification step. The size exclusion chromatography was performed in 20 mM histidine buffer, 0.14 M NaCl, pH 6.0. Size exclusion chromatography fractions were analyzed by CE-SDS LabChip GX II (PerkinElmer) and Crossmab containing fractions were pooled and stored at −80° C.

In case of a satisfying product quality after the POROS 50 HS (ThermoFisher Scientific) size exclusion chromatography on Superdex 200 (GE Healthcare) replaced by desalting chromatography on HiPrep 26/10 Desalting (GE Healthcare) in 20 mM histidine buffer, 0.14 M NaCl, pH 6.0.

The protein concentration of antibody preparations was determined by measuring the optical density (OD) at 280 nm, using the molar extinction coefficient calculated on the basis of the amino acid sequence.

Purity and integrity of the antibodies were analyzed by CE-SDS using a LabChip GX II (PerkinElmer) with Protein Express Chip and HT Protein Express Reagents Kit. Aggregate content of antibody preparations was determined by high-performance SEC using a Biosuite High Resolution SEC, 250 Å, 5 μm analytical size-exclusion column (Waters GmbH) using 200 mM K2HPO4/KH2PO4, 250 mM KCl, pH 7.0 as running buffer. Average purities were between 94-100% as analyzed by CE-SDS and monomer content >95% (SEC).

Functional Characterization of the Bispecific (Biparatopic) Anti-CCL2 Antibodies Affinity Measurement (Binding)

Around 1200 resonance units (RU) of the capturing system (20 μg/ml goat anti human IgG Fc; Order Code: 109-005-098; Jackson Immuno Research) were coupled on a C1 chip (GE Healthcare BR-1005-35) at pH 5.0 by using an amine coupling kit supplied by GE Healthcare. The sample and system buffer was PBS-T (10 mM phosphate buffered saline including 0.05% Tween20) pH 7.4. The flow cell was set to 25° C.—and the sample block set to 12° C.—and primed with running buffer twice. The bispecific antibody was captured by injecting a 2 μg/ml solution for 60 sec at a flow rate of 10 μl/min. Association was measured by injection of human CCL2 (wt) in various concentrations in solution for 150 sec at a flow rate of 30 μl/min starting with 30 nM in 1:10 dilutions. The dissociation phase was monitored for up to 1200 sec and triggered by switching from the sample solution to running buffer. The surface was regenerated by 60 sec washing with a 0.85% H3PO4 solution at a flow rate of 10 μl/min. Bulk refractive index differences were corrected by subtracting the response obtained from a goat anti human IgG Fc surface. Blank injections are also subtracted (=double referencing). For calculation of kinetic parameters, the Langmuir 1:1 model was used.

| Mono and bispecific anti-CCL2 antibodies | Alias | t 1/2* (min) | Ligand Level (RU) | Rmax (RU) |
|---|---|---|---|---|
| Humanized 11K2 (=11K2) | CCL2-0002 | no dissociation | 293.5 | 39.3 |
| ABN912 | CCL2-0003 | 27 | 307.0 | 33.6 |
| CNTO888 | CCL2-0004 | no dissociation | 272.8 | 31.9 |
| ABN912//11K2-PGLALA | CCL2-0041 | no dissociation | 212.2 | 21.1 |
| CNTO888//11K2-PGLALA | CCL2-0042 | no dissociation | 211.8 | 22.0 |
| 11K2//1G9-PGLALA | CCL2-0043 | no dissociation | 204.9 | 21.2 |
| CNTO888//1A5-PGLALA | CCL2-0044 | no dissociation | 207.3 | 20.0 |
| CNTO888//1G9-PGLALA | CCL2-0045 | no dissociation | 213.0 | 19.0 |
| 1A5//1G9-PGLALA | CCL2-0046 | no dissociation | 203.1 | 20.0 |
| ABN912//11K2-WT IgG1 | CCL2-0047 | no dissociation | 209.3 | 20.2 |
| CNTO888//11K2-WT IgG1 | CCL2-0048 | no dissociation | 226.1 | 22.9 |
| 11K2//1G9-WT IgG1 | CCL2-0049 | no dissociation | 206.1 | 21.1 |
| CNTO888//1A5-WT IgG1 | CCL2-0050 | no dissociation | 214.4 | 20.3 |
| CNTO888//1G9-WT IgG1 | CCL2-0051 | no dissociation | 215.8 | 20.7 |
| 1A5//1G9-WT IgG1 | CCL2-0052 | no dissociation | 211.7 | 21.0 |
| 11K2//2F6-PGLALA | CCL2-0053 | no dissociation | 201.9 | 19.8 |
| 1A4//2F6-PGLALA | CCL2-0054 | no dissociation | 194.7 | 18.8 |
| 1A5//2F6-PGLALA | CCL2-0055 | no dissociation | 203.5 | 20.1 |
| 11K2//2F6-WT IgG1 | CCL2-0056 | no dissociation | 205.3 | 20.2 |
| 1A4//2F6-WT IgG1 | CCL2-0057 | no dissociation | 199.0 | 19.5 |
| 1A5//2F6-WT IgG1 | CCL2-0058 | no dissociation | 202.8 | 19.8 |

Natural Immune Complex Formation in the Presence of Wild Type Antigen.

All protein samples (bispecific anti-CCL2 CrossMab antibodies and antigens) were re-buffered in 1×PBS, pH 7.4, using dialysis or centrifugal ultrafiltration devices.

A dilution series of the CrossMab samples from 2.0 to 0.1 mg/mL was prepared. Likewise, antigen solutions in PBS were prepared with concentrations ranging from 0.012 to 0.23 mg/mL. Concentrations were chosen to allow mixing of equivalent volumes to achieve a constant molar ratio of 1:1 (antibody:CCL2 complex). The following antigen was used in this study: wild type CCL2.

Equivalent volumes of the pre-diluted CrossMab and CCL2 preparation were mixed and incubated at 37° C. for 1 hour before samples were applied on a Superose6 (GE Healthcare #2039) column, pre-equilibrated with PBS and eluted at a flow rate of 0.5 mL/min. A total of 100 μg or the maximal possible volume of 250 μL was applied and the antibodies and antigens alone were used as a control.

SEC-MALLS data were recorded with an OptiLab rEX refractive index detector and with a miniDAWN Treos MALLS detector (both from Wyatt inc.). SEC-MALLS signals were processed using the Astra V5 software (Wyatt).

| Bispecific anti-CCL2 antibody | Alias | Interaction with CCL2wt (low conc.) |
|---|---|---|
| ABN912//11K2-WT IgG1 | CCL2-0047 | + |
| CNTO888//11K2-WT IgG1 | CCL2-0048 | +++ |
| 11K2//1G9-WT IgG1 | CCL2-0049 | ++ |
| CNTO888//1A5-WT IgG1 | CCL2-0050 | + |
| CNTO888//1G9-WT IgG1 | CCL2-0051 | + |
| 1A5//1G9-WT IgG1 | CCL2-0052 | ++ |
| 11K2//2F6-WT IgG1 | CCL2-0056 | ++ |
| 1A4//2F6-WT IgG1 | CCL2-0057 | + |
| 1A5//2F6-WT IgG1 | CCL2-0058 | + |

Legend
+++ large quantity of multi-/oligomers
++ medium quantity of multi-/oligomers
+ low quantity of multi-/oligomers
0 only dimers or less CCR2 Reporter Assay to Study the Neutralizing Characteristics of Anti-CCL2 Antibodies Tango™ CCR2-bla U2OS cells were purchased from Invitrogen, Germany, to study the impact of CCL2 neutralizing antibody constructs. Those reporter cells contain the human Chemokine (C—C Motif) Receptor 2 (CCR2) linked to a TEV protease site and a Gal4-VP16 transcription factor stably integrated into the Tango™ GPCR-bla U2OS parental cell line. This parental cell line stably expresses a beta-arrestin/TEV protease fusion protein and the beta-lactamase (bla) reporter gene under the control of a UAS response element. Adding the natural ligands MCP1=CCL2 resulted in an indication of the activity of the reporter gene, which can be measured by the cleavage of a FRET-enabled substrate.

Principally, assay and cell handling procedures were according the providers manual. In brief, CCR2-U2OS cells were seeded at a density of $2 \times 10^4$ cells/well (96er black clear bottom plate, cat. no. #655090, Greiner Bio-one) in 50 µl assay medium (Freestyle 293 Expression Medium, cat. no. #12338-018, Invitrogen). In parallel, serial dilutions of different test antibodies as well as the CCL2-antigen solution were prepared at c=4× final concentration. Then, CCL2-antigen/antibody mixtures were prepared and pre-incubated for two to three hours (hrs) at RT. 50 µl of indicated CCL2/antibody solutions were transferred to the CCR2 expressing U2OS cells and incubated for 18 hrs in a humidified incubator at 37° C. and 5% CO$_2$. As control only assay medium was used.

On the next day, the CCF4 substrate (cat. no. #K1089, Invitrogen) was prepared with ß-lactamase loading solution (cat. no. #K1085, Invitrogen) and 20 µl/well thereof were added to the cells. The substrate solution was incubated for two hrs at RT in the dark.

Finally, the fluorescence wavelengths were determined with a Spectra Max (M4) reader (Molecular devices) at the following wavelengths (Ex/Em=409 nm/460 nm=blue*; Ex/Em=409 nm/530 nm=green**) and the ratio of blue/green fluorescence after subtracting assay medium control was calculated according to the following equation: ratio=(sample-blue*−control-blue*)/(sample-green−control-green).

After the pH-engineering we characterized the final LO candidates (CKLO1-4) for their ability to inhibit CCL2-induced CCR2 signaling. In this case the neutralizing property was assessed by the monomeric variant of the rec. CCL2 protein, which was used at a final concentration of approx. 15 ng/ml.

| Bispecific Antibody | Alias | IC50 [ng/ml] | | |
|---|---|---|---|---|
| | | Exp 1 | Exp 2 | Exp3 |
| ABN912//11K2-PGLALA | CCL2-0041 | | 80.2 | |
| CNTO888//11K2-PGLALA | CCL2-0042 | | 84 | |
| 11K2//1G9-PGLALA | CCL2-0043 | | 57 | |
| CNTO888//1A5-PGLALA | CCL2-0044 | | 77.7 | 88 |
| CNTO888//1G9-PGLALA | CCL2-0045 | | 86.4 | 81.3 |
| 1A5//1G9-PGLALA | CCL2-0046 | | 75.8 | |
| ABN912//11K2-WT IgG1 | CCL2-0047 | 84.4 | | |
| CNTO888//11K2-WT IgG1 | CCL2-0048 | 92.9 | | |
| 11K2//1G9-WT IgG1 | CCL2-0049 | 82.2 | | |
| CNTO888//1A5-WT IgG1 | CCL2-0050 | 89.2 | | |
| CNTO888//1G9-WT IgG1 | CCL2-0051 | | 89.6 | 52.7/67.9 |
| 1A5//1G9-WT IgG1 | CCL2-0052 | 86.2 | | |
| 11K2//2F6-PGLALA | CCL2-0053 | | 26.3 | 49.6/70 |
| 1A4//2F6-PGLALA | CCL2-0054 | | 78.2 | |
| 1A5//2F6-PGLALA | CCL2-0055 | | 48.7 | |
| 11K2//2F6-WT IgG1 | CCL2-0056 | 93.9 | | |
| 1A4//2F6-WT IgG1 | CCL2-0057 | | 58.2 | |
| 1A5//2F6-WT IgG1 | CCL2-0058 | 93 | | |
| Monospecific control | CCL2-0002 | 76.1 | 79.1 | 56.9/58 |

Evaluation of Human CCL2 Immune Complex Sweeping with Biparatopic Antibody in Mice To evaluate the ability of biparatopic antibodies to form immune complex with wild type human CCL2, pre-formed immune complexes consisting of anti-CCL2 biparatopic antibody (20 mg/kg) and wild type human CCL2 (0.1 mg/kg) were administered at a single dose of 10 ml/kg into the caudal vein of Balb/c mice. Blood was collected 5 minutes, 7 hours, 1 day, 3 days and 7 days after administration. Serum was prepared by centrifuging the blood immediately at 14,000 rpm for 10 minutes in 4° C. The serum was stored at or below −80° C. until measurement. The biparatopic antibodies tested are listed in the Table 4 below. Antibodies with WT IgG1 Fc have Fc gamma receptor binding similar to wild-type while antibodies with PGLALA Fc are Fc gamma receptor binding silent. Results are shown in FIG. 4a-FIG. 4i.

The effect of immune complex sweeping of each anti-CCL2 biparatopic antibody on hCCL2 clearance in vivo were assessed by comparing anti-CCL2 antibody with Fc gamma receptor binding (solid line) and anti-CCL2 antibody with Fc gamma receptor binding silent (PGLALA, dotted line), as shown in FIG. 4a-FIG. 4i. The antibody profiles were analyzed by non-compartmental analysis using Phoenix 64 (Pharsight/Certara). The AUCinf was estimated by linear-log trapezoidal rule extrapolated to infinity. Clearance values are defined as Dose/AUCinf. This difference in clearance was also expressed as fold change, which is calculated by dividing the hCCL2 clearance of antibodies with Fc gamma receptor binding (SG1) by the hCCL2 clearance of antibodies with Fc gamma receptor binding silent (PGLALA) (Table 4 below). The data in the Table 4 below indicates that the clearance of human CCL2 by Fc gamma receptor (FcgR) binding antibodies (WT IgG1) was superior to that by Fc gamma receptor binding silent antibodies (PGLALA, with an IgG1 Fc domain comprising mutation L234A, L235A, P329G mutations (Kabat EU numbering)) for all the biparatopic antibodies tested. This suggests that immune complex-mediated sweeping of CCL2 achieved by the tested biparatopic antibodies was more efficient. Moreover, several biparatopic antibodies showed large fold change in clearance values, for example, CNTO/humanized 11K2 (CNTO/11K2).

Fold change is calculated by dividing the hCCL2 clearance of antibodies with WT FcgammaR (FcgR) binding with hCCL2 clearance of antibodies with PGLALA. As shown in FIG. 4a-FIG. 4i and the Table 4 below, CNTO/11k2 shows the largest fold change of 21.5 between the antibody with IgG1 wild type (WT) which has FcgR binding and antibody which is FcgR binding silent (PGLALA). This suggests that immune complex-mediated sweeping by CNTO/11k2-WT IgG1 is the most efficient among all variants.

TABLE 4

Clearance values of wild type CCL2 after administration of pre-formed immune complex of anti-CCL2 biparatopic antibody (20 mg/kg) and wild type human CCL2 (0.1 mg/kg)

| Antibodies | Alias | Clearance (ml/day/kg) | Fold change |
| --- | --- | --- | --- |
| 11K2//1G9-WT IgG1 | CCL2-0049 | 101.761 | 6.1 |
| 11K2//1G9-PGLALA | CCL2-0043 | 16.713 | |
| CNTO888//11K2-WT IgG1 | CCL2-0048 | 244.705 | 21.5 |
| CNTO888//11K2-PGLALA | CCL2-0042 | 11.374 | |
| CNTO888//1G9-WT IgG1 | CCL2-0051 | 31.085 | 7.8 |
| CNTO888//1G9-PGLALA | CCL2-0045 | 3.999 | |
| CNTO888//1A5-WT IgG1 | CCL2-0050 | 7.098 | 3.8 |
| CNTO888//1A5-PGLALA | CCL2-0044 | 1.892 | |
| 1A5//1G9-WT IgG1 | CCL2-0052 | 194.481 | 11.4 |
| 1A5//1G9-PGLALA | CCL2-0046 | 17.073 | |
| 11K2//2F6-WT IgG1 | CCL2-0056 | 14.442 | 4.9 |
| 11K2//2F6-PGLALA | CCL2-0053 | 2.964 | |
| ABN912//11K2-WT IgG1 | CCL2-0047 | 20.935 | 4.2 |
| ABN912//11K2-PGLALA | CCL2-0041 | 4.988 | |
| 1A4//2F6-WT IgG1 | CCL2-0057 | 19.606 | 3.3 |
| 1A4//2F6-PGLALA | CCL2-0054 | 5.933 | |
| 1A5//2F6-WT IgG1 | CCL2-0058 | 10.254 | 2.7 |
| 1A5//2F6-PGLALA | CCL2-0055 | 3.825 | |

Measurement of Total Human CCL2 Concentration in Serum by Electrochemiluminescence (ECL)

The concentration of total human CCL2 in mouse serum was measured by ECL. 3 ug/mL of anti-CCL2 antibody 2F2-SG1 was immobilized onto a MULTI-ARRAY 96-well plate (Meso Scale Discovery) overnight before incubating in blocking buffer for 2 hours at 30° C. Human CCL2 calibration curve samples, quality control samples and diluted mouse serum samples were incubated with denaturing buffer consisting of either 9% SDS for 30 minutes at 37° C., or pH2.0-2.5 Glycine HCl buffer for 10 minutes at 37° C. The purpose of the denaturing buffer is to dissociate human CCL2 from the biparatopic antibody. After that, the samples were diluted 10-fold and added onto anti-CCL2-immobilized plate, and allowed to bind for 1 hour at 30° C. before washing. Next, SULFO TAG labelled MCP-1 antibody was added and the plate was incubated for 1 hour at 30° C. before washing. Read Buffer T (×4) (Meso Scale Discovery) was immediately added to the plate and signal was detected by SECTOR Imager 2400 (Meso Scale Discovery). The human CCL2 concentration was calculated based on the response of the calibration curve using the analytical software SOFTmax PRO (Molecular Devices).

Measurement of Anti-CCL2 Antibody Concentration in Serum by Enzyme-Linked Immunosorbent Assay (ELISA)

The concentration of anti-CCL2 antibody in mouse serum was measured by ELISA. Anti-human IgG kappa-chain (Antibody Solutions) was dispensed onto a Nunc MaxiSorp plate (Thermofisher) and allowed to stand overnight at 4 degrees C. to prepare anti-human IgG-immobilized plates. Calibration curve and samples were prepared with 1% pooled mouse serum. Then, the samples were dispensed onto the anti-human IgG-immobilized plates, and allowed to stand for 1 hour at 30 degrees C. Subsequently, goat anti-human IgG (gamma-chain specific) with HRP conjugate (Southern Biotech) was added to react for 1 hour at 30 degrees C. Chromogenic reaction was carried out using ABTS substrate (KPL) as a substrate and absorbance at 450 nm was measured by a microplate reader. The concentration in mouse plasma was calculated from the absorbance of the calibration curve using the analytical software SOFTmax PRO (Molecular Devices).

Summary of the Studies

To summarize the mouse PK study data, sweeping of human CCL2 by the tested biparatopic antibodies was more efficient compared to monoparatopic antibodies at the same dose. With the monoparatopic antibodies, there were minimal difference in antigen clearance between antibodies with WT FcgR binding and FcgR binding silent (Table 3). In contrast, large difference in antigen clearance between biparatopic antibodies with WT FcgR binding and FcgR binding silent were obtained (Table 4), suggesting that the tested biparatopic antibodies could sweep human CCL2 efficiently. The combination of CNTO888/11K2 was chosen for further antibody engineering as it demonstrated the largest fold chance in clearance.

Example B-2 Anti-CCL2 Antibodies with Modified Variable Domains and CDRs (Ion Dependent/pH Dependent Binding)

Modification Leading to Ion Dependent/pH Dependent Binding

To generate pH-dependent anti-CCL2 antibodies, histidine scanning mutagenesis was conducted for all CDRs of mAbs CNTO888 and humanized 11K2. Each amino acid in the CDRs was individually mutated to histidine using In-Fusion HD Cloning Kit (Clontech Inc. or Takara Bio company) according to the manufacturer's instructions. After confirming through sequencing that each variant was mutated correctly, variants were transiently expressed and purified by the following method: Recombinant antibodies were expressed transiently using Freestyle FS293-F cells and 293Fectin (Life technologies), according to the manufacturer's instructions. Recombinant antibodies were purified with protein A (GE Healthcare) and eluted in D-PBS or His buffer (20 mM Histidine, 150 mM NaCl, pH6.0). Size exclusion chromatography was further conducted to remove high molecular weight and/or low molecular weight component, if necessary. All histidine-substituted variants were evaluated by a modified BIACORE® assay as compared to that described above. Briefly, an additional dissociation phase at pH5.8 was integrated into the BIACORE® assay immediately after the dissociation phase at pH7.4. This is to assess the pH-dependent dissociation between antibody (Ab) and antigen (Ag) from the complexes formed at pH7.4 as opposed to the corresponding dissociation at pH5.8. The dissociation rate at pH5.8 buffer was determined by processing and fitting data using the Scrubber 2.0 (BioLogic Software) curve fitting software.

Single histidine substitutions which resulted in reduction in binding response at pH5.8 compared to the pH7.4 dissociation phase were selected and combined. To identify mutations which improve affinity at pH7.4, more than 500 variants were generated for heavy and light chain respectively, using at least one variant generated during the histidine substitution step. These variants had each amino acid in the CDRs substituted with 18 other amino acids, excluding the original amino acid and Cysteine. The binding ability of variants to human CCL2 was assessed at 37 degrees C. under pH7.4 using BIACORE® 4000 instrument (GE Healthcare). As before, an additional dissociation phase at pH5.8 was integrated into the BIACORE® assay immediately after the dissociation phase at pH7.4. The dissociation rate at pH5.8 buffer was determined by processing and fitting data using the Scrubber 2.0 (BioLogic Software) curve fitting software.

Variants which improved affinity at pH7.4 and improved pH dependency were selected, and these mutations were combined. This is exemplified in four 11K2 variants and four CNTO888 variants in the following Table.

TABLE

Four modified 11K2 and four CNTO888 variants engineered for pH-dependent binding

| Modified 11K2 variants (VH/VL) | Modified CNTO888 variants (VH/VL) |
|---|---|
| 11K2H1503/11K2L1338 | CNTO888H0625/CNTO888L0616 |
| 11K2H1510/11K2L1338 | CNTO888H0634/CNTO888L0616 |
| 11K2H1503/11K2L1201 | CNTO888H0635/CNTO888L0616 |
| 11K2H1514/11K2L1338 | CNTO888H0695/CNTO888L0616 |

To evaluate the combination effect of modified 11K2 and CNTO888 variants, each 11K2 variant was combined with the four modified CNTO888 variants, and expressed as a biparatopic CCL2 antibody in CrossMab format. This is exemplified in the following Table, where the 4×4 combination results in the generation of 16 biparatopic antibodies, designated as CKLO81 to CKLO16.

TABLE

Combination of four modified 11K2 and four modified CNTO888 variants to generate 16 bispecific (biparatopic) antibodies.

| Bispecific anti-CCL2 antibody | Based on variable domains of |
|---|---|
| CKLO01 | 11K2H1503/11K2L1338//CNTO888H0695/CNTO888L0616 |
| CKLO02 | 11K2H1510/11K2L1338//CNTO888H0695/CNTO888L0616 |
| CKLO03 | 11K2H1503/11K2L1201//CNTO888H0695/CNTO888L0616 |
| CKLO04 | 11K2H1503/11K2L1201//CNTO888H0625/CNTO888L0616 |
| CKLO05 | 11K2H1503/11K2L1338//CNTO888H0634/CNTO888L0616 |
| CKLO06 | 11K2H1503/11K2L1201//CNTO888H0634/CNTO888L0616 |
| CKLO07 | 11K2H1514/11K2L1338//CNTO888H0634/CNTO888L0616 |
| CKLO08 | 11K2H1510/11K2L1338//CNTO888H0634/CNTO888L0616 |
| CKLO09 | 11K2H1503/11K2L1338//CNTO888H0625/CNTO888L0616 |
| CKLO10 | 11K2H1514/11K2L1338//CNTO888H0625/CNTO888L0616 |
| CKLO11 | 11K2H1510/11K2L1338//CNTO888H0625/CNTO888L0616 |
| CKLO12 | 11K2H1503/11K2L1338//CNTO888H0635/CNTO888L0616 |
| CKLO13 | 11K2H1503/11K2L1201//CNTO888H0635/CNTO888L0616 |
| CKLO14 | 11K2H1514/11K2L1338//CNTO888H0635/CNTO888L0616 |
| CKLO15 | 11K2H1510/11K2L1338//CNTO888H0635/CNTO888L0616 |
| CKLO16 | 11K2H1514/11K2L1338//CNTO888H0695/CNTO888L0616 |

To generate the bispecific antibodies, the CrossMab technology described in WO 2016/016299 was used, in which VH/VL have been exchanged in one antibody arm and the CH1/CL interface of the other antibody arm has been modified by charge modifications, in combination with the knobs-into holes technology in the CH3/CH3 interface to foster heterodimerization. An exemplary sequence for all four antibody chains where this technology was applied is given for CKLO2 IgG1 (see SEQ ID NO: 108 to SEQ ID NO:111). Depending on the heavy chain constant domain used (e.g. IgG1 wild type (without Fc receptor binding silencing mutations), PGLALA, SG1095, SG1099, 1100—for SG1095, SG1099, 1100 see description below or sequence description) the suffixes IgG1, PGLALA, SG1095, SG1099, 1100 are added Functional Characterization of the Biparatopic Anti-CCL2 Antibodies with Modified Variable Domains and CDRs (Ion Dependent/pH Dependent Binding)

Affinity Measurements (See Methods Above)

For all 16 generated bispecific anti-CCL2 antibodies as IgG1 wild type their pH dependent binding human CCL2 was determined.

FIG. 5*a* shows Biacore® sensorgrams showing binding profile to monomeric CCL2 at pH7.4 (black line) and pH5.8 (grey line) of the four modified 11K2 and four CNTO888 variants, and the 16 Crossmabs after combination.

FIG. 5*b* shows Biacore® sensorgrams showing binding profile of the four modified 11K2 and four CNTO888 variants, and the 16 Crossmabs after combination to monomeric CCL2, where an additional dissociation phase at pH5.8 was integrated into the BIACORE® assay immediately after the dissociation phase at pH7.4.

Cross-reactivity Binding to CCL8 pH dependency binding to recombinant monomeric human CCL2 and recombinant monomeric human CCL8 were assessed at 37° C. using Biacore T200 instrument (GE Healthcare). Anti-human Fc (GE Healthcare) was immobilized on each flow cells of a CM4 sensor chip using amine coupling kit (GE Healthcare) according to the recommended settings by the manufacturer. Antibodies and analytes were diluted into ACES pH 7.4 or pH 5.8 buffer (20 mM ACES, 150 mM NaCl, 1 mg/ml BSA, 0.05% Tween 20, 0.005% NaN3). Antibodies were captured onto the anti-Fc sensor surfaces, then recombinant monomeric human CCL2 was injected over the flow cell at 8 nM concentration. Association phase of analytes to antibodies was monitored for 120 s, followed by 180 s dissociation phase. Sensor surface was regenerated each cycle with 3M $MgCl_2$. Binding sensorgram was processed by TIBCO Spofire by normalization of binding response to the capture level.

Assessment of pH-dependent dissociation for antibody/antigen complexes formed at pH 7.4 was checked by a modified Biacore assay. Briefly, an additional dissociation phase at pH 5.8 was integrated into the Biacore assay immediately after dissociation phase at pH 7.4. Binding sensorgram was processed by TIBCO Spofire by normalization of binding response to the capture level.

Expression and purification of recombinant human CCL8 P8A monomer: The sequence for wild type human CCL8 was obtained from Genbank (NCBI: NP_005614.2). To make monomeric CCL8, proline at position 8 of the mature CCL8 protein was mutated to alanine. Expi 293 cells (Lifetech) were transfected according to the manufacturer's instructions. CCL8 wild type and P8A monomer protein were purified using the same method from cell culture supernatants by cation exchange chromatography using SP-Sepharose HP (GE Healthcare) and Superose 200 size exclusion (GE Healthcare) chromatography. Briefly, cell culture supernatants were diluted 2.5-fold with MilliQ water (Millipore), loaded on a Hi-Trap SP-HP column equilibrated with PBS, washed with equilibration buffer and eluted using a gradient of 0-2M NaCl. The eluted protein fractions were pooled and further purified by size exclusion chromatography using a HiLoad 16/600 Superose 200 (GE Healthcare) column equilibrated with 20 mM histidine, 150 mM NaCl, pH 6.0. Fractions were analyzed by size exclusion chromatography and SDS-PAGE. Fractions containing CCL8 protein were pooled, concentrated and stored at −80° C.

Human CCL8 shares a high degree of homology with CCL2 and is able bind to CCR2 as well. As the 11K2 arm is able to bind CCL8 (see FIG. 1, FIG. 1A, FIG. 1B, and FIG. 1C), it was necessary to identify mutations to reduce this binding to avoid possible off-target effects of neutralizing CCL8. In addition, removal of CCL8 binding on the 11K2 arm is important for efficient formation of immune complex with CCL2. As the CNTO arm does not bind CCL8, binding of CCL8 to the 11K2 arm will interfere with immune complex formation with CCL2, which may reduce the clearance rate of CCL2 from plasma.

Figure 6:
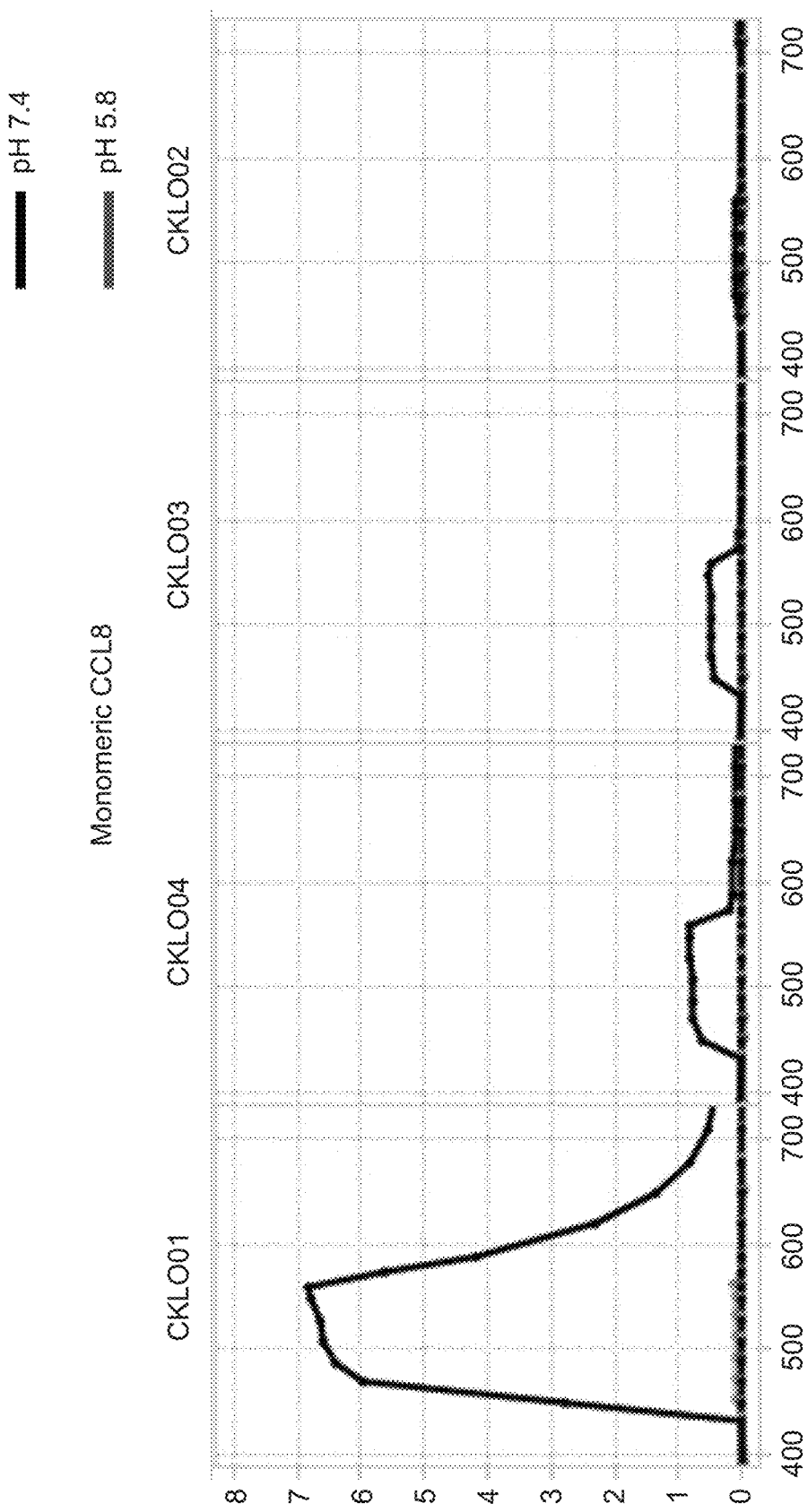
FIG. 6: Biacore® sensorgrams showing binding profile of bispecific anti-CCL2 antibodies CKLO01, CKLO02, CKLO03 and CKLO04 to monomeric CCL8 at pH7.4 (black line) and pH5.8 (grey line).

To identify mutations which reduce binding of 11K2 to human CCL8 and confer selectivity to human CCL2, some CDR positions were substituted like e.g. D101E in the 111K2 VH of CKLO02 or W92R in the 11K2 VL of CKLO03 to remove cross-reactivity to huCCL8. As shown in FIG. 6, CCL8 binding in the biparatopic Crossmab could be markedly reduced by engineering 11K2. The CKLO01 variant was not optimized to reduce CCL8 binding, whereas CKLO04, CKLO03, and CKLO02, contain mutations to reduce CCL8 binding. All four Crossmabs have pH-dependent binding to CCL8.

Binding Affinity of Anti-CCL2 Antibodies to Recombinant CCL2 and CCL8 at pH 7.4 & pH 5.8

To determine the affinity and pH dependent binding of parental CNTO888H/11K2H2, CKLO1, CKLO2 and CKLO3 to human CCL2 and CCL8 was assessed at 37° C. using Biacore T200 instrument (GE Healthcare). Anti-human Fc (GE Healthcare) was immobilized on each flow cells of a CM4 sensor chip using amine coupling kit (GE Healthcare) according to the recommended settings by the manufacturer. Antibodies and analytes were diluted into ACES pH 7.4 or pH 5.8 buffer (20 mM ACES, 150 mM NaCl, 1 mg/ml BSA, 0.05% Tween 20, 0.005% NaN3). Antibodies were captured onto the anti-Fc sensor surfaces, then recombinant human CCL2 P8A variant (monomer) or CCL8 P8A variant (monomer) was injected over the flow cell at 1.25 nM to 20 nM prepared by two-fold serial dilution. Sensor surface was regenerated each cycle with 3M MgCl2. Binding affinity were determined by processing and fitting the data to 1:1 binding model using Biacore T200 Evaluation software, version 2.0 (GE Healthcare). The binding affinity of anti-CCL2 antibodies to recombinant CCL2 and CCL8 at pH 7.4 & pH 5.8 are shown in the Table 5 below.

TABLE 5

Binding affinity of anti-CCL2 antibodies to recombinant CCL2 and CCL8 at pH 7.4 & pH 5.8

| Bispecific anti-CCL2 antibody | KD to human CCL2 | | KD to human CCL8 | |
| --- | --- | --- | --- | --- |
| | pH 7.4 | pH 5.8 | pH 7.4 | pH 5.8 |
| CNTO8888/11k2 | 1.28E−11 | 2.35E−13 | 1.47E−09 | 1.75E−09 |
| CKLO1 | 7.39E−12 | 9.32E−09 | 2.33E−08 | n.d. |
| CKLO2 | 4.32E−12 | n.d. | n.d. | n.d. |
| CKLO3 | 6.85E−12 | 2.17E−08 | n.d. | n.d. |

Note:
n.d. KD cannot be determined due to low binding response.

The data in the Table 5 show that binding to CCL8 at pH7.4 was abolished for CKLO2 and CKLO3, while maintaining strong affinity at pH7.4 and pH-dependent binding for CCL2. The results show the different modifications introduced in the variable regions and CDRs of the parental bispecific antibody based on CNTO888 and 11K2 successfully generated affinity matured variants, CKLO1, CKLO2, CKLO3 with enhanced binding affinity to CCL2 compared to parental Ab at pH 7.4. At the same time CKLO1, CKLO2, CKLO3 showed strong pH dependent binding to CCL2. A more than 1000-fold weaker KD of the binding affinity to CCL2 was observed at pH 5.8 compared to the KD value at pH 7.4

Clearance of Wild Type Human CCL2

To evaluate the ability of pH-dependent bispecific antibodies to enhance the clearance of wild type human CCL2, pre-formed immune complexes consisting of anti-CCL2 monoparatopic antibody (20 mg/kg) and wild type human CCL2 (0.1 mg/kg) were administered at a single dose of 10 ml/kg into the caudal vein of SCID mice. Blood was collected 5 minutes, 1 hour, 4 hours, 7 hours, 1 day, and 7 days after administration. The serum was stored at or below −80° C. until measurement. The Crossmab antibodies tested were parental CNTO/11K2, and four pH-engineered variants, CKLO01, CKLO02, CKLO03, and CKLO04. All antibodies had an IgG1 wild type Fc part (without mutations silencing/abolishing Fc (gamma) receptor binding). Measurement of total human CCL2 and anti-CCL2 antibody concentration in mouse serum was done as described above (under "Evaluation of human CCL2 immune complex sweeping with biparatopic antibody in mice" following Table 4).

Figure 7A:
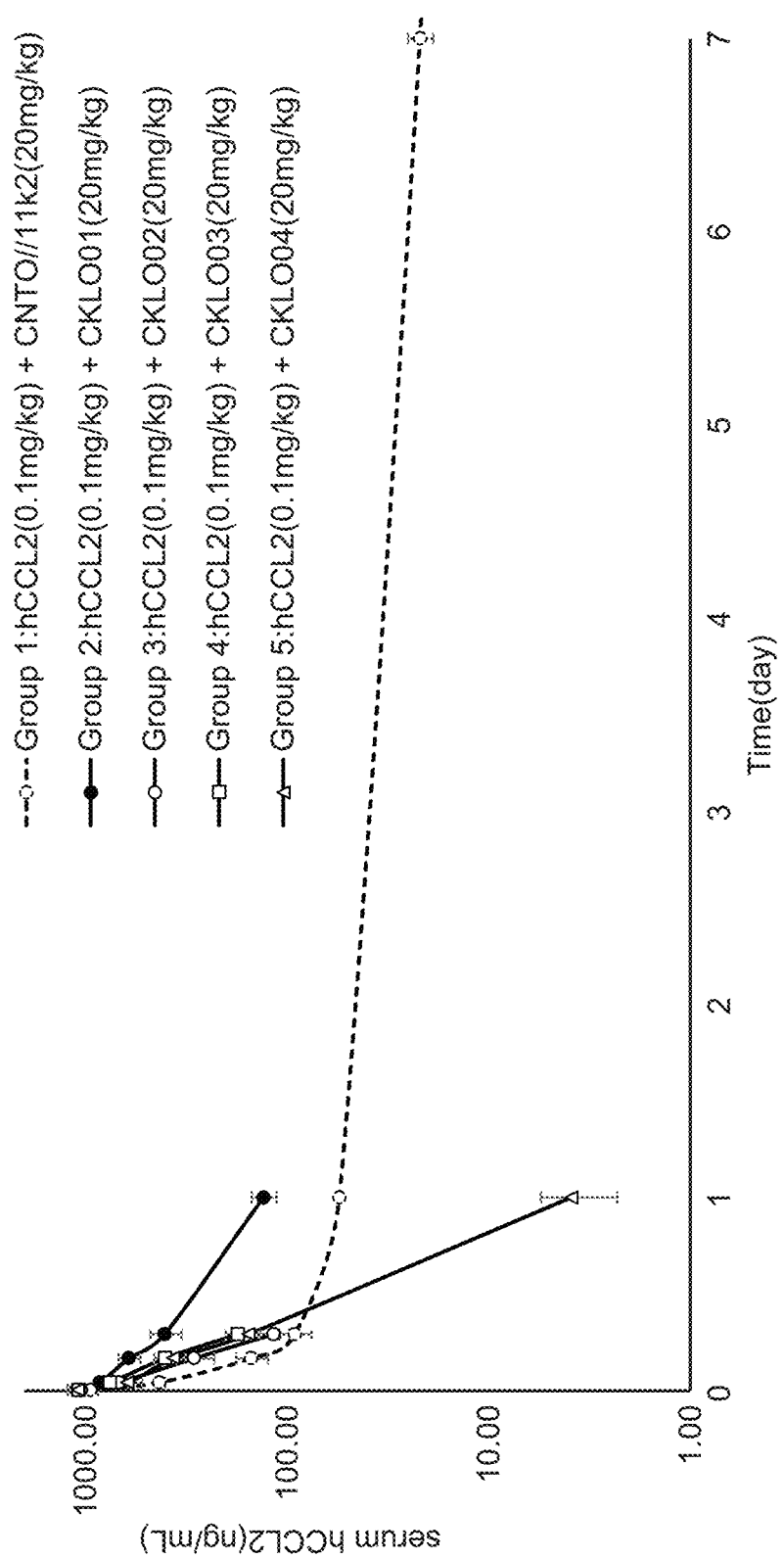
FIG. 7a: Serum concentration of hCCL2 over time after injection of pre-formed immune complex consisting of hCCL2 and bispecific anti-CCL2 antibodies (parental CNTO/11K2 and pH dependent variants CKLO01, CKLO02, CKLO03 and CKLO04) into SCID mice.

Results are shown in FIG. 7a: Serum concentration of hCCL2 over time after injection of pre-formed immune complex consisting of hCCL2 and bispecific anti-CCL2 antibodies (parental CNTO/11K2 and pH dependent variants CKLO01, CKLO02, CKLO03 and CKLO04) into SCID mice. All four pH-engineered variants showed rapid clearance of human CCL2. For CKL002, CKLO03, human CCL2 was below the detection limit by day 1. For the parental CNTO/11K2, rapid clearance of human CCL2 was initially observed till day 1, but thereafter, clearance of human CCL2 was slow.

Example B-3 Anti-CCL2 Antibodies with Modified Variable Domains and CDRs (Ion Dependent/pH Dependent Binding) and Fc Mediated Sweeping Modification of the Bispecific Anti-CCL2 Antibodies Via Sweeping Technology The bispecific anti-CCL2 antibodies were modified using the sweeping technology to enable the bispecific anti-CCL2 antibodies to abrogate free CCl2 over longer time periods to enable sustained a biological effect like anti-cancer efficacy or anti-inflammatory efficacy in vivo.

The Sweeping concept is described e.g. in Igawa et al, Immunological Reviews 270 (2016) 132-151, WO2012/122011, WO2016/098357, and WO2013/081143 which are incorporated herein by reference.

pI Fc Mediated Sweeping

Having demonstrated the pH-engineered biparatopic antibodies can accelerate CCL2 clearance in vivo, we next evaluated the ability of antibodies with pI-increasing substitutions to enhance the clearance of wild type human CCL2. Pre-formed immune complexes consisting of anti-CCL2 monoparatopic antibody (20 mg/kg) and wild type human CCL2 (0.1 mg/kg) were administered at a single dose of 10 ml/kg into the caudal vein of SCID mice. Blood was collected 5 minutes, 30 minutes, 1 hour, 2 hours, 4 hours, and 7 days after administration. The serum was stored at or below −80° C. until measurement. The Crossmab antibodies tested were parental CKLO03 with IgG1, and CKLO03 with pI enhanced Fc, CKLO03-SG1099. Measurement of total human CCL2 and anti-CCL2 antibody concentration in mouse serum was done as described above (under "Evaluation of human CCL2 immune complex sweeping with biparatopic antibody in mice" following Table 4).

Figure 7B:
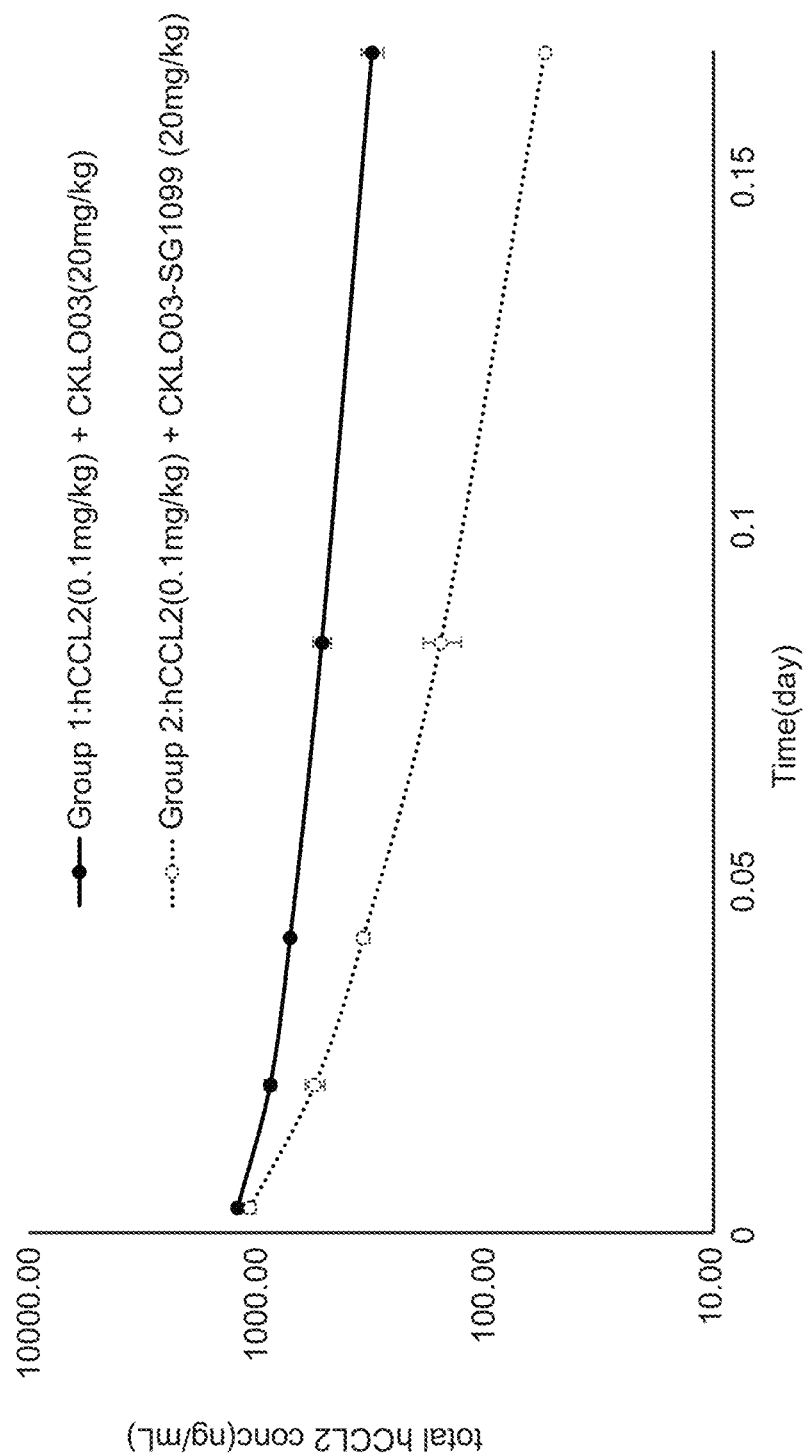
FIG. 7b: Serum concentration of hCCL2 over time after injection of pre-formed immune complex consisting of hCCL2 and CKLO03 (with IgG1 wild type Fc) or CKLO03-SG1099, (CKLO03 with enhanced pI Fc) into SCID mice.

Results are shown in FIG. 7b. Serum concentration of hCCL2 over time after injection of pre-formed immune complex consisting of hCCL2 and CKLO03 (with IgG1 wild type Fc) or CKLO03-SG1099, (CKLO03 with enhanced pI Fc) into SCID mice. CKLO03-SG1099, which contain Fc substitutions Q311R/P343R (EU Kabat numb.) showed faster clearance/reduction of human CCL2 compared to CKLO03 with IgG1. This demonstrates that pH-dependent biparatopic antibody with pI-increasing mutations can accelerate the clearance of CCL2.

Generation of Biparatopic Anti-CCL2 Antibodies with FcgammaRIIb-Enhanced Fc Variants and Further Fc Modifications In this example, Fc engineering to enhance CCL2 clearance is illustrated.

It has been demonstrated in WO 2013/125667 that clearance of a soluble antigen can be enhanced by its administration of antigen-binding molecules (e.g. antibodies) comprising an Fc domain displaying an increased affinity for FcgammaRIIb. Furthermore, Fc variants that can show enhanced binding to human FcgammaRIIb have been illustrated in WO 2012/115241 and WO 2014/030728. It has been also illustrated that these Fc variants can show selectively enhanced binding to human FcgammaRIIb and decreased binding to other active Fc gamma Receptors (Fc gamma Rs). This selective enhancement of FcgammaRIIb binding can be favorable not only for clearance of soluble antigen but also for decreasing the risk of undesired effector functions and immune response.

For development of an antibody drug, efficacy, pharmacokinetics, and safety should be evaluated in non-human animals in which the drug is pharmacologically active. If it is active only in human, alternative approaches such as the use of a surrogate antibody must be considered (Int. J. Tox. 28: 230-253 (2009)). However, it would not be easy to precisely predict the effects of the interaction between the Fc region and Fc gamma Rs in human using a surrogate antibody, because the expression patterns and/or functions of Fc gamma Rs in non-human animals are not always the same as in human. It would be preferable that the Fc regions of antibody drugs should have cross-reactivity to non-human animals, especially to cynomolgus monkey which has close expression patterns and functions of Fc gamma Rs to human, so that the results obtained in non-human animals could be extrapolated into human.

The following IgG1 constant domain/Fc variants of the bispecific anti-CCL2 antibodies were generated with mutations at positions of the Fc part (EU Kabat numbering)

SG1095—derived from IgG1 including the mutations (Kabat EU numbering):
  L235W/G236N/H268D/Q295L/A330K/K326T (suitable for increase affinity to human FcgRIIb and decreasing affinity to other human FcgR);
  Q311R/P343R (suitable for increasing isoelectric point (pI) for enhancing uptake of antigen);
  N434A (suitable for increasing affinity to FcRn for longer plasma half-life of antibody); and
  Q438R/S440E (suitable for suppressing rheumatoid factor binding)

SG1099—derived from IgG1 including mutations (Kabat EU numbering):
  Q311R/P343R (suitable for increasing pI for enhancing uptake of antigen)

SG1100—derived from IgG1 including the mutations (Kabat EU numbering):
  Q311R/P343R (suitable for increasing pI for enhancing uptake of antigen);
  N434A (suitable for increasing affinity to FcRn for longer plasma half-life of antibody; and
  Q438R/S440E (suitable for suppressing rheumatoid factor binding)

GG01—derived from IgG1 including the mutations (Kabat EU numbering):
  L234Y/P238D/T250V/V264I/T307P/A330K (suitable for increasing affinity to human FcgRIIb and decreasing affinity to other human FcgR);
  Q311R/P343R (suitable for increasing isoelectric point (pI) for enhancing uptake of antigen);
  N434A (suitable for increasing affinity to FcRn for longer plasma half-life of antibody); and
  Q438R/S440E (suitable for suppressing rheumatoid factor binding)

GG02—derived from IgG1 including mutations (Kabat EU numbering):
  L234Y/P238D/T250V/V264I/T307P/A330K (suitable for increasing affinity to human FcgRIIb and decreasing affinity to other human FcgR);
  Q311R/P343R (suitable for increasing isoelectric point (pI) for enhancing uptake of antigen);
  M428L/N434A/Y436T (suitable for increasing affinity to FcRn for longer plasma half-life of antibody); and
  Q438R/S440E (suitable for suppressing rheumatoid factor binding)

GG03—derived from IgG1 (SG1-IgG1 allotype) including the mutations (Kabat EU numbering):
  L234Y/P238D/T250V/V264I/T307P/A330K (suitable for increasing affinity to human FcgRIIb and decreasing affinity to other human FcgR);
  Q311R/P343R (suitable for increasing isoelectric point (pI) for enhancing uptake of antigen);
  N434A (suitable for increasing affinity to FcRn for longer plasma half-life of antibody); and
  Q438R/S440E (suitable for suppressing rheumatoid factor binding)

GG04—derived from IgG1 (SG1-IgG1 allotype) including mutations (Kabat EU numbering):
  L234Y/P238D/T250V/V264I/T307P/A330K (suitable for increasing affinity to human FcgRIIb and decreasing affinity to other human FcgR);
  Q311R/P343R (suitable for increasing isoelectric point (pI) for enhancing uptake of antigen);

M428L/N434A/Y436T (suitable for increasing affinity to FcRn for longer plasma half-life of antibody); and Q438R/S440E (suitable for suppressing rheumatoid factor binding)

Functional Characterization of the Bispecific Anti-CCL2 Antibodies with Modified Variable Domains and CDRs (Ion Dependent/pH Dependent Binding) and with or without Fc Mediated Sweeping SPR Binding of Fc Variants SG1095, GG01, GG02, GG03/04 of CKLO2

In an SPR assay at a Biacore 8K instrument, binding of monomeric human and cyno CCL2 to the 4 different antibodies P1AD8325, P1AF8137, P1AF8139, and P1AF8140 at pH 7.4 and 5.8 was investigated.

In this set-up, CaptureSelect™ Human Fab-kappa (ThermoFisher Scientific) was immobilized on a CM3 sensor chip using the amine coupling method, the diverse antibodies were captured as ligands, and measurements were performed with 0, 10, 100 and 1000 nM monomeric human or cyno CCL2 as an analyte at two different pH values.

CKLO2-SG1095, CKLO2-GG01, CKLO2-GG02, CKLO2-GG03/04 show almost identical binding profiles to monomeric human and cyno CCL2 which bind at 10, 100 and 1000 nM and dissociate equally fast at pH 7.4, whereas no stable binding was observed at pH 5.8. Results are shown in the table below.

TABLE

Binding to monomeric human and cyno CCL2 of CKLO2-SG1095, CKLO2-GG01, CKLO2-GG02, CKLO2-GG03/04 show almost identical binding profiles to monomeric human and cyno CCL2

| Antibody | Antigen | Rmax (RU) @ pH 7.4 | t 1/2 (s) @ pH 7.4 | Rmax (RU) @ pH 5.8 | t 1/2 (s) @ pH 5.8 |
|---|---|---|---|---|---|
| CKLO2-GG01 | Monomeric human CCL2 | 15.9 | 6.18 | 29.8 | 3.29 |
| CKLO2-GG02 | Monomeric human CCL2 | 16.8 | 4.04 | 28.8 | 3.29 |
| CKLO2-GG03/04 | Monomeric human CCL2 | 17.6 | 5.90 | 29.6 | 3.24 |
| CKLO2-SG1095 | Monomeric human CCL2 | 19.0 | 5.49 | 35.3 | 3.51 |
| CKLO2-GG01, | Monomeric cyno CCL2 | 16.5 | 7.10 | 30.7 | 3.22 |
| CKLO2-GG02, | Monomeric cyno CCL2 | 17.2 | 5.97 | 29.5 | 3.14 |
| CKLO2-GG03/04 | Monomeric cyno CCL2 | 17.9 | 6.48 | 30.4 | 3.12 |
| CKLO2-SG1095 | Monomeric cyno CCL2 | 19.5 | 6.07 | 36.0 | 3.41 |

Chemotaxis Assay
Description of Method

THP-1 cells were cultured for 3 days up to 8×10E5 cells/ml. A total cell number of 5000 cells/well were seeded in the upper chamber of a microtiter plate and let settle at 37° C. Recombinant huCCL2 was pipetted in the bottom chamber at a final concentration of 50 ng/ml in the presence or not of anti-CCL2 antibodies (when the assay was performed to test surrogate antibodies, recombinant muCCL2 was used instead, at 100 ng/ml). Upper and bottom chambers were brought together avoiding the formation of air bubbles and the plate was then incubated at 37° C. for 24 h. Migrated cells were quantified by the Cell Titer Glo method according to manufacturer's recommendation, and luminescence measured with the Tecan Infinite 200 Reader.

Results are shown in FIG. 8: Chemotaxis Assay: Bispecific anti-CCL2 antibodies with identical CDRs and variable regions VH/VL, namely CKLO2-IgG1 wild type and CKLO2-SG1095, but different Fc moieties, can inhibit the migration of THP-1 cells with identical potencies ($IC_{50}$=0.2 µg/ml; FIG. 8, left panel).

Similarly, CCL2-0048, the parent VH/VL-unmodified bispecific antibody CNTO888/11k2 of CKLO2, which is non-pH dependent, also shows an $IC_{50}$ of 0.2 µg/ml, since pH-dependency is critical for antigen sweeping, a phenomenon that does not take place in this assay.

The corresponding monoparatopic antibodies CNTO888 IgG1 and humanized 11k2 IgG1 display $IC_{50}$ values of 0.3 and 0.7 µg/ml, respectively, while the huIgG1 isotype control shows no inhibition (FIG. 8, right panel).

In additional analogous experiments the $IC_{50}$ values of CKLO2-GG01 (0.2 µg/ml), CKLO2-GG02 (0.2 µg/ml), and GG03/GG04 (0.3 µg/ml), were determined.

In Vivo Biological Activity in a Genetically-Modified Mouse Model
Material and Methods
B16-huCCL2/CCL2-Null Model The present model was generated with the aim of testing anti-human CCL2 antibodies without the interference of mouse CCL2 in, otherwise, immune competent tumor-bearing mice. For this, the mouse tumor cell line B16-F10 was chosen since it does not secrete mCCL2 and is known to grow in vivo in mice of the C57/B16 strain, which is the genetic background of the CCL2 knock-out mice.

To generate stable pools of B16F10 tumor cells expressing huCCL2 they were transfected with plasmid DNA encoding for huCCL2 and a Hygromycin-B selection cassette. Therefore, cells were seeded into 6-well plates with 2.0E+05 cells/well in growth medium (DMEM+10% FCS+2 mM L-glutamine). After 24 h a transfection mix composed of 1 µg DNA per well and Lipofectamine 2000 in Opti-MEM medium was added to the cells. Subsequently, the cells were put under selection with medium containing Hygromycin-B (0.5 mg/ml). After 20 days of culture living single cells were sorted based on FSC/SSC-scatter using a BD FACS Aria III. Twelve days later, cell culture supernatants from single cell clones were screened for expression of human CCL2 using the ELISA Ready-SET-Go from ebioscience (Cat #88-7399-86) in comparison to wild type B16F10 cells (data not shown).

The selected B16-F10_HOMSA_CCL2 tumor cell clones 1A5, 2A3 and 2B2 were routinely cultured in DMEM containing 10% FCS and 2 mM L-Glutamine (PAN Biotech GmbH, Germany) at 37° C. in a water-saturated atmosphere at 5% CO2. Culture passage was performed with trypsin/EDTA 1×(PAN Biotech GmbH, Germany) splitting twice/week.

Female B6.129S4-Ccl2tm1Rol/J mice (Jackson Laboratories), age 7-10 weeks at arrival, were inoculated with the B16-F10_HOMSA_CCL2 tumor cell clones: on that day (study day 0), tumor cells were harvested from culture flasks and transferred into culture medium, washed once and resuspended in PBS. Cell numbers were determined using a cell counter and analyzer system (Vi-CELL, Beckman Coulter). For s.c. injection cell titer was adjusted to 1×10E7 cells/ml and 100 µl were injected subcutaneously into the right flank of mice using a cooled 1.0 ml tuberculin syringe (Dispomed, Germany) and a small needle (0.45×12 mm). Cell inoculation was performed under general anesthesia by isoflurane (CP Pharma, Germany) in an inhalation unit for small animals.

Tumor growth was monitored daily and mice were sacrificed on study day 15, when tumors reached about 1000 mm3 for B16-F10_HOMSA_CCL2 tumor cell clones 1A5 and 2A3 (at this time point 2B2 tumors were about 600 mm3 due to a slower growth rate). At endpoint, blood samples were taken for CCL2 measurement and tumors were explanted and analyzed by flow cytometry, as described in above.

Mouse immune cells were found to infiltrate all tumors, confirming the notion that human CCL2 is able to attract mouse CCR2+ cells. B16-F10_HOMSA_CCL2 tumor cell clone 1A5 displayed the highest CD45+ total infiltrate with the highest relative mMDSC (monocytic myeloid-derived suppressor cells) composition (FIG. 2a-FIG. 2g). Clones 2A3 and 2B2 had lower frequencies of immune cells in the tumor even though 2A3 cells led to similar levels of serum total CCL2 like 1A5 cells, while the 2B2 clone showed a significantly lower CCL2 serum concentration (data not shown).

Female B6.129S4-Ccl2tm1Rol/J mice were inoculated with the B16-F10_HOMSA_CCL2 tumor cell clone 1A5, as described in above.

Treatment of study groups started 5 days after cell inoculation. Group 1 received human IgG vehicle control treatment whereas groups 2 and 3 were treated i.p. with Mab CKLO2-IgG1 (Fc wild type IgG1) and CKLO2-SG1099 ((CKLO2 pI-enhanced Fc based on IgG1 with mutations Q311R/P343R (Kabat EU numbering)), respectively, at 3.7 mg/kg daily for 9 days. On study day 14, mice were sacrificed and tumors were explanted. Enzymatic digestions and cell strainers were used to generate single cell suspensions from each tumor mass to be analyzed non-pooled by flow cytometry. For the detection of immune cell populations of interest following markers and fluorochromes were used: CD45-BUV395, CD11b-BUV737, F4/80-BV421, CD11c-BV605, Ly6C-AF488, Ly6G-PerCP-Cy5.5, CD206-BV711, CD4-BV510, CD8a-APC-H7, NK1.1-PE-Cy7, CD279-APC and CD274-PE.

Samples were acquired with a BD LSR-Fortessa flow cytometer and analyze using the BD Diva Software.

Serum samples were withdrawn on study days 6, 8 11 and 14 to measure total and free huCCL2.

The method to detect free CCL2 is described in detail under "Proof of concept study of CCL2 sweeping efficiency in cynomolgus monkeys" below. For analysis of free human CCL2 in this study recombinant cynomolgus CCL2 was replaced by recombinant human CCL2 to prepare the calibrators and QCs.

Total CCL2 serum samples were analyzed with a non-validated, but qualified, specific sandwich ELISA. Briefly, biotinylated anti-CCL2 capture antibody (CNTO888 CCL2-0004), blocking buffer, pretreated test sample and detection reagent (digoxigenylated anti-CCL2 antibody (M-1H11-IgG)), were added stepwise to 384-well streptavidin-coated microtiter plate and incubated on a non-vigorous shaker for 1 hour in each step. To dissociate CCL2-drug complexes in the pre-treatment step samples, calibrators or QCs were acidified in pH 5.5 at 37° C. for 10 minutes. Acidified samples were added to the SA-MTP. For detection of immobilized immune complexes, a polyclonal anti-digoxigenin-POD conjugate was added and the plate was incubated for 60 minutes. The plate was washed three times after each step to remove unbound substances.

ABTS was added to the plate and incubated at room temperature with shaking. Absorption was measured at 405/490 nm wavelength. The human CCL2 concentrations were calculated based on the response of the calibration curve using the analytical software XLFit (IDBS).

Depending on the data sets being analyzed statistically a t-test or one-way ANOVA with Tukey's test for multiple comparisons were applied, accordingly.

Results

At end of the study, tumor volumes and tumor weights were significantly reduced in those mice receiving CKLO2-SG1099 (CKLO2 pI-enhanced Fc) (FIG. 9). A closer look at the tumor infiltrate revealed a decreased tumor infiltrate of monocytic myeloid-derived suppressor cells (M-MDSCs), as expected upon CCL2 blockade (FIG. 9).

Furthermore, serum analytics confirmed the efficacy of the therapy: pI optimization leads indeed to a reduction in the accumulation of total CCL2 as compared to the IgG1 wild type Fc CKLO2 molecule, while free-CCL2 (not bound to antibody) is completely suppressed under limit of detection (FIG. 10). Therefore, the present model is suited to investigate the effects of CCL2 blockade in a tumor context, using anti-huCCL2 biparatopic sweeping antibody CKLO2-SG1099 (CKLO2 pI-enhanced Fc). In subsequent studies the optimal dose regimen is investigated in which CKLO2-SG1099 (CKLO2 pI-enhanced Fc) is given at a lower dose once or twice per week and the extension of free-CCL2 suppression is monitored over weeks. Furthermore, combination with T cell activating therapies (i.e. T cell bispecifics, PD-L1 blockade) is also explored in this model.

In additional analogous experiments other variants like CKLO2-SG1095, CKLO2-GG01, GG02 and GG03/GG04 are analyzed.

Proof of Concept (POC) Study of CCL2 Sweeping Efficiency in Cynomolgus Monkeys

Methods. The main objective of this study was to evaluate the extend of CCL2 suppression and sweeping efficiency of four anti-CCL2 (MCP-1) antibodies in cynomolgus monkeys. The secondary objective was to evaluate the pharmacokinetic (PK) properties of these antibodies. All antibodies were administered as single IV infusions of 25 mg/kg over a period of 30 minutes to 3-4-year-old male animals and total CCL2 and antibody concentrations were measured in serum over 70 days. The anti-CCL2 antibodies studied comprised of control antibodies (groups 1 and 2) as well as antibodies specifically engineered to provide enhanced elimination of CCL2-drug complexes (referred to hereafter as antigen sweeping or simply sweeping). Group 1: CNTO888-SG1 (=IgG1 wild type) anti-CCL2 antibody (n=3 animals) as control of maximal total CCL2 accumulation; group 2: a biparatopic anti-CCL2 antibody CKLO2-SG1 (IgG1 wild type) with pH dependent target binding but no Fc-modifications (n=3); group 3: a biparatopic anti-CCL2 antibody CKLO2-SG1100 with pH dependent target binding and Fc-pI and further modifications (n=4) and group 4: biparatopic anti-CCL2 antibody CKLO2-SG1095 with pH dependent target binding, Fc-pI and FcγRII and further modifications (n=4).

In this study, the total serum concentrations of the antibodies, the total (free and antibody-bound CCL2) and free target were quantified. Furthermore, presence of anti-drug antibodies (ADA) was assessed. The antibody, total and free CCL2 profiles were analyzed by non-compartmental analysis using Phoenix 64 (Pharsight/Certara); data were illustrated using GraphPad Prism v. 6.07 (GraphPad Software).

For the antibodies, serum samples were analyzed using a generic human sandwich ELISA method. The concentrations of total antibody in monkey serum were measured by ELISA. 2 µg/mL of anti-human kappa chain antibody was immobilized onto maxisorp 96-well plate overnight before incubating in blocking buffer for 2 hours at 30° C. Antibody calibration curve samples, quality control samples and monkey serum samples were incubated on plate for 1 hour at 30° C. before washing. Next, anti-human IgG-HRP was added and incubated for 1 hour at 30° C. before washing. ABTS substrate was incubated for 10, 20 and 30 minutes before detection with microplate reader at 405 nm. The antibody concentrations were calculated based on the response of the calibration curve using the analytical software SOFTmax PRO (Molecular Devices).

Total CCL2 serum samples were analyzed with a non-validated, but qualified, specific sandwich ECL method assay. 3 µg/mL of anti-CCL2 antibody (r2F2-SG1) was immobilized onto a MULTI-ARRAY 96-well plate (Meso Scale Discovery) overnight before incubating in blocking buffer for 2 hours at 30° C. Cynomolgus monkey CCL2 calibration curve samples, quality control samples and diluted cynomolgus monkey serum samples were incubated with pH5.5 acid buffer for 10 minutes at 37° C. After that, the samples were incubated onto anti-CCL2-immobilized plate for 1 hour at 30° C. before washing. Next, SULFO TAG labelled MCP-1 antibody was added and incubated for 1 hour at 30° C. before washing. Read Buffer T (×4) (Meso Scale Discovery) was immediately added to the plate and signal was detected by SECTOR Imager 2400 (Meso Scale Discovery). The cynomolgus monkey CCL2 concentrations were calculated based on the response of the calibration curve using the analytical software SOFTmax PRO (Molecular Devices).

Free CCL2 serum samples were analyzed with a non-validated, but qualified, Gyrolab™ immunoassay run on a Gyrolab Xplore. A biotinylated anti-CCL2 antibody (M-2F6-IgG) was used as capture reagent and for detection an Alexa647 labeled anti-CCL2 antibody (M-1H11-IgG) was selected. Both reagents were diluted to 1 µg/mL in PBS, 0.1% Tween, 1% BSA and transferred to a 96-well PCR plate (Fisher Scientific). Cynomolgus monkey CCL2 calibration curve samples, QCs and undiluted serum samples were also transferred to a 96-well PCR plate. Both plates were loaded into the instrument together with a Gyrolab Bioaffy 200 nl disc (Gyros Protein Technologies AB). A three step assay protocol (200-3W-001) was selected. Briefly the protocol describes the sequential addition of capture reagent, sample and detection reagent to designated streptavidin columns of the Gyrolab Bio Affy 200 disc. Each reagent reaches the column at the same time after a short spinning step is applied to the disc. The columns were washed with PBS 0.05% Tween after each step and finally laser induced fluorescence values were recorded within the instrument. The free cynomolgus monkey CCL2 concentration was calculated based on the response of the calibration curve using XL Fit software (IDBS).

ADA were analyzed using a method described elsewhere (Stubenrauch et al., 2010). In summary, biotinylated mAb anti-human Fcγ-pan R10Z8E9 was bound to streptavidin-coated high bind plate at a concentration of 0.5 µg/mL and incubated for 1 h. Samples and standards were diluted with assay buffer to 5% cynomolgus monkey serum and added to each well of the coated plate after washing and incubated for 1 h with shaking. After washing, digoxigenylated anti-cynomolgus(cyno) IgG at 0.1 µg/mL were added and incubated for 1 h with shaking. After washing, the polyclonal anti-digoxigenin-HRP conjugate at 25 mU/mL were added and incubated for 1 h with shaking. ABTS was added to the plate and incubated for 10 minutes at room temperature with shaking. Absorption was measured by microplate reader at 405/490 nm wavelength. The ADA concentration was calculated based on the response of the calibration curve using the analytical software SOFTmax PRO (Molecular Devices).

Results. The PK behaviour was assessed during the time in which animals were free of ADA (i.e., before day 14). During this period, the serum concentration-time profiles of all anti-CCL2 antibodies were similar (see FIG. 11 left panel) and partial average AUC values ($AUC_{0-7d}$) were comparable between the different groups 1490, 1810, 1210 and 1320 day. µg/mL for groups 1, 2, 3, and 4 respectively. Similarly, the average $C_{max}$ values were comparable with values of 620, 764, 616 and 664 µg/mL for the groups 1, 2, 4 and 4, respectively. The extent of ADA development was highly variable between animals and groups and resulted in highly variable PK profiles beyond day 7 (data not shown). One animal from group 2 was ADA-negative throughout the entire observation period of 70 days (see FIG. 11 right panel). In this animal the clearance, volume of distribution and terminal half-life of anti-CCL2 antibodies was estimated by non-compartmental analysis at 7.34 mL/(day·kg), 76.2 mL/kg and 10.9 days, respectively.

Baseline levels of CCL2 in serum were assessed for each animal before antibody treatment started. Basal CCL2 levels ranged from 0.126 to 0.357 ng/mL (geometric mean (% CV): 0.199 ng/mL (32.2%, N=14)). As the free form of CCL2 has a higher elimination rate than the antibody-bound form of CCL2, an increase of total CCL2 serum concentrations following antibody treatment was expected. This was indeed observed in all groups (FIG. 12 left panel), demonstrating engagement of the target by all antibodies. Under treatment, the $C_{max}$ values of total CCL2 increased to 824, 575, 106, 32.7 ng/mL for groups 1, 2, 3 and 4, respectively. The $AUC_{0-7d}$ values were 3060, 2970, 522 and 181 day·ng/mL for groups 1, 2, 3 and 4, respectively. During the time that animals were ADA negative, the molar drug concentrations remained in excess of the total CCL2 concentrations. The two sweeping anti-CCL2 antibodies (groups 3 and 4) showed a considerable reduction in total CCL2 serum concentrations compared to the conventional antibody (group 1) of approximately 8- and 25-fold, respectively based on serum $C_{max}$ values and approximately 6- to 17-fold based on the $AUC_{0-7d}$ values of total CCL2. The ADA-negative animal of Group 2 displayed a sustained target engagement (apparent by the plateau) of total CCL2 concentrations (FIG. 12 right panel).

Treatments with all antibodies led to a substantial reduction of free CCL2 levels in serum (FIG. 13 left panel), however the reduction was in part only initially. In group 1, all individuals had quantifiable levels of free CCL2 again after one day. In group 2, all individuals had quantifiable levels of free CCL2 again after two days. In groups 3 and 4, two individuals of each group showed suppression of free CCL2 for seven days. In group 3, two animals with a moderate ADA response, maintaining sufficient antibody concentrations, showed free CCL2 suppression below the detection limit for 21 days. In ADA positive animals, antibody elimination was significantly increased and as a consequence of loss of target engagement CCL2 levels returned rapidly to their original baseline (not shown here).

In additional analogous experiments other variants like CKLO2-SG1099, CKLO2-GG01, GG02 and GG03/GG04 are analyzed.

PK/PD Study of CCL2 Sweeping Efficiency in Cynomolgus Monkeys

Study outline and aims. The PK/PD study was designed based on the results of the POC study using anti-CCL2 antibody CKL02-SG1095. As the POC study had demonstrated a high extent of anti-drug antibody (ADA) formation, a Gazyva® (obinituzumab) treatment was included in the PK/PD study with the intention to reduce the ADA response. For this purpose, 30 mg/kg doses of Gazyva were administered by intravenous infusions four time throughout the study: on days −14, −7, 8 and 36. CKL02-SG1095 was administered at 2.5, 10 and 25 mg/kg dose levels to four animals (2/2 male and female) per dose group as IV infusion over 30 minutes on day 1 (groups 1-3). For comparison a conventional anti-CCL2 antibody (CNTO888-IgG1) was administered at 25 mg/kg as IV infusion over 30 minutes on day 1 (group 4; same control as group 1 of the POC study described above). Total PK (CKL02-SG1095), total and free CCL2 concentrations were assessed until day 99 (i.e., 14 weeks post dose).

The aim of the PK/PD study was to demonstrate a prolonged duration of free CCL2 suppression of CKL02-SG1095 in comparison to a conventional anti-CCL2 antibody (CNTO888 with wild type IgG1 Fc part) in non-human primates.

Methods. Total PK as well as total and free CCL2 were quantified in this study. However, due to the presence of Gazyva in the serum samples some modifications were made to the total PK assay, the total CCL2 assay and the ADA assay in comparison to the POC study, which are described herein. For CNTO888 IgG1 no PK assay was developed.

The concentration of total antibody CKL02-SG1095 in monkey serum was measured by ELISA. For the ELISA biotinylated recombinant human CCL2 (Antigen), pre-treated test samples, positive control standards (calibrator) or QCs (quality controls) and digoxigenylated anti-human IgG (M-1.19.31-IgG) were successively added to a 384 well streptavidin coated microtiter plate (SA-MTP). To dissociate CCL2-drug complexes a pre-treatment of test samples was performed at pH 5.5 for 20 minutes. Before addition to the SA-MTP the acidified samples were neutralized. Immobilized immune complexes were detected with a polyclonal anti-digoxigenin-POD conjugate. The plate was washed three times after each step to remove unbound substances. ABTS was added to the plate as substrate and incubated at room temperature. Absorption was measured at 405/490 nm wavelength. The antibody concentrations were calculated based on the response of the calibration curve using the analytical software XLFit (IDBS).

Total CCL2 serum samples were analyzed with a non-validated, but qualified, specific sandwich ELISA. Briefly, biotinylated anti-CCL2 capture antibody*, pretreated test sample and detection reagent (digoxigenylated anti-CCL2 antibody (1H11-IgG1)), were added stepwise to a 384-well streptavidin-coated microtiter plate and incubated on a non-vigorous shaker for 1 hour for capture and sample step and 50 minutes for the detection reagent respectively. To dissociate CCL2-drug complexes in the pre-treatment step samples, calibrators or QCs were acidified in pH 5.5 for 20 minutes. Acidified samples were added to the SA-MTP. For detection of immobilized immune complexes, a polyclonal anti-digoxigenin-POD conjugate was added and the plate was incubated for 50 minutes. The plate was washed three times after each step to remove unbound substances.

ABTS was added to the plate and incubated at room temperature with shaking. Absorption was measured at 405/490 nm wavelength. The cynomolgus monkey CCL2 concentrations were calculated based on the response of the calibration curve using the analytical software XLFit (IDBS). *Capture antibody for analysis of Group 1-Group 3: anti-CCL2 CNTO8888 IgG1, Capture antibody for analysis of Group 4: anti-CCL2 2F2 IgG1.

ADAs were screened with a bridging sandwich ELISA in 384-well plates. Test samples of animals of group 1, 2 and 3, quality control samples and positive controls were incubated overnight with biotinylated capture antibody CKL02-SG1095 and digoxigenylated detection antibody CKL02-SG1095 together with two additional anti CCL2 antibodies (2F6-IgG1 and 1H11-IgG1) at RT, 500 rpm on a MTP-shaker; these antibodies were added to neutralize CCL2. For samples of animals of group 4 biotin labelled CNTO888-SG1 and digoxigenylated CNTO888-SG1 were used respectively. Formed immune complexes were transferred to a Streptavidin (SA)-coated MTP to immobilize the immune complexes via the biotin-labelled (Bi) capture antibody. Following aspiration of the supernatant, unbound substances were removed by repeated washing. Detection was accomplished by addition of an anti-digoxigenin POD(p) conjugated antibody and ABTS substrate solution. The color intensity of the reaction was photometrically determined (absorption at 405 nm-490 nm reference wavelength). A sample was defined ADA positive if the signal was found to be above a plate specific cut-point. This cut point was defined during assay qualification.

Results. In spite of the Gazyva® (obinituzumab) pre-treatment, 10 out of 12 animals of the CKL02-SG1095 treated and 1 out of 4 of the CNTO888 treated animals developed ADA with influence on the drug and biomarker concentrations. However, the two ADA-negative animals for CKL02-SG1095 were in the 25 mg/kg dose group allowing a direct comparison to the ADA-negative animals of the CNTO888 group. The PK behaviour was assessed during the time in which animals were free of ADAs (i.e., before day 10). The PK profiles of the three different dose groups for CKL02-SG1095 are shown in FIG. 14, left panel. The partial average AUC values ($AUC_{0-7d}$) were 229/191 (male/female), 696/813 and 1492/1346 day·µg/mL for the dose levels 2.5, 10 and 25 mg/kg, respectively. The $C_{max}$ values were 115/122 (male/female), 369/491 and 869/941 µg/mL for the dose levels 2.5, 10 and 25 mg/kg, respectively. At the highest dose level, these findings are consistent with the POC study. For the two ADA-negative animals the clearance, volume of distribution and terminal half-life of CKL02-SG1095 was estimated by non-compartmental analysis at 10.5-17.4 mL/(day·kg), 116-118 mL/kg and 5.8-11.6 days, respectively (see FIG. 14 right panel).

As for the POC study describe above, accumulation of total CCL2 was observed upon treatment with anti-CCL2 antibodies (see FIG. 15 left panel). Baseline levels of CCL2 were assessed on five occasions before drug administration (including one occasion before Gazyva® (obinituzumab) treatment); the average CCL2 baseline value was 0.742 ng/mL and Gazyva® (obinituzumab) treatment did not affect basal CCL2 levels. The extent of total CCL2 accumulation (values in parenthesis indicate the median fold-change from individual baselines) was dose and construct dependent. For CKL02-SG1095, total CCL2 levels increased to 22.4 (22), 67.2 (105) and 54.9 (76) ng/mL (median of four animals) for 2.5, 10 and 25 mg/kg dose levels. For CNTO888 IgG1, total CCL2 level increased to 1490 (3160) ng/mL (median of 4 animals). Comparison of the ADA-negative animals of groups 3 and 4 showed a considerably lower level of accumulation for CKL02-SG1095 compared to CNTO888 (FIG. 15 right panel).

Treatments of all study groups lead to a substantial, transient reduction of free CCL2 levels in serum (see FIG. 16 left panel; typically, below the limit of detection (0.01 ng/mL). For all ADA-positive animals, free CCL2 levels rapidly returned to baseline values after ADA developed (consistent with the loss of drug exposure and a rapid target turnover). For ADA-negative animals (2/4 in group 3) and (3/4 in group 4) the duration of free CCL2 suppression could be assessed throughout the study duration. For the conventional antibody CNTO888 (group 4), the duration of CCL2 suppression was short, presumably due to the extensive accumulation of the total target (FIG. 15). While the drug concentration was not quantified (no specific assay available for CNTO888), the POC study suggests similar PK properties between CNTO888 and CKL02-SG1095. For the two ADA-negative animals of group 3 on the other hand, long lasting free CCL2 suppression was observed. For one animal, free CCL2 levels remained below the limit of detection for 29 days (FIG. 16 right panel).

In additional analogous experiments other variants like CKLO2-SG1099, CKLO2-GG01, GG02 and GG03/GG04 are analyzed.

Prevalence Study of CCL2 in Different Tumor Types

The following IHC prevalence study of CCL2 and its receptor CCR2, including macrophages analysis using CD163/CD68 and CD14, was performed on 121 human matched tumor and serum samples of 6 different indications:
pancreatic cancer (PaC)
colorectal cancer (CRC)
breast cancer (BC)
prostate cancer (PrC)
ovarian cancer (OvC)
gastric cancer (GC)
the following questions were addressed:
 do these tumors (over)express CCL2?
 is the blood CCL2 level elevated in these tumor patients?
 is there a correlation between blood and tumor CCL2 levels?
 is there a correlation between tumor CCL2 and infiltrating $CCR2^+$ immune cells?
 is there a correlation between tumor CCL2 and infiltrating myeloid cells?

Material and Methods

Histopathological scoring was done semiquantitatively. Additionally, automatical multiplex image analysis was used for CD163/CD68 IHC, and tested for CD14 and CCR2 for immune cell quantification, as well as for CCL2 quantification.

The immunohistological investigation was performed on a set of resection specimens of 121 human tumors of 6 different indications: 31 Pancreatic cancer (PaC), 30 colorectal cancer (CRC), 30 breast cancer (BC), 29 prostate cancer (PrC), 20 ovarian cancer (OvC), and 10 gastric cancer (GC), provided by Indivumed (Hamburg) and Asterand (Royston/Herts, UK). Tumors were fixed in 4% buffered formaldehyde, paraffin-embedded, cut at 2.5 µm thickness, and mounted on Superfrost Plus slides. The mouse monoclonal antibody against CCL2 (clone 2D8, Novusbio NBP2-22115) was used on the Ventana BXT, following a standard staining Protocol (CC1 for 32', concentration of 1 µg/mL in VBX, Optiview DAB detection system). The rabbit monoclonal antibody against CCR2 (E68, Abcam ab32144) was used on the Ventana Discovery XT, following a standard staining protocol (CC1 for 32', concentration 0.8 ug/ml in DS2, Omni-UltraMap HRP DAB detection system). The mouse monoclonal antibody against the monocytic marker CD14 (Cell Marque EPR3653, RTU) was used on the Ventana Discovery Ultra, following a standard staining protocol (CC1 for 64', Omni-UltraMap HRP DAB detection system detection system). The double staining against macrophages and M2-like TAMs (tumor-associated macrophages) CD163/CD68 (DAB CD163 Mouse MRQ-26 Cell Marque RTU/red CD68 Mouse PG-M1 Dako) was used on the Ventana BXT, following a standard staining protocol (CC1 for 32', CD163 RTU/CD68 concentration 0.6 µg/ml in DS2, Detection with DAB and Red detection systems). All images were scanned using the Ventana iScan HT®. The tissue sections were analyzed semi-quantitatively.

1. Results

CCL2 and CCR2 Prevalence

All analyzed tumor indications showed some tumors with up-regulation of CCL2 at variable levels and presence of CCR2 on TAMs at variable amount (Table 6 below). For both, CCL2 and CCR2, the highest expression was observed in ovarian carcinoma, followed by PDAC and GC Tumor Type-Specific Characteristics Tumors with high activity of CCL2-CCR2, associated with a tumor-growth enhancing immunological status of high MDSC attraction and M2 polarization, represent the preferred of tumors for CCL2-blocking therapy. CCR2 IHC showed a good correlation to MDSCs and M2-like macrophages confirming its biological role, and demonstrated a higher relevance as biomarker for this pathway than CCL2 IHC measurement. Concluding from the present study, the following recommendations for CCL2-therapy can be summarized:

OvC can be recommended for CCL2-targeted therapy because of the highest CCL2 and CCR2 prevalence and M2 polarization;

PDAC can be recommended for CCL2-targeted therapy due to the highest amount of MDSCs compared to the other analyzed tumor types, and because CCR2 and M2 were present at considerable high levels and amounts. CCL2 was high in PDAC as well and showed, in contrast to the other tumor types, an extraordinary higher presence in immune cells than in tumor cells. PaC showed a very good correlation between CCL2/CCR2 and MDSC attraction/M2-polarization. These results support that in the analyzed PDACs, the role of CCL2-CCR2 is highly focused on immune cell attraction.

BC, especially TNBC, can be recommended for CCL2-targeted therapy: BC showed CCL2, CCR2, MDSCs and M2 at considerable high levels and amounts. Especially TNBC cases were characterized by higher amounts of M2 and MDSC than non-TNBC, although non-TNBC showed the highest CCL2 production in tumor cells compared to other tumor indications.

The following tumor indications seemed to be less dependent from the CCL2-CCR2-axis and, therefore, might be less recommended for CCL2 targeted therapy:

CRC: CCL2 was low compared to the other tumor types, especially when compared to PaC. Also here, the lowest amount of M2-like macrophages was measured compared to the other tumor types. CCR2 and MDSCs were present at variable amounts. Interestingly, in this indication only, a trend of a positive correlation between CCL2 and CCR2 was detectable. However, the overall findings support that in CRC, the role of CCL2-CCR2 is focused on tumor cell survival and not on immune cell attraction.

Although high for CCL2, GC was observed to be low for CCR2 and showed the lowest amount of MDSCs. M2-like macrophages were present at variable amounts.

| Tumor type: | CCL2 | | | | | CCR2 | | |
|---|---|---|---|---|---|---|---|---|
| | In tumor cells (TC) (manual score) | | | In immune cells (IC) (manual score) | | In immune cells (manual score) | | |
| | % of positive cases | % of mod to hi pos cases | Mean score | % of positive cases | Mean score | % of positive cases | % of mod to hi pos cases | Mean Score |
| OvC | 100% | 42% | 1.3 | 100% | 0.9 | 100% | 63 | 1.7 |
| PaC | 90% | 9% | 0.8 (PDAC 0.8 and PNET 0.9) | 97% | 2.0 (PDAC 2.2 and PNET 0.6) | 90% | 55 | 1.5 (PDAC 1.7 and PNET 0.3) |
| GC | 91% | 45% | 1.3 | 91% | 1.9 | 91% | 18 | 0.8 |
| BC | 78% | 46% | 1.1 (TNBC 0.9 non-TNBC 1.6) | 61% | 0.6 (TNBC 0.5 non-TNBC 0.9) | 96% | 38 | 1.3 (TNBC 1.2 non-TNBC 1.5) |
| CRC | 76% | 24% | 0.8 | 72% | 0.7 | 96% | 39 | 1.2 |
| PrC | 72% | 10% | 0.7 | 79% | 0.5 | 72% | 10 | 0.6 |

Pr CCR2 was present at variable levels. (M2 and MDSC were not measured)

Correlation Analyses

The study outcome can be summarized as follows:

Between tumor CCL2 and CCR2 (IHC), the only positive correlation was existent in CRC.

Serum CCL2 (ELISA) did not correlate with any of the measured parameters in the tumor, including CCL2, CCR2, macrophages, and MDSCs. A trend of positive correlation to tumor CCL2 was found only in PrC, where both methods show very low values.

CCR2 expression correlates positively with the presence of M2-like macrophages and CD14$^+$ cells, and negatively with the M1/M2-ratio, and confirms the biological role of CCR2. The level of CCR2 correlates better with M2 polarization than with MDSC attraction.

CCL2 showed a trend of positive correlation with MDSC attraction and M2 polarization. Thus, the CCL2 level alone seemed not to be the main factor for the presence of MDSCs and M2-like polarization.

The invention claimed is:

1. An isolated bispecific antibody comprising a first antigen-binding site that binds to a first epitope on human CCL2 and a second antigen-binding site that binds a second epitope on human CCL2,
wherein
A) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;
or
B) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;
or
C) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;
or
D) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;
or
E) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;
or
F) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;
or
G) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93;
or
H) i) said first antigen-binding site comprises
a VH domain comprising the amino acid sequence of SEQ ID NO:73;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;
or
I) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:93;
or
J) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93;
or
K) i) said first antigen-binding site comprises
a VH domain comprising the amino acid sequence of SEQ ID NO:72;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;
or
L) i) said first antigen-binding site comprises
a VH domain comprising the amino acid sequence of SEQ ID NO:74;
and a VL domain comprising the amino acid sequence of SEQ ID NO:75; and ii) said second antigen-binding site comprises
a VH domain comprising the amino acid sequence of SEQ ID NO:90;
and a VL domain comprising the amino acid sequence of SEQ ID NO:93;

or

M) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:90;
and a VL domain comprising the amino acid sequence of SEQ ID NO:94;

or

N) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93;

or

O) i) said first antigen-binding site comprises
a VH domain comprising the amino acid sequence of SEQ ID NO:74;
and a VL domain comprising the amino acid sequence of SEQ ID NO:75; and
ii) said second antigen-binding site comprises
a VH domain comprising the amino acid sequence of SEQ ID NO:91;
and a VL domain comprising the amino acid sequence of SEQ ID NO:93;

or

P) i) said first antigen-binding site comprises
a VH domain comprising the amino acid sequence of SEQ ID NO:71;
and a VL domain comprising the amino acid sequence of SEQ ID NO:75; and
ii) said second antigen-binding site comprises
a VH domain comprising the amino acid sequence of SEQ ID NO:92;
and a VL domain comprising the amino acid sequence of SEQ ID NO:93.

2. A composition comprising the bispecific antibody of claim 1, and a carrier.

* * * * *

SEQUENCE LISTING

```
<160> NUMBER OF SEQ ID NOS: 174

<210> SEQ ID NO 1
<211> LENGTH: 3
<212> TYPE: PRT
<213> ORGANISM: Artificial
<220> FEATURE:
<223> OTHER INFORMATION: heavy chain CDR-H1 1A4

<400> SEQUENCE: 1

Trp Ile Cys
1

<210> SEQ ID NO 2
<211> LENGTH: 18
<212> TYPE: PRT
<213> ORGANISM: Artificial
<220> FEATURE:
<223> OTHER INFORMATION: heavy chain CDR-H2    1A4

<400> SEQUENCE: 2

Cys Ile Gly Ala Gly Ser Ser Gly Ser Thr Tyr Tyr Ala Ser Trp Ala
1               5                   10                  15

Lys Gly

<210> SEQ ID NO 3
<211> LENGTH: 10
<212> TYPE: PRT
```

```
<213> ORGANISM: Artificial
<220> FEATURE:
<223> OTHER INFORMATION: heavy chain CDR-H3 1A4

<400> SEQUENCE: 3

Thr Gly Thr Glu Phe Thr Tyr Tyr Ser Leu
1               5                   10

<210> SEQ ID NO 4
<211> LENGTH: 12
<212> TYPE: PRT
<213> ORGANISM: Artificial
<220> FEATURE:
<223> OTHER INFORMATION: light chain CDR-L1 1A4

<400> SEQUENCE: 4

Gln Ala Ser Gln Ser Val Tyr Asn Asn Met Ala
1               5                   10

<210> SEQ ID NO 5
<211> LENGTH: 7
<212> TYPE: PRT
<213> ORGANISM: Artificial
<220> FEATURE:
<223> OTHER INFORMATION: light chain CDR-L2 1A4

<400> SEQUENCE: 5

Thr Ala Ser Ser Leu Ala Ser
1               5

<210> SEQ ID NO 6
<211> LENGTH: 12
<212> TYPE: PRT
<213> ORGANISM: Artificial
<220> FEATURE:
<223> OTHER INFORMATION: light chain CDR-L3 1A4

<400> SEQUENCE: 6

Ala Gly Tyr Lys Ser Tyr Ser Asn Asp Glu Tyr Gly
1               5                   10

<210> SEQ ID NO 7
<211> LENGTH: 116
<212> TYPE: PRT
<213> ORGANISM: Artificial
<220> FEATURE:
<223> OTHER INFORMATION: heavy chain variable domain VH 1A4

<400> SEQUENCE: 7

Gln Ser Leu Glu Glu Ser Gly Gly Asp Leu Val Lys Pro Gly Ala Ser
1               5                   10                  15

Leu Thr Leu Thr Cys Thr Ala Ser Glu Leu Asp Phe Tyr Trp Ile Cys
                20                  25                  30

Trp Val Arg Gln Ala Pro Gly Lys Gly Leu Glu Trp Ile Ala Cys Ile
            35                  40                  45

Gly Ala Gly Ser Ser Gly Ser Thr Tyr Tyr Ala Ser Trp Ala Lys Gly
        50                  55                  60

Arg Phe Thr Val Ser Lys Thr Ser Ser Thr Val Thr Leu Gln Met
65                  70                  75                  80

Thr Ser Leu Thr Ala Ala Asp Thr Ala Thr Tyr Phe Cys Ala Arg Thr
                85                  90                  95

Gly Thr Glu Phe Thr Tyr Tyr Ser Leu Trp Gly Pro Gly Thr Leu Val
            100                 105                 110
```

Thr Val Ser Ser
        115

<210> SEQ ID NO 8
<211> LENGTH: 111
<212> TYPE: PRT
<213> ORGANISM: Artificial
<220> FEATURE:
<223> OTHER INFORMATION: light chain variable domain VL 1A4

<400> SEQUENCE: 8

Ala Leu Val Met Thr Gln Thr Pro Ser Ser Val Ser Ala Ala Val Gly
1               5                   10                  15

Gly Thr Val Thr Ile Asn Cys Gln Ala Ser Gln Ser Val Tyr Asn Asn
            20                  25                  30

Asn Met Ala Trp Tyr Gln Gln Lys Pro Gly Gln Pro Pro Lys Leu Leu
        35                  40                  45

Ile Tyr Thr Ala Ser Ser Leu Ala Ser Gly Val Pro Ser His Phe Arg
    50                  55                  60

Gly Ser Gly Ser Gly Thr Gln Phe Thr Leu Thr Ile Ser Asp Leu Glu
65                  70                  75                  80

Ser Asp Asp Ala Ala Thr Tyr Tyr Cys Ala Gly Tyr Lys Ser Tyr Ser
                85                  90                  95

Asn Asp Glu Tyr Gly Phe Gly Gly Gly Thr Glu Val Val Val Lys
            100                 105                 110

<210> SEQ ID NO 9
<211> LENGTH: 6
<212> TYPE: PRT
<213> ORGANISM: Artificial
<220> FEATURE:
<223> OTHER INFORMATION: heavy chain CDR-H1 1A5

<400> SEQUENCE: 9

Thr Ser Tyr Trp Met Cys
1               5

<210> SEQ ID NO 10
<211> LENGTH: 17
<212> TYPE: PRT
<213> ORGANISM: Artificial
<220> FEATURE:
<223> OTHER INFORMATION: heavy chain CDR-H2 1A5

<400> SEQUENCE: 10

Cys Ile Ser Ser Ser Ile Gly Val Thr Tyr Tyr Ala Ser Trp Ala Glu
1               5                   10                  15

Gly

<210> SEQ ID NO 11
<211> LENGTH: 12
<212> TYPE: PRT
<213> ORGANISM: Artificial
<220> FEATURE:
<223> OTHER INFORMATION: heavy chain CDR-H3 1A5

<400> SEQUENCE: 11

Thr Thr Asp Asp Asn Trp Asn Val Gly Phe Asn Leu
1               5                   10

<210> SEQ ID NO 12
<211> LENGTH: 12
<212> TYPE: PRT

<213> ORGANISM: Artificial
<220> FEATURE:
<223> OTHER INFORMATION: light chain CDR-L1 1A5

<400> SEQUENCE: 12

Gln Ala Ser Gln Ser Ile Gly Asn Arg Tyr Leu Ser
1               5                   10

<210> SEQ ID NO 13
<211> LENGTH: 7
<212> TYPE: PRT
<213> ORGANISM: Artificial
<220> FEATURE:
<223> OTHER INFORMATION: light chain CDR-L2 1A5

<400> SEQUENCE: 13

Gly Thr Ser Thr Leu Ala Ser
1               5

<210> SEQ ID NO 14
<211> LENGTH: 12
<212> TYPE: PRT
<213> ORGANISM: Artificial
<220> FEATURE:
<223> OTHER INFORMATION: light chain CDR-L3 1A5

<400> SEQUENCE: 14

Gln Gln Gly Ala Thr Ile Ser Tyr Leu Asp Asn Ala
1               5                   10

<210> SEQ ID NO 15
<211> LENGTH: 121
<212> TYPE: PRT
<213> ORGANISM: Artificial
<220> FEATURE:
<223> OTHER INFORMATION: heavy chain variable domain VH 1A5

<400> SEQUENCE: 15

Gln Glu Gln Leu Val Glu Ser Gly Gly Asp Leu Val Lys Pro Glu Gly
1               5                   10                  15

Ser Leu Thr Leu Thr Cys Thr Ala Ser Gly Phe Ser Phe Ser Thr Ser
            20                  25                  30

Tyr Trp Met Cys Trp Val Arg Gln Ala Pro Gly Lys Gly Leu Glu Leu
        35                  40                  45

Ile Ala Cys Ile Ser Ser Ser Ile Gly Val Thr Tyr Tyr Ala Ser Trp
    50                  55                  60

Ala Glu Gly Arg Phe Thr Ile Ser Lys Thr Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Thr Thr Asp Asp Asn Trp Asn Val Gly Phe Asn Leu Trp Gly
            100                 105                 110

Pro Gly Thr Leu Val Thr Val Ser Ser
        115                 120

<210> SEQ ID NO 16
<211> LENGTH: 111
<212> TYPE: PRT
<213> ORGANISM: Artificial
<220> FEATURE:
<223> OTHER INFORMATION: light chain variable domain VL 1A5

<400> SEQUENCE: 16

Ala Tyr Asp Met Thr Gln Thr Pro Ala Ser Val Glu Val Gly Val Gly
1               5                   10                  15

Gly Thr Val Thr Ile Lys Cys Gln Ala Ser Gln Ser Ile Gly Asn Arg
            20                  25                  30

Tyr Leu Ser Trp Tyr Gln Gln Lys Pro Gly Gln Pro Pro Lys Leu Leu
        35                  40                  45

Ile Tyr Gly Thr Ser Thr Leu Ala Ser Gly Val Ser Ser Arg Phe Lys
50                  55                  60

Gly Ser Gly Ser Gly Thr Gln Phe Thr Leu Thr Ile Ser Gly Val Glu
65                  70                  75                  80

Ser Ala Asp Ser Ala Thr Tyr Tyr Cys Gln Gln Gly Ala Thr Ile Ser
                85                  90                  95

Tyr Leu Asp Asn Ala Phe Gly Gly Thr Glu Val Val Val Lys
            100                 105                 110

<210> SEQ ID NO 17
<211> LENGTH: 6
<212> TYPE: PRT
<213> ORGANISM: Artificial
<220> FEATURE:
<223> OTHER INFORMATION: heavy chain CDR-H1 1G9

<400> SEQUENCE: 17

Leu Tyr Ser Tyr Met Cys
1               5

<210> SEQ ID NO 18
<211> LENGTH: 18
<212> TYPE: PRT
<213> ORGANISM: Artificial
<220> FEATURE:
<223> OTHER INFORMATION: heavy chain CDR-H2 1G9

<400> SEQUENCE: 18

Cys Val Asp Ala Gly Ala Ser Gly Ser Thr Tyr Tyr Ala Ser Trp Ala
1               5                   10                  15

Lys Gly

<210> SEQ ID NO 19
<211> LENGTH: 19
<212> TYPE: PRT
<213> ORGANISM: Artificial
<220> FEATURE:
<223> OTHER INFORMATION: heavy chain CDR-H3 1G9

<400> SEQUENCE: 19

Gly Ile Leu Tyr Tyr Thr Trp Pro Tyr Pro Ala Gly Ala Ile Asp Ala
1               5                   10                  15

Phe Asp Ser

<210> SEQ ID NO 20
<211> LENGTH: 11
<212> TYPE: PRT
<213> ORGANISM: Artificial
<220> FEATURE:
<223> OTHER INFORMATION: light chain CDR-L1 1G9

<400> SEQUENCE: 20

Gln Ala Ser Glu Ser Ile Ser Asn Tyr Leu Ser
1               5                   10

<210> SEQ ID NO 21

```
<211> LENGTH: 7
<212> TYPE: PRT
<213> ORGANISM: Artificial
<220> FEATURE:
<223> OTHER INFORMATION: light chain CDR-L2 1G9

<400> SEQUENCE: 21

Lys Ala Ser Thr Leu Ala Ser
1               5

<210> SEQ ID NO 22
<211> LENGTH: 12
<212> TYPE: PRT
<213> ORGANISM: Artificial
<220> FEATURE:
<223> OTHER INFORMATION: light chain CDR-L3 1G9

<400> SEQUENCE: 22

Gln Gln Ser Tyr Ser Ser Ser Asn Val Phe Asn Thr
1               5                  10

<210> SEQ ID NO 23
<211> LENGTH: 128
<212> TYPE: PRT
<213> ORGANISM: Artificial
<220> FEATURE:
<223> OTHER INFORMATION: heavy chain variable domain VH 1G9

<400> SEQUENCE: 23

Gln Ser Leu Glu Glu Ser Gly Gly Asp Leu Val Lys Pro Gly Ala Ser
1               5                  10                  15

Leu Thr Leu Thr Cys Lys Ala Ser Gly Ile Asp Phe Ser Leu Tyr Ser
            20                  25                  30

Tyr Met Cys Trp Val Arg Gln Ala Pro Gly Lys Gly Leu Glu Trp Ile
        35                  40                  45

Ala Cys Val Asp Ala Gly Ala Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Ile Leu Tyr Tyr Thr Trp Pro Tyr Pro Ala Gly Ala Ile
            100                 105                 110

Asp Ala Phe Asp Ser Trp Gly Pro Gly Thr Leu Val Thr Val Ser Ser
        115                 120                 125

<210> SEQ ID NO 24
<211> LENGTH: 110
<212> TYPE: PRT
<213> ORGANISM: Artificial
<220> FEATURE:
<223> OTHER INFORMATION: light chain variable domain VL 1G9

<400> SEQUENCE: 24

Ala Tyr Asp Met Thr Gln Thr Pro Ala Ser Val Ser Glu Pro Val Gly
1               5                  10                  15

Gly Thr Val Thr Ile Lys Cys Gln Ala Ser Glu Ser Ile Ser Asn Tyr
            20                  25                  30

Leu Ser Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60
```

Ser Gly Ser Gly Thr Glu Tyr Thr Val Thr Ile Ser Gly Val Gln Ser
65                  70                  75                  80

Asp Asp Ala Ala Thr Tyr Tyr Cys Gln Gln Ser Tyr Ser Ser Ser Asn
                85                  90                  95

Val Phe Asn Thr Phe Gly Gly Gly Thr Glu Val Val Val Lys
            100                 105                 110

<210> SEQ ID NO 25
<211> LENGTH: 6
<212> TYPE: PRT
<213> ORGANISM: Artificial
<220> FEATURE:
<223> OTHER INFORMATION: heavy chain CDR-H1 2F6

<400> SEQUENCE: 25

Asn Asn Tyr Tyr Met Cys
1               5

<210> SEQ ID NO 26
<211> LENGTH: 17
<212> TYPE: PRT
<213> ORGANISM: Artificial
<220> FEATURE:
<223> OTHER INFORMATION: heavy chain CDR-H2 2F6

<400> SEQUENCE: 26

Cys Ile Ser Thr Asp Asp Ser Asn Thr His Tyr Ala Ser Trp Ala Gln
1               5                   10                  15

Gly

<210> SEQ ID NO 27
<211> LENGTH: 13
<212> TYPE: PRT
<213> ORGANISM: Artificial
<220> FEATURE:
<223> OTHER INFORMATION: heavy chain CDR-H3 2F6

<400> SEQUENCE: 27

Asp Ala His Phe Thr Ser Tyr Gly Tyr Gly Phe Asp Leu
1               5                   10

<210> SEQ ID NO 28
<211> LENGTH: 11
<212> TYPE: PRT
<213> ORGANISM: Artificial
<220> FEATURE:
<223> OTHER INFORMATION: light chain CDR-L1 2F6

<400> SEQUENCE: 28

Arg Ala Ser Glu Asp Ile Glu Asn Leu Val Ala
1               5                   10

<210> SEQ ID NO 29
<211> LENGTH: 7
<212> TYPE: PRT
<213> ORGANISM: Artificial
<220> FEATURE:
<223> OTHER INFORMATION: light chain CDR-L2 2F6

<400> SEQUENCE: 29

Gln Ala Ser Lys Leu Ala Ser
1               5

<210> SEQ ID NO 30

```
<211> LENGTH: 12
<212> TYPE: PRT
<213> ORGANISM: Artificial
<220> FEATURE:
<223> OTHER INFORMATION: light chain CDR-L3 2F6

<400> SEQUENCE: 30

Gln Gly Asp Tyr Gly Ser Gly Trp Ile Met Tyr Ser
1               5                   10

<210> SEQ ID NO 31
<211> LENGTH: 121
<212> TYPE: PRT
<213> ORGANISM: Artificial
<220> FEATURE:
<223> OTHER INFORMATION: heavy chain variable domain VH 2F6

<400> SEQUENCE: 31

Gln Ser Leu Glu Glu Ser Gly Gly Leu Val Gln Pro Glu Gly Ser
1               5                   10                  15

Leu Thr Leu Thr Cys Thr Ala Ser Gly Phe Ser Phe Asn Asn Tyr
                20                  25                  30

Tyr Met Cys Trp Val Arg Gln Ala Pro Gly Lys Gly Leu Glu Trp Ile
                35                  40                  45

Gly Cys Ile Ser Thr Asp Asp Ser Asn Thr His Tyr Ala Ser Trp Ala
        50                  55                  60

Gln Gly Arg Phe Thr Ile Ser Lys Ala Ser Ser Thr Ala Leu Thr Leu
65                  70                  75                  80

Gln Val Ala Gly Leu Thr Val Ala Asp Met Ala Thr Tyr Phe Cys Ala
                85                  90                  95

Arg Asp Ala His Phe Thr Ser Tyr Gly Tyr Gly Phe Asp Leu Trp Gly
                100                 105                 110

Pro Gly Thr Leu Val Thr Val Ser Ser
            115                 120

<210> SEQ ID NO 32
<211> LENGTH: 110
<212> TYPE: PRT
<213> ORGANISM: Artificial
<220> FEATURE:
<223> OTHER INFORMATION: light chain variable domain VL 2F6

<400> SEQUENCE: 32

Asp Ile Val Met Thr Gln Thr Pro Ala Ser Val Ser Ala Ala Val Gly
1               5                   10                  15

Gly Thr Val Ser Ile Asn Cys Arg Ala Ser Glu Asp Ile Glu Asn Leu
                20                  25                  30

Val Ala Trp Tyr Gln Gln Lys Pro Gly Gln Pro Pro Lys Leu Leu Ile
                35                  40                  45

Tyr Gln Ala Ser Lys Leu Ala Ser Gly Val Pro Ser Arg Phe Lys Gly
        50                  55                  60

Ser Gly Ser Gly Ala Glu Phe Thr Leu Thr Ile Gly Asp Leu Glu Ser
65                  70                  75                  80

Ala Asp Ala Ala Thr Tyr Tyr Cys Gln Gly Asp Tyr Gly Ser Gly Trp
                85                  90                  95

Ile Met Tyr Ser Phe Gly Gly Gly Thr Asp Leu Val Val Lys
                100                 105                 110

<210> SEQ ID NO 33
<211> LENGTH: 5
```

```
<212> TYPE: PRT
<213> ORGANISM: Artificial
<220> FEATURE:
<223> OTHER INFORMATION: heavy chain CDR-H1 CNTO888

<400> SEQUENCE: 33

Ser Tyr Gly Ile Ser
1               5

<210> SEQ ID NO 34
<211> LENGTH: 17
<212> TYPE: PRT
<213> ORGANISM: Artificial
<220> FEATURE:
<223> OTHER INFORMATION: heavy chain CDR-H2 CNTO888

<400> SEQUENCE: 34

Gly Ile Ile Pro Ile Phe Gly Thr Ala Asn Tyr Ala Gln Lys Phe Gln
1               5                   10                  15

Gly

<210> SEQ ID NO 35
<211> LENGTH: 10
<212> TYPE: PRT
<213> ORGANISM: Artificial
<220> FEATURE:
<223> OTHER INFORMATION: heavy chain CDR-H3 CNTO888

<400> SEQUENCE: 35

Tyr Asp Gly Ile Tyr Gly Glu Leu Asp Phe
1               5                   10

<210> SEQ ID NO 36
<211> LENGTH: 12
<212> TYPE: PRT
<213> ORGANISM: Artificial
<220> FEATURE:
<223> OTHER INFORMATION: light chain CDR-L1 CNTO888

<400> SEQUENCE: 36

Arg Ala Ser Gln Ser Val Ser Asp Ala Tyr Leu Ala
1               5                   10

<210> SEQ ID NO 37
<211> LENGTH: 7
<212> TYPE: PRT
<213> ORGANISM: Artificial
<220> FEATURE:
<223> OTHER INFORMATION: light chain CDR-L2 CNTO888

<400> SEQUENCE: 37

Asp Ala Ser Ser Arg Ala Thr
1               5

<210> SEQ ID NO 38
<211> LENGTH: 10
<212> TYPE: PRT
<213> ORGANISM: Artificial
<220> FEATURE:
<223> OTHER INFORMATION: light chain CDR-L3 CNTO888

<400> SEQUENCE: 38

His Gln Tyr Ile Gln Leu His Ser Phe Thr
1               5                   10

<210> SEQ ID NO 39
```

```
<211> LENGTH: 119
<212> TYPE: PRT
<213> ORGANISM: Artificial
<220> FEATURE:
<223> OTHER INFORMATION: heavy chain variable domain VH CNTO888

<400> SEQUENCE: 39

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Gly Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Tyr Asp Gly Ile Tyr Gly Glu Leu Asp Phe Trp Gly Gln Gly
            100                 105                 110
Thr Leu Val Thr Val Ser Ser
        115

<210> SEQ ID NO 40
<211> LENGTH: 109
<212> TYPE: PRT
<213> ORGANISM: Artificial
<220> FEATURE:
<223> OTHER INFORMATION: light chain variable domain VL CNTO888

<400> SEQUENCE: 40

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Asp Ala
            20                  25                  30
Tyr Leu Ala Trp Tyr Gln Gln Lys Pro Gly Gln Ala Pro Arg Leu Leu
        35                  40                  45
Ile Tyr Asp Ala Ser Ser Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys His Gln Tyr Ile Gln Leu His
                85                  90                  95
Ser Phe Thr Phe Gly Gln Gly Thr Lys Val Glu Ile Lys
            100                 105

<210> SEQ ID NO 41
<211> LENGTH: 5
<212> TYPE: PRT
<213> ORGANISM: Artificial
<220> FEATURE:
<223> OTHER INFORMATION: heavy chain CDR-H1 Humanized 11K2 (= 11K2)

<400> SEQUENCE: 41

Asp Thr Tyr Met His
1               5

<210> SEQ ID NO 42
<211> LENGTH: 17
```

```
<212> TYPE: PRT
<213> ORGANISM: Artificial
<220> FEATURE:
<223> OTHER INFORMATION: heavy chain CDR-H2 Humanized 11K2 (= 11K2)

<400> SEQUENCE: 42

Arg Ile Asp Pro Ala Asn Gly Asn Thr Lys Phe Asp Pro Lys Phe Gln
1               5                   10                  15

Gly

<210> SEQ ID NO 43
<211> LENGTH: 8
<212> TYPE: PRT
<213> ORGANISM: Artificial
<220> FEATURE:
<223> OTHER INFORMATION: heavy chain CDR-H3 Humanized 11K2 (= 11K2)

<400> SEQUENCE: 43

Gly Val Phe Gly Phe Phe Asp Tyr
1               5

<210> SEQ ID NO 44
<211> LENGTH: 11
<212> TYPE: PRT
<213> ORGANISM: Artificial
<220> FEATURE:
<223> OTHER INFORMATION: light chain CDR-L1 Humanized 11K2 (= 11K2)

<400> SEQUENCE: 44

Lys Ala Thr Glu Asp Ile Tyr Asn Arg Leu Ala
1               5                   10

<210> SEQ ID NO 45
<211> LENGTH: 7
<212> TYPE: PRT
<213> ORGANISM: Artificial
<220> FEATURE:
<223> OTHER INFORMATION: light chain CDR-L2 Humanized 11K2 (= 11K2)

<400> SEQUENCE: 45

Gly Ala Thr Ser Leu Glu Thr
1               5

<210> SEQ ID NO 46
<211> LENGTH: 9
<212> TYPE: PRT
<213> ORGANISM: Artificial
<220> FEATURE:
<223> OTHER INFORMATION: light chain CDR-L3 Humanized 11K2 (= 11K2)

<400> SEQUENCE: 46

Gln Gln Phe Trp Ser Ala Pro Tyr Thr
1               5

<210> SEQ ID NO 47
<211> LENGTH: 117
<212> TYPE: PRT
<213> ORGANISM: Artificial
<220> FEATURE:
<223> OTHER INFORMATION: heavy chain variable domain VH Humanized 11K2
      (= 11K2)

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser Asp Thr
```

```
                    20                  25                  30
Tyr Met His Trp Val Arg Gln Ala Pro Gly Gln Gly Leu Glu Trp Met
            35                  40                  45

Gly Arg Ile Asp Pro Ala Asn Gly Asn Thr Lys Phe Asp Pro Lys Phe
        50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Asp Tyr Trp Gly Gln Gly Thr Thr
            100                 105                 110

Val Thr Val Ser Ser
        115

<210> SEQ ID NO 48
<211> LENGTH: 107
<212> TYPE: PRT
<213> ORGANISM: Artificial
<220> FEATURE:
<223> OTHER INFORMATION: light chain variable domain VL Humanized 11K2
      (= 11K2)

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Trp Ser Ala Pro Tyr
                85                  90                  95

Thr Phe Gly Gly Gly Thr Lys Val Glu Ile Lys
            100                 105

<210> SEQ ID NO 49
<211> LENGTH: 5
<212> TYPE: PRT
<213> ORGANISM: Artificial
<220> FEATURE:
<223> OTHER INFORMATION: heavy chain CDR-H1 ABN912

<400> SEQUENCE: 49

His Tyr Trp Met Ser
1               5

<210> SEQ ID NO 50
<211> LENGTH: 17
<212> TYPE: PRT
<213> ORGANISM: Artificial
<220> FEATURE:
<223> OTHER INFORMATION: heavy chain CDR-H2 ABN912

<400> SEQUENCE: 50

Asn Ile Glu Gln Asp Gly Ser Glu Lys Tyr Tyr Val Asp Ser Val Lys
1               5                   10                  15

Gly
```

<210> SEQ ID NO 51
<211> LENGTH: 13
<212> TYPE: PRT
<213> ORGANISM: Artificial
<220> FEATURE:
<223> OTHER INFORMATION: heavy chain CDR-H3 ABN912

<400> SEQUENCE: 51

Asp Leu Glu Gly Leu His Gly Asp Gly Tyr Phe Asp Leu
1               5                   10

<210> SEQ ID NO 52
<211> LENGTH: 11
<212> TYPE: PRT
<213> ORGANISM: Artificial
<220> FEATURE:
<223> OTHER INFORMATION: light chain CDR-L1 ABN912

<400> SEQUENCE: 52

Arg Ala Ser Gln Gly Val Ser Ser Ala Leu Ala
1               5                   10

<210> SEQ ID NO 53
<211> LENGTH: 7
<212> TYPE: PRT
<213> ORGANISM: Artificial
<220> FEATURE:
<223> OTHER INFORMATION: light chain CDR-L2 ABN912

<400> SEQUENCE: 53

Asp Ala Ser Ser Leu Glu Ser
1               5

<210> SEQ ID NO 54
<211> LENGTH: 9
<212> TYPE: PRT
<213> ORGANISM: Artificial
<220> FEATURE:
<223> OTHER INFORMATION: light chain CDR-L3 ABN912

<400> SEQUENCE: 54

Gln Gln Phe Asn Ser Tyr Pro Leu Thr
1               5

<210> SEQ ID NO 55
<211> LENGTH: 122
<212> TYPE: PRT
<213> ORGANISM: Artificial
<220> FEATURE:
<223> OTHER INFORMATION: heavy chain variable domain VH ABN912

<400> SEQUENCE: 55

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Trp Met Ser Trp Val Arg Gln Ala Pro Gly Lys Gly Leu Glu Trp Leu
        35                  40                  45

Ala Asn Ile Glu Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys

```
                85                  90                  95
Ala Arg Asp Leu Glu Gly Leu His Gly Asp Gly Tyr Phe Asp Leu Trp
            100                 105                 110
Gly Arg Gly Thr Leu Val Thr Val Ser Ser
        115                 120
```

<210> SEQ ID NO 56
<211> LENGTH: 107
<212> TYPE: PRT
<213> ORGANISM: Artificial
<220> FEATURE:
<223> OTHER INFORMATION: light chain variable domain VL ABN912

<400> SEQUENCE: 56

```
Ala Ile Gln Leu Thr Gln Ser Pro Ser Leu Ser Ala Ser Val Gly
1               5                   10                  15
Asp Arg Val Ile Leu Thr Cys Arg Ala Ser Gln Gly Val Ser Ser Ala
            20                  25                  30
Leu Ala Trp Tyr Gln Gln Lys Pro Gly Lys Ala Pro Lys Leu Leu Ile
        35                  40                  45
Tyr Asp Ala Ser Ser Leu Glu Ser Gly Val Pro Ser Arg Phe Ser Gly
    50                  55                  60
Ser Gly Ser Gly Pro Asp Phe Thr Leu Thr Ile Ser Ser Leu Gln Pro
65                  70                  75                  80
Glu Asp Phe Ala Thr Tyr Phe Cys Gln Gln Phe Asn Ser Tyr Pro Leu
                85                  90                  95
Thr Phe Gly Gly Gly Thr Lys Val Glu Ile Lys
            100                 105
```

<210> SEQ ID NO 57
<211> LENGTH: 6
<212> TYPE: PRT
<213> ORGANISM: Artificial
<220> FEATURE:
<223> OTHER INFORMATION: heavy chain CDR-H1 mutated variant CNTO888
<220> FEATURE:
<221> NAME/KEY: MISC_FEATURE
<222> LOCATION: (5)..(5)
<223> OTHER INFORMATION: X is I or T

<400> SEQUENCE: 57

```
Ser His Tyr Gly Xaa Ser
1               5
```

<210> SEQ ID NO 58
<211> LENGTH: 17
<212> TYPE: PRT
<213> ORGANISM: Artificial
<220> FEATURE:
<223> OTHER INFORMATION: heavy chain CDR-H2 mutated variant CNTO888
<220> FEATURE:
<221> NAME/KEY: MISC_FEATURE
<222> LOCATION: (2)..(2)
<223> OTHER INFORMATION: X is V or I or H
<220> FEATURE:
<221> NAME/KEY: MISC_FEATURE
<222> LOCATION: (4)..(4)
<223> OTHER INFORMATION: X is P or H
<220> FEATURE:
<221> NAME/KEY: MISC_FEATURE
<222> LOCATION: (7)..(7)
<223> OTHER INFORMATION: X is H or G

<400> SEQUENCE: 58

Gly Xaa Ile Xaa Ile Phe Xaa Thr Ala Asn Tyr Ala Gln Lys Phe Gln

```
1               5                  10                  15
Gly

<210> SEQ ID NO 59
<211> LENGTH: 10
<212> TYPE: PRT
<213> ORGANISM: Artificial
<220> FEATURE:
<223> OTHER INFORMATION: heavy chain CDR-H3 mutated variant  CNTO888

<400> SEQUENCE: 59

Tyr Asp Ala His Tyr Gly Glu Leu Asp Phe
1               5                  10

<210> SEQ ID NO 60
<211> LENGTH: 12
<212> TYPE: PRT
<213> ORGANISM: Artificial
<220> FEATURE:
<223> OTHER INFORMATION: light chain CDR-L1 mutated variant  CNTO888

<400> SEQUENCE: 60

Arg Ala Ser Gln His Val Ser Asp Ala Tyr Leu Ala
1               5                  10

<210> SEQ ID NO 61
<211> LENGTH: 7
<212> TYPE: PRT
<213> ORGANISM: Artificial
<220> FEATURE:
<223> OTHER INFORMATION: light chain CDR-L2 mutated variant  CNTO888

<400> SEQUENCE: 61

Asp Ala Ser Asp Arg Ala Glu
1               5

<210> SEQ ID NO 62
<211> LENGTH: 10
<212> TYPE: PRT
<213> ORGANISM: Artificial
<220> FEATURE:
<223> OTHER INFORMATION: light chain CDR-L3 mutated variant  CNTO888

<400> SEQUENCE: 62

His Gln Tyr Ile His Leu His Ser Phe Thr
1               5                  10

<210> SEQ ID NO 63
<211> LENGTH: 29
<212> TYPE: PRT
<213> ORGANISM: Artificial
<220> FEATURE:
<223> OTHER INFORMATION: heavy chain FR-H1 mutated variant  CNTO888

<400> SEQUENCE: 63

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe
            20                  25

<210> SEQ ID NO 64
<211> LENGTH: 14
<212> TYPE: PRT
<213> ORGANISM: Artificial
<220> FEATURE:
<223> OTHER INFORMATION: heavy chain FR-H2 mutated variant  CNTO888
```

```
<400> SEQUENCE: 64

Trp Val Arg Gln Ala Pro Gly Gln Gly Leu Glu Trp Met Gly
1               5                   10

<210> SEQ ID NO 65
<211> LENGTH: 32
<212> TYPE: PRT
<213> ORGANISM: Artificial
<220> FEATURE:
<223> OTHER INFORMATION: heavy chain FR-H3 mutated variant  CNTO888

<400> SEQUENCE: 65

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 66
<211> LENGTH: 11
<212> TYPE: PRT
<213> ORGANISM: Artificial
<220> FEATURE:
<223> OTHER INFORMATION: heavy chain FR-H4 mutated variant  CNTO888

<400> SEQUENCE: 66

Trp Gly Gln Gly Thr Leu Val Thr Val Ser Ser
1               5                   10

<210> SEQ ID NO 67
<211> LENGTH: 23
<212> TYPE: PRT
<213> ORGANISM: Artificial
<220> FEATURE:
<223> OTHER INFORMATION: light chain FR-L1 mutated variant  CNTO888

<400> SEQUENCE: 67

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 68
<211> LENGTH: 15
<212> TYPE: PRT
<213> ORGANISM: Artificial
<220> FEATURE:
<223> OTHER INFORMATION: light chain FR-L2 mutated variant  CNTO888

<400> SEQUENCE: 68

Trp Tyr Gln Gln Lys Pro Gly Gln Ala Pro Arg Leu Leu Ile Tyr
1               5                   10                  15

<210> SEQ ID NO 69
<211> LENGTH: 32
<212> TYPE: PRT
<213> ORGANISM: Artificial
<220> FEATURE:
<223> OTHER INFORMATION: light chain FR-L3 mutated variant  CNTO888

<400> SEQUENCE: 69

Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 70
<211> LENGTH: 9
<212> TYPE: PRT
<213> ORGANISM: Artificial
<220> FEATURE:
<223> OTHER INFORMATION: light chain FR-L4 mutated variant CNTO888

<400> SEQUENCE: 70

Gly Gln Gly Thr Lys Val Glu Ile Lys
1               5

<210> SEQ ID NO 71
<211> LENGTH: 119
<212> TYPE: PRT
<213> ORGANISM: Artificial
<220> FEATURE:
<223> OTHER INFORMATION: heavy chain variable domain VH mutated variant
      CNTO888 H0695

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser
        115

<210> SEQ ID NO 72
<211> LENGTH: 119
<212> TYPE: PRT
<213> ORGANISM: Artificial
<220> FEATURE:
<223> OTHER INFORMATION: heavy chain variable domain VH mutated variant
      CNTO888 H0625

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Ile Ile His Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly

```
                    100                 105                 110

Thr Leu Val Thr Val Ser Ser
        115

<210> SEQ ID NO 73
<211> LENGTH: 119
<212> TYPE: PRT
<213> ORGANISM: Artificial
<220> FEATURE:
<223> OTHER INFORMATION: heavy chain variable domain VH mutated variant
      CNTO888 H0634

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Thr Ser Trp Val Arg Gln Ala Pro Gly Gln Gly Leu Glu Trp Met
        35                  40                  45

Gly Gly Ile Ile His Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser
        115

<210> SEQ ID NO 74
<211> LENGTH: 119
<212> TYPE: PRT
<213> ORGANISM: Artificial
<220> FEATURE:
<223> OTHER INFORMATION: heavy chain variable domain VH mutated variant
      CNTO888 H0635

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly His Ile His Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser
        115

<210> SEQ ID NO 75
<211> LENGTH: 109
<212> TYPE: PRT
```

<213> ORGANISM: Artificial
<220> FEATURE:
<223> OTHER INFORMATION: light chain variable domain VL mutated variant
      CNTO888 L0616

<400> SEQUENCE: 75

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Asp Arg Ala Glu Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Ile His Leu His
                85                  90                  95

Ser Phe Thr Phe Gly Gln Gly Thr Lys Val Glu Ile Lys
            100                 105

<210> SEQ ID NO 76
<211> LENGTH: 5
<212> TYPE: PRT
<213> ORGANISM: Artificial
<220> FEATURE:
<223> OTHER INFORMATION: heavy chain CDR-H1 mutated variant humanized
      11K2

<400> SEQUENCE: 76

His Thr Tyr Met His
1               5

<210> SEQ ID NO 77
<211> LENGTH: 17
<212> TYPE: PRT
<213> ORGANISM: Artificial
<220> FEATURE:
<223> OTHER INFORMATION: heavy chain CDR-H2 mutated variant humanized
      11K2
<220> FEATURE:
<221> NAME/KEY: MISC_FEATURE
<222> LOCATION: (5)..(5)
<223> OTHER INFORMATION: X is D or E

<400> SEQUENCE: 77

Arg Ile Asp Pro Xaa Asn His Asn Thr Lys Phe Asp Pro Lys Phe Gln
1               5                   10                  15

Gly

<210> SEQ ID NO 78
<211> LENGTH: 8
<212> TYPE: PRT
<213> ORGANISM: Artificial
<220> FEATURE:
<223> OTHER INFORMATION: heavy chain CDR-H3 mutated variant humanized
      11K2
<220> FEATURE:
<221> NAME/KEY: MISC_FEATURE
<222> LOCATION: (7)..(7)
<223> OTHER INFORMATION: X is D or E

<400> SEQUENCE: 78

Gly Val Phe Gly Phe Phe Xaa His
1               5

<210> SEQ ID NO 79
<211> LENGTH: 11
<212> TYPE: PRT
<213> ORGANISM: Artificial
<220> FEATURE:
<223> OTHER INFORMATION: light chain CDR-L1 mutated variant humanized 11K2
<220> FEATURE:
<221> NAME/KEY: MISC_FEATURE
<222> LOCATION: (3)..(3)
<223> OTHER INFORMATION: X is F or T
<220> FEATURE:
<221> NAME/KEY: MISC_FEATURE
<222> LOCATION: (10)..(10)
<223> OTHER INFORMATION: X is R or L

<400> SEQUENCE: 79

Lys Ala Xaa Glu Asp Ile Tyr Asn Arg Xaa Ala
1               5                   10

<210> SEQ ID NO 80
<211> LENGTH: 7
<212> TYPE: PRT
<213> ORGANISM: Artificial
<220> FEATURE:
<223> OTHER INFORMATION: light chain CDR-L2 mutated variant humanized 11K2

<400> SEQUENCE: 80

Gly Ala Thr Ser Leu Glu His
1               5

<210> SEQ ID NO 81
<211> LENGTH: 9
<212> TYPE: PRT
<213> ORGANISM: Artificial
<220> FEATURE:
<223> OTHER INFORMATION: light chain CDR-L3 mutated variant humanized 11K2
<220> FEATURE:
<221> NAME/KEY: MISC_FEATURE
<222> LOCATION: (4)..(4)
<223> OTHER INFORMATION: X is W or R

<400> SEQUENCE: 81

Gln Gln Phe Xaa Ser Ala Pro Tyr Thr
1               5

<210> SEQ ID NO 82
<211> LENGTH: 30
<212> TYPE: PRT
<213> ORGANISM: Artificial
<220> FEATURE:
<223> OTHER INFORMATION: heavy chain FR-H1 mutated variant humanized 11K2

<400> SEQUENCE: 82

Gln Val Gln Leu Val Gln Ser Gly Ala Glu Val Lys Lys Pro Gly Ser
1               5                   10                  15
Ser Val Lys Val Ser Cys Lys Ala Ser Gly Leu Thr Ile Ser
            20                  25                  30

<210> SEQ ID NO 83
<211> LENGTH: 14
<212> TYPE: PRT
<213> ORGANISM: Artificial
<220> FEATURE:
<223> OTHER INFORMATION: heavy chain FR-H2 mutated variant humanized

11K2

<400> SEQUENCE: 83

Trp Val Arg Gln Ala Pro Gly Gln Gly Leu Glu Trp Met Gly
1               5                   10

<210> SEQ ID NO 84
<211> LENGTH: 32
<212> TYPE: PRT
<213> ORGANISM: Artificial
<220> FEATURE:
<223> OTHER INFORMATION: heavy chain FR-H3 mutated variant humanized
      11K2

<400> SEQUENCE: 84

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 85
<211> LENGTH: 11
<212> TYPE: PRT
<213> ORGANISM: Artificial
<220> FEATURE:
<223> OTHER INFORMATION: heavy chain FR-H4 mutated variant humanized
      11K2

<400> SEQUENCE: 85

Trp Gly Gln Gly Thr Thr Val Thr Val Ser Ser
1               5                   10

<210> SEQ ID NO 86
<211> LENGTH: 23
<212> TYPE: PRT
<213> ORGANISM: Artificial
<220> FEATURE:
<223> OTHER INFORMATION: light chain FR-L1 mutated variant  11K2

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 87
<211> LENGTH: 15
<212> TYPE: PRT
<213> ORGANISM: Artificial
<220> FEATURE:
<223> OTHER INFORMATION: light chain FR-L2 mutated variant humanized
      11K2

<400> SEQUENCE: 87

Trp Tyr Gln Gln Lys Pro Gly Lys Ala Pro Lys Leu Leu Ile His
1               5                   10                  15

<210> SEQ ID NO 88
<211> LENGTH: 32
<212> TYPE: PRT
<213> ORGANISM: Artificial
<220> FEATURE:
<223> OTHER INFORMATION: light chain FR-L3 mutated variant humanized
      11K2

<400> SEQUENCE: 88

```
Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30
```

```
<210> SEQ ID NO 89
<211> LENGTH: 10
<212> TYPE: PRT
<213> ORGANISM: Artificial
<220> FEATURE:
<223> OTHER INFORMATION: light chain FR-L4 mutated variant humanized
      11K2

<400> SEQUENCE: 89

Phe Gly Gly Gly Thr Lys Val Glu Ile Lys
1               5                   10
```

```
<210> SEQ ID NO 90
<211> LENGTH: 117
<212> TYPE: PRT
<213> ORGANISM: Artificial
<220> FEATURE:
<223> OTHER INFORMATION: heavy chain variable domain VH mutated variant
      humanized 11K2 H1503

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
        35                  40                  45

Gly Arg Ile Asp Pro Asp Asn His Asn Thr Lys Phe Asp Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Asp His Trp Gly Gln Gly Thr Thr
            100                 105                 110

Val Thr Val Ser Ser
        115
```

```
<210> SEQ ID NO 91
<211> LENGTH: 117
<212> TYPE: PRT
<213> ORGANISM: Artificial
<220> FEATURE:
<223> OTHER INFORMATION: heavy chain variable domain VH mutated variant
      humanized 11K2 H1510

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
        35                  40                  45

Gly Arg Ile Asp Pro Asp Asn His Asn Thr Lys Phe Asp Pro Lys Phe
    50                  55                  60

Gln Gly Arg Val Thr Ile Thr Ala Asp Thr Ser Thr Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Gly Val Phe Gly Phe Glu His Trp Gly Gln Gly Thr Thr
                    100                 105                 110

Val Thr Val Ser Ser
        115

<210> SEQ ID NO 92
<211> LENGTH: 117
<212> TYPE: PRT
<213> ORGANISM: Artificial
<220> FEATURE:
<223> OTHER INFORMATION: heavy chain variable domain VH mutated variant
      humanized 11K2 H1514

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
                20                  25                  30

Tyr Met His Trp Val Arg Gln Ala Pro Gly Gln Gly Leu Glu Trp Met
                35                  40                  45

Gly Arg Ile Asp Pro Glu Asn His Asn Thr Lys Phe Asp Pro Lys Phe
            50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Gly Val Phe Gly Phe Glu His Trp Gly Gln Gly Thr Thr
                    100                 105                 110

Val Thr Val Ser Ser
        115

<210> SEQ ID NO 93
<211> LENGTH: 107
<212> TYPE: PRT
<213> ORGANISM: Artificial
<220> FEATURE:
<223> OTHER INFORMATION: light chain variable domain VL mutated variant
      humanized 11K2 L1338

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ala Phe Glu Asp Ile Tyr Asn Arg
                20                  25                  30

Arg Ala Trp Tyr Gln Gln Lys Pro Gly Lys Ala Pro Lys Leu Leu Ile
                35                  40                  45

His Gly Ala Thr Ser Leu Glu His Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Trp Ser Ala Pro Tyr
                    85                  90                  95

Thr Phe Gly Gly Gly Thr Lys Val Glu Ile Lys
                    100                 105
```

```
<210> SEQ ID NO 94
<211> LENGTH: 107
<212> TYPE: PRT
<213> ORGANISM: Artificial
<220> FEATURE:
<223> OTHER INFORMATION: light chain variable domain VL mutated variant
      humanized 11K2 L1201

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Lys Ala Pro Lys Leu Leu Ile
        35                  40                  45

His Gly Ala Thr Ser Leu Glu His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Arg Ser Ala Pro Tyr
                85                  90                  95

Thr Phe Gly Gly Gly Thr Lys Val Glu Ile Lys
            100                 105

<210> SEQ ID NO 95
<211> LENGTH: 107
<212> TYPE: PRT
<213> ORGANISM: homo sapiens

<400> SEQUENCE: 95

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 96
<211> LENGTH: 105
<212> TYPE: PRT
<213> ORGANISM: homo sapiens

<400> SEQUENCE: 96

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60
```

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 97
<211> LENGTH: 328
<212> TYPE: PRT
<213> ORGANISM: homo sapiens

<400> SEQUENCE: 97

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro

<210> SEQ ID NO 98
<211> LENGTH: 328
<212> TYPE: PRT
<213> ORGANISM: Artificial
<220> FEATURE:
<223> OTHER INFORMATION: exemplary human heavy chain constant region
      derived from IgG1 with mutations L234A, L235A and P329G (Fcgamma
      receptor silenced)

<400> SEQUENCE: 98

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 99

```
<211> LENGTH: 328
<212> TYPE: PRT
<213> ORGANISM: homo sapiens

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 100
<211> LENGTH: 328
<212> TYPE: PRT
<213> ORGANISM: Artificial
<220> FEATURE:
<223> OTHER INFORMATION: exemplary human heavy chain constant region
      derived from IgG1 with mutations (SG105-IgG1 allotype - Fcgamma
      receptor silenced)
```

<400> SEQUENCE: 100

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Arg Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 101
<211> LENGTH: 328
<212> TYPE: PRT
<213> ORGANISM: Artificial
<220> FEATURE:
<223> OTHER INFORMATION: SG1095-exemplary human heavy chain constant
      region derived from IgG1 including the mutations (Kabat EU
      numbering) L235W/G236N/H268D/Q295L/A330K/K326T, Q311R/P343R,
      N434A, Q438R/S440E

<400> SEQUENCE: 101

Ala Ser Thr Lys Gly Pro Ser Val Phe Pro Leu Ala Pro Ser Ser Lys

```
                1               5                  10                 15
            Ser Thr Ser Gly Gly Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                            35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
            65                  70                  75                  80

Tyr Ile Cys Asn Val Asn His Lys Pro Ser Asn Thr Lys Val Asp Lys
                            85                  90                  95

Lys Val Glu Pro Lys Ser Cys Asp Lys Thr His Thr Cys Pro Pro Cys
                            100                 105                 110

Pro Ala Pro Glu Leu Trp Asn Gly Pro Ser Val Phe Leu Phe Pro Pro
                            115                 120                 125

Lys Pro Lys Asp Thr Leu Met Ile Ser Arg Thr Pro Glu Val Thr Cys
            130                 135                 140

Val Val Val Asp Val Ser Asp Glu Asp Pro Glu Val Lys Phe Asn Trp
            145                 150                 155                 160

Tyr Val Asp Gly Val Glu Val His Asn Ala Lys Thr Lys Pro Arg Glu
                            165                 170                 175

Glu Leu Tyr Asn Ser Thr Tyr Arg Val Val Ser Val Leu Thr Val Leu
                            180                 185                 190

His Arg Asp Trp Leu Asn Gly Lys Glu Tyr Lys Cys Lys Val Ser Asn
                            195                 200                 205

Thr Ala Leu Pro Lys Pro Ile Glu Lys Thr Ile Ser Lys Ala Lys Gly
                            210                 215                 220

Gln Arg Arg Glu Pro Gln Val Tyr Thr Leu Pro Pro Ser Arg Asp Glu
            225                 230                 235                 240

Leu Thr Lys Asn Gln Val Ser Leu Thr Cys Leu Val Lys Gly Phe Tyr
                            245                 250                 255

Pro Ser Asp Ile Ala Val Glu Trp Glu Ser Asn Gly Gln Pro Glu Asn
                            260                 265                 270

Asn Tyr Lys Thr Thr Pro Pro Val Leu Asp Ser Asp Gly Ser Phe Phe
                            275                 280                 285

Leu Tyr Ser Lys Leu Thr Val Asp Lys Ser Arg Trp Gln Gln Gly Asn
                            290                 295                 300

Val Phe Ser Cys Ser Val Met His Glu Ala Leu His Ala His Tyr Thr
            305                 310                 315                 320

Arg Lys Glu Leu Ser Leu Ser Pro
                            325

<210> SEQ ID NO 102
<211> LENGTH: 328
<212> TYPE: PRT
<213> ORGANISM: Artificial
<220> FEATURE:
<223> OTHER INFORMATION: SG1099-exemplary human heavy chain constant
      region derived from IgG1 including mutations (Kabat EU numbering)
      Q311R/P343R

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Arg Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Arg Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 103
<211> LENGTH: 328
<212> TYPE: PRT
<213> ORGANISM: Artificial
<220> FEATURE:
<223> OTHER INFORMATION: SG1100-exemplary human heavy chain constant
      region derived from IgG1 including the mutations (Kabat EU
      numbering) Q311R/P343R, N434A, Q438R/S440E

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Arg Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Arg Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Ala His Tyr Thr
305                 310                 315                 320

Arg Lys Glu Leu Ser Leu Ser Pro
                325

<210> SEQ ID NO 104
<211> LENGTH: 437
<212> TYPE: PRT
<213> ORGANISM: Artificial
<220> FEATURE:
<223> OTHER INFORMATION: heavy chain 1- CNTO888//11K2-WT IgG1

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Lys Ala Pro Lys Leu Leu Ile
            35                  40                  45

Ser Gly Ala Thr Ser Leu Glu Thr Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Gln Phe Trp Ser Ala Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
            195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
            275                 280                 285

Asn Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Cys Arg Asp Glu Leu Thr Lys
            340                 345                 350

Asn Gln Val Ser Leu Trp Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro
            435

<210> SEQ ID NO 105
<211> LENGTH: 447
<212> TYPE: PRT
<213> ORGANISM: Artificial
<220> FEATURE:
<223> OTHER INFORMATION: heavy chain 2- CNTO888//11K2-WT IgG1

<400> SEQUENCE: 105
```

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Gly Ile Tyr Gly Glu Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
```

```
                    420             425             430
Ala Leu His Asn His Tyr Thr Gln Lys Ser Leu Ser Leu Ser Pro
        435                 440                 445
```

<210> SEQ ID NO 106
<211> LENGTH: 224
<212> TYPE: PRT
<213> ORGANISM: Artificial
<220> FEATURE:
<223> OTHER INFORMATION: light chain 1- CNTO888//11K2-WT IgG1

<400> SEQUENCE: 106

```
Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Thr Lys Phe Asp Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Asp Tyr Trp Gly Gln Gly Thr Thr
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220
```

<210> SEQ ID NO 107
<211> LENGTH: 216
<212> TYPE: PRT
<213> ORGANISM: Artificial
<220> FEATURE:
<223> OTHER INFORMATION: light chain 2- CNTO888//11K2-WT IgG1

<400> SEQUENCE: 107

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Val Pro Ala Arg Phe Ser
    50                  55                  60
```

```
Gly Ser Gly Ser Gly Thr Asp Phe Thr Leu Thr Ile Ser Ser Leu Glu
 65                  70                  75                  80

Pro Glu Asp Phe Ala Val Tyr Tyr Cys His Gln Tyr Ile Gln Leu His
                 85                  90                  95

Ser Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 108
<211> LENGTH: 437
<212> TYPE: PRT
<213> ORGANISM: Artificial
<220> FEATURE:
<223> OTHER INFORMATION: heavy chain 1- CKLO2 IgG1

<400> SEQUENCE: 108

Asp Ile Gln Met Thr Gln Ser Pro Ser Ser Leu Ser Ala Ser Val Gly
  1               5                  10                  15

Asp Arg Val Thr Ile Thr Cys Lys Ala Phe Glu Asp Ile Tyr Asn Arg
             20                  25                  30

Arg Ala Trp Tyr Gln Gln Lys Pro Gly Lys Ala Pro Lys Leu Leu Ile
         35                  40                  45

His Gly Ala Thr Ser Leu Glu His Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Phe Trp Ser Ala Pro Tyr
                 85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205
```

```
Pro Lys Ser Cys Asp Lys Thr His Thr Cys Pro Pro Cys Pro Ala Pro
    210                 215                 220
Glu Leu Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                245                 250                 255
Asp Val Ser His Glu Asp Pro Glu Val Lys Phe Asn Trp Tyr Val Asp
            260                 265                 270
Gly Val Glu Val His Asn Ala Lys Thr Lys Pro Arg Glu Glu Gln Tyr
        275                 280                 285
Asn Ser Thr Tyr Arg Val Val Ser Val Leu Thr Val Leu His Gln Asp
    290                 295                 300
Trp Leu Asn Gly Lys Glu Tyr Lys Cys Lys Val Ser Asn Lys Ala Leu
305                 310                 315                 320
Pro Ala Pro Ile Glu Lys Thr Ile Ser Lys Ala Lys Gly Gln Pro Arg
                325                 330                 335
Glu Pro Gln Val Tyr Thr Leu Pro Pro Cys Arg Asp Glu Leu Thr Lys
            340                 345                 350
Asn Gln Val Ser Leu Trp Cys Leu Val Lys Gly Phe Tyr Pro Ser Asp
        355                 360                 365
Ile Ala Val Glu Trp Glu Ser Asn Gly Gln Pro Glu Asn Asn Tyr Lys
    370                 375                 380
Thr Thr Pro Pro Val Leu Asp Ser Asp Gly Ser Phe Phe Leu Tyr Ser
385                 390                 395                 400
Lys Leu Thr Val Asp Lys Ser Arg Trp Gln Gln Gly Asn Val Phe Ser
                405                 410                 415
Cys Ser Val Met His Glu Ala Leu His Asn His Tyr Thr Gln Lys Ser
            420                 425                 430
Leu Ser Leu Ser Pro
        435

<210> SEQ ID NO 109
<211> LENGTH: 447
<212> TYPE: PRT
<213> ORGANISM: Artificial
<220> FEATURE:
<223> OTHER INFORMATION: heavy chain 2- CKLO2 IgG1

<400> SEQUENCE: 109

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser His Tyr
                20                  25                  30
Gly Ile Ser Trp Val Arg Gln Ala Pro Gly Gln Gly Leu Glu Trp Met
            35                  40                  45
Gly Gly Val Ile Pro Ile Phe His Thr Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Tyr Asp Ala His Tyr Gly Glu Leu Asp Phe Trp Gly Gln Gly
            100                 105                 110
Thr Leu Val Thr Val Ser Ser Ala Ser Thr Lys Gly Pro Ser Val Phe
        115                 120                 125
```

Pro Leu Ala Pro Ser Ser Lys Ser Thr Ser Gly Gly Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 110
<211> LENGTH: 224
<212> TYPE: PRT
<213> ORGANISM: Artificial
<220> FEATURE:
<223> OTHER INFORMATION: light chain 1- CKLO2 IgG1

<400> SEQUENCE: 110

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
                20                  25                  30

Tyr Met His Trp Val Arg Gln Ala Pro Gly Gln Gly Leu Glu Trp Met
            35                  40                  45

```
Gly Arg Ile Asp Pro Asp Asn His Asn Thr Lys Phe Asp Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Glu His Trp Gly Gln Gly Thr Thr
            100                 105                 110

Val Thr Val Ser Ser Ala Ser Val Ala Ala Pro Ser Val Phe Ile Phe
            115                 120                 125

Pro Pro Ser Asp Glu Gln Leu Lys Ser Gly Thr Ala Ser Val Val Cys
130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
210                 215                 220

<210> SEQ ID NO 111
<211> LENGTH: 216
<212> TYPE: PRT
<213> ORGANISM: Artificial
<220> FEATURE:
<223> OTHER INFORMATION: light chain 2- CKLO2 IgG1

<400> SEQUENCE: 111

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Asp Arg Ala Glu Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Ile His Leu His
                85                  90                  95

Ser Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190
```

Val Tyr Ala Cys Glu Val Thr His Gln Gly Leu Ser Ser Pro Val Thr
            195                 200                 205

Lys Ser Phe Asn Arg Gly Glu Cys
    210                 215

<210> SEQ ID NO 112
<211> LENGTH: 437
<212> TYPE: PRT
<213> ORGANISM: Artificial
<220> FEATURE:
<223> OTHER INFORMATION: heavy chain 1- CKLO2 - SG1095

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Lys Ala Phe Glu Asp Ile Tyr Asn Arg
            20                  25                  30

Arg Ala Trp Tyr Gln Gln Lys Pro Gly Lys Ala Pro Lys Leu Leu Ile
        35                  40                  45

His Gly Ala Thr Ser Leu Glu His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Trp Ser Ala Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
    210                 215                 220

Glu Leu Trp Asn Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Asp Glu Asp Pro Glu Val Lys Phe Asn Trp Tyr Val Asp
            260                 265                 270

Gly Val Glu Val His Asn Ala Lys Thr Lys Pro Arg Glu Glu Leu Tyr
        275                 280                 285

Asn Ser Thr Tyr Arg Val Val Ser Val Leu Thr Val Leu His Arg Asp
    290                 295                 300

Trp Leu Asn Gly Lys Glu Tyr Lys Cys Lys Val Ser Asn Thr Ala Leu
305                 310                 315                 320

Pro Lys Pro Ile Glu Lys Thr Ile Ser Lys Ala Lys Gly Gln Arg Arg
                325                 330                 335

```
Glu Pro Gln Val Tyr Thr Leu Pro Pro Cys Arg Asp Glu Leu Thr Lys
            340                 345                 350

Asn Gln Val Ser Leu Trp Cys Leu Val Lys Gly Phe Tyr Pro Ser Asp
        355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Ala His Tyr Thr Arg Lys Glu
            420                 425                 430

Leu Ser Leu Ser Pro
            435

<210> SEQ ID NO 113
<211> LENGTH: 447
<212> TYPE: PRT
<213> ORGANISM: Artificial
<220> FEATURE:
<223> OTHER INFORMATION: heavy chain 2- CKLO2 - SG1095

<400> SEQUENCE: 113

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Trp Asn Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser Asp Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Leu Tyr Asn Ser Thr Tyr Arg Val
            290                 295                 300

Val Ser Val Leu Thr Val Leu His Arg Asp Trp Leu Asn Gly Lys Glu
305                 310                 315                 320

Tyr Lys Cys Lys Val Ser Asn Thr Ala Leu Pro Lys Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
            370                 375                 380

Ser Asn Gly Gln Pro Glu Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Ala His Tyr Thr Arg Lys Glu Leu Ser Leu Ser Pro
            435                 440                 445

<210> SEQ ID NO 114
<211> LENGTH: 224
<212> TYPE: PRT
<213> ORGANISM: Artificial
<220> FEATURE:
<223> OTHER INFORMATION: light chain 1- CKLO2 - SG1095

<400> SEQUENCE: 114

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
            35                  40                  45

Gly Arg Ile Asp Pro Asp Asn His Asn Thr Lys Phe Asp Pro Lys Phe
        50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Glu His Trp Gly Gln Gly Thr Thr
            100                 105                 110

Val Thr Val Ser Ser Ala Ser Val Ala Ala Pro Ser Val Phe Ile Phe
            115                 120                 125

Pro Pro Ser Asp Glu Gln Leu Lys Ser Gly Thr Ala Ser Val Val Cys
            130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175
```

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
            195                 200                 205

Gln Gly Leu Ser Ser Pro Val Thr Lys Ser Phe Asn Arg Gly Glu Cys
            210                 215                 220

<210> SEQ ID NO 115
<211> LENGTH: 216
<212> TYPE: PRT
<213> ORGANISM: Artificial
<220> FEATURE:
<223> OTHER INFORMATION: light chain 2- CKLO2 - SG1095

<400> SEQUENCE: 115

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Asp Arg Ala Glu Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Ile His Leu His
                85                  90                  95

Ser Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 116
<211> LENGTH: 437
<212> TYPE: PRT
<213> ORGANISM: Artificial
<220> FEATURE:
<223> OTHER INFORMATION: heavy chain 1- CKLO2 - SG1099

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Lys Ala Phe Glu Asp Ile Tyr Asn Arg
            20                  25                  30

Arg Ala Trp Tyr Gln Gln Lys Pro Gly Lys Ala Pro Lys Leu Leu Ile
        35                  40                  45

```
His Gly Ala Thr Ser Leu Glu His Gly Val Pro Ser Arg Phe Ser Gly
     50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Tyr Cys Gln Gln Phe Trp Ser Ala Pro Tyr
                 85                  90                  95
Thr Phe Gly Gly Gly Thr Lys Val Glu Ile Lys Ser Ser Ala Ser Thr
            100                 105                 110
Lys Gly Pro Ser Val Phe Pro Leu Ala Pro Ser Ser Lys Ser Thr Ser
        115                 120                 125
Gly Gly Thr Ala Ala Leu Gly Cys Leu Val Lys Asp Tyr Phe Pro Glu
    130                 135                 140
Pro Val Thr Val Ser Trp Asn Ser Gly Ala Leu Thr Ser Gly Val His
145                 150                 155                 160
Thr Phe Pro Ala Val Leu Gln Ser Ser Gly Leu Tyr Ser Leu Ser Ser
                165                 170                 175
Val Val Thr Val Pro Ser Ser Leu Gly Thr Gln Thr Tyr Ile Cys
            180                 185                 190
Asn Val Asn His Lys Pro Ser Asn Thr Lys Val Asp Lys Lys Val Glu
        195                 200                 205
Pro Lys Ser Cys Asp Lys Thr His Thr Cys Pro Pro Cys Pro Ala Pro
    210                 215                 220
Glu Leu Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                245                 250                 255
Asp Val Ser His Glu Asp Pro Glu Val Lys Phe Asn Trp Tyr Val Asp
            260                 265                 270
Gly Val Glu Val His Asn Ala Lys Thr Lys Pro Arg Glu Glu Gln Tyr
        275                 280                 285
Asn Ser Thr Tyr Arg Val Val Ser Val Leu Thr Val Leu His Arg Asp
    290                 295                 300
Trp Leu Asn Gly Lys Glu Tyr Lys Cys Lys Val Ser Asn Lys Ala Leu
305                 310                 315                 320
Pro Ala Pro Ile Glu Lys Thr Ile Ser Lys Ala Lys Gly Gln Arg Arg
                325                 330                 335
Glu Pro Gln Val Tyr Thr Leu Pro Pro Cys Arg Asp Glu Leu Thr Lys
            340                 345                 350
Asn Gln Val Ser Leu Trp Cys Leu Val Lys Gly Phe Tyr Pro Ser Asp
        355                 360                 365
Ile Ala Val Glu Trp Glu Ser Asn Gly Gln Pro Glu Asn Asn Tyr Lys
    370                 375                 380
Thr Thr Pro Pro Val Leu Asp Ser Asp Gly Ser Phe Phe Leu Tyr Ser
385                 390                 395                 400
Lys Leu Thr Val Asp Lys Ser Arg Trp Gln Gln Gly Asn Val Phe Ser
                405                 410                 415
Cys Ser Val Met His Glu Ala Leu His Asn His Tyr Thr Gln Lys Ser
            420                 425                 430
Leu Ser Leu Ser Pro
        435

<210> SEQ ID NO 117
<211> LENGTH: 447
```

<212> TYPE: PRT
<213> ORGANISM: Artificial
<220> FEATURE:
<223> OTHER INFORMATION: heavy chain 2- CKLO2 - SG1099

<400> SEQUENCE: 117

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Arg Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380
```

```
Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 118
<211> LENGTH: 224
<212> TYPE: PRT
<213> ORGANISM: Artificial
<220> FEATURE:
<223> OTHER INFORMATION: light chain 1- CKLO2 - SG1099

<400> SEQUENCE: 118

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
        35                  40                  45

Gly Arg Ile Asp Pro Asp Asn His Asn Thr Lys Phe Asp Pro Lys Phe
50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Glu His Trp Gly Gln Gly Thr Thr
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220

<210> SEQ ID NO 119
<211> LENGTH: 216
<212> TYPE: PRT
<213> ORGANISM: Artificial
<220> FEATURE:
<223> OTHER INFORMATION: light chain 2- CKLO2 - SG1099

<400> SEQUENCE: 119

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
            20                  25                  30
```

Tyr Leu Ala Trp Tyr Gln Gln Lys Pro Gly Gln Ala Pro Arg Leu Leu
                35                  40                  45

Ile Tyr Asp Ala Ser Asp Arg Ala Glu Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Ile His Leu His
                85                  90                  95

Ser Phe Thr Phe Gly Gln Gly Thr Lys Val Glu Ile Lys Arg Thr Val
                100                 105                 110

Ala Ala Pro Ser Val Phe Ile Phe Pro Pro Ser Asp Arg Lys Leu Lys
                115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
210                 215

<210> SEQ ID NO 120
<211> LENGTH: 437
<212> TYPE: PRT
<213> ORGANISM: Artificial
<220> FEATURE:
<223> OTHER INFORMATION: heavy chain 1- CKLO2 - SG1100

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Lys Ala Phe Glu Asp Ile Tyr Asn Arg
                20                  25                  30

Arg Ala Trp Tyr Gln Gln Lys Pro Gly Lys Ala Pro Lys Leu Leu Ile
                35                  40                  45

His Gly Ala Thr Ser Leu Glu His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Trp Ser Ala Pro Tyr
                85                  90                  95

Thr Phe Gly Gly Gly Thr Lys Val Glu Ile Lys Ser Ser Ala Ser Thr
                100                 105                 110

Lys Gly Pro Ser Val Phe Pro Leu Ala Pro Ser Ser Lys Ser Thr Ser
                115                 120                 125

Gly Gly Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

```
Val Val Thr Val Pro Ser Ser Leu Gly Thr Gln Thr Tyr Ile Cys
            180                 185                 190

Asn Val Asn His Lys Pro Ser Asn Thr Lys Val Asp Lys Lys Val Glu
            195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
            245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
            275                 280                 285

Asn Ser Thr Tyr Arg Val Val Ser Val Leu Thr Val Leu His Arg Asp
            290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Arg Arg
                325                 330                 335

Glu Pro Gln Val Tyr Thr Leu Pro Pro Cys Arg Asp Glu Leu Thr Lys
                340                 345                 350

Asn Gln Val Ser Leu Trp Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Ala His Tyr Thr Arg Lys Glu
                420                 425                 430

Leu Ser Leu Ser Pro
            435

<210> SEQ ID NO 121
<211> LENGTH: 447
<212> TYPE: PRT
<213> ORGANISM: Artificial
<220> FEATURE:
<223> OTHER INFORMATION: heavy chain 2- CKLO2 - SG1100

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

Ala Arg Tyr Asp Ala His Tyr Gly Glu Leu Asp Phe Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Arg Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Ala His Tyr Thr Arg Lys Glu Leu Ser Leu Ser Pro
        435                 440                 445

<210> SEQ ID NO 122
<211> LENGTH: 224
<212> TYPE: PRT
<213> ORGANISM: Artificial
<220> FEATURE:
<223> OTHER INFORMATION: light chain 1- CKLO2 - SG1100

<400> SEQUENCE: 122

Gln Val Gln Leu Val Gln Ser Gly Ala Glu Val Lys Lys Pro Gly Ser
1               5                   10                  15

```
Ser Val Lys Val Ser Cys Lys Ala Ser Gly Leu Thr Ile Ser His Thr
         20                  25                  30

Tyr Met His Trp Val Arg Gln Ala Pro Gly Gln Gly Leu Glu Trp Met
         35                  40                  45

Gly Arg Ile Asp Pro Asp Asn His Asn Thr Lys Phe Asp Pro Lys Phe
 50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Val Phe Gly Phe Phe Glu His Trp Gly Gln Gly Thr Thr
             100                 105                 110

Val Thr Val Ser Ser Ala Ser Val Ala Ala Pro Ser Val Phe Ile Phe
         115                 120                 125

Pro Pro Ser Asp Glu Gln Leu Lys Ser Gly Thr Ala Ser Val Val Cys
 130                 135                 140

Leu Leu Asn Asn Phe Tyr Pro Arg Glu Ala Lys Val Gln Trp Lys Val
 145                 150                 155                 160

Asp Asn Ala Leu Gln Ser Gly Asn Ser Gln Glu Ser Val Thr Glu Gln
                 165                 170                 175

Asp Ser Lys Asp Ser Thr Tyr Ser Leu Ser Ser Thr Leu Thr Leu Ser
             180                 185                 190

Lys Ala Asp Tyr Glu Lys His Lys Val Tyr Ala Cys Glu Val Thr His
             195                 200                 205

Gln Gly Leu Ser Ser Pro Val Thr Lys Ser Phe Asn Arg Gly Glu Cys
         210                 215                 220

<210> SEQ ID NO 123
<211> LENGTH: 216
<212> TYPE: PRT
<213> ORGANISM: Artificial
<220> FEATURE:
<223> OTHER INFORMATION: light chain 2- CKLO2 - SG1100

<400> SEQUENCE: 123

Glu Ile Val Leu Thr Gln Ser Pro Ala Thr Leu Ser Leu Ser Pro Gly
 1               5                   10                  15

Glu Arg Ala Thr Leu Ser Cys Arg Ala Ser Gln His Val Ser Asp Ala
             20                  25                  30

Tyr Leu Ala Trp Tyr Gln Gln Lys Pro Gly Gln Ala Pro Arg Leu Leu
         35                  40                  45

Ile Tyr Asp Ala Ser Asp Arg Ala Glu Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys His Gln Tyr Ile His Leu His
             85                  90                  95

Ser Phe Thr Phe Gly Gln Gly Thr Lys Val Glu Ile Lys Arg Thr Val
             100                 105                 110

Ala Ala Pro Ser Val Phe Ile Phe Pro Pro Ser Asp Arg Lys Leu Lys
         115                 120                 125

Ser Gly Thr Ala Ser Val Val Cys Leu Leu Asn Asn Phe Tyr Pro Arg
 130                 135                 140

Glu Ala Lys Val Gln Trp Lys Val Asp Asn Ala Leu Gln Ser Gly Asn
 145                 150                 155                 160
```

```
Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 124
<211> LENGTH: 437
<212> TYPE: PRT
<213> ORGANISM: Artificial
<220> FEATURE:
<223> OTHER INFORMATION: heavy chain 1- CKLO3 - SG1095

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Lys Ala Pro Lys Leu Leu Ile
        35                  40                  45

His Gly Ala Thr Ser Leu Glu His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Arg Ser Ala Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
    210                 215                 220

Glu Leu Trp Asn Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Asp Glu Asp Pro Glu Val Lys Phe Asn Trp Tyr Val Asp
            260                 265                 270

Gly Val Glu Val His Asn Ala Lys Thr Lys Pro Arg Glu Glu Leu Tyr
        275                 280                 285

Asn Ser Thr Tyr Arg Val Val Ser Val Leu Thr Val Leu His Arg Asp
    290                 295                 300
```

```
Trp Leu Asn Gly Lys Glu Tyr Lys Cys Lys Val Ser Asn Thr Ala Leu
305                 310                 315                 320

Pro Lys Pro Ile Glu Lys Thr Ile Ser Lys Ala Lys Gly Gln Arg Arg
            325                 330                 335

Glu Pro Gln Val Tyr Thr Leu Pro Pro Cys Arg Asp Glu Leu Thr Lys
        340                 345                 350

Asn Gln Val Ser Leu Trp Cys Leu Val Lys Gly Phe Tyr Pro Ser Asp
    355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
            405                 410                 415

Cys Ser Val Met His Glu Ala Leu His Ala His Tyr Thr Arg Lys Glu
        420                 425                 430

Leu Ser Leu Ser Pro
        435

<210> SEQ ID NO 125
<211> LENGTH: 447
<212> TYPE: PRT
<213> ORGANISM: Artificial
<220> FEATURE:
<223> OTHER INFORMATION: heavy chain 2- CKLO3 - SG1095

<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220
```

```
Thr His Thr Cys Pro Pro Cys Pro Ala Pro Glu Leu Trp Asn Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Asp Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Leu Tyr Asn Ser Thr Tyr Arg Val
        290                 295                 300

Val Ser Val Leu Thr Val Leu His Arg Asp Trp Leu Asn Gly Lys Glu
305                 310                 315                 320

Tyr Lys Cys Lys Val Ser Asn Thr Ala Leu Pro Lys Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Ala His Tyr Thr Arg Lys Glu Leu Ser Leu Ser Pro
        435                 440                 445

<210> SEQ ID NO 126
<211> LENGTH: 224
<212> TYPE: PRT
<213> ORGANISM: Artificial
<220> FEATURE:
<223> OTHER INFORMATION: light chain 1- CKLO3 - SG1095

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
        35                  40                  45

Gly Arg Ile Asp Pro Asp Asn His Asn Thr Lys Phe Asp Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Asp His Trp Gly Gln Gly Thr Thr
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
130                 135                 140
```

-continued

```
Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
            165                 170                 175

Asp Ser Lys Asp Ser Thr Tyr Ser Leu Ser Ser Thr Leu Thr Leu Ser
        180                 185                 190

Lys Ala Asp Tyr Glu Lys His Lys Val Tyr Ala Cys Glu Val Thr His
    195                 200                 205

Gln Gly Leu Ser Ser Pro Val Thr Lys Ser Phe Asn Arg Gly Glu Cys
210                 215                 220
```

<210> SEQ ID NO 127
<211> LENGTH: 216
<212> TYPE: PRT
<213> ORGANISM: Artificial
<220> FEATURE:
<223> OTHER INFORMATION: light chain 2- CKLO3 - SG1095

<400> SEQUENCE: 127

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Asp Arg Ala Glu Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Ile His Leu His
                85                  90                  95

Ser Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 128
<211> LENGTH: 437
<212> TYPE: PRT
<213> ORGANISM: Artificial
<220> FEATURE:
<223> OTHER INFORMATION: heavy chain 1- CKLO3 - SG1099

<400> SEQUENCE: 128

Asp Ile Gln Met Thr Gln Ser Pro Ser Ser Leu Ser Ala Ser Val Gly

```
1               5                   10                  15
Asp Arg Val Thr Ile Thr Cys Lys Ala Thr Glu Asp Ile Tyr Asn Arg
                20                  25                  30
Leu Ala Trp Tyr Gln Gln Lys Pro Gly Lys Ala Pro Lys Leu Leu Ile
            35                  40                  45
His Gly Ala Thr Ser Leu Glu His Gly Val Pro Ser Arg Phe Ser Gly
        50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Phe Arg Ser Ala Pro Tyr
                85                  90                  95
Thr Phe Gly Gly Gly Thr Lys Val Glu Ile Lys Ser Ser Ala Ser Thr
            100                 105                 110
Lys Gly Pro Ser Val Phe Pro Leu Ala Pro Ser Ser Lys Ser Thr Ser
        115                 120                 125
Gly Gly Thr Ala Ala Leu Gly Cys Leu Val Lys Asp Tyr Phe Pro Glu
    130                 135                 140
Pro Val Thr Val Ser Trp Asn Ser Gly Ala Leu Thr Ser Gly Val His
145                 150                 155                 160
Thr Phe Pro Ala Val Leu Gln Ser Ser Gly Leu Tyr Ser Leu Ser Ser
                165                 170                 175
Val Val Thr Val Pro Ser Ser Ser Leu Gly Thr Gln Thr Tyr Ile Cys
            180                 185                 190
Asn Val Asn His Lys Pro Ser Asn Thr Lys Val Asp Lys Lys Val Glu
        195                 200                 205
Pro Lys Ser Cys Asp Lys Thr His Thr Cys Pro Pro Cys Pro Ala Pro
    210                 215                 220
Glu Leu Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                245                 250                 255
Asp Val Ser His Glu Asp Pro Glu Val Lys Phe Asn Trp Tyr Val Asp
            260                 265                 270
Gly Val Glu Val His Asn Ala Lys Thr Lys Pro Arg Glu Glu Gln Tyr
        275                 280                 285
Asn Ser Thr Tyr Arg Val Val Ser Val Leu Thr Val Leu His Arg Asp
    290                 295                 300
Trp Leu Asn Gly Lys Glu Tyr Lys Cys Lys Val Ser Asn Lys Ala Leu
305                 310                 315                 320
Pro Ala Pro Ile Glu Lys Thr Ile Ser Lys Ala Lys Gly Gln Arg Arg
                325                 330                 335
Glu Pro Gln Val Tyr Thr Leu Pro Pro Cys Arg Asp Glu Leu Thr Lys
            340                 345                 350
Asn Gln Val Ser Leu Trp Cys Leu Val Lys Gly Phe Tyr Pro Ser Asp
        355                 360                 365
Ile Ala Val Glu Trp Glu Ser Asn Gly Gln Pro Glu Asn Asn Tyr Lys
    370                 375                 380
Thr Thr Pro Pro Val Leu Asp Ser Asp Gly Ser Phe Phe Leu Tyr Ser
385                 390                 395                 400
Lys Leu Thr Val Asp Lys Ser Arg Trp Gln Gln Gly Asn Val Phe Ser
                405                 410                 415
Cys Ser Val Met His Glu Ala Leu His Asn His Tyr Thr Gln Lys Ser
            420                 425                 430
```

Leu Ser Leu Ser Pro
        435

<210> SEQ ID NO 129
<211> LENGTH: 447
<212> TYPE: PRT
<213> ORGANISM: Artificial
<220> FEATURE:
<223> OTHER INFORMATION: heavy chain 2- CKLO3 - SG1099

<400> SEQUENCE: 129

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Arg Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Asp Glu Leu Thr Lys Asn Gln Val Ser Leu Ser
              355                 360                 365

Cys Ala Val Lys Gly Phe Tyr Pro Ser Asp Ile Ala Val Glu Trp Glu
              370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro
              435                 440                 445

<210> SEQ ID NO 130
<211> LENGTH: 224
<212> TYPE: PRT
<213> ORGANISM: Artificial
<220> FEATURE:
<223> OTHER INFORMATION: light chain 1- CKLO3 - SG1099

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
        35                  40                  45

Gly Arg Ile Asp Pro Asp Asn His Asn Thr Lys Phe Asp Pro Lys Phe
50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Asp His Trp Gly Gln Gly Thr Thr
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220

<210> SEQ ID NO 131
<211> LENGTH: 216
<212> TYPE: PRT
<213> ORGANISM: Artificial
<220> FEATURE:
<223> OTHER INFORMATION: light chain 2- CKLO3 - SG1099

```
<400> SEQUENCE: 131

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Asp Arg Ala Glu Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Ile His Leu His
                85                  90                  95

Ser Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 132
<211> LENGTH: 437
<212> TYPE: PRT
<213> ORGANISM: Artificial
<220> FEATURE:
<223> OTHER INFORMATION: heavy chain 1- CKLO3 - SG1100

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Lys Ala Pro Lys Leu Leu Ile
        35                  40                  45

His Gly Ala Thr Ser Leu Glu His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Arg Ser Ala Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
```

```
            130                 135                 140
Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
                180                 185                 190

Asn Val Asn His Lys Pro Ser Asn Thr Lys Val Asp Lys Lys Val Glu
                195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
                275                 280                 285

Asn Ser Thr Tyr Arg Val Val Ser Val Leu Thr Val Leu His Arg Asp
                290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Arg Arg
                325                 330                 335

Glu Pro Gln Val Tyr Thr Leu Pro Pro Cys Arg Asp Glu Leu Thr Lys
                340                 345                 350

Asn Gln Val Ser Leu Trp Cys Leu Val Lys Gly Phe Tyr Pro Ser Asp
                355                 360                 365

Ile Ala Val Glu Trp Glu Ser Asn Gly Gln Pro Glu Asn Asn Tyr Lys
                370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Ala His Tyr Thr Arg Lys Glu
                420                 425                 430

Leu Ser Leu Ser Pro
                435

<210> SEQ ID NO 133
<211> LENGTH: 447
<212> TYPE: PRT
<213> ORGANISM: Artificial
<220> FEATURE:
<223> OTHER INFORMATION: heavy chain 2- CKLO3 - SG1100

<400> SEQUENCE: 133

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
                20                  25                  30

Gly Ile Ser Trp Val Arg Gln Ala Pro Gly Gln Gly Leu Glu Trp Met
            35                  40                  45

Gly Gly Val Ile Pro Ile Phe His Thr Ala Asn Tyr Ala Gln Lys Phe
```

```
            50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Tyr Asp Ala His Tyr Gly Glu Leu Asp Phe Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
130                 135                 140
Gly Cys Leu Val Glu Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Glu Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Arg Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Arg Arg Glu Pro Gln Val Cys Thr
                340                 345                 350
Leu Pro Pro Ser Arg Asp Glu Leu Thr Lys Asn Gln Val Ser Leu Ser
                355                 360                 365
Cys Ala Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Ala His Tyr Thr Arg Lys Glu Leu Ser Leu Ser Pro
                435                 440                 445

<210> SEQ ID NO 134
<211> LENGTH: 224
<212> TYPE: PRT
<213> ORGANISM: Artificial
```

```
<220> FEATURE:
<223> OTHER INFORMATION: light chain 1- CKL03- SG1100

<400> SEQUENCE: 134
```

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Pro|Gly|Ser|
|1| | | |5| | | | |10| | | | |15|
|Ser|Val|Lys|Val|Ser|Cys|Lys|Ala|Ser|Gly|Leu|Thr|Ile|Ser|His|Thr|
| | | |20| | | | |25| | | | |30| |
|Tyr|Met|His|Trp|Val|Arg|Gln|Ala|Pro|Gly|Gln|Gly|Leu|Glu|Trp|Met|
| | |35| | | | |40| | | | |45| | |
|Gly|Arg|Ile|Asp|Pro|Asp|Asn|His|Asn|Thr|Lys|Phe|Asp|Pro|Lys|Phe|
| |50| | | | |55| | | | |60| | | |
|Gln|Gly|Arg|Val|Thr|Ile|Thr|Ala|Asp|Thr|Ser|Ser|Thr|Ala|Tyr|
|65| | | | |70| | | | |75| | | | |80|
|Met|Glu|Leu|Ser|Ser|Leu|Arg|Ser|Glu|Asp|Thr|Ala|Val|Tyr|Tyr|Cys|
| | | | |85| | | | |90| | | | |95| |
|Ala|Arg|Gly|Val|Phe|Gly|Phe|Phe|Asp|His|Trp|Gly|Gln|Gly|Thr|Thr|
| | | |100| | | | |105| | | | |110| | |
|Val|Thr|Val|Ser|Ser|Ala|Ser|Val|Ala|Ala|Pro|Ser|Val|Phe|Ile|Phe|
| | |115| | | | |120| | | | |125| | | |
|Pro|Pro|Ser|Asp|Glu|Gln|Leu|Lys|Ser|Gly|Thr|Ala|Ser|Val|Val|Cys|
| |130| | | | |135| | | | |140| | | | |
|Leu|Leu|Asn|Asn|Phe|Tyr|Pro|Arg|Glu|Ala|Lys|Val|Gln|Trp|Lys|Val|
|145| | | | |150| | | | |155| | | | |160|
|Asp|Asn|Ala|Leu|Gln|Ser|Gly|Asn|Ser|Gln|Glu|Ser|Val|Thr|Glu|Gln|
| | | |165| | | | |170| | | | |175| | |
|Asp|Ser|Lys|Asp|Ser|Thr|Tyr|Ser|Leu|Ser|Ser|Thr|Leu|Thr|Leu|Ser|
| | |180| | | | |185| | | | |190| | | |
|Lys|Ala|Asp|Tyr|Glu|Lys|His|Lys|Val|Tyr|Ala|Cys|Glu|Val|Thr|His|
| |195| | | | |200| | | | |205| | | | |
|Gln|Gly|Leu|Ser|Ser|Pro|Val|Thr|Lys|Ser|Phe|Asn|Arg|Gly|Glu|Cys|
|210| | | | |215| | | | |220| | | | | |

```
<210> SEQ ID NO 135
<211> LENGTH: 216
<212> TYPE: PRT
<213> ORGANISM: Artificial
<220> FEATURE:
<223> OTHER INFORMATION: light chain 2- CKL03 - SG1100

<400> SEQUENCE: 135
```

| | | | | | | | | | | | | | | | |
|---|---|---|---|---|---|---|---|---|---|---|---|---|---|---|---|
|Glu|Ile|Val|Leu|Thr|Gln|Ser|Pro|Ala|Thr|Leu|Ser|Leu|Ser|Pro|Gly|
|1| | | |5| | | | |10| | | | |15| |
|Glu|Arg|Ala|Thr|Leu|Ser|Cys|Arg|Ala|Ser|Gln|His|Val|Ser|Asp|Ala|
| | | |20| | | | |25| | | | |30| | |
|Tyr|Leu|Ala|Trp|Tyr|Gln|Gln|Lys|Pro|Gly|Gln|Ala|Pro|Arg|Leu|Leu|
| | |35| | | | |40| | | | |45| | | |
|Ile|Tyr|Asp|Ala|Ser|Asp|Arg|Ala|Glu|Gly|Val|Pro|Ala|Arg|Phe|Ser|
| |50| | | | |55| | | | |60| | | | |
|Gly|Ser|Gly|Ser|Gly|Thr|Asp|Phe|Thr|Leu|Thr|Ile|Ser|Ser|Leu|Glu|
|65| | | | |70| | | | |75| | | | |80| |
|Pro|Glu|Asp|Phe|Ala|Val|Tyr|Tyr|Cys|His|Gln|Tyr|Ile|His|Leu|His|
| | | | |85| | | | |90| | | | |95| | |
|Ser|Phe|Thr|Phe|Gly|Gln|Gly|Thr|Lys|Val|Glu|Ile|Lys|Arg|Thr|Val|
| | | |100| | | | |105| | | | |110| | | |
|Ala|Ala|Pro|Ser|Val|Phe|Ile|Phe|Pro|Pro|Ser|Asp|Arg|Lys|Leu|Lys|

```
                115                 120                 125
Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 136
<211> LENGTH: 115
<212> TYPE: PRT
<213> ORGANISM: Artificial
<220> FEATURE:
<223> OTHER INFORMATION: heavy chain variable domain VH 2F2

<400> SEQUENCE: 136

Gln Glu Gln Leu Glu Glu Ser Gly Gly Gly Leu Val Lys Pro Gly Gly
1               5                   10                  15

Thr Leu Thr Leu Thr Cys Lys Ala Ser Gly Phe Ser Phe Ile Asp His
            20                  25                  30

Tyr Ala Ser Trp Val Arg Gln Ala Pro Gly Lys Gly Leu Glu Trp Ile
        35                  40                  45

Ala Tyr Ile Gly Gly Ser Gly Thr Thr Tyr Tyr Ala Asn Arg Ala Lys
    50                  55                  60

Gly Arg Phe Thr Ile Ser Arg Thr Ser Thr Thr Val Thr Leu Gln
65              70                  75                  80

Met Thr Ser Leu Thr Ala Ala Asp Thr Ala Thr Tyr Phe Cys Ala Arg
                85                  90                  95

Asn Leu Asp Val Ser Ala Ser Leu Trp Gly Pro Gly Thr Leu Val Thr
            100                 105                 110

Val Ser Ser
        115

<210> SEQ ID NO 137
<211> LENGTH: 112
<212> TYPE: PRT
<213> ORGANISM: Artificial
<220> FEATURE:
<223> OTHER INFORMATION: light chain variable domain VL 2F2

<400> SEQUENCE: 137

Gln Val Leu Thr Gln Thr Pro Ala Ser Val Ser Ala Ala Val Gly Gly
1               5                   10                  15

Thr Val Thr Ile Ser Cys Gln Ser Ser Gln Ser Val Tyr Asn Asn Asn
            20                  25                  30

Leu Leu Ser Trp Phe Gln Gln Lys Pro Gly Gln Pro Pro Lys Leu Leu
        35                  40                  45

Ile Tyr Glu Ala Ser Lys Leu Ala Ser Gly Val Pro Pro Arg Phe Ser
    50                  55                  60

Gly Ser Gly Ser Gly Thr Gln Ser Thr Leu Thr Ile Ser Gly Val Gln
65              70                  75                  80
```

```
Cys Asp Asp Ala Ala Thr Tyr Tyr Cys Glu Gly Ala Phe Leu Cys Thr
                85                  90                  95

Thr Tyr Asp Cys Phe Val Phe Gly Gly Gly Thr Glu Val Val Val Lys
            100                 105                 110

<210> SEQ ID NO 138
<211> LENGTH: 117
<212> TYPE: PRT
<213> ORGANISM: mus musculus

<400> SEQUENCE: 138

Glu Val Gln Leu Gln Gln Ser Gly Ala Glu Leu Val Lys Ala Gly Ala
1               5                   10                  15

Ser Val Lys Leu Ser Cys Pro Ala Ser Gly Leu Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Val Phe Gly Phe Asp Tyr Trp Gly Gln Gly Thr Thr
            100                 105                 110

Leu Thr Val Ser Ser
        115

<210> SEQ ID NO 139
<211> LENGTH: 107
<212> TYPE: PRT
<213> ORGANISM: mus musculus

<400> SEQUENCE: 139

Asp Ile Gln Met Thr Gln Ser Ser Ser Phe Ser Val Ser Leu Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Ser Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Phe Trp Ser Ala Pro Tyr
                85                  90                  95

Thr Phe Gly Gly Gly Thr Lys Leu Glu Ile Lys
            100                 105

<210> SEQ ID NO 140
<211> LENGTH: 121
<212> TYPE: PRT
<213> ORGANISM: Artificial
<220> FEATURE:
<223> OTHER INFORMATION: heavy chain variable domain VH 1H11

<400> SEQUENCE: 140

Gln Glu Gln Leu Val Glu Ser Gly Gly Asp Leu Val Lys Pro Glu Gly
1               5                   10                  15
```

-continued

```
Ser Leu Thr Leu Thr Cys Thr Ala Ser Gly Phe Ser Phe Ser Thr Ser
            20                  25                  30

Tyr Trp Met Cys Trp Val Arg Gln Ala Pro Gly Lys Gly Leu Glu Leu
        35                  40                  45

Ile Ala Cys Ile Ser Ser Ser Ile Gly Val Thr Tyr Tyr Ala Ser Trp
 50                  55                  60

Ala Glu Gly Arg Phe Thr Ile Ser Lys Thr Ser Thr Thr Val Thr
 65                  70                  75                  80

Leu Gln Met Thr Ser Leu Thr Val Ala Asp Thr Ala Thr Tyr Phe Cys
                85                  90                  95

Ala Arg Thr Thr Asp Asp Asn Trp Asn Val Gly Phe Asn Leu Trp Gly
                100                 105                 110

Pro Gly Thr Leu Val Thr Val Ser Ser
            115                 120
```

<210> SEQ ID NO 141
<211> LENGTH: 110
<212> TYPE: PRT
<213> ORGANISM: Artificial
<220> FEATURE:
<223> OTHER INFORMATION: light chain variable domain VL 1H11

<400> SEQUENCE: 141

```
Tyr Asp Met Thr Gln Thr Pro Ala Ser Val Glu Val Gly Val Gly Gly
 1               5                  10                  15

Thr Val Thr Ile Lys Cys Gln Ala Ser Gln Ser Ile Gly Asn Arg Tyr
            20                  25                  30

Leu Ser Trp Tyr Gln Gln Lys Pro Gly Gln Pro Pro Lys Leu Leu Ile
        35                  40                  45

Tyr Gly Thr Ser Thr Leu Ala Ser Gly Val Ser Ser Arg Phe Lys Gly
 50                  55                  60

Ser Gly Ser Gly Thr Gln Phe Thr Leu Thr Ile Ser Gly Val Glu Cys
 65                  70                  75                  80

Ala Asp Ser Ala Thr Tyr Tyr Cys Gln Gln Gly Ala Thr Ile Ser Tyr
                85                  90                  95

Leu Asp Asn Ala Phe Gly Gly Gly Thr Glu Val Val Val Lys
                100                 105                 110
```

<210> SEQ ID NO 142
<211> LENGTH: 76
<212> TYPE: PRT
<213> ORGANISM: homo sapiens

<400> SEQUENCE: 142

```
Gln Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
 65                  70                  75
```

<210> SEQ ID NO 143
<211> LENGTH: 76

```
<212> TYPE: PRT
<213> ORGANISM: Artificial
<220> FEATURE:
<223> OTHER INFORMATION: exemplary human CCL2 (MCP1) - P8A variant

<400> SEQUENCE: 143

Gln Pro Asp Ala Ile Asn Ala Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 144
<211> LENGTH: 76
<212> TYPE: PRT
<213> ORGANISM: Artificial
<220> FEATURE:
<223> OTHER INFORMATION: exemplary human CCL2 (MCP1) - T10C variant

<400> SEQUENCE: 144

Gln Pro Asp Ala Ile Asn Ala Pro Val Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 145
<211> LENGTH: 76
<212> TYPE: PRT
<213> ORGANISM: homo sapiens

<400> SEQUENCE: 145

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
50                  55                  60

Lys His Leu Asp Gln Ile Phe Gln Asn Leu Lys Pro
65                  70                  75

<210> SEQ ID NO 146
<211> LENGTH: 76
<212> TYPE: PRT
<213> ORGANISM: Artificial
<220> FEATURE:
<223> OTHER INFORMATION: SEQ ID NO: 146 exemplary human CCL8 (MCP2) -
      P8A variant
```

```
<400> SEQUENCE: 146

Gln Pro Asp Ser Val Ser Ile Ala Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
50                  55                  60

Lys His Leu Asp Gln Ile Phe Gln Asn Leu Lys Pro
65                  70                  75

<210> SEQ ID NO 147
<211> LENGTH: 76
<212> TYPE: PRT
<213> ORGANISM: homo sapiens

<400> SEQUENCE: 147

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
                20                  25                  30

Ser Ser His Cys Pro Arg Glu Ala Val Ile Phe Lys Thr Lys Leu Asp
            35                  40                  45

Lys Glu Ile Cys Ala Asp Pro Thr Gln Lys Trp Val Gln Asp Phe Met
50                  55                  60

Lys His Leu Asp Lys Lys Thr Gln Thr Pro Lys Leu
65                  70                  75

<210> SEQ ID NO 148
<211> LENGTH: 82
<212> TYPE: PRT
<213> ORGANISM: homo sapiens

<400> SEQUENCE: 148

Phe Asn Pro Gln Gly Leu Ala Gln Pro Asp Ala Leu Asn Val Pro Ser
1               5                   10                  15

Thr Cys Cys Phe Thr Phe Ser Ser Lys Lys Ile Ser Leu Gln Arg Leu
                20                  25                  30

Lys Ser Tyr Val Ile Thr Thr Ser Arg Cys Pro Gln Lys Ala Val Ile
            35                  40                  45

Phe Arg Thr Lys Leu Gly Lys Glu Ile Cys Ala Asp Pro Lys Glu Lys
50                  55                  60

Trp Val Gln Asn Tyr Met Lys His Leu Gly Arg Lys Ala His Thr Leu
65                  70                  75                  80

Lys Thr

<210> SEQ ID NO 149
<211> LENGTH: 76
<212> TYPE: PRT
<213> ORGANISM: macaca fascicularis

<400> SEQUENCE: 149

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30
```

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
 50                  55                  60

Asp His Leu Asp Lys Gln Ile Gln Thr Pro Lys Pro
 65                  70                  75

<210> SEQ ID NO 150
<211> LENGTH: 125
<212> TYPE: PRT
<213> ORGANISM: mus musculus

<400> SEQUENCE: 150

Gln Pro Asp Ala Val Asn Ala Pro Leu Thr Cys Cys Tyr Ser Phe Thr
1               5                   10                  15

Ser Lys Met Ile Pro Met Ser Arg Leu Glu Ser Tyr Lys Arg Ile Thr
            20                  25                  30

Ser Ser Arg Cys Pro Lys Glu Ala Val Val Phe Val Thr Lys Leu Lys
        35                  40                  45

Arg Glu Val Cys Ala Asp Pro Lys Lys Glu Trp Val Gln Thr Tyr Ile
 50                  55                  60

Lys Asn Leu Asp Arg Asn Gln Met Arg Ser Glu Pro Thr Thr Leu Phe
65                  70                  75                  80

Lys Thr Ala Ser Ala Leu Arg Ser Ser Ala Pro Leu Asn Val Lys Leu
                85                  90                  95

Thr Arg Lys Ser Glu Ala Asn Ala Ser Thr Thr Phe Ser Thr Thr Thr
            100                 105                 110

Ser Ser Thr Ser Val Gly Val Thr Ser Val Thr Val Asn
        115                 120                 125

<210> SEQ ID NO 151
<211> LENGTH: 328
<212> TYPE: PRT
<213> ORGANISM: Artificial
<220> FEATURE:
<223> OTHER INFORMATION: GG01 - exemplary human heavy chain constant
      region derived from IgG1 including the mutations (Kabat EU
      numbering) L234Y/P238D/T250V/V264I/T307P/A330K, Q311R/P343R,
      N434A, Q438R/S440E

<400> SEQUENCE: 151

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Tyr Leu Gly Gly Asp Ser Val Phe Leu Phe Pro Pro
        115                 120                 125

Lys Pro Lys Asp Val Leu Met Ile Ser Arg Thr Pro Glu Val Thr Cys

```
                130               135               140
Val Val Ile Asp Val Ser His Glu Asp Pro Glu Val Lys Phe Asn Trp
145               150               155               160

Tyr Val Asp Gly Val Glu Val His Asn Ala Lys Thr Lys Pro Arg Glu
                165               170               175

Glu Gln Tyr Asn Ser Thr Tyr Arg Val Val Ser Val Leu Pro Val Leu
                180               185               190

His Arg Asp Trp Leu Asn Gly Lys Glu Tyr Lys Cys Lys Val Ser Asn
            195               200               205

Lys Ala Leu Pro Lys Pro Ile Glu Lys Thr Ile Ser Lys Ala Lys Gly
            210               215               220

Gln Arg Arg Glu Pro Gln Val Tyr Thr Leu Pro Pro Ser Arg Asp Glu
225               230               235               240

Leu Thr Lys Asn Gln Val Ser Leu Thr Cys Leu Val Lys Gly Phe Tyr
                245               250               255

Pro Ser Asp Ile Ala Val Glu Trp Glu Ser Asn Gly Gln Pro Glu Asn
                260               265               270

Asn Tyr Lys Thr Thr Pro Pro Val Leu Asp Ser Asp Gly Ser Phe Phe
            275               280               285

Leu Tyr Ser Lys Leu Thr Val Asp Lys Ser Arg Trp Gln Gln Gly Asn
            290               295               300

Val Phe Ser Cys Ser Val Met His Glu Ala Leu His Ala His Tyr Thr
305               310               315               320

Arg Lys Glu Leu Ser Leu Ser Pro
                325

<210> SEQ ID NO 152
<211> LENGTH: 328
<212> TYPE: PRT
<213> ORGANISM: Artificial
<220> FEATURE:
<223> OTHER INFORMATION: GG02 - exemplary human heavy chain constant
      region derived from IgG1 including mutations (Kabat EU numbering)
      L234Y/P238D/T250V/V264I/T307P/A330K, Q311R/P343R,
      M428L/N434A/Y436T,Q438R/S440E

<400> SEQUENCE: 152

Ala Ser Thr Lys Gly Pro Ser Val Phe Pro Leu Ala Pro Ser Ser Lys
1               5                 10                15

Ser Thr Ser Gly Gly Thr Ala Ala Leu Gly Cys Leu Val Lys Asp Tyr
                20                25                30

Phe Pro Glu Pro Val Thr Val Ser Trp Asn Ser Gly Ala Leu Thr Ser
            35                40                45

Gly Val His Thr Phe Pro Ala Val Leu Gln Ser Ser Gly Leu Tyr Ser
        50                55                60

Leu Ser Ser Val Val Thr Val Pro Ser Ser Leu Gly Thr Gln Thr
65              70                75                80

Tyr Ile Cys Asn Val Asn His Lys Pro Ser Asn Thr Lys Val Asp Lys
                85                90                95

Lys Val Glu Pro Lys Ser Cys Asp Lys Thr His Thr Cys Pro Pro Cys
                100               105               110

Pro Ala Pro Glu Tyr Leu Gly Gly Asp Ser Val Phe Leu Phe Pro Pro
            115               120               125

Lys Pro Lys Asp Val Leu Met Ile Ser Arg Thr Pro Glu Val Thr Cys
            130               135               140

Val Val Ile Asp Val Ser His Glu Asp Pro Glu Val Lys Phe Asn Trp
```

```
145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Pro Val Leu
                180                 185                 190

His Arg Asp Trp Leu Asn Gly Lys Glu Tyr Lys Cys Lys Val Ser Asn
                195                 200                 205

Lys Ala Leu Pro Lys Pro Ile Glu Lys Thr Ile Ser Lys Ala Lys Gly
                210                 215                 220

Gln Arg Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Leu His Glu Ala Leu His Ala His Thr Thr
305                 310                 315                 320

Arg Lys Glu Leu Ser Leu Ser Pro
                325

<210> SEQ ID NO 153
<211> LENGTH: 328
<212> TYPE: PRT
<213> ORGANISM: Artificial
<220> FEATURE:
<223> OTHER INFORMATION: GG03 -exemplary human heavy chain constant
      region derived from IgG1 (comprising-IgG1 allotype sequences)
      including the mutations (Kabat EU numbering)
      L234Y/P238D/T250V/V264I/T307P/A330K, Q311R/P343R, N434A,
      Q438R/S440E

<400> SEQUENCE: 153

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Tyr Leu Gly Gly Asp Ser Val Phe Leu Phe Pro Pro
                115                 120                 125

Lys Pro Lys Asp Val Leu Met Ile Ser Arg Thr Pro Glu Val Thr Cys
                130                 135                 140

Val Val Ile Asp Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
              165                 170                 175

Glu Gln Tyr Asn Ser Thr Tyr Arg Val Val Ser Val Leu Pro Val Leu
            180                 185                 190

His Arg Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Ala His Tyr Thr
305                 310                 315                 320

Arg Lys Glu Leu Ser Leu Ser Pro
                325

<210> SEQ ID NO 154
<211> LENGTH: 328
<212> TYPE: PRT
<213> ORGANISM: Artificial
<220> FEATURE:
<223> OTHER INFORMATION: GG04 -exemplary human heavy chain constant
      region derived from IgG1 (comprising-IgG1 allotype sequences)
      including mutations (Kabat EU numbering)
      L234Y/P238D/T250V/V264I/T307P/A330K, Q311R/P343R,
      M428L/N434A/Y436T, Q438R/S440E

<400> SEQUENCE: 154

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Tyr Leu Gly Gly Asp Ser Val Phe Leu Phe Pro Pro
        115                 120                 125

Lys Pro Lys Asp Val Leu Met Ile Ser Arg Thr Pro Glu Val Thr Cys
    130                 135                 140

Val Val Ile Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Pro Val Leu
            180                 185                 190

His Arg Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ala His Thr Thr
305                 310                 315                 320

Arg Lys Glu Leu Ser Leu Ser Pro
                325

<210> SEQ ID NO 155
<211> LENGTH: 437
<212> TYPE: PRT
<213> ORGANISM: Artificial
<220> FEATURE:
<223> OTHER INFORMATION: heavy chain 1- CKLO2 - GG01

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Lys Ala Phe Glu Asp Ile Tyr Asn Arg
            20                  25                  30

Arg Ala Trp Tyr Gln Gln Lys Pro Gly Lys Ala Pro Lys Leu Leu Ile
        35                  40                  45

His Gly Ala Thr Ser Leu Glu His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Trp Ser Ala Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205
```

```
Pro Lys Ser Cys Asp Lys Thr His Thr Cys Pro Pro Cys Pro Ala Pro
        210                 215                 220

Glu Tyr Leu Gly Gly Asp Ser Val Phe Leu Phe Pro Pro Lys Pro Lys
225                 230                 235                 240

Asp Val Leu Met Ile Ser Arg Thr Pro Glu Val Thr Cys Val Val Ile
                245                 250                 255

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
            275                 280                 285

Asn Ser Thr Tyr Arg Val Val Ser Val Leu Pro Val Leu His Arg Asp
    290                 295                 300

Trp Leu Asn Gly Lys Glu Tyr Lys Cys Lys Val Ser Asn Lys Ala Leu
305                 310                 315                 320

Pro Lys Pro Ile Glu Lys Thr Ile Ser Lys Ala Lys Gly Gln Arg Arg
                325                 330                 335

Glu Pro Gln Val Tyr Thr Leu Pro Pro Cys Arg Asp Glu Leu Thr Lys
                340                 345                 350

Asn Gln Val Ser Leu Trp Cys Leu Val Lys Gly Phe Tyr Pro Ser Asp
            355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Ala His Tyr Thr Arg Lys Glu
                420                 425                 430

Leu Ser Leu Ser Pro
            435

<210> SEQ ID NO 156
<211> LENGTH: 447
<212> TYPE: PRT
<213> ORGANISM: Artificial
<220> FEATURE:
<223> OTHER INFORMATION: heavy chain 2- CKL02 - GG01

<400> SEQUENCE: 156

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
                20                  25                  30

Gly Ile Ser Trp Val Arg Gln Ala Pro Gly Gln Gly Leu Glu Trp Met
            35                  40                  45

Gly Gly Val Ile Pro Ile Phe His Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
                100                 105                 110

Thr Leu Val Thr Val Ser Ser Ala Ser Thr Lys Gly Pro Ser Val Phe
            115                 120                 125
```

```
Pro Leu Ala Pro Ser Ser Lys Ser Thr Ser Gly Gly Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Val Leu Met Ile Ser
                245                 250                 255

Arg Thr Pro Glu Val Thr Cys Val Val Ile Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Pro Val Leu His Arg Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Ala His Tyr Thr Arg Lys Glu Leu Ser Leu Ser Pro
        435                 440                 445

<210> SEQ ID NO 157
<211> LENGTH: 224
<212> TYPE: PRT
<213> ORGANISM: Artificial
<220> FEATURE:
<223> OTHER INFORMATION: light chain 1- CKLO2 GG01

<400> SEQUENCE: 157

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
        35                  40                  45
```

```
Gly Arg Ile Asp Pro Asp Asn His Asn Thr Lys Phe Asp Pro Lys Phe
 50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Val Phe Gly Phe Phe Glu His Trp Gly Gln Gly Thr Thr
                100                 105                 110

Val Thr Val Ser Ser Ala Ser Val Ala Ala Pro Ser Val Phe Ile Phe
            115                 120                 125

Pro Pro Ser Asp Glu Gln Leu Lys Ser Gly Thr Ala Ser Val Val Cys
130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220
```

<210> SEQ ID NO 158
<211> LENGTH: 216
<212> TYPE: PRT
<213> ORGANISM: Artificial
<220> FEATURE:
<223> OTHER INFORMATION: light chain 2- CKLO2 GG01

<400> SEQUENCE: 158

```
Glu Ile Val Leu Thr Gln Ser Pro Ala Thr Leu Ser Leu Ser Pro Gly
 1               5                   10                  15

Glu Arg Ala Thr Leu Ser Cys Arg Ala Ser Gln His Val Ser Asp Ala
                 20                  25                  30

Tyr Leu Ala Trp Tyr Gln Gln Lys Pro Gly Gln Ala Pro Arg Leu Leu
             35                  40                  45

Ile Tyr Asp Ala Ser Asp Arg Ala Glu Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys His Gln Tyr Ile His Leu His
                 85                  90                  95

Ser Phe Thr Phe Gly Gln Gly Thr Lys Val Glu Ile Lys Arg Thr Val
                100                 105                 110

Ala Ala Pro Ser Val Phe Ile Phe Pro Pro Ser Asp Arg Lys Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190
```

-continued

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 159
<211> LENGTH: 437
<212> TYPE: PRT
<213> ORGANISM: Artificial
<220> FEATURE:
<223> OTHER INFORMATION: heavy chain 1- CKL02 GG02

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Lys Ala Phe Glu Asp Ile Tyr Asn Arg
            20                  25                  30

Arg Ala Trp Tyr Gln Gln Lys Pro Gly Lys Ala Pro Lys Leu Leu Ile
        35                  40                  45

His Gly Ala Thr Ser Leu Glu His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Trp Ser Ala Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
    210                 215                 220

Glu Tyr Leu Gly Gly Asp Ser Val Phe Leu Phe Pro Pro Lys Pro Lys
225                 230                 235                 240

Asp Val Leu Met Ile Ser Arg Thr Pro Glu Val Thr Cys Val Val Ile
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Pro Val Leu His Arg Asp
    290                 295                 300

Trp Leu Asn Gly Lys Glu Tyr Lys Cys Lys Val Ser Asn Lys Ala Leu
305                 310                 315                 320

Pro Lys Pro Ile Glu Lys Thr Ile Ser Lys Ala Lys Gly Gln Arg Arg
                325                 330                 335

Glu Pro Gln Val Tyr Thr Leu Pro Pro Cys Arg Asp Glu Leu Thr Lys
                340                 345                 350

Asn Gln Val Ser Leu Trp Cys Leu Val Lys Gly Phe Tyr Pro Ser Asp
            355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Leu His Glu Ala Leu His Ala His Thr Arg Lys Glu
            420                 425                 430

Leu Ser Leu Ser Pro
            435

<210> SEQ ID NO 160
<211> LENGTH: 447
<212> TYPE: PRT
<213> ORGANISM: Artificial
<220> FEATURE:
<223> OTHER INFORMATION: heavy chain 2- CKLO2 GG02

<400> SEQUENCE: 160

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Val Leu Met Ile Ser
                245                 250                 255

```
Arg Thr Pro Glu Val Thr Cys Val Val Ile Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Pro Val Leu His Arg Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ala His Thr Thr Arg Lys Glu Leu Ser Leu Ser Pro
            435                 440                 445

<210> SEQ ID NO 161
<211> LENGTH: 224
<212> TYPE: PRT
<213> ORGANISM: Artificial
<220> FEATURE:
<223> OTHER INFORMATION: light chain 1- CKLO2 - GG02

<400> SEQUENCE: 161

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
        35                  40                  45

Gly Arg Ile Asp Pro Asp Asn His Asn Thr Lys Phe Asp Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Glu His Trp Gly Gln Gly Thr Thr
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175
```

-continued

Asp Ser Lys Asp Ser Thr Tyr Ser Leu Ser Ser Thr Leu Thr Leu Ser
                180                 185                 190

Lys Ala Asp Tyr Glu Lys His Lys Val Tyr Ala Cys Glu Val Thr His
            195                 200                 205

Gln Gly Leu Ser Ser Pro Val Thr Lys Ser Phe Asn Arg Gly Glu Cys
        210                 215                 220

<210> SEQ ID NO 162
<211> LENGTH: 216
<212> TYPE: PRT
<213> ORGANISM: Artificial
<220> FEATURE:
<223> OTHER INFORMATION: light chain 2- CKLO2 - GG02

<400> SEQUENCE: 162

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Asp Arg Ala Glu Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Ile His Leu His
                85                  90                  95

Ser Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 163
<211> LENGTH: 437
<212> TYPE: PRT
<213> ORGANISM: Artificial
<220> FEATURE:
<223> OTHER INFORMATION: heavy chain 1- CKLO2 - GG03

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Lys Ala Phe Glu Asp Ile Tyr Asn Arg
            20                  25                  30

Arg Ala Trp Tyr Gln Gln Lys Pro Gly Lys Ala Pro Lys Leu Leu Ile

```
                35                  40                  45
His Gly Ala Thr Ser Leu Glu His Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Phe Trp Ser Ala Pro Tyr
                 85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
210                 215                 220

Glu Tyr Leu Gly Gly Asp Ser Val Phe Leu Phe Pro Pro Lys Pro Lys
225                 230                 235                 240

Asp Val Leu Met Ile Ser Arg Thr Pro Glu Val Thr Cys Val Val Ile
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Pro Val Leu His Arg Asp
290                 295                 300

Trp Leu Asn Gly Lys Glu Tyr Lys Cys Lys Val Ser Asn Lys Ala Leu
305                 310                 315                 320

Pro Lys Pro Ile Glu Lys Thr Ile Ser Lys Ala Lys Gly Gln Arg Arg
                325                 330                 335

Glu Pro Gln Val Tyr Thr Leu Pro Pro Cys Arg Glu Glu Met Thr Lys
            340                 345                 350

Asn Gln Val Ser Leu Trp Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Ala His Tyr Thr Arg Lys Glu
            420                 425                 430

Leu Ser Leu Ser Pro
        435

<210> SEQ ID NO 164
```

<211> LENGTH: 447
<212> TYPE: PRT
<213> ORGANISM: Artificial
<220> FEATURE:
<223> OTHER INFORMATION: heavy chain 2- CKLO2 - GG03

<400> SEQUENCE: 164

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Val Leu Met Ile Ser
                245                 250                 255

Arg Thr Pro Glu Val Thr Cys Val Val Ile Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Pro Val Leu His Arg Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380
```

-continued

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Ala His Tyr Thr Arg Lys Glu Leu Ser Leu Ser Pro
    435                 440                 445

<210> SEQ ID NO 165
<211> LENGTH: 224
<212> TYPE: PRT
<213> ORGANISM: Artificial
<220> FEATURE:
<223> OTHER INFORMATION: light chain 1- CKLO2 - GG03

<400> SEQUENCE: 165

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
            20                  25                  30

Tyr Met His Trp Val Arg Gln Ala Pro Gly Gln Gly Leu Glu Trp Met
        35                  40                  45

Gly Arg Ile Asp Pro Asp Asn His Asn Thr Lys Phe Asp Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Glu His Trp Gly Gln Gly Thr Thr
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220

<210> SEQ ID NO 166
<211> LENGTH: 216
<212> TYPE: PRT
<213> ORGANISM: Artificial
<220> FEATURE:
<223> OTHER INFORMATION: light chain 2- CKLO2 - GG03

<400> SEQUENCE: 166

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala

```
                    20                  25                  30
Tyr Leu Ala Trp Tyr Gln Gln Lys Pro Gly Gln Ala Pro Arg Leu Leu
            35                  40                  45
Ile Tyr Asp Ala Ser Asp Arg Ala Glu Gly Val Pro Ala Arg Phe Ser
        50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys His Gln Tyr Ile His Leu His
                85                  90                  95
Ser Phe Thr Phe Gly Gln Gly Thr Lys Val Glu Ile Lys Arg Thr Val
            100                 105                 110
Ala Ala Pro Ser Val Phe Ile Phe Pro Pro Ser Asp Arg Lys Leu Lys
        115                 120                 125
Ser Gly Thr Ala Ser Val Val Cys Leu Leu Asn Asn Phe Tyr Pro Arg
    130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Asp Tyr Glu Lys His Lys
            180                 185                 190
Val Tyr Ala Cys Glu Val Thr His Gln Gly Leu Ser Ser Pro Val Thr
        195                 200                 205
Lys Ser Phe Asn Arg Gly Glu Cys
    210                 215

<210> SEQ ID NO 167
<211> LENGTH: 437
<212> TYPE: PRT
<213> ORGANISM: Artificial
<220> FEATURE:
<223> OTHER INFORMATION: heavy chain 1- CKLO2 - GG04

<400> SEQUENCE: 167

Asp Ile Gln Met Thr Gln Ser Pro Ser Ser Leu Ser Ala Ser Val Gly
1               5                   10                  15
Asp Arg Val Thr Ile Thr Cys Lys Ala Phe Glu Asp Ile Tyr Asn Arg
            20                  25                  30
Arg Ala Trp Tyr Gln Gln Lys Pro Gly Lys Ala Pro Lys Leu Leu Ile
        35                  40                  45
His Gly Ala Thr Ser Leu Glu His Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Phe Trp Ser Ala Pro Tyr
                85                  90                  95
Thr Phe Gly Gly Gly Thr Lys Val Glu Ile Lys Ser Ser Ala Ser Thr
            100                 105                 110
Lys Gly Pro Ser Val Phe Pro Leu Ala Pro Ser Ser Lys Ser Thr Ser
        115                 120                 125
Gly Gly Thr Ala Ala Leu Gly Cys Leu Val Lys Asp Tyr Phe Pro Glu
    130                 135                 140
Pro Val Thr Val Ser Trp Asn Ser Gly Ala Leu Thr Ser Gly Val His
145                 150                 155                 160
Thr Phe Pro Ala Val Leu Gln Ser Ser Gly Leu Tyr Ser Leu Ser Ser
```

```
                    165                 170                 175
Val Val Thr Val Pro Ser Ser Leu Gly Thr Gln Thr Tyr Ile Cys
            180                 185                 190

Asn Val Asn His Lys Pro Ser Asn Thr Lys Val Asp Lys Val Glu
            195                 200                 205

Pro Lys Ser Cys Asp Lys Thr His Thr Cys Pro Pro Cys Pro Ala Pro
210                 215                 220

Glu Tyr Leu Gly Gly Asp Ser Val Phe Leu Phe Pro Pro Lys Pro Lys
225                 230                 235                 240

Asp Val Leu Met Ile Ser Arg Thr Pro Glu Val Thr Cys Val Val Ile
            245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
            275                 280                 285

Asn Ser Thr Tyr Arg Val Val Ser Val Leu Pro Val Leu His Arg Asp
            290                 295                 300

Trp Leu Asn Gly Lys Glu Tyr Lys Cys Lys Val Ser Asn Lys Ala Leu
305                 310                 315                 320

Pro Lys Pro Ile Glu Lys Thr Ile Ser Lys Ala Lys Gly Gln Arg Arg
            325                 330                 335

Glu Pro Gln Val Tyr Thr Leu Pro Pro Cys Arg Glu Glu Met Thr Lys
            340                 345                 350

Asn Gln Val Ser Leu Trp Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
            405                 410                 415

Cys Ser Val Leu His Glu Ala Leu His Ala His Thr Thr Arg Lys Glu
            420                 425                 430

Leu Ser Leu Ser Pro
            435

<210> SEQ ID NO 168
<211> LENGTH: 447
<212> TYPE: PRT
<213> ORGANISM: Artificial
<220> FEATURE:
<223> OTHER INFORMATION: heavy chain 2- CKLO2 - GG04

<400> SEQUENCE: 168

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe His Thr Ala Asn Tyr Ala Gln Lys Phe
    50                  55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
```

85                  90                  95

Ala Arg Tyr Asp Ala His Tyr Gly Glu Leu Asp Phe Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Val Leu Met Ile Ser
                245                 250                 255

Arg Thr Pro Glu Val Thr Cys Val Val Ile Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Pro Val Leu His Arg Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Arg Arg Glu Pro Gln Val Cys Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ala His Thr Thr Arg Lys Glu Leu Ser Leu Ser Pro
        435                 440                 445

<210> SEQ ID NO 169
<211> LENGTH: 224
<212> TYPE: PRT
<213> ORGANISM: Artificial
<220> FEATURE:
<223> OTHER INFORMATION: light chain 1- CKLO2 - GG04

<400> SEQUENCE: 169

Gln Val Gln Leu Val Gln Ser Gly Ala Glu Val Lys Lys Pro Gly Ser

```
1               5                   10                  15
Ser Val Lys Val Ser Cys Lys Ala Ser Gly Leu Thr Ile Ser His Thr
                20                  25                  30

Tyr Met His Trp Val Arg Gln Ala Pro Gly Gln Gly Leu Glu Trp Met
            35                  40                  45

Gly Arg Ile Asp Pro Asp Asn His Asn Thr Lys Phe Asp Pro Lys Phe
        50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Phe Gly Phe Phe Glu His Trp Gly Gln Gly Thr Thr
                100                 105                 110

Val Thr Val Ser Ser Ala Ser Val Ala Ala Pro Ser Val Phe Ile Phe
            115                 120                 125

Pro Pro Ser Asp Glu Gln Leu Lys Ser Gly Thr Ala Ser Val Val Cys
130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220

<210> SEQ ID NO 170
<211> LENGTH: 216
<212> TYPE: PRT
<213> ORGANISM: Artificial
<220> FEATURE:
<223> OTHER INFORMATION: light chain 2- CKLO2 - GG04

<400> SEQUENCE: 170

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
                20                  25                  30

Tyr Leu Ala Trp Tyr Gln Gln Lys Pro Gly Gln Ala Pro Arg Leu Leu
            35                  40                  45

Ile Tyr Asp Ala Ser Asp Arg Ala Glu Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gly Tyr Ile His Leu His
                85                  90                  95

Ser Phe Thr Phe Gly Gln Gly Thr Lys Val Glu Ile Lys Arg Thr Val
                100                 105                 110

Ala Ala Pro Ser Val Phe Ile Phe Pro Pro Ser Asp Arg Lys Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
```

```
145                 150                 155                 160
Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
    210                 215

<210> SEQ ID NO 171
<211> LENGTH: 437
<212> TYPE: PRT
<213> ORGANISM: Artificial
<220> FEATURE:
<223> OTHER INFORMATION: heavy chain 1- CKLO2 - GG03/GG04

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Lys Ala Phe Glu Asp Ile Tyr Asn Arg
            20                  25                  30

Arg Ala Trp Tyr Gln Gln Lys Pro Gly Lys Ala Pro Lys Leu Leu Ile
        35                  40                  45

His Gly Ala Thr Ser Leu Glu His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Trp Ser Ala Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
    210                 215                 220

Glu Tyr Leu Gly Gly Asp Ser Val Phe Leu Phe Pro Pro Lys Pro Lys
225                 230                 235                 240

Asp Val Leu Met Ile Ser Arg Thr Pro Glu Val Thr Cys Val Val Ile
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Pro Val Leu His Arg Asp
```

```
                 290                 295                 300

Trp Leu Asn Gly Lys Glu Tyr Lys Cys Lys Val Ser Asn Lys Ala Leu
305                 310                 315                 320

Pro Lys Pro Ile Glu Lys Thr Ile Ser Lys Ala Lys Gly Gln Arg Arg
                325                 330                 335

Glu Pro Gln Val Tyr Thr Leu Pro Pro Cys Arg Glu Glu Met Thr Lys
                340                 345                 350

Asn Gln Val Ser Leu Trp Cys Leu Val Lys Gly Phe Tyr Pro Ser Asp
                355                 360                 365

Ile Ala Val Glu Trp Glu Ser Asn Gly Gln Pro Glu Asn Asn Tyr Lys
        370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Ala His Tyr Thr Arg Lys Glu
                420                 425                 430

Leu Ser Leu Ser Pro
        435

<210> SEQ ID NO 172
<211> LENGTH: 447
<212> TYPE: PRT
<213> ORGANISM: Artificial
<220> FEATURE:
<223> OTHER INFORMATION: heavy chain 2- CKLO2 - GG03/GG04

<400> SEQUENCE: 172

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Tyr
                20                  25                  30

Gly Ile Ser Trp Val Arg Gln Ala Pro Gly Gln Gly Leu Glu Trp Met
            35                  40                  45

Gly Gly Val Ile Pro Ile Phe His Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala His Tyr Gly Glu Leu Asp Phe Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Lys
```

```
            210                 215                 220
Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Val Leu Met Ile Ser
                245                 250                 255

Arg Thr Pro Glu Val Thr Cys Val Val Ile Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Pro Val Leu His Arg Asp Trp Leu Asn Gly Lys Glu
305                 310                 315                 320

Tyr Lys Cys Lys Val Ser Asn Lys Ala Leu Pro Lys Pro Ile Glu Lys
                325                 330                 335

Thr Ile Ser Lys Ala Lys Gly Gln Arg Arg Glu Pro Gln Val Cys Thr
                340                 345                 350

Leu Pro Pro Ser Arg Glu Glu Met Thr Lys Asn Gln Val Ser Leu Ser
                355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Leu His Glu
                420                 425                 430

Ala Leu His Ala His Thr Thr Arg Lys Glu Leu Ser Leu Ser Pro
            435                 440                 445

<210> SEQ ID NO 173
<211> LENGTH: 224
<212> TYPE: PRT
<213> ORGANISM: Artificial
<220> FEATURE:
<223> OTHER INFORMATION: light chain 1- CKLO2 - GG03/GG04

<400> SEQUENCE: 173

Gln Val Gln Leu Val Gln Ser Gly Ala Glu Val Lys Lys Pro Gly Ser
1               5                   10                  15

Ser Val Lys Val Ser Cys Lys Ala Ser Gly Leu Thr Ile Ser His Thr
                20                  25                  30

Tyr Met His Trp Val Arg Gln Ala Pro Gly Gln Gly Leu Glu Trp Met
            35                  40                  45

Gly Arg Ile Asp Pro Asp Asn His Asn Thr Lys Phe Asp Pro Lys Phe
        50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Gly Val Phe Gly Phe Glu His Trp Gln Gly Thr Thr
            100                 105                 110

Val Thr Val Ser Ser Ala Ser Val Ala Ala Pro Ser Val Phe Ile Phe
            115                 120                 125

Pro Pro Ser Asp Glu Gln Leu Lys Ser Gly Thr Ala Ser Val Val Cys
130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
            165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
            195                 200                 205

Gln Gly Leu Ser Ser Pro Val Thr Lys Ser Phe Asn Arg Gly Glu Cys
            210                 215                 220

<210> SEQ ID NO 174
<211> LENGTH: 216
<212> TYPE: PRT
<213> ORGANISM: Artificial
<220> FEATURE:
<223> OTHER INFORMATION: light chain 2- CKLO2 - GG03/GG04

<400> SEQUENCE: 174

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln His Val Ser Asp Ala
            20                  25                  30

Tyr Leu Ala Trp Tyr Gln Gln Lys Pro Gly Gln Ala Pro Arg Leu Leu
        35                  40                  45

Ile Tyr Asp Ala Ser Asp Arg Ala Glu Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Ile His Leu His
                85                  90                  95

Ser Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
            165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
210                 215